(12) United States Patent
Yakovlev et al.

(10) Patent No.: US 10,967,183 B2
(45) Date of Patent: *Apr. 6, 2021

(54) METHOD AND APPARATUS FOR NEUROMODULATION TREATMENTS OF PAIN AND OTHER CONDITIONS

(71) Applicant: Nalu Medical, Inc., Carlsbad, CA (US)

(72) Inventors: Anatoly Yakovlev, Santa Clara, CA (US); Daniel Pivonka, Palo Alto, CA (US); Logan Palmer, Santa Monica, CA (US)

(73) Assignee: Nalu Medical, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/408,989

(22) Filed: May 10, 2019

(65) Prior Publication Data

US 2020/0101291 A1    Apr. 2, 2020

Related U.S. Application Data

(63) Continuation of application No. 15/385,729, filed on Dec. 20, 2016, now Pat. No. 10,335,596, which is a (Continued)

(51) Int. Cl.
*A61N 1/378* (2006.01)
*A61N 1/36* (2006.01)
(Continued)

(52) U.S. Cl.
CPC ........ *A61N 1/36071* (2013.01); *A61B 5/0022* (2013.01); *A61B 5/0031* (2013.01); *A61B 5/04001* (2013.01); *A61B 5/0488* (2013.01); *A61B 5/0538* (2013.01); *A61B 5/1118* (2013.01); *A61B 5/14539* (2013.01); *A61B 5/40* (2013.01); *A61B 5/4824* (2013.01); *A61B 5/4836* (2013.01); *A61N 1/0551* (2013.01); *A61N 1/0553* (2013.01); *A61N 1/0558* (2013.01); *A61N 1/36125* (2013.01); *A61N 1/3787* (2013.01); *A61N 1/37229* (2013.01); *A61N 1/37235* (2013.01); *A61N 1/37288* (2013.01); *A61N 2/002* (2013.01);
(Continued)

(58) Field of Classification Search
CPC .................................................. A61N 1/3787
See application file for complete search history.

(56) References Cited

U.S. PATENT DOCUMENTS

| 5,193,539 A | 3/1993 | Schulman et al. |
| 8,452,421 B2 | 5/2013 | Thenuwara et al. |

(Continued)

FOREIGN PATENT DOCUMENTS

| WO | WO-2014205129 A1 | 12/2014 |
| WO | WO-2015139053 A1 | 9/2015 |

(Continued)

OTHER PUBLICATIONS

EP15809379.9 European Search Report dated Mar. 9, 2018.
(Continued)

*Primary Examiner* — Allen Porter
(74) *Attorney, Agent, or Firm* — Wilson Sonsini Goodrich and Rosati, P.C.

(57) ABSTRACT

Systems, devices, and methods for neurostimulation using a combination of implantable and external devices to treat pain are disclosed.

21 Claims, 56 Drawing Sheets

Related U.S. Application Data continuation of application No. PCT/US2015/036821, filed on Jun. 19, 2015.

(60) Provisional application No. 62/077,181, filed on Nov. 8, 2014, provisional application No. 62/053,085, filed on Sep. 19, 2014, provisional application No. 62/015,392, filed on Jun. 21, 2014.

(51) Int. Cl.

| | |
|---|---|
| *G16H 40/67* | (2018.01) |
| *A61B 5/00* | (2006.01) |
| *A61B 5/04* | (2006.01) |
| *A61B 5/0488* | (2006.01) |
| *A61B 5/0538* | (2021.01) |
| *A61B 5/11* | (2006.01) |
| *A61B 5/145* | (2006.01) |
| *A61N 1/05* | (2006.01) |
| *A61N 1/372* | (2006.01) |
| *A61N 2/00* | (2006.01) |
| *H02J 50/00* | (2016.01) |

(52) U.S. Cl.
CPC ............ *A61N 2/006* (2013.01); *A61N 2/008* (2013.01); *G16H 40/67* (2018.01); *A61B 2560/0219* (2013.01); *A61B 2560/0242* (2013.01); *A61N 1/36007* (2013.01); *A61N 1/36057* (2013.01); *A61N 1/36064* (2013.01); *A61N 1/36067* (2013.01); *H02J 50/00* (2016.02)

(56) References Cited

U.S. PATENT DOCUMENTS

| | | |
|---|---|---|
| 8,634,928 B1 | 1/2014 | O'Driscoll et al. |
| 8,972,502 B2 | 3/2015 | Beslic et al. |
| 10,238,872 B2 | 3/2019 | Pivonka et al. |
| 10,335,596 B2 | 7/2019 | Yakovlev et al. |
| 2003/0085684 A1 | 5/2003 | Tsukamoto et al. |
| 2006/0074450 A1 | 4/2006 | Boveja et al. |
| 2008/0300654 A1 | 12/2008 | Lambert et al. |
| 2008/0300660 A1 | 12/2008 | John |
| 2009/0187230 A1 | 7/2009 | Dilorenzo |
| 2010/0137948 A1 | 6/2010 | Aghassian et al. |
| 2010/0305663 A1 | 12/2010 | Aghassian et al. |
| 2011/0190849 A1 | 8/2011 | Faltys et al. |
| 2012/0283800 A1 | 11/2012 | Perryman et al. |
| 2013/0193914 A1 | 8/2013 | Gaddam et al. |
| 2013/0215979 A1 | 8/2013 | Yakovlev et al. |
| 2013/0310901 A1 | 11/2013 | Perryma et al. |
| 2014/0142507 A1 | 5/2014 | Armes |
| 2014/0330348 A1 | 11/2014 | Shelton et al. |
| 2015/0028798 A1 | 1/2015 | Dearden et al. |
| 2016/0331956 A1 | 11/2016 | Yakovlev et al. |
| 2018/0028824 A1 | 2/2018 | Pivonka et al. |
| 2018/0256906 A1 | 9/2018 | Pivonka et al. |
| 2018/0368875 A1 | 12/2018 | Castillo et al. |
| 2019/0001139 A1 | 1/2019 | Lakshmi et al. |
| 2019/0009097 A1 | 1/2019 | Hartley et al. |
| 2019/0151659 A1 | 5/2019 | Lakshmi et al. |
| 2019/0269913 A1 | 9/2019 | Daniel et al. |
| 2019/0374776 A1 | 12/2019 | Lakshmi et al. |
| 2020/0139138 A1 | 5/2020 | Sit et al. |
| 2020/0306528 A1 | 10/2020 | Linden et al. |

FOREIGN PATENT DOCUMENTS

| | | |
|---|---|---|
| WO | WO-2015196164 | 12/2015 |
| WO | WO-2015196164 A2 | 12/2015 |
| WO | WO-2016127130 A1 | 8/2016 |
| WO | WO-2017044904 A1 | 3/2017 |
| WO | WO-2017142948 A1 | 8/2017 |
| WO | WO-2017165410 A1 | 9/2017 |
| WO | WO-2017205675 A1 | 11/2017 |
| WO | WO-2018017463 A1 | 1/2018 |
| WO | WO-2018126062 A1 | 7/2018 |
| WO | WO-2018156953 A1 | 8/2018 |
| WO | WO-2018208992 A1 | 11/2018 |

OTHER PUBLICATIONS

International search report and written opinion dated Dec. 18, 2015 for PCT/US2015/036821.
EP20160001.2 Extended Search Report dated Jul. 31, 2020.
U.S. Appl. No. 15/385,719 Office Action dated Oct. 12, 2019.
U.S. Appl. No. 15/385,729 Notice of Allowance dated Feb. 19, 2019.

$V_{rf}(t) = V_{rf+} = V_{rf-} = A[1+k_a m(t)]\cos(\omega_2 t)$ Modulation Depth = $[k_a m(t)] \leq 1.0$

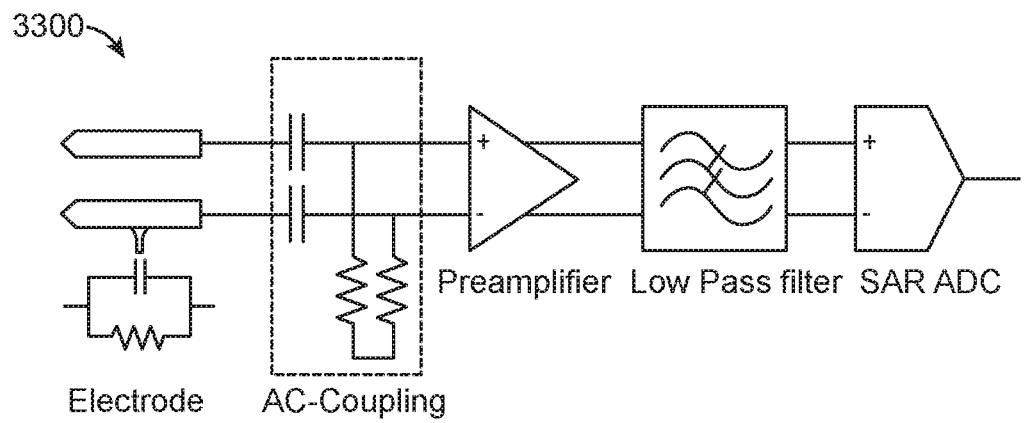
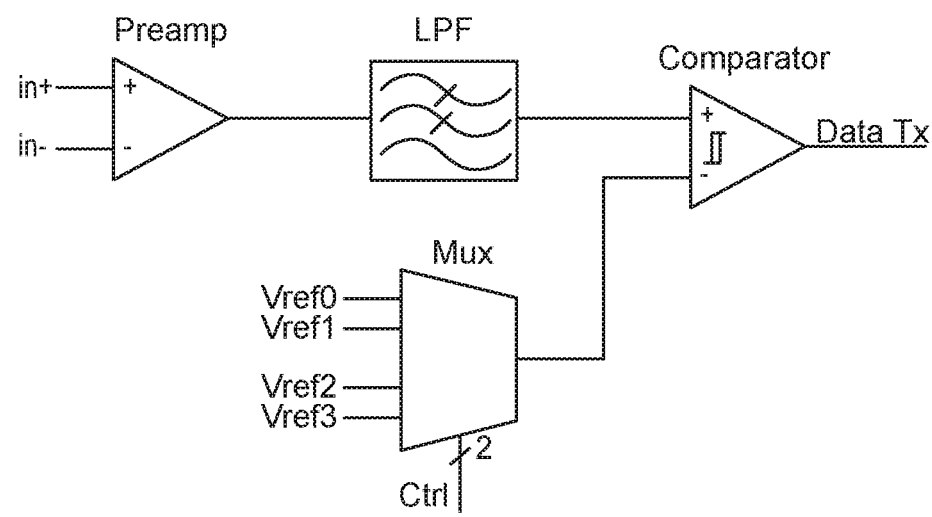
Fig. 33
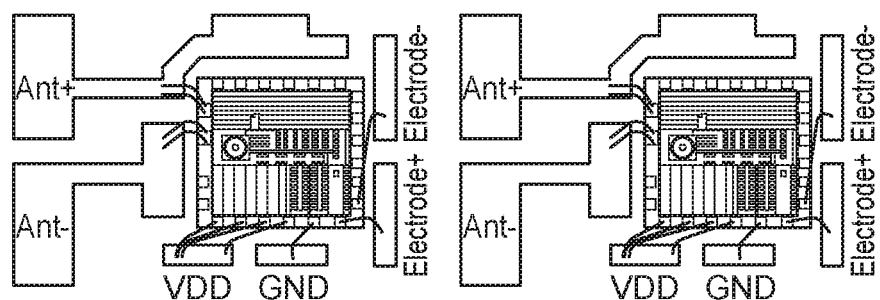
Fig. 34

Single-channel Stimulator, Stimulation Phase

Single-channel Stimulator, Recovery Phase

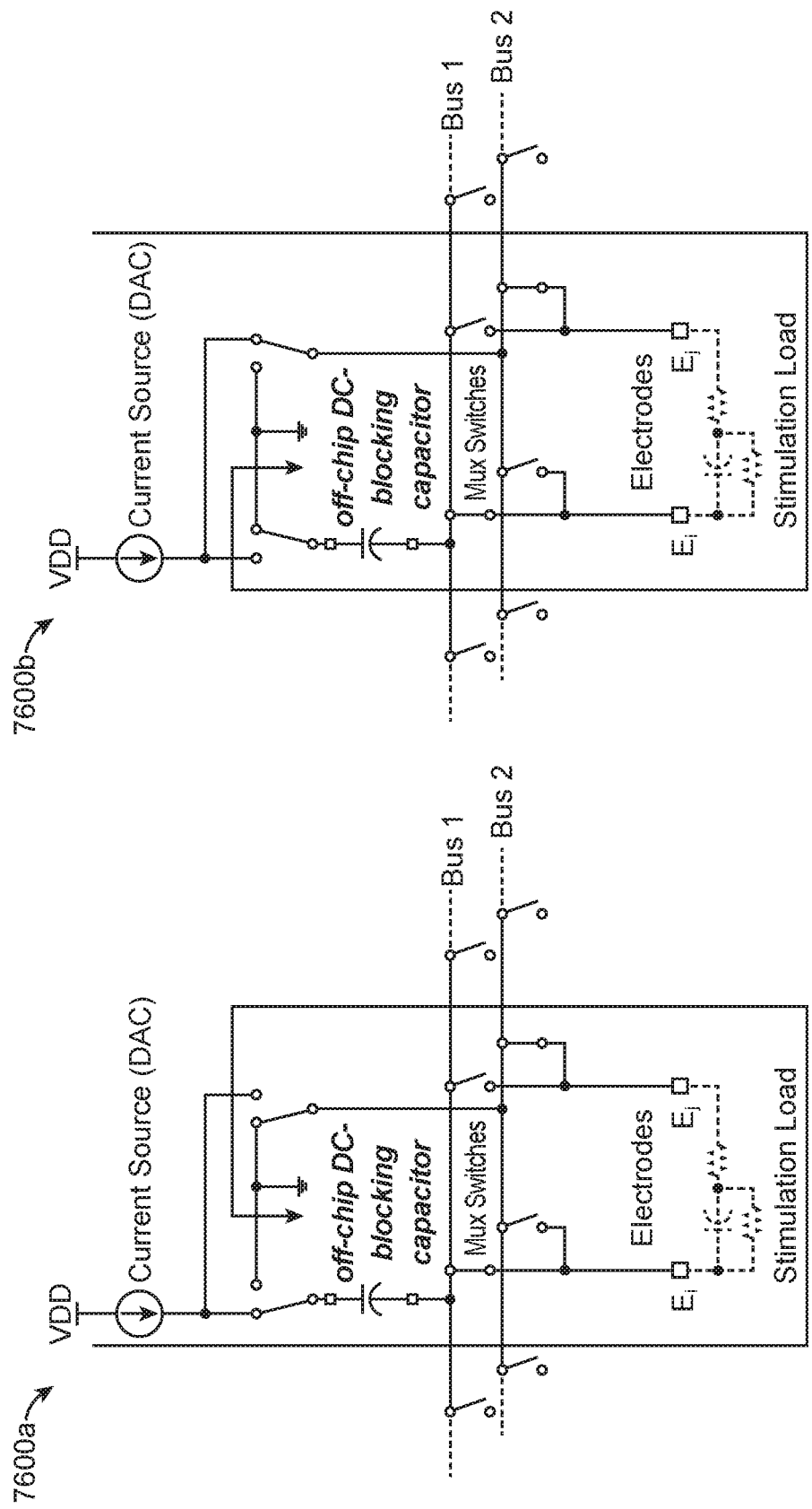

Grounding Load, Recovery Phase

Leakage Monitoring Scheme

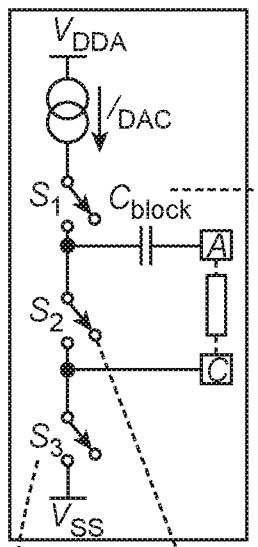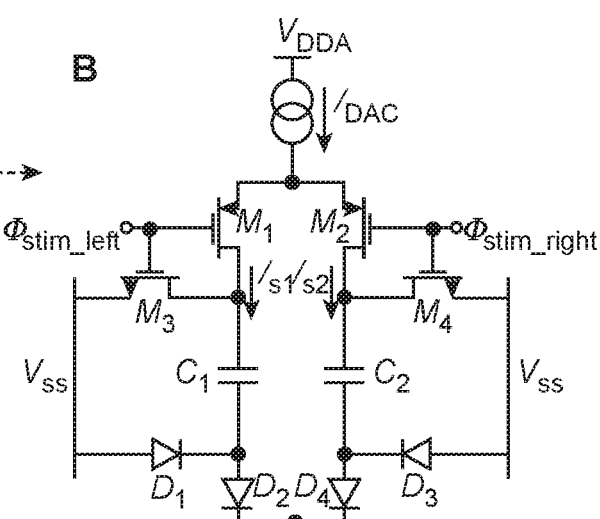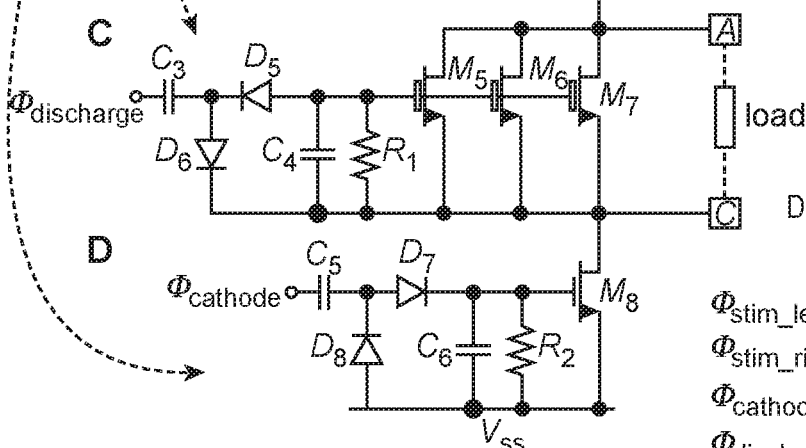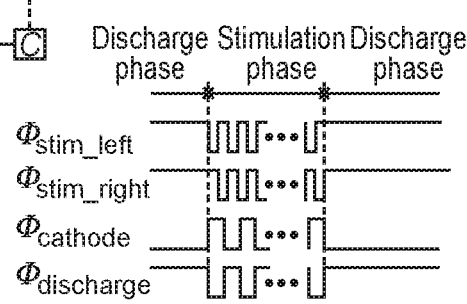
Fig. 80

METHOD AND APPARATUS FOR NEUROMODULATION TREATMENTS OF PAIN AND OTHER CONDITIONS

CROSS-REFERENCE

This application is a continuation of U.S. patent application Ser. No. 15/385,729, filed Dec. 20, 2016, now U.S. Pat. No. 10,335,596; which is a continuation of PCT Application No. PCT/US2015/036821, filed Jun. 19, 2015; which claims the benefit of U.S. Provisional Application Nos. 62/015,392, filed Jun. 21, 2014; 62/053,085, filed Sep. 19, 2014; and 62/077,181, filed Nov. 8, 2014; which applications are fully incorporated herein by reference.

The subject matter of this application is also related to the subject matter of U.S. Provisional Application No. 61/953,702, filed Mar. 14, 2014 and entitled "Method and Apparatus for Versatile Minimally Invasive Neuromodulators", which application is fully incorporated herein by reference.

BACKGROUND

Neuromodulation treatments for chronic pain are known and are frequently used for treating patients. Most use large devices with batteries and long leads to electrically stimulate nerves inside the body. These devices require invasive implantation, which are very costly. They also require periodic battery replacement, which requires additional surgery. The large sizes of these devices and their high costs have prevented their use in a variety of applications that have demonstrated effective neurostimulation treatments. Additionally, most of these devices stimulate large areas of non-target nerves in addition to the desired nerves, which can have negative effects on the patient and reduce the efficacy of the therapy.

The therapeutic treatment of chronic or acute pain is the single most common reason patients seek medical care, accounting for approximately 50% of all physician office visits. Chronic pain in particular is often disabling with the associated economic impact estimated at over $100 billion. A large portion (25% to 50%) of the population that is over the age of 65 suffers from health problems that predispose them to pain. An even greater portion (45%-85%) of the nursing home population suffers from chronic pain.

The primary treatments for chronic pain are pharmaceutical analgesics and electrical/neurostimulation. While both of these methods provide some level of relief, they are not without their drawbacks. Pharmaceuticals can have a wide range of systemic side effects such as GI bleeding as well as interactions with other drugs, etc. Opioid analgesics can be addictive and can they be debilitating. Also, the analgesic effect provided by pharmaceuticals is relatively transient making them cost prohibitive, particularly for the aging population.

Neurolysis is a technique that is growing in popularity whereby a particular nerve is temporarily damaged so that it can no longer transmit pain. One method gaining in popularity is the use of neurotoxins such as botulinum toxin which must be used in large volumes on a regular basis and has a number of risks, side effects, and contraindications associated with its use. Additionally, neurolysis is primarily used to treat chronic pain, but may also have applications in acute pain under certain conditions such as those where a nerve block (such as an epidural) would be used.

Another method is the use of thermal injury from an energy source such as radio frequency or cryoablation. The procedure is minimally invasive and can be performed under local anesthesia. It has no systemic effects and does not cause permanent damage; however, there are several aspects of the existing technology available to perform such a procedure that could be improved upon.

Neurostimulators can be used for at least three different applications: neuromuscular stimulation, peripheral nerve stimulation, or spinal cord stimulation. The major drawback is that they must be surgically implanted resulting in an expensive procedure which has serious risks, side effects, contraindications, and ongoing maintenance or upgrades.

Nerve stimulation treatments have shown increasing promise recently, showing potential in the treatment of many chronic pain conditions such as neuromuscular stimulation, peripheral nerve stimulation, or spinal cord stimulation. Other conditions have also shown promise though are in much earlier stages, including drug-resistant hypertension, motility disorders in the intestinal system, and metabolic disorders arising from diabetes and obesity. The primary drawback is that they must be surgically implanted resulting in an expensive procedure which has serious risks, side effects, contraindications, and ongoing maintenance or upgrades. These treatments also have difficulty in targeting and attaching to the specific nerves for the therapy as well as delivering the appropriate energy to these nerves. Minimally invasive methods can reduce cost and risk, and improve performance by selectively modulating the proper nerves. Delivering the appropriate energy is also essential, as activity can be up-regulated or down-regulated based on the parameters of stimulation. Wirelessly powered devices with communication can be desirable because they can be miniaturized and have no need for battery replacements. However, wireless devices have an even more restrictive power budget.

Implantable devices that perform various treatments such as neuromodulation treatments are known. Most use large devices with batteries and long leads to electrically stimulate nerves inside the body. These devices require invasive implantation, which are very costly. They also require periodic battery replacement, which requires additional surgery. The large sizes of these devices and their high costs have prevented their use in a variety of applications that have demonstrated effective neurostimulation treatments.

Nerve stimulation treatments have shown increasing promise recently, showing potential in the treatment of many chronic diseases including drug-resistant hypertension, motility disorders in the intestinal system, metabolic disorders arising from diabetes and obesity, and chronic pain conditions among others. Many of these treatments have not been developed effectively because of the lack of miniaturization and power efficiency, in addition to other factors. Wirelessly powered implantables with communication are desirable because they can be miniaturized and have no need for battery replacements. However, wireless implantables have an even more restrictive power budget.

There have also been several attempts at developing miniature wireless implantable, neurostimulators, including the device described in U.S. Pat. No. 5,193,539. This device receives power wirelessly, configures stimulation, and performs electrical stimulation in a needle injectable form factor. However, the systems in place for power delivery are highly sensitive to placement and alignment, and offer limited bandwidth for data communications. The receiver operates at MHz frequencies through an inductive link, requiring multiple coils and ferrite cores. More recently, new neurostimulation devices have transitioned to operation at higher frequencies, though these devices presently rely on dipole antennas and struggle with data transfer because of challenges with high-frequency operation. Furthermore, these devices provide stimulation from directly rectifying the power waveform, reducing the precision of control and introducing additional complexity and overhead in the overall system. These systems can also have limitations in the duration of pulses that can be delivered, and long pulses can be necessary to induce therapeutic effects for many applications, including gastric stimulation. These systems also may rely on instantaneously received power to stimulate excitable tissue and do not aggregate received energy for use in therapy. Additionally, these systems may not provide for a way to use larger non-dipole antennas.

The above described miniaturized neuromodulators can achieve miniaturization in part by relying on external power source to either recharge batteries or energy storage components such as capacitors, or to instantaneously power the implant. Additionally, much of the control for proper implant operation is typically located on the controller which is external to the patient body. Therefore, the external system should have several important characteristics, such as ability to wirelessly supply power to implants, communicate with implants to program their operation and receive feedback about therapy and status of the implant, interface with the user which could be a doctor who programs and monitors the therapy or actual patient. Physically, the external system should be comfortable to wear, light weight and portable, have easy and intuitive maintenance and interface. Also, the overall system should be safe and secure for the patient and compliant with a variety of regulations while being very robust and versatile to accommodate a variety of patients, conditions, uses and applications.

There is a need for apparatus form factors that are designed for simplicity of implantation as well as effective delivery to specific locations with proper electrical connectivity to tissue. Different patients and different treatments have different requirements, and there is a need to accommodate the needs of different operating conditions.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

The present inventions relate to neuromodulation methods, systems, and apparatus for the treatment of chronic pain conditions as well as other conditions or disorders. In particular, embodiments of the invention provide for precise, controlled modulation of specific nerves or tissues to induce physiological effects for therapies. Additionally, methods for incorporating information for diagnostics or improved therapeutic efficacy are described. In the preferred embodiment, the methods described herein are accomplished with a minimally invasive neuromodulation system that can target specific nerves with configurable modulation parameters and/or sensors for diagnostics or adaptations to the therapy.

The present inventions relate to neuromodulation methods, systems, and apparatus for the treatment of pain management as well as other conditions or disorders. In particular, embodiments of the invention provide for precise, controlled modulation of specific nerves or tissues to induce physiological effects for therapies. Additionally, embodiments that incorporate information for diagnostics or improved therapeutic efficacy are described. Also, systems, apparatus, and devices that improve the therapies or the diagnostics are described.

The modulating energy for these therapies may directly or indirectly effect the composition or behavior of the targeted nerve or tissue, and specific parameters will be described in more detail for different treatment modalities. This may include placing the modulators in, around, or in the proximity of nerves or tissues to be influenced. The modulators may be directly or indirectly attached to the nerves through a variety of methods based on the specific type of nerve or tissue as well as the intended therapy. Close proximity to nerves can reduce energy requirements and can eliminate unwanted stimulation of surrounding nerve tissue. The modulators may be placed at a multitude of locations and configured with multiple parameters to increase the configurability of the treatment. For example, high frequency stimulation can block signals, while low frequency stimulation can mask symptoms. Devices or apparatuses may have specifically designed coatings to reduce tissue interface impedance, which can in turn reduce the power required for the system, devices, or apparatuses. Multiple nerves can be stimulated in coordination, which may be provided with multiple modulators or interfaces. Real-time information, which may be provided by sensors in the devices or apparatuses, can further enhance the efficacy of therapy and may be applied for guided placement of an interface.

The conditions to be treated by the various systems, devices, apparatuses, and methods of the present disclosure include chronic and acute pain. Chronic pain may include but is not limited to lower back pain, migraine headaches, pain associated with herniated discs, muscle spasm or pinched nerve anywhere in the body, foot pain such as plantar fasciitis, plantar fibroma, neuromas, neuritis, bursitis, and ingrown toenails. Also addressed may be pain associated with malignant tumors. Acute pain may include but is not limited to post-surgical pain such as pain associated with thoracotomy or inguinal hernia repair, pain associated with procedures where an epidural block is used. This may be particularly and uniquely applicable in pregnancy to preliminarily disable the sensory nerves without the use of drugs and prior to delivery to avoid the potential for missing the window of time where an epidural can be administered.

A variety of treatment locations and other pain conditions are contemplated, including but not limited to the dorsal root ganglion or a location proximal to the dorsal root ganglion; somatic, afferent, nociceptive, and neuropathic pain; and, diabetic, abdominal, and cancer related pain. Systems, devices, and apparatuses of the present disclosure may have a diverse feature set to accommodate to the needs of the variety of indications.

The methods described also involve the location of placement of the modulating device and its interface with nerves or tissue, the specific nerves or tissues that are being targeted for the therapy, the modalities for modulating the nerves or tissue, and the techniques for attaching the device to the desired sites for the modulation system and its interface. Many of the devices, apparatuses, and tissue interfaces described herein may be delivered in a minimally invasive manner through an introducer with anatomical guidance. The delivery of the interfaces may be simple and minimally invasive and the interfaces may be delivered in conjunction with the wireless devices of the system.

The apparatus and systems described herein include electrodes, connectors, anchors, and other devices and materials that allow for improved therapies or diagnostics. In some cases, the apparatuses and systems may be configured to be powered wirelessly, transmit data wirelessly, have energy storage, and/or have local generation of the modulation, thereby providing miniaturized devices capable of precise therapies and feedback systems. In some cases, the devices described are specially designed for specific locations or nerves inside the body. Anatomical considerations for each application can be important for implantation procedures and the location site of any implantable device, and can dramatically influence efficacy of the implantable device. The systems and apparatuses for different anatomical sites associated with the therapies may include at least one specific attachment device that these interfaces can accommodate.

The present inventions relate to methods of making and using a system or apparatus for minimally invasive neuromodulation devices with sensing capabilities and versatility for operation with a wide variety of applications, and to the external system which powers such implants, controls their operation, gathers information from them, provides an interface for a patient and a doctor to control the therapy and monitor its effectiveness. These implantable devices are versatile and can be implanted in a variety of organs and body areas to treat a variety of conditions and diseases. The external system, which may include one or more of the external devices, therefore, may have different embodiments for all these various applications. However, the core components and functionality of the external system which are critical to the operation of versatile minimally invasive neuromodulators are described in this invention.

According to one aspect of the present inventive concepts, a stimulation or diagnostic system comprises an external device (such as a patch) configured to transmit and/or receive wireless transcutaneous transmissions, and at least one implantable device or implant configured to receive wireless transcutaneous transmissions from the at least one external device and/or to transmit wireless transcutaneous transmissions to the at least one external device.

In some embodiments, the implantable device comprises a stimulator for neuromodulation of tissue.

In some embodiments, the implantable device includes one or more independently controlled electrodes.

In some embodiments, the wireless transmissions operate in one or more of the industrial, scientific, and medical (ISM) radio bands.

In some embodiments, the implantable device comprises one or more of: pulse generator; extension; leads; patient programmer.

In some embodiments, the system or apparatus is configured to adhere to ANSI standards for spinal cord stimulators.

In some embodiments, the implantable device comprises a therapeutic element.

In some embodiments, the system or apparatus further comprises a positioning algorithm configured to position the at least one external patch device relative to the at least one implantable device. Better links between the external device(s) and the implantable device(s) can dramatically increase system efficiency, which can increase battery life and reliability. In some embodiments, the positioning algorithm can position the at least one external device relative to multiple implantable devices. In multi-component or multi-device systems such as these, positioning can be important to ensure that each individual component or device is receiving sufficient power. In some embodiments, the positioning algorithm can be configured to optimize link gain. In some embodiments, the positioning algorithm can be configured to maximize the average rate of charge among the implantable devices. In some embodiments, the positioning algorithm can be configured to maximize the minimum received power among the implantable devices. In some embodiments, the positioning algorithm can be configured to maximize a weighted rate of charge for the implantable devices. In some embodiments, the positioning algorithm comprises a gradient search algorithm. In some embodiments, the system or apparatus is configured to take a measurement while transmitting power at a higher than average power level. In some embodiments, the system or apparatus can be configured to optimize one or more of: antenna position; EM focusing such as beam steering and/or midfield focusing; electrical lens adjustment such as an adjustment caused by phase change materials or adjust to focus and/or beam steer in tissue; antenna reconfiguration, such as through segmentation, to modify antenna geometry; control of enabled antennas; control in phase and amplitude of signal transmitted from one or more antennas. Midfield powering or focusing, for example, can allow multiple devices to be powered and communicated with through a high bandwidth channel. External control devices and the communication protocols they use may allow for independent control of the functional components on the implant while minimizing disturbances in power transfer.

In some embodiments, the at least one external device is configured to adjustably control power transfer from the at least one external patch to the at least one implantable device. In some embodiments, the control of power transfer comprises closed loop power transfer. The precise amount of necessary power can be delivered, ensuring that the system can operate with maximum efficiency. Power usage and management can be optimized over multi-component or multi-device systems, delivering power preferentially to components or devices that require more power. In some embodiments, the at least one implantable device further comprises a power supply, and the power transfer is configured based on the charge and/or discharge rate of the at least one implantable device power supply. In some embodiments, the adjustable control of power transfer comprises an adjustment to a parameter selected from the group consisting of: transmitted power level; frequency; envelope of the transmitted carrier; duty cycle; number of carriers transmitted and their parameters; and combinations thereof. In some embodiments, the adjustable control of power transfer comprises adjusting a matching network parameter. In some embodiments, the adjustable control of power is performed by sensing a reflection coefficient and/or standing waves on the at least one external device. In some embodiments, the at least one external device is configured to deliver a first wireless transmission at a first frequency and a second wireless transmission at a second frequency, wherein the system or apparatus is configured to compare the first wireless transmission to the second wireless transmission. In some embodiments, the comparison of performance at different frequencies comprises a comparison of power transferred at each frequency. In some embodiments, the comparison of performance at different frequencies comprises a comparison of data transferred at each frequency. In some embodiments, the system or apparatus is further configured to select the first frequency or the second frequency to satisfy a minimum power requirement of the at least one implantable device. In some embodiments, the at least one implantable device comprises multiple implantable devices, wherein the at least one external device is configured to adjustably control power transfer from the at least one external device to the multiple implantable devices. In the some embodiments, the at least one external patch device is configured to increase the power delivered to a first implantable device as compared to a second implantable device. In some embodiments, the first implantable device is receiving less power than the second implantable device. In some embodiments, the first implantable device comprises a higher power requirement than the second implantable device.

In some embodiments, the at least one external device and the at least one implantable device comprise a matching network, wherein the system or apparatus is configured to determine a mismatch in the impedances and determine desired adjustments to the at least one external device and/or the at least one implantable device matching networks. Impedance mismatching can result in efficiency losses of 50% or more, and antenna impedances can vary with the environment, particularly the external. Adjustable impedance matching can minimize losses and allow for adaptations from patient to patient and over time. In some embodiments, the system or apparatus is configured to determine the mismatch by monitoring reflected power, wherein the system or apparatus comprises multiple matching network elements, and wherein the adjustment comprises a selection of one or more of the multiple matching network elements that reduce the mismatch. In some embodiments, the at least one external device comprises an antenna and/or antenna circuitry, and wherein the system or apparatus is configured to monitor the temperature of the antenna and/or antenna circuity and detect a mismatch, improper operation, and/or failure when the temperature level exceeds a threshold.

In some embodiments, the overall system further comprises a handheld interface configured to transmit and/or receive transmissions to and/or from the at least one external device. In some embodiments, the transmissions transmitted and/or received by the handheld device comprise wireless transmissions. In some embodiments, the transmissions transmitted and/or received by the handheld device comprise wired transmissions. In some embodiments, the transmitted and/or received transmissions comprise a protocol and/or standard selected from the group consisting of: Bluetooth; WiFi, ZigBee; Qualcomm 2net; MICS; ISM; WMTS; MedRadio; MNN; MBAN; cellular communications; RFID communications; and combinations thereof. In some embodiments, the handheld interface is further configured to transmit and/or receive wireless transmissions to and/or from the at least one implantable device.

In some embodiments, the system or apparatus further comprises a user interface configured to provide information to a user. In some embodiments, the user interface may provide real-time feedback of the operation of the implantable system of device(s). In some embodiments, the user interface simplifies device usage and can take several user-friendly form factors, which can allow for more convenient devices. In some embodiments, the user comprises a user selected from the group consisting of: clinician; patient; caregiver; family member; and combinations thereof. In some embodiments, the provided information comprises information selected from the group consisting of: stimulation parameters; energy transmission parameters such as energy transmission power level; power supply level; information transmission parameters such as information transmission power level; stimulation history information; patient compliance information; schedule of future stimulation; sensor information; alarm and alert information; and combinations thereof. In some embodiments, the provided information comprises information selected from the group consisting of: treatment delivered over time; delivered energy; therapy parameters; visualization of sensed activity in tissue; an operating parameter of the at least one implantable device; an operating parameter of the at least one external patch device; and combinations thereof. In some embodiments, the system or apparatus further comprises a user input device configured to allow a user to change a system or an apparatus parameter. The feedback information can allow doctors or patients to make informed changes to the system operation and can allow for sophisticated monitoring of the therapy. In some embodiments, the user input device comprises a device selected from the group consisting of: touchscreen; controllable cursor; mouse; keyboard, switch; and combinations thereof. In some embodiments, the system or apparatus parameter to be changed comprises a parameter selected from the group consisting of: stimulation parameters of one or more implants; transmitted power parameter; antenna position; nerve interface configuration; and combinations thereof. In some embodiments, the at least one external device comprises multiple external devices, such as multiple external patches, wherein the at least one implantable device comprises multiple implantable devices; and wherein each external device communicates with at least one implantable device. In some embodiments, the multiple external devices and the multiple implantable devices are configured as a network to coordinate therapeutic and/or diagnostic information. In some embodiments, the system or apparatus further comprises a master clock configured to synchronize the multiple external patch devices. In some embodiments, the multiple implantable devices are synchronized. In some embodiments, the system or apparatus further comprises a master clock, wherein each external device comprises a local clock which is phase and/or frequency synchronized to the master clock. In some embodiments, the multiple external devices are synchronized, wherein calibration of the system or apparatus parameters accomplished by operating the multiple external devices in a synchronized manner.

In some embodiments, the at least one external device further comprises an electronic component selected from the group consisting of: sensor; power supply; transmitter; receiver; signal conditioner; multiplexor; controller; memory; user interface; tissue interface; and combinations thereof.

In some embodiments, the at least one external device further comprises an attachable battery.

In some embodiments, the at least one external device comprises a rechargeable battery. In some embodiments, the rechargeable battery comprises an attachable rechargeable battery. In some embodiments, the system or apparatus further comprises a charging device configured to charge the rechargeable battery. In some embodiments, the charging device is configured to wirelessly transfer power to the rechargeable battery. In some embodiments, the charging device can comprise an inductive and/or mid-field coupling link and/or far-field link configured to transfer power to the rechargeable battery. In some embodiments, the charging device comprises a first coil and a first mating portion, and the at least one external device comprises a second coil and a second mating portion constructed and arranged to align the first coil with the second coil during charging. In some embodiments, the first mating portion comprises at least one of a projection or a recess and the second mating portion comprises a mating recess or projection. In some embodiments, the first mating portion comprises at least one of a magnet or magnetic material and the second mating portion comprises a mating magnetic material or magnet. In some embodiments, the first mating portion comprises a magnet and the second mating portion comprises a magnet. In some embodiments, the charging device is configured as a bedside monitor.

In some embodiments, the at least one external device or patch comprises a flexible substrate configured to attach the at least one external device to the patient. In some embodiments, the at least one external patch device further comprises skin contacts attached to the flexible substrate. In some embodiments, the at least one external patch device further comprise an adhesive layer. In some embodiments, the adhesive layer comprises impedance matching gels and/or hydrogels. In some embodiments, the at least one external patch device further comprises one or more electronic components selected from the group consisting of: sensor; power supply; transmitter; receiver; signal conditioner; multiplexor; controller; memory; antenna; and combinations thereof. In some embodiments, the one or more electronic components are positioned on and/or within the substrate. In some embodiments, the at least one external patch device can further comprise an antenna. In some embodiments, the at least one external patch device further comprises a cable attaching the one or more of the electronic components to the antenna. In some embodiments, the cable comprises one or more portions that are rigid, semi-rigid or flexible. In some embodiments, the cable comprises an e-textile cable, and/or antenna. In some embodiments, the at least one external patch device further comprises a power supply. In some embodiments, the power supply comprises a component selected from the group consisting of: battery; attachable power supply; multiple attachable power supplies; rechargeable power supply; wirelessly rechargeable power supply; and combinations thereof. In some embodiments, the at least one external patch device further comprises an antenna and gel, wherein the gel is configured to improve performance of antenna, tissue contacts (electrodes), heat removal; reduction of irritation; etc. In some embodiments, the gel comprises a gel selected from the group consisting of: contact gels; matching gels; and combinations thereof. The external patch device(s) may come in multiple form factors, including necessary electronics, rechargeable batteries, flexible substrates, garments, and multiple antenna arrays. The external patch device(s) may provide a comfortable system that can be flexibly designed based on patient feedback and usability testing. Rechargeable, replaceable batteries can simplify the recharging protocols for the external patch device(s).

In some embodiments, the at least one external device further comprises at least one antenna. The external device(s) may comprise multiple antennas or distributed antennas in different locations around the body of the patient. The external device(s) may form a network and may perform coordinated therapies with implants distributed in different locations around the body. The external device(s) may coordinate with one another based on sensed information and alter their operation as necessary. The configurations of the antennas may be sophisticated so as to desensitize placement and alignment, and to focus energy to improve power transfer. In some embodiments, the at least one antenna comprises a positionable antenna. In some embodiments, the at least one antenna comprises an adjustable antenna. In some embodiments, the adjustable antenna comprises an electrical lens. In some embodiments, the adjustable antenna comprises energy focusing antenna. In some embodiments, the energy focusing is configured to maximize electric or magnetic field distribution at a particular location inside tissue to localize energy delivery to one or more implantable devices. In some embodiments, the energy focusing utilizes midfield wireless powering. In some embodiments, the energy focusing utilizes nearfield wireless powering. In some embodiments, the energy focusing utilizes far-field wireless powering. In some embodiments, the energy focusing is reconfigurable or adjustable. In some embodiments, the adjustable antenna comprises a self-adjusting antenna. In some embodiments, the at least one external device comprises a ferrite core, wherein the at least one implantable device comprises a magnet, and wherein the adjustable antenna self-adjusts through magnetic alignment of the ferrite core and magnet. In some embodiments, the self-adjusting antenna is electrically steered. In some embodiments, the self-adjusting antenna comprises an array of antennas each configured for phase adjustment to accomplish beam steering and/or beam focusing. In some embodiments, the system or apparatus further comprises a patient worn device, wherein the at least one antenna is embedded in the patient worn device. In some embodiments, the patient worn device comprises a device selected from the group consisting of: shirt; belt; cloth band; hat; and other wearable items; and combinations thereof. In some embodiments, the at least one antenna comprises multiple antennas. In some embodiments, the system or apparatus further comprises an algorithm configured to coordinate activation of one or more antennas to optimize delivery of power to the at least one implantable device. In some embodiments, the algorithm is configured to activate the one or more antennas based on coupling efficiency with the at least one implantable device. In some embodiments, the activation results in a focusing effect and/or a beam steering effect. In some embodiments, the at least one antenna comprises multiple selectable conducting elements. In some embodiments, one or more of the selectable conducting elements are selected to optimize coupling with the at least one implantable device. In some embodiments, the system or apparatus further comprises a separator between the at least one antenna and tissue of the patient. In some embodiments, the separator comprises an element selected from the group consisting of: air; soft pad; gel; matching gel; contact gel; thermal insulator; fluid; recirculating fluid; and combinations thereof. In some embodiments, the separator is constructed and arranged to improve performance of the at least one antenna. In some embodiments, the separator is constructed and arranged to insulate the patient tissue from heat generated by the at least one external patch device. In some embodiments, the separator is constructed and arranged to maintain constant relative position with respect to tissue and at least one implantable device. In some embodiments, the separator is constructed and arranged to remove excess heating from tissue.

In some embodiments, the system or apparatus further comprises at least one body electrode configured to be positioned on the patient's skin and to produce a signal to be transmitted to the at least one device. The body electrode(s) can provide a potential alternative communication path for information between the implant(s) and the external patch device(s) or device (s). The body electrode(s) can monitor the stimulation therapy or other patient parameters during the operation of the device, ensuring the proper functioning of the device. The body electrode(s) can provide stochastic resonance, which can prime the nerves for stimulation, reducing the required energy for therapy. In some embodiments, the at least one body electrode comprises a component selected from the group consisting of: volume conduction electrodes; EKG-type contact electrode; hydrogel; adhesive; and combinations thereof. In some embodiments, the at least one body electrode comprises multiple body electrodes. In some embodiments, the at least one body electrode comprises an attachment element. In some embodiments, the attachment element comprises an element selected from the group consisting of: adhesive; conductive adhesive; gel; hydrogel; conductive gel; short-wear gel; extended-wear gel; and combinations thereof. In some embodiments, the attachment element comprises a conductive material whose impedance is configured to minimize reflections at an interface with the patient's skin. In some embodiments, the at least one body electrode is further configured to receive data from the at least one implantable device. In some embodiments, the at least one body electrode is configured to sense and/or monitor the therapy delivered by the implantable device. In some embodiments, the data is received via body conduction communication. In some embodiments, the at least one implantable device is configured to send data to the at least one body electrode by modulating its stimulation signal. In some embodiments, the at least one implantable device is configured to modulate the voltage and/or current of its stimulation signal. In some embodiments, the at least one implantable device is configured to modulate the stimulation signal without interfering with the therapy delivered by the stimulation signal. In some embodiments, the system or apparatus is configured to adjust the at least one implantable device based on the body electrode received signal. In some embodiments, the adjustment to the at least one implantable device comprises an adjustment to one or more of: voltage; current; frequency; duty cycle; pulse shape; duration of therapy and/or start and stop times of therapy. In some embodiments, the adjustment to the at least one implantable device comprises a calibration of one or more of: the at least one external patch device; the at least one implantable device; and/or the coupling between the at least one external device and the at least one implantable device. In some embodiments, the system or apparatus is configured to adjust the at least one implantable device to compensate for an event selected from the group consisting of: patient physical activity; electrode migration; tissue interface impedance; a time-varying parameter affecting therapeutic outcome; and combinations thereof. In some embodiments, the system or apparatus is configured to locate the at least one implantable device using the body electrode received and/or produced signal. In some embodiments, the system or apparatus is configured to locate the at least one implantable device using multiple stimulation signals comprising different stimulation parameters. In some embodiments, the system or apparatus is configured to locate the depth and/or position in tissue of the at least one implantable device. In some embodiments, the at least one body electrode is further configured to deliver energy to tissue and/or the at least one implantable device. In some embodiments, the delivered energy is configured to perform a function selected from the group consisting of: communicate with the at least one implantable device; modulate tissue; improve therapy produced by the at least one implantable device by reducing the activation threshold of excitable tissue; block neural activity; stimulate neural activity; improve efficiency of the at least one implantable device and/or the system or apparatus; interact with one or more sensors; improve therapeutic outcomes; inhibit and/or promote one or more nerve activation thresholds; and combinations thereof.

In some embodiments, the at least one implantable device comprises multiple implantable device.

In some embodiments, the at least one implantable device comprises an energy storage element.

In some embodiments, the at least one implantable device comprises an integrated circuit assembly comprising one or more elements selected from the group consisting of: power management circuitry; implant controller circuitry; sensor interface circuitry; sensor; transmitter; receiver; pulse generator circuitry; electrode; electrode drive circuitry; energy storage element; matching network; kill switch; unique identification storing circuitry and/or elements; power-on-reset circuit; bandgap reference circuit; calibration circuit; timing circuit; antenna; charge balance circuit; safety and failure prevention and detection circuits; overvoltage protection circuit; overcurrent protection circuit; interference detection circuit; chip auxiliary circuitry; and combinations thereof. Implantable device s should be safe and reliable and fail-safe protocols can ensure that the devices do not harm the patient. Monitoring of the patient and the implantable device can ensure that it functions as detected and can allow for immediate detection of malfunctions.

In some embodiments, the at least one implantable device comprises at least one antenna. In some embodiments, the at least one antenna comprises a positionable antenna. In some embodiments, the at least one antenna comprises an adjustable antenna. In some embodiments, the adjustable antenna comprises an electrical lens. In some embodiments, the adjustable antenna comprises a self-adjusting antenna. In some embodiments, the at least one external patch device comprises a ferrite core, wherein the at least one implantable device comprises a magnet, and wherein the adjustable antenna self-adjusts through magnetic alignment of the ferrite core and magnet. In some embodiments, the self-adjusting antenna is electrically steered. In some embodiments, the self-adjusting antenna comprises an array of antennas each configured for phase adjustment to accomplish beam steering and/or beam focusing. In some embodiments, the at least one antenna comprises multiple antennas. In some embodiments, the system or apparatus further comprises an algorithm configured to coordinate activation of one or more antennas to optimize delivery of power to the at least one implantable device. In some embodiments, the algorithm is configured to activate the one or more antennas based on coupling efficiency with the at least one implantable device. In some embodiments, the activation results in a focusing effect and/or a beam steering effect. In some embodiments, the at least one antenna comprises multiple selectable conducting elements. In some embodiments, one or more of the selectable conducting elements are selected to optimize coupling with the at least one implantable device. One or more implantable device configurations with midfield wireless transmissions and techniques for optimizing the antenna link may be provided. Multi-device systems may introduce complexity in the functionality of the overall system and may require an intelligent system to operate effectively. The antenna sub-systems may define the power budget of the overall system, and improvements in the link may result in better usability with increased reliability.

In some embodiments, the wireless transcutaneous transmissions received by the at least one implantable device comprise both data and power.

In some embodiments, the wireless transcutaneous transmissions received by the at least one implantable device comprise at a distance smaller than one hundredth of the wavelength.

In some embodiments, the wireless transcutaneous transmissions received by the at least one implantable device operate at a distance within 100× the size of a wavelength.

In some embodiments, the wireless transcutaneous transmissions received by the at least one implantable device operate at a distance greater than 100× the size of a wavelength.

In some embodiments, the wireless transcutaneous transmissions transmitted by the at least one implantable device comprises data. In some embodiments, the data is related to the status of the at least one implantable device on state. In some embodiments, the data is related to a POR triggered signal. In some embodiments, the data is related to the rate of charge of the at least one implantable device.

In some embodiments, the system or apparatus further comprises a sensor. In some embodiments, the sensor comprises multiple sensors. In some embodiments, the sensor comprises a temperature sensor configured to produce a temperature signal. In some embodiments, the system or apparatus is configured to prevent tissue of the patient from exceeding a threshold based on the temperature signal. In some embodiments, the temperature sensor comprises a sensor selected from the group consisting of: thermocouple; temperature dependent resistor (thermistor); infrared sensor; semiconductor; thermopile; and combinations thereof. In some embodiments, the system or apparatus further comprises a recirculating fluid supply configured to cool tissue based on the temperature signal. In some embodiments, the system or apparatus is configured to adjust energy delivered by the at least one external device based on the temperature signal.

In some embodiments, the system or apparatus further comprises a fault assembly configured to prevent and/or detect a fault in the system or apparatus. In some embodiments, the fault assembly is positioned in a location selected from the group consisting of: the at least one external device; the at least one implantable device; and combinations thereof. In some embodiments, the fault assembly is configured to detect improper relative positioning between the at least one external device and the at least one device. In some embodiments, the fault assembly comprises electronic circuitry configured to perform a function selected from the group consisting of: overcurrent protection; overvoltage protection; charge imbalance detection; short circuit protection; heating detection; unauthorized programming detection; detection of loss in link; electrode-tissue interface impedance malfunction detection; circuit miscalibration and/or malfunction detection; detection and/or correction of errors in data; and combinations thereof. In some embodiments, the fault assembly is configured to detect an inadequate power link and/or an inadequate data link. In some embodiments, the fault assembly is configured to detect an inadequate data link using a method selected from the group consisting of: repetition codes; parity bits; checksums; cyclic redundancy checks (CRC); cryptographic hash functions; error-correcting codes; automatic repeat requests; and combinations thereof. In some embodiments, the fault assembly is configured to detect improper program settings. In some embodiments, the fault assembly is configured to detect potentially harmful environment for the implantable device selected from a group of: electric field; magnetic field, such as during MRI; radiation; interference; and combinations thereof. In some embodiments, the fault assembly is configured to disable system or apparatus operation upon detection of a fault condition. In some embodiments, the fault assembly comprises non-volatile memory. In some embodiments, the fault assembly is configured to prevent adverse events resulting from environmental electromagnetic fields. In some embodiments, the fault assembly is configured to temporarily disable system or apparatus operation. In some embodiments, the fault assembly comprises a remotely controllable switch configured to allow programming via a method selected from a group of: magnetic field; magnetic field gradient; electric field; electric field gradient; and combinations thereof. In some embodiments, the switch comprises a magnetic switch. In some embodiments, the at least one implantable device is configured to communicate the fault condition to the at least one external patch device. In some embodiments, the communication method can be selected from a group of: electromagnetic signal; body conduction signal; sound signal; optical signal; mechanical signal, such as vibration and/or rotation or movement; and combinations thereof. In some embodiments, the system or apparatus further comprises a handheld device comprising a display, wherein the system or apparatus is configured to present the fault condition on the handheld device display. In some embodiments, the fault assembly is configured to monitor one or more of: antenna radiation; energy reflections; data transmission; data reception; tissue temperature; and/or SAR.

In some embodiments, the at least one implantable device is implantable in (e.g., within, on and/or proximate) one or more of the following sites: the tibial nerve (and/or sensory fibers that lead to the tibial nerve); the occipital nerve; the sphenopalatine ganglion; the sacral and/or pudendal nerve; target sites in the brain, such as the thalamus; the vagus nerve; baroreceptors in a blood vessel wall, such as in the carotid artery; along, in, or proximal to the spinal cord; one or more muscles; the medial nerve; the hypoglossal nerve and/or one or more muscles of the tongue; cardiac tissue; the anal sphincter; peripheral nerves of the spinal cord, including locations around the back; the dorsal root ganglion; and motor nerves and/or muscles. The flexibility of the devices and systems described herein can allow for a variety of therapies throughout the body.

In some embodiments, the system or apparatus is configured to stimulate one or more of: tibial nerve (and/or sensory fibers that lead to the tibial nerve); the occipital nerve; the sphenopalatine ganglion; the sacral and/or pudendal nerve; target sites in the brain, such as the thalamus; the vagus nerve; baroreceptors in a blood vessel wall; the spinal cord; one or more muscles; the medial nerve; the hypoglossal nerve and/or one or more muscles of the tongue; cardiac tissue; the anal sphincter; peripheral nerves of the spinal cord; the dorsal root ganglion; and motor nerves and/or muscles.

In some embodiments, the overall system is configured to stimulate to treat one or more of: migraine; cluster headaches; urge incontinence; tremor; obsessive compulsive disorder; depression; epilepsy; inflammation; tinnitus; high blood pressure; pain; muscle pain; carpal tunnel syndrome; obstructive sleep apnea; cardiac arrhythmia or other cardiac disease or disorder that could benefit from pacing or defibrillation; dystonia; interstitial cystitis; gastroparesis; obesity; fecal incontinence; bowel disorders; chronic pain; and/or compromised mobility.

The present inventions relate to methods of making and using a system or an apparatus for powering, controlling, and receiving information from minimally invasive devices, which have the capability of activation and suppression of tissue or cellular activity and/or sensing with versatility for operation with a wide variety of applications. The implantable devices are versatile in their applications and are highly configurable to accommodate a variety of therapies and potentially diagnoses. Alternatively or additionally, the external system can also be versatile, can have the ability to wirelessly power these implants, can have high data rate communications to be able to control and receive information from one or more implants, can have an intuitive user interface for a doctor, or other user, can provide feedback and recommendations for users, can monitor therapy progress and update the patient and/or doctor of its efficacy and safety and the status of one or more implants. The external system of device(s) can also be comfortable for short term, prolonged term, and potentially chronic use. The present invention will, therefore, address these important considerations and describe an embodiment which encompasses these important features.

The present inventions relate to systems or apparatuses for treating a patient, such as systems or apparatuses for neuromodulating nerve or other tissue for treating pain and/or other patient diseases and disorders.

According to aspects of the present disclosure, an overall system for a patient comprises at least one external system of device(s) configured to transmit and receive wireless transcutaneous transmissions and at least one implanted system of device(s) configured to be implanted in the patient and receive wireless transcutaneous transmissions from the at least one external device and/or to transmit wireless transcutaneous transmissions to the at least one external device.

In some embodiments, the overall system comprises a stimulation apparatus configured for the neuromodulation of tissue.

In some embodiments, the overall system comprises a stimulation apparatus configured for the treatment of pain.

In some embodiments, the at least one implantable system comprises multiple discrete components and/or the at least one external system comprises multiple discrete components, and the multiple discrete components are configured as a network of components.

In some embodiments, the overall system is configured to transmit power and data between the at least one implantable system and the at least one external system.

In some embodiments, the at least one implantable system comprises multiple discrete components each comprising a sealed enclosure. The implantable system can be configured to transfer data to the multiple discrete components simultaneously. The sealed enclosures can comprise glass.

In some embodiments, the at least one implantable device of the implantable system comprises one or more components selected from the group consisting of: one or more antennas; one or more electrodes; energy harvesting circuit; energy management circuit; one or more energy storage elements; pulse generator; controller, stimulation current driver; one or more sensors; communications circuits for receiving and sending data; calibration circuits; startup and power-on-reset circuits; memory circuits; timing circuits; other auxiliary circuits, such as a matching network, that are necessary for proper implantable system operation and a particular application; and combinations thereof.

In some embodiments, the at least one implantable device of the implantable system comprises at least one electrode configured to independently deliver energy to tissue. The at least one electrode can comprise a paddle electrode. The at least one electrode can comprise an anchorable electrode. The at least one electrode can comprise a coating. The coating can comprise platinum, iridium, gold, alloys, carbon nanotubes, or combinations thereof. The electrode can comprise a microelectrode. The microelectrode can protrude from the enclosure or the lead. The at least one electrode can be constructed and/or arranged to stimulate the dorsal root ganglion. The at least one electrode can comprise multiple electrodes. The multiple electrodes can be placed 10-50 cm apart across the patient's back or torso. The multiple electrodes can be placed in a pattern across the patient's back, wherein the pattern is selected from the group consisting of: square; rectangular; diamond; circular; elliptical; regular; irregular pattern; and combinations thereof. The multiple electrodes can be implanted to provide cross-talk. The multiple electrodes can be implanted to steer current from one electrode to a second electrode. The multiple electrodes can each generate voltage or current in reference to a common reference node. The multiple electrodes can be positioned on the multiple leads. The multiple leads can comprise bifurcated leads. The multiple leads can be electrically connected in series. The multiple leads can each have a unique addressable ID. The implantable system can comprise an implantable connector assembly including multiple connectors and a plug, wherein the plug is configured to seal unused connectors. The multiple electrodes can be positioned on an active lead configured to send and/or receive commands to and/or from a portion of the at least one implantable lead. The implantable system can comprise a serial communication protocol for sending and/or receiving information. The at least one electrode can be implanted at a location in proximity to tissue to be stimulated. The at least one electrode can be implanted at a location at least partially surrounding the tissue to be stimulated.

In some embodiments, the at least one implantable device of the implantable system comprises at least one antenna. The at least one implantable system can comprise an implantable enclosure, and wherein the at least one antenna is tethered to the implantable enclosure. The at least one antenna can be implanted closer to the skin surface than the implantable enclosure is implanted. The at least one antenna can comprise multiple antennas connected to the implantable enclosure by a connecting element comprising one or more of: connecting interface; cable; wires; conductive lead; transmission line; waveguide; distributed matching network; transformer; lumped matching network; and combinations thereof. The connecting element can be configured as a matching network. The connecting element can comprise at least a flexible portion. The multiple antennas can be implanted at locations to optimize link gain. The multiple antennas can be implanted at locations to decrease sensitivity to position, orientation and/or rotation of one or more external system components. The multiple antennas can comprise at least two antennas configured to be implanted orthogonal to each other. The at least two antennas can be implanted to minimize sensitivity to the position of one or more external system components. The multiple antennas can be configured as an antenna selected from the group consisting of: loop antenna; multi-loop antenna; orthogonal antennas; polarized antenna structures; dipole antenna; multi-coil antenna; helical antenna; patch antenna; and combinations thereof. The at least one antenna can comprise a foldable and unfoldable antenna. The antenna can comprise an impedance that matches and/or is resonant with at least a portion of the at least one implantable system. The antenna can be configured as an interposer matching network. The implantable system can comprise multiple components with different characteristics. The at least one implantable device of the implantable system can comprise an enclosure, and the antenna can comprise an electrical connector configured to electrically attach to the enclosure.

In some embodiments, the at least one implantable device of the implantable system comprises a controller and an on-board power management assembly, wherein the controller is configured to control the power management assembly.

In some embodiments, the at least one implantable device of the implantable system comprises a pulse generator configured to produce custom stimulation waveforms. The pulse generator can be configured to operatively adjust a stimulation parameter selected from the group consisting of: amplitude; timing; frequency; pulse duration; duty cycle; polarity; and combinations thereof.

In some embodiments, the implantable system is constructed and arranged to be delivered through a component selected from the group consisting of: needle; endoscope; laparoscope; and combinations thereof.

In some embodiments, the implantable device(s) of the implantable system comprises a lead comprising at least one electrode. The lead further can comprise a cross section with a geometry selected from the group consisting of: circular, oval, rectangular; and combinations thereof. The lead further can comprise one or more electronic components and an outer surface surrounding the one or more electronic components. The lead further can comprise one or more antennas and an outer surface surrounding the one or more antennas. The one or more antennas can comprise multiple antennas distributed along the length of the lead to increase its radar cross section. The lead further can comprise a proximal end and a housing positioned on the proximal end. The housing can comprise a sealed housing. The housing can comprise one or more feed through configured for: AC coupled channels, such as RF inputs for an antenna; stimulation channels; and/or sensors. The housing can comprise a shape selected from the group consisting of: cylindrical; rectangular; elliptical; spherical; an irregular shape; and combinations thereof. The system or apparatus can further comprise a delivery needle assembly for implanting the lead. The delivery needle assembly can comprise a first portion and a second portion, wherein the first portion is configured to detach from the second portion after placement of the lead into the patient. The delivery needle assembly can comprise a covering surrounding a needle, wherein the covering is configured to be cut such that the needle can be removed from the lead. The delivery needle assembly can comprise a needle comprising the first portion and the second portion, and a hinge rotatably attaching the first portion to the second portion such that the needle can be removed from the lead. The housing can comprise a connector electrically attached to the at least one electrode. The lead further can comprise a proximal end and a connector positioned on the proximal end. The connector can comprise a connector configured to seal with a mating connector. The at least one implantable device can comprise an enclosure comprising the mating connector. The connector can be configured to attach to an accessory component selected from the group consisting of: lead splitter; active lead interface; passive lead interface; serializer; deserializer; lead extension; lead diagnostic interface; charge balance device; pulse conversion device; pulse shaping device; DC to pulse burst pulse shaping device; a filter; an AC coupling capacitor assembly for charge balancing; and combinations thereof. The implantable device can further comprise an active and/or passive distribution circuit configured to operably attach to the lead. The lead further can comprise at least one lumen. The implantable device can further comprise a filament slidingly received by the lumen and configured to aid in implantation of the lead. The filament can be constructed and arranged to adjust the stiffness of the lead. The filament can comprise a curved distal portion. The lumen can comprise a cross section with a geometry selected from the group consisting of: circular, oval, rectangular; and combinations thereof. The lead further can comprise a sensor. The sensor can be constructed and arranged to produce a signal corresponding to a parameter selected from the group consisting of: action potential; neural activity; muscle activity; pressure; temperature; pH; and combinations thereof. The lead can comprise a first lead and the at least one implantable device comprises a second lead and an implantable enclosure, wherein the first lead and the second lead are each configured to operably attach to the enclosure. The first lead and the second lead can comprise a different property selected from the group consisting of: length; diameter; electrode shapes; electrode sizes; electrode configurations; and combinations thereof. The lead further can comprise an antenna. The antenna can comprise an elongated antenna. The elongated antenna can comprise an antenna selected from the group consisting of: dipole antenna; elongated loop antenna; elongated multi-loop antenna; and combinations thereof. The lead further can comprise a flexible PCB operably connected to the at least one electrode.

In some embodiments, the at least one implantable device of the implantable system comprises at least a portion with a controllable stiffness and/or shape. The at least a portion can comprise a shaped memory alloy.

In some embodiments, further comprising a sheath, the at least one implantable device comprises a portion surrounded by the sheath. The sheath can be stiffer than the surrounded portion of the at least one implantable device. The sheath can comprise a biased portion. The sheath can be constructed and arranged to provide support for a component selected from the group consisting of: camera; fiber; visible light fiber; ultrasound fiber; a sensing lead; a tool; implantable device; at least one portion of implantable device; and combinations thereof. The sheath can comprise a sensor. The sensor can be constructed and arranged to produce a signal corresponding to a parameter selected from the group consisting of: action potential; neural activity; muscle activity; pressure; temperature; pH; and combinations thereof.

In some embodiments, the at least one implantable device comprises at least four stimulation channels. The at least one implantable device can comprise at least eight stimulation channels.

In some embodiments, the at least one implantable device comprises an AC coupled interface. The AC coupled interface can comprise primary and secondary coils. The at least one implantable device can comprise an enclosure with an extension extending from the enclosure, wherein the primary coil can be positioned in the enclosure and the secondary coil can be positioned in the extension. The extension can comprise at least one of a lead or an antenna. The primary and second coils can comprise planar coils. The planar coils can comprise matching planar coils. The primary and secondary coils can comprise co-planar coils. The at least one implantable device can comprise an enclosure, wherein the enclosure can comprise a convex and/or concave port proximate a co-planar coil. The AC coupled interface further can comprise a ferrite core. The AC coupling interface can comprise a capacitive coupling interface. The at least one implantable device can comprise an implantable enclosure and an extension, wherein the AC coupling interface comprises a first plate in the enclosure and a second plate in the extension.

In some embodiments, the at least one implantable device is configured to electrically stimulate tissue. The electrical stimulation can be controllable by configuring parameters wherein the configurable parameters are selected from the group consisting of: amplitude; frequency; pulse width; polarity; pulse shape; and combinations thereof. The electrical stimulation parameters can be configured to have the following parameters: frequency in the range between 1 Hz and 50 kHz; pulse width in the range between 1 microsecond and 50 milliseconds; amplitude in the range of 0.1 and 20 mA. The electrical stimulation parameters can be configured to have the following parameters: frequency in the range between 40 and 150 Hz; pulse width in the range between 100 and 500 microseconds; amplitude in the range of 0.2 and 10 mA. The electrical stimulation parameters can be configured to have the following parameters: frequency in the range between 2 and 20 kHz; pulse width in the range between 10 and 500 microseconds; amplitude in the range of 0.1 and 10 mA.

In some embodiments, the at least one implantable device is configured to mechanically interact with tissue. In some embodiments, the at least one implantable device is constructed and arranged to achieve an interaction with tissue selected from the group consisting of: inducing motion; moving tissue; rotating tissue; squeezing tissue; expanding tissue; repositioning at least a portion of the implantable device within tissue; and combinations thereof. The at least one implantable device can be constructed and arranged to provide motion selected from the group consisting of: vibrations; impulses; linear displacements; angular displacement; and combinations thereof. The at least one implantable device can be constructed and arranged to provide motion at one or more frequencies between 1 Hz and 50 KHz. The at least one implantable device can be constructed and arranged to provide motion with adjustable duty cycles. The at least one implantable device can cause the mechanical interaction by application of a force selected from the group consisting of: electromagnetics force; magnetic force; piezoelectric force; thermal expansion force; and combinations thereof. The at least one implantable device can comprise a lead with a tip portion, and the mechanical interaction with tissue comprises imparting of a force on tissue by the tip portion. The at least one implantable device can be further constructed and arranged to electrically stimulate tissue.

In some embodiments, the at least one implantable device comprises a connection hub. The at least one implantable device further can comprise multiple leads and a controller, wherein the connection hub is configured to operably connect the multiple leads to the controller. The connection hub can comprise a first connection hub, wherein the at least one implantable device further comprises a second connection hub connected to the first connection hub.

In some embodiments, the at least one implantable device further comprises an MRI effect reducing assembly. The MRI effect reducing assembly can comprise a component selected from the group consisting of: heat sink; heat spreader; shielding; high heat conduction element; active shorting element; passive shorting element; reed switch; mechanical switch; switch activated before and/or during MRI use; parallel electrical connections; current diverters; and combinations thereof.

In some embodiments, the at least one implantable device further comprises an anchor element configured to attached at least a portion of the at least one implantable device to tissue. The anchor element can comprise an element selected from the group consisting of: element with texturized pattern; eyelet; suture hole; suture; barb; clamp; clamp with suture hole; staple; and combinations thereof. The at least one implantable device can comprise a lead, wherein the lead is positioned on the anchor element.

In some embodiments, the at least one implantable device further comprises a marker configured to identify the three dimensional orientation of at least a portion of the at least one implantable device. The marker can comprise a radiopaque marker. The at least one implantable device can comprise a lead with a tip portion, wherein the marker is positioned on the lead tip portion.

In some embodiments, the at least one implantable device further comprises a needle injection assembly configured to slidingly receive at least a portion of the at least one implantable device and position the at least a portion in tissue.

In some embodiments, the at least one external system comprises a single discrete component.

In some embodiments, the at least one external system comprises multiple discrete components such as multiple external devices or patches. In some embodiments, the at least one external system comprises a first discrete component, a second discrete component and a tether configured to transfer power and/or communication between the first discrete component and the second discrete component. In some embodiments, the at least one external system comprises a first discrete component, a second discrete component and a wireless link configured to transfer power and/or communication between the first discrete component and the second discrete component. The at least one external system can be configured to transfer data between the multiple discrete components.

In some embodiments, the at least one external device comprises a transmission antenna configured to be positioned proximate the patient's skin. The at least one implantable device can comprise an implantable antenna, wherein the transmission antenna is configured to be positioned proximate the patient's skin at a location proximate the implantable antenna.

In some embodiments, the at least one external system comprises a communication protocol for interfacing with a component selected from the group consisting of: computer; smart phone; handheld device; Internet; LAN; and combinations thereof. The communication protocol can be configured to transfer data at a rate up to and exceeding 20 Mbps. The communication protocol can be configured to transfer data at a rate in the range of 0.1 and 50 Mbps.

In some embodiments, the at least one external device comprises at least one antenna. The at least one antenna can be constructed and arranged to be removably attached to the patient's skin. The at least one antenna can comprise an attachment element selected from the group consisting of: adhesive; belt; band; strap; and combinations thereof. The at least one external system can comprise a controller, wherein the at least one antenna is configured to send and/or receive information to and/or from the controller. The at least one antenna can be configured to send and/or receive the information via a wired connection. The at least one antenna can be configured to send and/or receive the information via a wireless connection. The wireless connection can comprise a connection selected from the group consisting of: Bluetooth; WiFi; ZigBee; Qualcomm 2net; MICS; ISM; WMTS; MedRadio; MNN; MBAN; cellular communications; RFID; and combinations thereof. The at least one antenna can comprise a power supply. The at least one antenna can comprise a flexible substrate. The at least one antenna can comprise a skin-printed antenna comprising epidermal electronics. The at least one antenna can comprise multiple antennas. The multiple antennas can be configured to transmit power and/or communication simultaneously. The multiple antennas can be configured to relay received commands from one or more controllers to one or more implantable devices or from one or more implantable devices to one or more controllers while powering one or more implantable devices. The multiple antennas can be configured to function as part of a network. The at least one antenna can comprise a tuning element. The tuning element can be configured to tune performance based on antenna position, orientation and/or operating environment. The tuning element can be configured to automatically tune the performance.

In some embodiments, the at least one external device comprises a disposable portion. The disposable portion can comprise a component selected from the group consisting of: at least one antenna; multiple antennas; an attachment element; an adhesive attachment element; and combinations thereof. The at least one external device further can comprise a reusable portion. The reusable portion can comprise a component selected from the group consisting of: power supply; rechargeable battery; controller; electronics; one or more antennas; user interface; and combinations thereof.

In some embodiments, the at least one external device comprises at least one enclosure. The at least one enclosure can surround at least one of a power supply or a controller. The apparatus can further comprise an antenna tethered to the at least one enclosure. The apparatus can further comprise an antenna positioned in the enclosure.

In some embodiments, the at least one external system comprises a user interface. The user interface can comprise at least one user input component. The user interface can comprise at least one user output component. The user interface can comprise a component selected from the group consisting of: button; touchscreen display; knob; keyboard; keypad; display; microphone; light; speaker; and combinations thereof. The at least one external device can comprise an attachment assembly, wherein the user interface is positioned on the attachment assembly.

In some embodiments, the at least one external device further comprises an attachment assembly, at least one antenna, a controller and a power supply. The attachment assembly can position the antenna proximate the patient's skin. The attachment assembly can position the controller relative to the patient. The at least one antenna can comprise an attachment element configured to attach the antenna on the patient's skin at a location remote from the attachment assembly. The at least one implantable system can comprise multiple implants, wherein the at least one antenna can comprise multiple antennas each comprising an attachment element and each configured to be positioned on the patient's skin at locations proximate different of the multiple implants. The attachment assembly can position the power supply relative to the patient. The attachment assembly can comprise an attachment element selected from the group consisting of: belt; band; strap; article of clothing; adhesive; and combinations thereof. The power supply can comprise multiple power supplies positioned on different locations of the attachment assembly.

In some embodiments, the wireless transcutaneous transmissions comprise transmissions selected from the group consisting of: power transmissions; data transmissions; transmissions of synchronization markers; transmission of a training sequence; and combinations thereof.

In some embodiments, the overall system further comprises at least one sensor configured to provide a signal. The apparatus can be configured to provide apparatus diagnostic information based on the sensor signal. The implantable device can comprise the at least one sensor. The overall system can be configured to provide patient physiologic information based on the sensor signal.

In some embodiments, the overall system further comprises a trialing interface configured to operate the at least one implantable device during implantation of the at least one implantable system. The trialing interface can be configured to enable the patient to provide feedback about sensation of paresthesia, its location and/or comfort level. The trialing interface can be configured to provide information related to multiple stimulation parameters and/or multiple electrode configurations. The trialing interface can be configured to provide information related to the acceptability of one or more stimulation parameters and/or placement of the at least one implantable system. The at least one implantable device can comprise at least one electrode, wherein the trialing interface can be configured to provide information related to placement of the at least one electrode. The trialing interface can comprise a docking element configured to operatively engage the at least one implantable device. The at least one implantable device can comprise a lead, wherein the docking element can be configured to operatively engage the lead. The docking element can be configured to at least partially surround a portion of the at least one implantable device. The docking element can be configured to wirelessly couple to the at least one implantable device. The docking element can comprise radio-absorptive and/or radio-reflective materials. The docking element can comprise a connector configured to electrically connect to the at least one implantable device. The trialing interface can comprise a search algorithm configured to provide information related to the acceptability of one or more stimulation parameters and/or placement of the at least one implantable device. At least a portion of the at least one implantable device can be re-positionable, wherein the trialing interface can be configured to provide re-positioning information. The at least one implantable device can comprise a lead comprising one or more electrodes, wherein the trialing interface can be configured to mate with the lead and directly drive the electrodes. The at least one implantable device can comprise an antenna interface, wherein the trialing interface can provide an RF signal to the antenna interface. The external device can provide an RF signal with a similar carrier frequency to the RF signal of the trialing interface.

In some embodiments, the overall system further comprises a testing assembly comprising a power supply and an RF interface, wherein the RF interface is configured to mimic an antenna of the at least one external device. The testing assembly can be configured to provide a signal to the at least one implantable device.

In some embodiments, the at least one implantable device is implantable in (e.g. within, on and/or proximate) one or more of the following sites: the tibial nerve (and/or sensory fibers that lead to the tibial nerve); the occipital nerve; the sphenopalatine ganglion; the sacral and/or pudendal nerve; target sites in the brain, such as the thalamus; the vagus nerve; baroreceptors in a blood vessel wall, such as in the carotid artery; along, in, or proximal to the spinal cord; one or more muscles; the medial nerve; the hypoglossal nerve and/or one or more muscles of the tongue; cardiac tissue; the anal sphincter; peripheral nerves of the spinal cord, including locations around the back; the dorsal root ganglion; and motor nerves and/or muscles.

In some embodiments, the overall system is configured to stimulate one or more of: tibial nerve (and/or sensory fibers that lead to the tibial nerve); the occipital nerve; the sphenopalatine ganglion; the sacral and/or pudendal nerve; target sites in the brain, such as the thalamus; the vagus nerve; baroreceptors in a blood vessel wall; the spinal cord; one or more muscles; the medial nerve; the hypoglossal nerve and/or one or more muscles of the tongue; cardiac tissue; the anal sphincter; peripheral nerves of the spinal cord; the dorsal root ganglion; and motor nerves and/or muscles.

In some embodiments, the overall system is configured to stimulate to treat one or more of: migraine; cluster headaches; urge incontinence; tremor; obsessive compulsive disorder; depression; epilepsy; inflammation; tinnitus; high blood pressure; pain; muscle pain; carpal tunnel syndrome; obstructive sleep apnea; cardiac arrhythmia or other cardiac disease or disorder that could benefit from pacing or defibrillation; dystonia; interstitial cystitis; gastroparesis; obesity; fecal incontinence; bowel disorders; chronic pain; compromised mobility; spinal cord stimulation (SCS) for heart failure.

In some embodiments, an implantable device may comprise a sealed (e.g., hermetically sealed) enclosure and one or more of the implantable devices may form a network with external components, forming a wirelessly communicating system that may allow accommodation of different patients and therapies and ensure reliability, precise therapy, and enable many treatment options.

In some embodiments, provided are electrode configurations for tissue interfaces and patterns of electric field coverage, and lead constructions including standard leads, paddles, bifurcated leads, and connectorized interfaces. Spinal cord stimulation (SCS) treatments often require multiple leads, and interfacing the systems and devices described herein with standard approaches can greatly simplify their use. SCS and peripheral nerve stimulation can both take advantage of multi-channel stimulation among multiple leads, making this capability important for the systems and devices described herein. Additional configurability in both electrodes and leads can support new treatment options and refinements.

In some embodiments, provided are implantable antennas constructed in enclosures with orthogonal orientations and tethering options for connections. Sealed devices can ensure longevity of the implant, minimize the need for explantation, and increase safety. Configurations with multiple antennas, particularly in orthogonal orientations, can increase reliability and make the overall system more user-friendly.

In some embodiments, provided are power management systems with an onboard controller and pulse generator on the implant capable of producing custom waveforms. Energy storage can allow for an intelligently designed system that decouples power transfer from stimulation waveforms or sensor operation. Custom waveforms can allow for adaptive and emerging therapies.

In some embodiments, provided are implantable devices with an attached/connected lead and delivery assemblies that include one or more of: functional elements, such as electronics or antennas; connectorized interchangeable interfaces; sensing elements or other accessories; or, custom, modified delivery needles. Interchangeable operation with a variety of standard interfaces or leads can increase the versatility of the overall system. Functional elements distributed along leads can increase functionality or address specific use cases while operating with the same implantable system. The modified delivery system can allow for simple, minimally-invasive delivery that is very similar to the standard of care.

In some embodiments, the delivered or implantable device includes elements with controllable stiffness or designed stiffness that supports the implantation location. Controllable stiffness and rigidity can guide and anchor the implant to precise locations. Using a sheath or separate structural component can aid the implantation procedure and be removed after the desired location is reached.

In some embodiments, provided are four or more stimulation channels that can be configured with an AC-coupled interface in the device or in the structural connection. Multi-channel stimulation can be enabled by the intelligence of the overall system, and can complicate charge balance. AC-coupling can be a fail-safe charge balance mechanism, and incorporating it in structural elements can minimize physical size.

In some embodiments, the implantable device can provide configurable neuromodulation at low and high frequency with different nerve interfaces. Paresthesia therapies can operate with lower frequencies, and pain-blocking therapies can operate at high frequencies, and the overall system can be capable of both. Mechanical nueromodulation and interfaces can induce therapies without electrical contact to nerves and with significantly less power.

In some embodiments, the implantable system can incorporate a connection hub that can connect multiple implantable devices and leads together. Interchangeable components can allow for extendable systems with a variable number of leads and devices working together, which can useful for spinal cord stimulation (SCS) because patients often require multiple leads.

In some embodiments, an implantable device comprises one or more of: MRI compatibility elements, tissue anchors, markers for detecting orientation, and/or sliding delivery system. Short leads and avoidance of magnetic materials can minimize risks associated with MRI compatibility, though additional elements can provide further protection. Tissue anchors can minimize lead migration and motion of the antennas. The ability to detect orientation can assist implantation and can inform the operation of the external, for example, by adjusting polarization of the antennas. Versatile delivery systems can allow for new implantation sites and new treatments, or differently structured implants.

In some embodiments, the external device configurations may include: one or more discrete components/enclosures; one or more antenna configurations/attachments outside the body; wired or wireless connections with a controller or peripheral devices; antenna arrays; tunable elements on the antenna; disposable and/or reusable portions; and/or, multiple user interface configurations. Configurations with multiple discrete components (e.g., smaller components) may be more comfortable to the patient because less bulky components can be more flexibly placed. Multiple discrete components can form a network and operate with multiple implantable devices. Different configurations for attaching the antenna can give the overall system flexibility during usability testing. The external system configuration can include multiple discrete components that are attached with wires and/or it can include elements that communicate without wires, allowing for significant flexibility. The ability to communicate peripherally can allow for remote programming from existing devices, such as with a Bluetooth connection to a tablet. Antenna arrays can desensitize positioning requirements and simplify powering of multiple devices. The tunable elements can allow for increased link performance, improved efficiency and reliability. Disposable elements may offer advantages from a cost or business perspective, and may simplify certain design elements. User interfaces can be custom designed or implemented through existing devices, and can include standard protocols.

In some embodiments, provided is an external device with an attachment assembly, one or more antennas, a controller, and a power supply. The garment or system for attaching can distribute the power supplies and/or antennas in the most comfortable way while maintaining reliable operation with one or more implants.

In some embodiments, provided may be wireless transcutaneous transmissions that include power and/or data with optional sensing elements that can collect diagnostic or physiological parameters. Wireless power combined with data can enable the described benefits of midfield operation, and incorporating sensors enables closed-loop systems.

In some embodiments, provided may be a trialing interface for the implantable device that can include: a wireless or wired connection with the implant; elements for feedback of electrode positioning; docking interface; and/or, information for re-positioning the implant. A trialing interface can ensure seamless operation of our device in a surgical setting, simplifying use by the doctor. Feedback of electrode positioning can ensure the electrodes have good contact with tissue and are placed appropriately. A wireless docking port can allow the form-factor system to be tested in a controlled way prior to implantation, and can allow the therapy coverage to be evaluated. Implant positioning can influence the antenna link performance, and having readily available information during implantation can ensure the antenna link functions reliably.

In some embodiments, provided may be a testing assembly comprising an RF testing interface for the device prior to or after implantation. The testing assembly can verify implant functionality immediately preceding implantation, and can provide other diagnostics on the device performance. This verification can ensure devices are implanted in an effective (e.g., working) configuration, and can allow for easy verification of implantable devices.

The systems, devices, and methods described herein may be appropriate for a variety of implantation sites, nerves for stimulation, and targeted indications. The flexibility of the systems and devices described herein can allow for a variety of therapies to be provided throughout the body.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the present disclosure are set forth with particularity in the appended claims. A better understanding of the features and advantages of the inventions of present disclosure will be obtained by reference to the following detailed description that sets forth illustrative embodiments, in which the principles of the present disclosure are utilized, and the accompanying drawings of which:

FIG. 33 shows circuit diagrams of an analog sensor or body conduction interface.

FIG. 34 shows schematics of a method for assigning a unique ID to devices.

FIGS. 76a and 76b show current paths for a single-channel stimulator using a hybrid approach for stimulation and recovery, according to many embodiments.

FIG. 80 shows a circuit diagram of scheme to achieve charge-balanced stimulation and protect tissue against DC current, according to many embodiments.

DETAILED DESCRIPTION

The present disclosure relate to neuromodulation methods, systems, and apparatus for the treatment of pain management as well as other conditions or disorders. In particular, many embodiments provide for precise, controlled modulation of specific nerves or tissues to induce physiological effects. Additionally, embodiments that incorporate information for diagnostics or improved therapeutic efficacy are described. Also, apparatus and devices are described that improve the therapies or the diagnostics.

Figure 11:
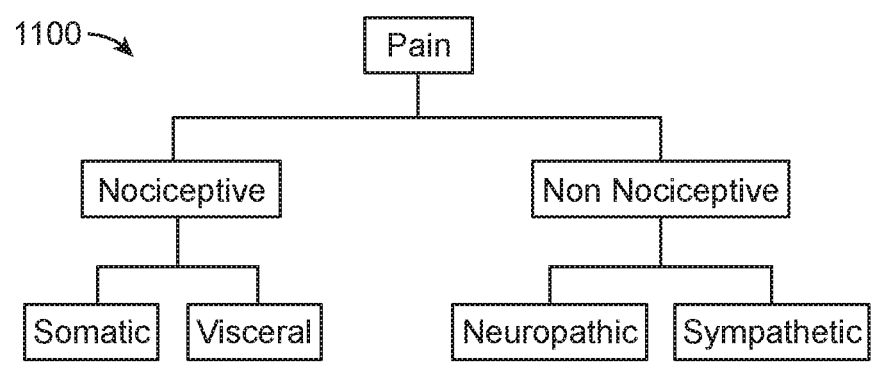
FIG. 11 illustrates the classifications of different types of pain.

There are different types of pain which are classified into two major categories: nociceptive and non-nociceptive pain, as can be seen in pain classification 1100 shown in FIG. 11. Nociceptive pain can arise from the stimulation of specific pain receptors. These receptors can respond to heat, cold, vibration, stretch, and chemical stimuli released from damaged cells. Non-nociceptive pain can arise from within the peripheral and/or central nervous system. Specific receptors do not exist here, with pain being generated by nerve cell dysfunction. Nociceptive pain can be further categorized into somatic and visceral pain. Non-nociceptive pain can be further categorized into neuropathic and sympathetic pain. Based on these classifications and on the actual origins of pain, various treatments may be more effective than others.

Somatic pain typically originates in tissue such as skin, muscle, joints, bones, and ligaments and is commonly referred to as musculo-skeletal pain. In this pain process, specific receptors, known as nociceptors, may be activated for heat, cold, vibration, stretch (muscles), inflammations (such as cuts and sprains which cause tissue disruption), and oxygen starvation (ischaemic muscle cramps), causing the sensation of pain. The characteristics of pain may be that it is often sharp and well-localized, and can often be reproduced by touching or moving the area or tissue involved. While there are some known useful medications to treat somatic pain, such as combinations of paracetomol, weak or strong opioids, and NSAIDs, it may be more preferable to treat this pain via neuromodulation. This way of treatment may especially be useful in cases of patients who have side effects to medication, medically refractive pain cases, chronic pain, and other cases where medication is not effective or not preferred.

Visceral pain typically originates from internal organs of the main body cavities. There are three main cavities— thorax (heart and lungs), abdomen (liver, kidneys, spleen and bowels), and pelvis (bladder, womb, and ovaries). The receptors activated in this type of pain may be specific receptors (nociceptors) for stretch, inflammation, and oxygen starvation (ischemia). The characteristics of this pain may include pain that is often poorly localized, and may feel like a vague deep ache, sometimes being cramping or colicky in nature. It can frequently produce referred pain to the back, with pelvic pain referring pain to the lower back, abdominal pain referring pain to the mid-back, and thoracic pain referring pain to the upper back. Some useful medications to which visceral pain responds are weak and strong opioids.

Nerve pain, which falls under non-nociceptive pain category, can originate from within the nervous system itself— also known as pinched nerve or a trapped nerve. The pain may originate from the peripheral nervous system (the nerves between the tissues and the spinal cord), or from the central nervous system (the nerves between the spinal cord and the brain). The causes may be due to any of the following processes: Nerve Degeneration—multiple sclerosis, stroke, brain hemorrhage, oxygen starvation; Nerve Pressure—trapped nerve; Nerve Inflammation—torn or slipped disc; Nerve Infection—shingles and other viral infections. The nervous system itself does not have specific receptors for pain (non-nociceptive). Instead, when a nerve becomes injured by one of the processes named above, it becomes electrically unstable, firing off signals in a completely inappropriate, random, and disordered fashion. Characteristics of this pain after being interpreted by the brain as pain can be associated with signs of nerve malfunction such as hypersensitivity (touch, vibration, hot and cold), tingling, numbness, and weakness. There is often referred pain to an area where that nerve would normally supply e.g. sciatica from a slipped disc irritating the L5 spinal nerve produces pain down the leg to the outside shin and big toe i.e. the normal territory in the leg supplied by the L5 spinal nerve. Spinal nerve root pain can also often be associated with intense itching in the distribution of a particular dermatome. People often describe nerve pain as lancinating, shooting, burning, and hypersensitive. This pain can only be partially sensitive to paracetamol, NSAIDs, opioids. It can be more sensitive to anti-depressants, anti-convulsants, anti-arrhythmics, and NMDA antagonists. Topical capsaicin may also be helpful.

Another type of pain which falls under non-nociceptive pain category is sympathetic pain. The reason and source of this pain may be due to possible over-activity in sympathetic nervous system, and central/peripheral nervous system mechanisms. The sympathetic nervous system controls blood flow to tissues such as skin and muscle, sweating by the skin, and the speed and responsiveness of the peripheral nervous system. This type of pain occurs more commonly after fractures and soft tissue injuries of the arms and legs, and these injuries may lead to Complex Regional Pain Syndrome (CRPS). CRPS was previously known as Reflex Sympathetic Dystrophy (RSD). Like nerve pain there are no specific pain receptors (non-nociceptive). The same processes as mentioned above in nerve pain may operate in CRPS. Sympathetic pain presents as extreme hypersensitivity in the skin around the injury and also peripherally in the limb (allodynia), and is associated with abnormalities of sweating and temperature control in the area. The limb is usually so painful, that the sufferer refuses to use it, causing secondary problems after a period of time with muscle wasting, joint contractures, and osteoporosis of the bones. It is possible that the syndrome is initiated by trauma to small peripheral nerves close to the injury. Many of the features of sympathetic pain are similar to those of nerve pain, and therefore nerve pain medications may be useful (anti-depressants, anti-convulsants, and anti-arrhythmics). Drugs which lower blood pressure by causing vasodilatation (nifedipine) may also be useful when used in combination. Treatment should include appropriate multi-modal medications, sympathetic nerve blocks, and intensive rehabilitation combining occupational and physiotherapy. Neuromodulation of these nerves offers an attractive alternative by mitigating or blocking the pain without the side effects of medication.

Figure 12:
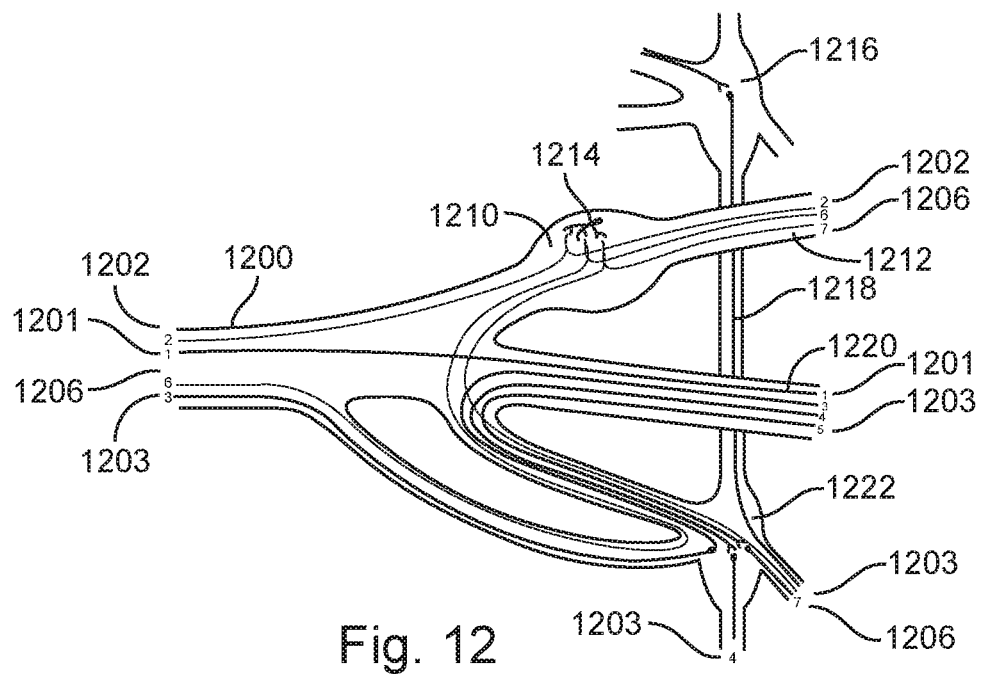
FIG. 12 illustrates ramus communicans depicted as a schematic.

It can be important to target the right nerves when treating specific pain. For instance, inside a body, somatic pain information is transferred from the origin of pain at nociceptors to the brain via somatic afferent nerves and nerve structures. Therefore, it can be important to target somatic afferent nerves. Posterior nerve root contains nerves and nerve bundles that have somatic and sympathetic afferent nerves physically separated from other types of nerves. Targeted nerve modulation of this posterior nerve root can treat pain only without affecting efferent nerves. Therefore, dorsal root, dorsal root ganglion, pre- or post-ganglionic neural tissue can be modulated to suppress pain propagation or mask pain. An example is spinal ganglion 1210 on the posterior nerve root 1212 as shown in FIG. 12 and other perspective views including spinal structure 1300 shown in FIG. 13. It is also possible to modulate spinal nerve, gray and/or white ramus communicans to treat pain. However, this modulation may require modification in treatment parameters to achieve the same therapeutic effect without affecting efferent nerves because afferent nerves are only slightly physically separated from efferent nerves in these other anatomical structures. In order to target only sympathetic afferent nerves and not somatic afferent nerves, it is possible to target gray and white rami communicantes, which do not contain somatic afferent nerves.

FIG. 12 shows ramus communications as a schematic. The general somatic afferent somatic sensory fibers 1202 may arise from cells in the spinal ganglia and may be found in all the spinal nerves, except occasionally the first cervical, and may conduct impulses of pain, touch, temperature, etc. from the surface of the body through the posterior roots to the spinal cord and impulses of muscle sense, tendon sense, and joint sense from the deeper structure. The spinal nerve 1200 may further include somatic efferent nerves 1201, sympathetic efferent nerves 1203, sympathetic afferent nerves 1206, the cell of dogiel 1214, the sympathetic ganglion 1216, the sympathetic cord 1218, the anterior nerve root 1220, and the sympathetic ganglion 1222.

Figure 13:
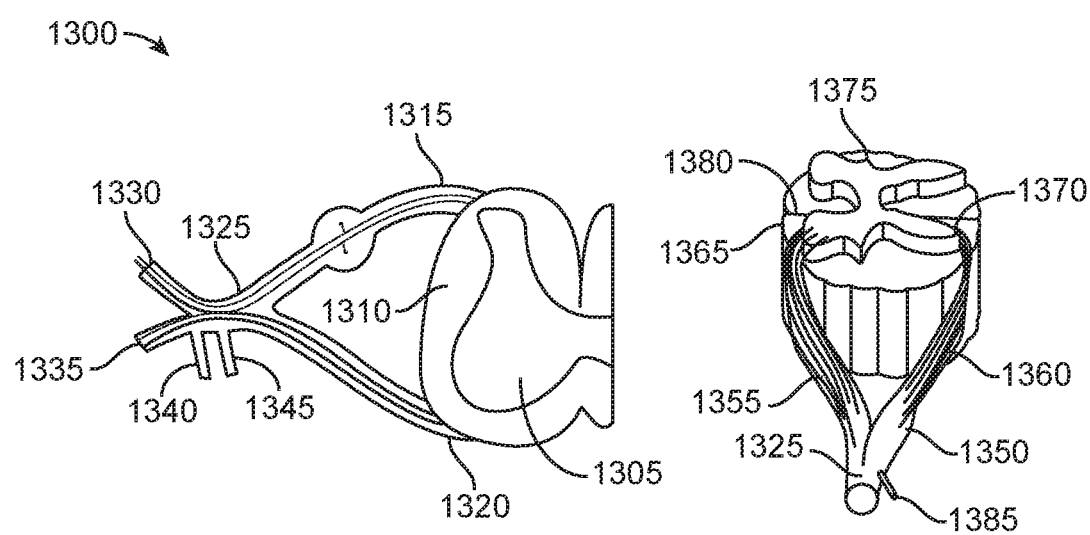
FIG. 13 illustrates additional depictions of spinal nerves and structures.

FIG. 13 shows other another schematic and a perspective view of the spinal nerve and adjacent anatomical structures 1300. The spinal nerve and the adjacent anatomical structures may comprise grey matter 1305, white matter 1310, the dorsal root 1315, the ventral root 1320, the spinal nerve 1325, the dorsal ramus 1330, the ventral ramus 1335, the white ramus 1340, and the gray ramus 1345. The spinal nerve and the adjacent anatomical structures may further comprise the spinal ganglion 1350, the anterior root 1355, the posterior root 1360, the posterior division 1365, the anterior column 1385 of the vertebrae, the posterior column 1370 of the vertebrae, the lateral column 1375 of the vertebrae, and the anterior medial fissure 1380.

Figure 9:
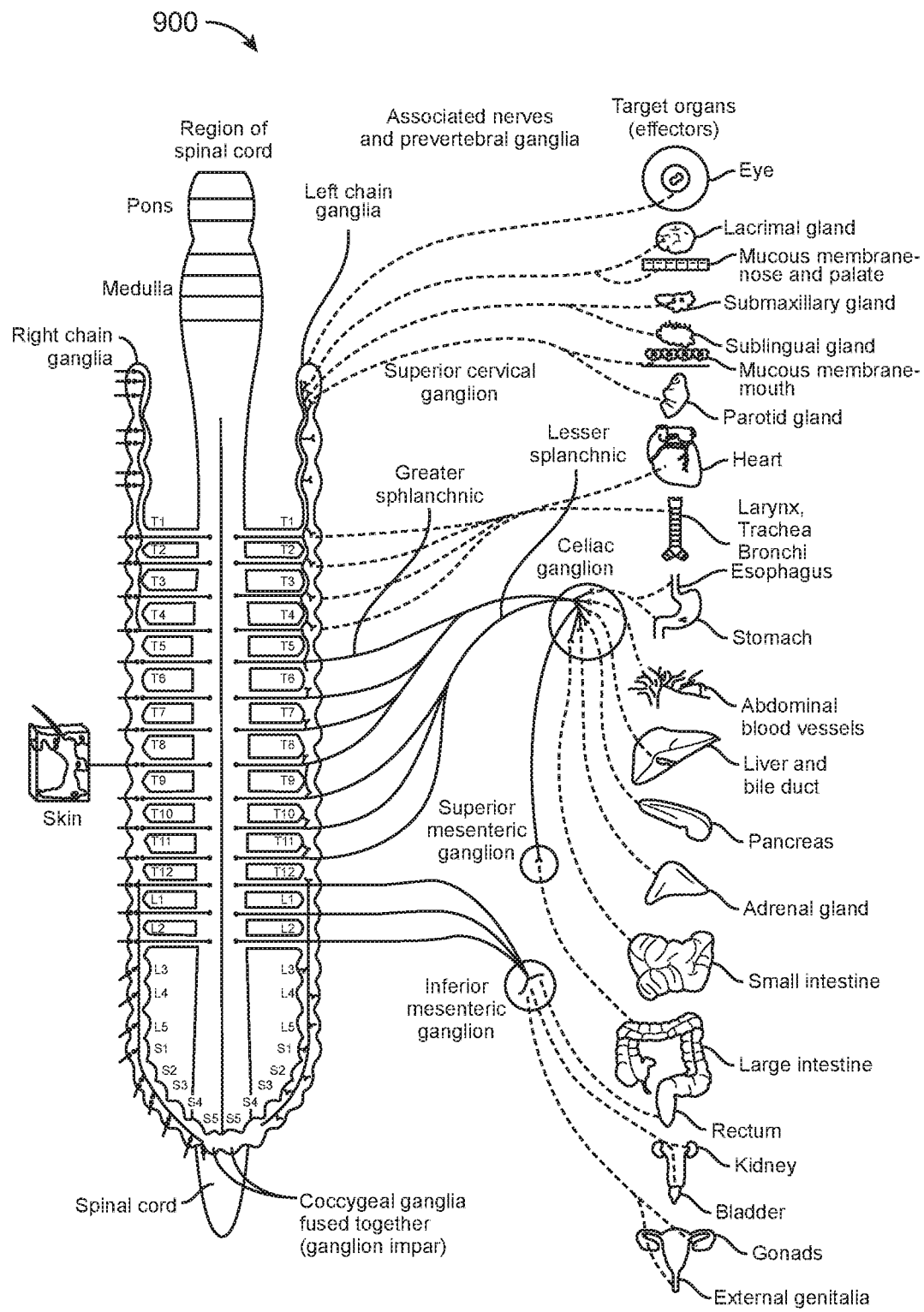
FIG. 9 illustrates a diagram of the sympathetic nervous system to highlight which nerves can be targeted for different therapies or diagnostics.
Figure 10:
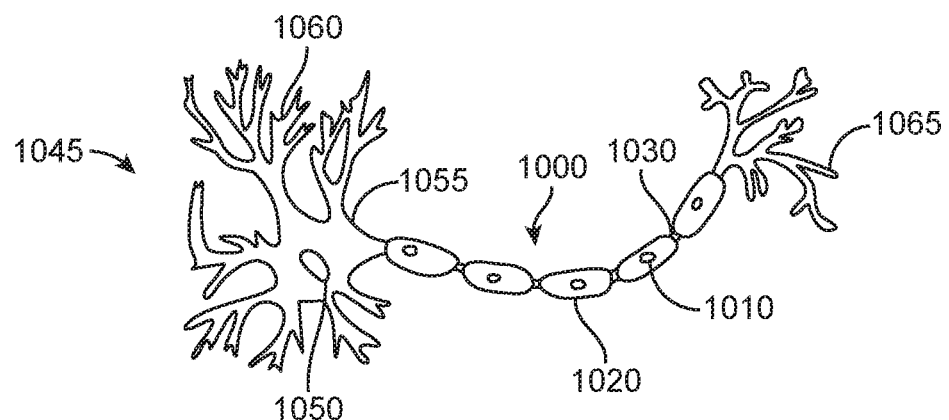
FIG. 10 illustrates the basic structure of a neuron with labeled parts.

Particular organs can be targeted via neuromodulation of sympathetic nervous system (SNS). Electrodes or interfaces can be placed at the origin of SNS, next to thoracolumbar region of the spinal cord (levels T1-L2), where the shorter preganglionic neurons originate. In addition or instead, electrodes or interfaces can be placed downstream from the preganglionic neurons, such as at a ganglion, such as one or more of the paravertebral ganglia, where preganglionic neurons synapse with a postganglionic neuron. The electrode positioning can also be done, in addition to or instead of previously mentioned locations, along the long postganglionic neurons which extend across most of the body as can be seen in schematic 900 of FIG. 9. The schematic 900 shows the various regions of the spinal cord and how they affect various target organs. The general illustration of a neuron 1000 is shown in FIG. 10. The attachment of electrodes to the above-described regions and locations of the sympathetic nervous system can be accomplished using methods described herein. The attachment can be done to ganglia, axons, or other parts of neurons as seen in FIG. 10. As shown in FIG. 10, the axon 100 may comprise a plurality of Schwann cells 1010 covered by myelin sheaths 1020. The axon 100 may further comprise nodes of Ranvier 1030. As shown in FIG. 10, the nerve cell 1045 may comprise a nucleus 1050, a soma 1055, dendrites 1060, and axon terminals 1065.

Chronic back pain has several existing neuromodulation therapies that target nerves in the back and in the spine. Some methods are placed in the vicinity of these nerves, and some are placed inside specific nerves. There are at least several elements that can dramatically improve the efficacy and safety of these therapies. Precisely locating the neuromodulation sites can ensure that only the nerves inducing pain or carrying pain signals are targeted and minimize unnecessary and unwanted neuromodulation of surrounding tissues. This precise location can potentially reduce the power requirements of the neuromodulation system, and can improve efficacy by focusing the energy at the desired site, and improves patient comfort by minimizing extraneous neuromodulation, which could affect motor function or induce other sensations. Additionally, the ability to selectively configure the neuromodulation at multiple targeted sites can give flexibility that can greatly enhance the therapy. Each patient is different and it can be difficult or impossible to identify the exact type of neuromodulation ahead of time, so this flexibility is often crucial. One of the more effective sites for treating chronic back pain may be in or around the vicinity of the dorsal root and the dorsal root ganglia. Placing the neuromodulator proximal or distal to either the dorsal root or the dorsal root ganglia as previously described can induce similar therapy to modulating these nerves specifically, and may even be advantageous in certain cases. Additionally, locations on the nerve upstream or downstream (in relation to the spinal cord) of either the dorsal root ganglia or dorsal root can achieve similar or better efficacy. It can be difficult to know exactly which dorsal root or dorsal root ganglia should be targeted ahead of time, and in some cases multiple sites can be targeted for effective treatment. Therefore, methods with controlled modulation of multiple sites either simultaneously or sequentially can be important for more effective treatments. Combining any and all of these techniques can result in improvement, and the preferred method can make use of multiple elements with innovative new devices. Methods for attaching, modulating, sensing, and adapting the therapy delivered to these sites are described in the following sections, as well as apparatus and devices that improve on existing technology.

Chronic pain can also surface in a number of other locations in the body for a variety of reasons. Some cases may be neuropathic in nature, and can be caused by damage or disease to parts of the somatosensory system. Neuropathic pain can include phantom pain, which is an experience of pain felt from a part of the body that has been lost or is no longer connected to the brain through the nervous system. Alternatively, these cases can be from nociceptive pain, which is caused by stimulation of nociceptors, which only respond to stimuli of excessive intensity. Another form of chronic pain is psychogenic, which results from certain types of mental, emotional, or behavioral factors. Psychogenic pain can be just as debilitating as pain from other sources. For all these types of pain, active research is showing promise for neuromodulation therapies. The higher the precision of the location and profile of the neuromodulation, the higher the efficacy and lower the risk of the treatment can be. For pain experienced in a specific location, neuromodulation sites could target the specific location of the nerve, as well as in close proximity, including both upstream and downstream locations (closer or farther to the spinal cord and brain). Additionally, neuromodulation treatments can target tissues other than nerves, and induce activity that accelerates healing and minimizes discomfort. Multiple sites can be targeted either sequentially or simultaneously with configurable neuromodulation treatments that are based on physiological responses or other information. This could be especially useful when the healing occurs in multiple phases, and different tissues are responsible for different aspects of the healing process. Combining any and all of these techniques results in improvement, and the preferred method would make use of multiple elements with innovative new devices. Methods for attaching, modulating, sensing, and adapting the therapy delivered to these sites are described in the following sections, as well as apparatus and devices that improve on existing technology.

Similarly to chronic pain, many types of acute pain can be treated with neuromodulation methods as well. As an example, research has shown evidence that migraines can be mitigated or eliminated through modulation of nerves in the nasal passage, which is likely because of their direct connections to the brain. Sphenopalatine ganglion or sphenopalatine nerves are examples of specific nerve structures that can be stimulated to stop migraines and other headaches. In cases of acute pain, giving the patient or doctor real-time control of the neuromodulation parameters is essential, and having the ability to target multiple sites can be essential in an effective treatment. Using any number of methods of modulating nerves, the precise location and control of the parameters can greatly enhance the therapeutic outcome. A feedback system can incorporate information from the patient in response to changes in the pain or from directly sensing signals from the tissues or nerves. The location of the stimulation sites can be at the site of the pain or downstream or upstream from it in the nervous system, as in the example of the treatment for migraines. Methods for attaching, modulating, sensing, and adapting the therapy delivered to these sites are described in the following sections, as well as apparatus and devices that improve on existing technology.

In particular methods, the modulation system interface may comprise several semi-rigid wires or structures which can extend out of a lumen, which can be flexible, rigid, or semi-rigid. The modulation system interface can be placed inside of a delivery system, which may be a needle, a cannula, introducer, or other system. The curved ends of wires can allow them to grab around and onto a nerve, ganglion, bundle, or other tissue or anatomical structure, such as around a dorsal root ganglion, dorsal root, muscle, or bone. When the wires are retracted, they may compress together. This mechanism of action can allows the interface to attach to tissue without needing an explicit anchoring mechanism. The mechanism of action and design is substantially similar to the Screw or Part Grabber devices 100a and 100b (also referred to as screw-grabber) that are shown in FIG. 1.

Figure 1:
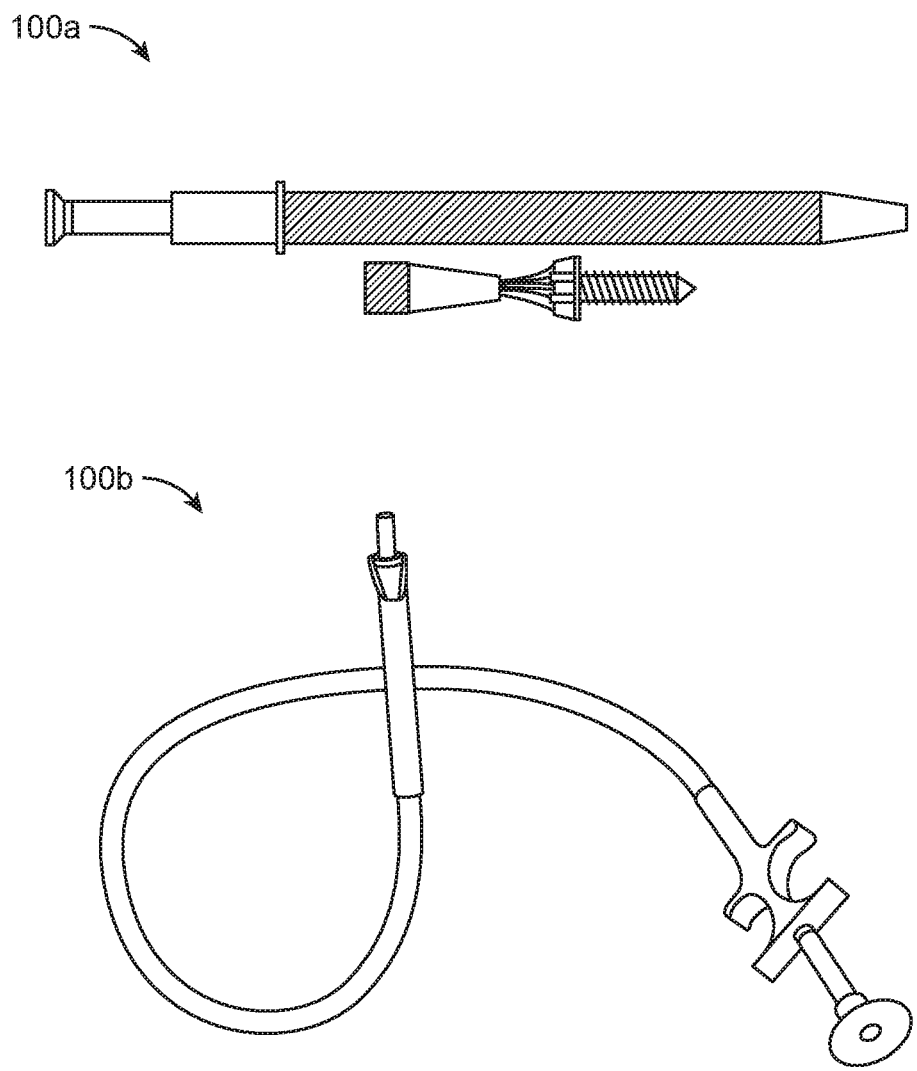
FIG. 1 shows Screw or Part Grabber devices that have a similar mechanism of action compared to embodiments of tissue attachment method, according to many embodiments.
Figure 2:
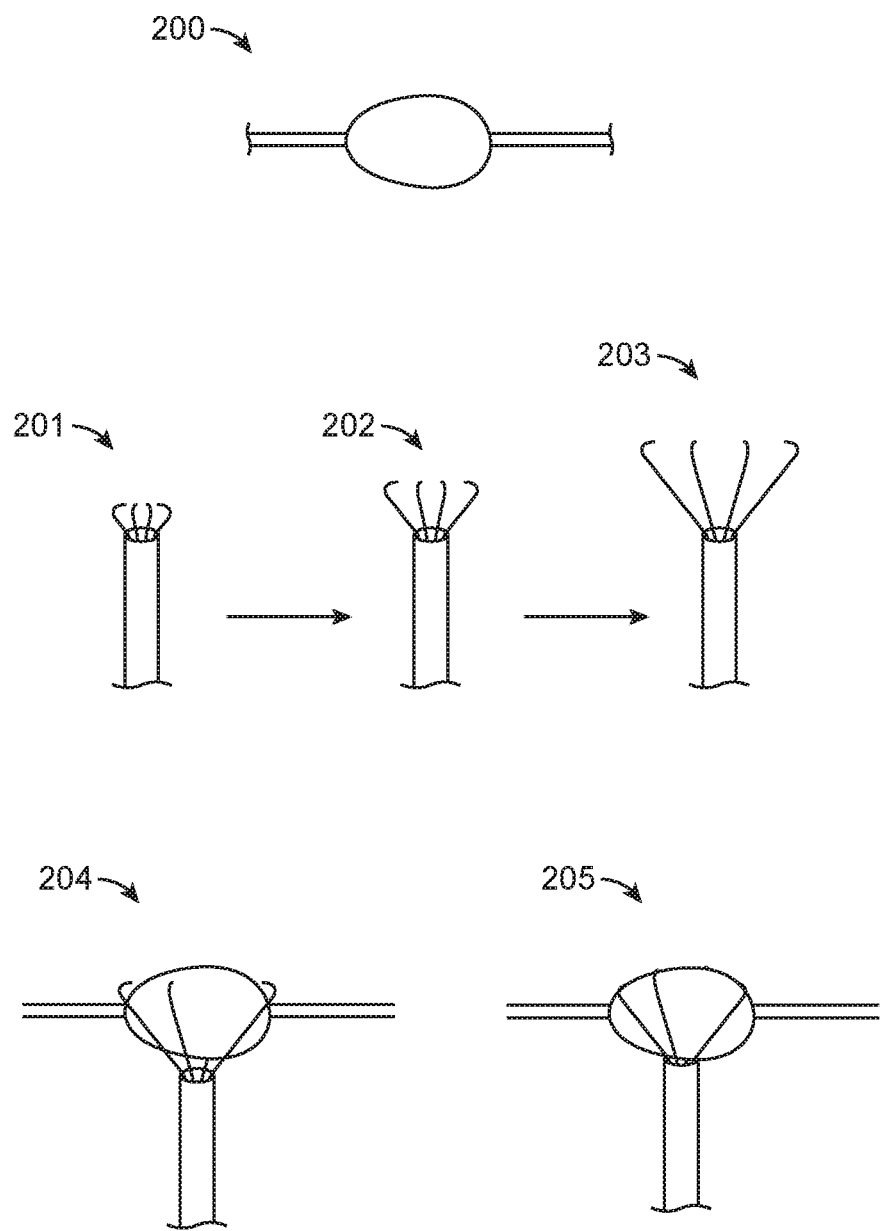
FIG. 2 illustrates the described attachment mechanism operating with tissue.

As shown in FIG. 1, the screw-grabber 100a may be rigid and the screw-grabber 100b may be flexible and bendable. Electrodes may be configured with similar mechanisms of action to the screw-grabbers 100a and 100b and have adapted and modified functionality of grabbing onto nerve ganglia, nerve bundles, nerve tissues, or other tissues. The wires which extend out of leads may be isolated at least partially to prevent shorting. The tips of the wires can be non-insulated to enable energy delivery to tissue. Alternatively, the wires may simply function as an anchor and/or inactive electrode (ground or reference electrode). The active electrode could be placed within nerve tissue and can be in the form of a needle which can penetrate through neural tissue, thereby enabling current flow from the inside of the neural tissue to the reference electrodes which are positioned on the outside of the neural tissue.

Figure 8:
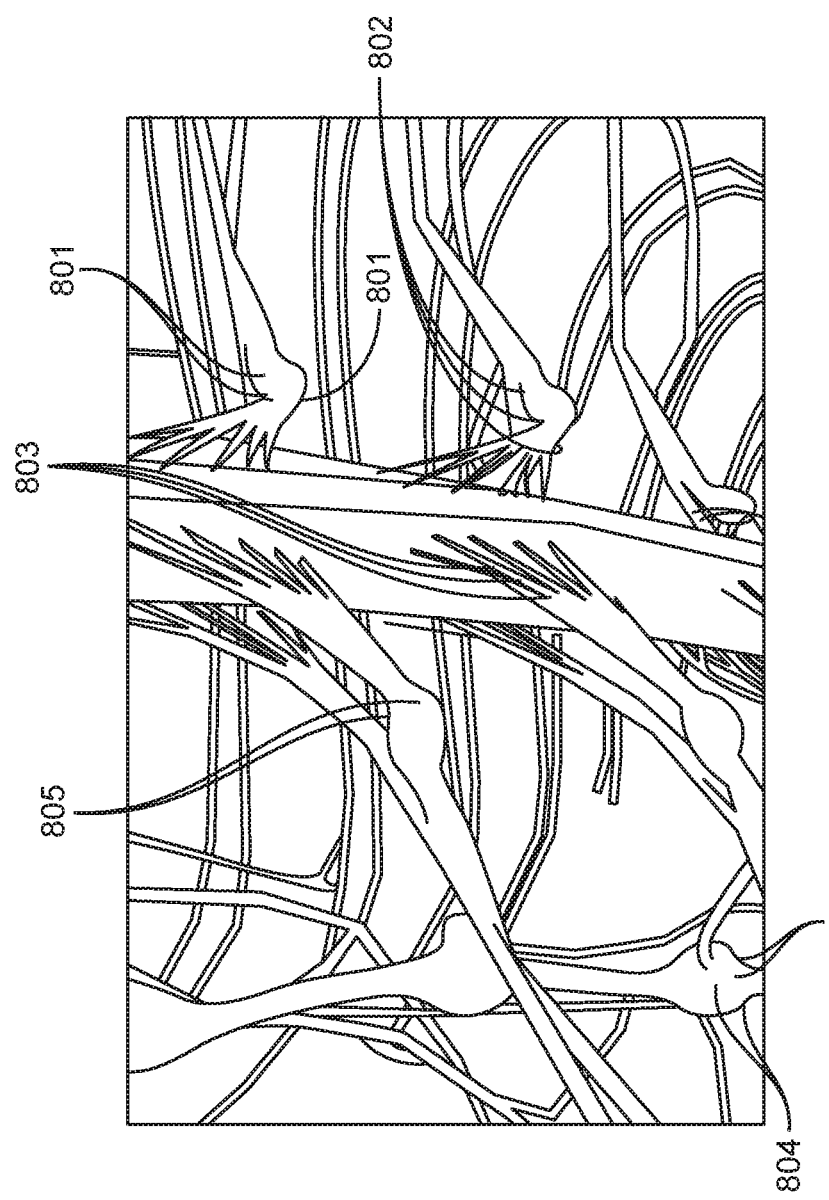
FIG. 8 illustrates several attachments to different tissues, nerves, or nerve bundles using the methods described herein.

For neuromodulation, the attaching structures can comprise wires that are conductive and can be electrically connected to the same contact or connected to separate contacts on the neuromodulator system. Some possible connection mechanisms and method examples are shown in FIGS. 2, 3A, 3B, 3C, 4A, 4B, and 4C. If connected to different contacts, each wire can have a potential to be individually controlled and thus can enable current steering which can be beneficially used to target energy delivery to particular nerves and avoid delivery to unintended nerves and tissue. If electrically connected together, all the wires do not have to be isolated and can act as a single (distributed) electrode. This connection configuration would increase the surface area of the electrode and lower tissue/electrode impedance. This option, however, may require another electrode (e.g. a return electrode) to complete the electrical circuit. Such a circuit-completing electrode can be placed on a side of the neuromodulator (e.g. on the housing of the neuromodulator) away from attached electrodes, can be selected as one of the attached electrodes, can be positioned in the center of the attached electrodes, or can be a separate attached electrode using any attachment method. The method similar to a Screw or Part Grabber can also feature one or more internal needle-like (or bayonet-like) extensions in the middle of the wires, for example similar in structure to a BNC connector. This central extension can penetrate through tissue when attaching the electrode to the desired tissue, and eventually reside inside of the tissue. The extension protruding into the tissue could be programmed to source and/or sink current, while external anchoring (grabbing) wires or a separately attached system would have the opposite polarity to the central extensions. In other implementations, multiple center wires or needle-like extensions could be included and could act as separate electrodes. Some of the potential advantages of a tissue grabbing system are that these elements provide a way to anchor the modulation interface without a complex procedure. Also, the electrodes of the present invention can be in a compact form which is well-suited for delivery through a lumen, such as a lumen of a cannula, catheter, needle, or introducer. A simple mechanism, such as a mechanism enabling pressing of a button, can open up the wires or electrodes in proportion to level of activation of the mechanism (such as the amount of depression of the button). Upon release of the mechanism, the electrodes transition to their original state of compression. When advanced close to a nerve, nerve bundle, or other tissue and upon release of the mechanism, the electrodes or wires wrap around the tissue and secure them in place. Additionally, when the needle-like center electrode is not used, or otherwise when the tissue is not penetrated, undesirable side-effects can be reduced and/or the healing process can be accelerated. Also, this method can provide a self-adjustable way to anchor the modulation interface to varying size tissue or nerves without having to customize these electrodes for a particular patient. Multiple attached modulator system configurations utilizing a variety of screw-grabber anchoring mechanisms are illustrated in FIG. 8.

Referring back to FIG. 2, screw-grabber connectors or electrodes (anchoring mechanisms) can be used to attach to any tissue, such as a nerve and nerve ganglion 200. In a step 201, the electrode may be advanced so that its tip is in proximity to a nerve. In a step 202, the connecting elements may be opened by engaging a remote activator such as a button. In a step 203, the connecting elements may be opened sufficiently wide to be able to grab onto the desired tissue (nerve ganglion in this case). In a step 204, the connecting elements may start closing by disengaging the remote activator (releasing the button). In a step 205, the remote activator may be completely disengaged to anchor the electrodes in place, completing the procedure. The screw-grabber connectors or electrodes may be removed by inversing these steps. Specifically, to remove these interfaces, one would first start engaging the remote activator until connecting elements are sufficiently open to be able to remove them from the target tissue. Then, the connecting elements may be removed from the target tissue. Once connecting elements are no longer overlapping with the target tissue, the removal activator can be fully or partially disengaged to close the connecting elements, reverting it back to the step 201. The screw-grabber connectors or electrodes can then be completely removed from the body.

Figure 3A:
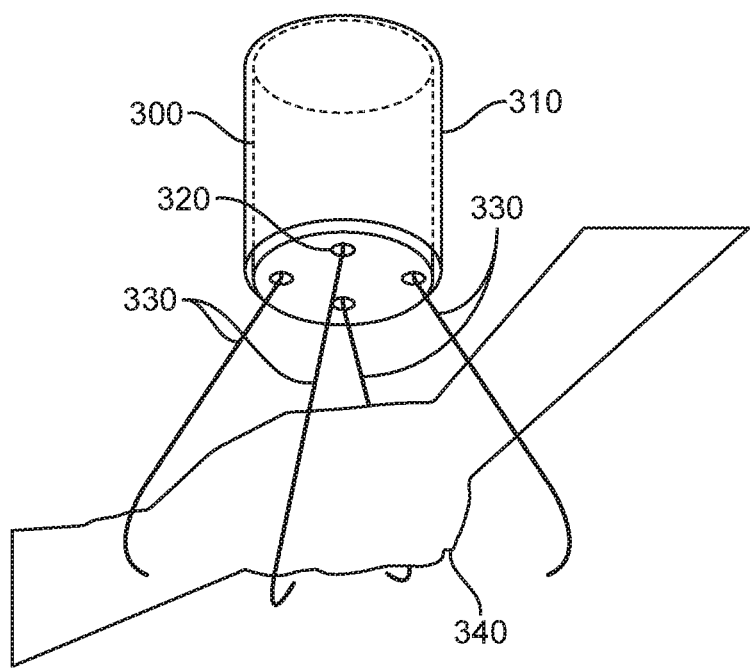
FIGS. 3A, 3B, and 3C illustrate the described attachment apparatus with a single group of attaching elements and a method of attachment to tissue.
Figure 3B:
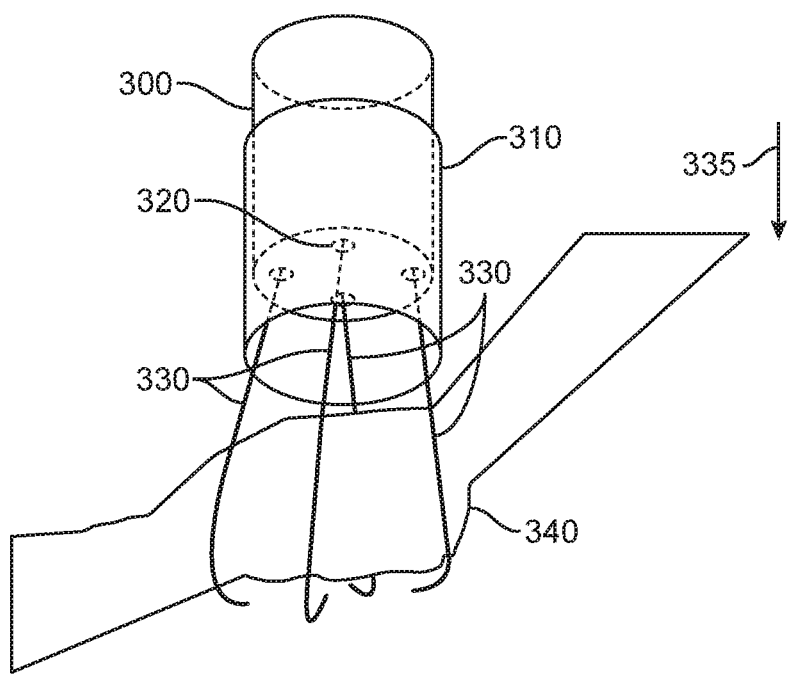
Figure 3C:
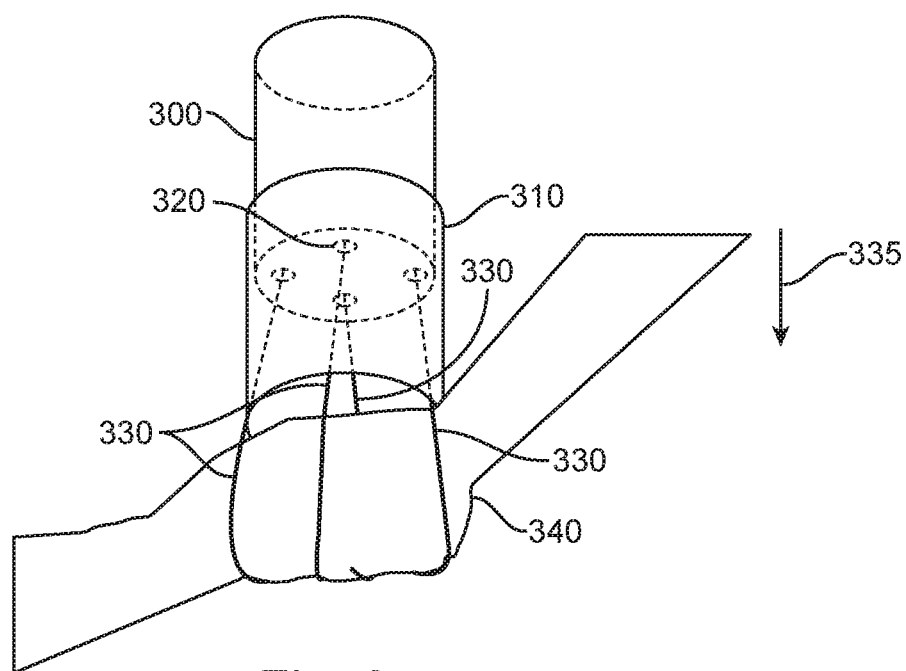

FIGS. 3A-3C show an apparatus and method of securing an implant body 300 to target tissue 340. The implant body 300 may be positioned within a sliding tube 310. The implant body 300 may comprise feed-throughs 320 for connecting elements 330 for grabbing on to target tissue 340, such as nerve ganglion. As shown in FIGS. 3B and 3C, the sliding tube 310 can be advanced in the direction of arrow 335 to secure the connecting elements 330 to the target tissue 340. FIG. 3B shows the sliding tube 310 slightly advanced to push the connecting elements 330 to the target tissue. FIG. 3C shows the sliding tube 310 fully advanced to fully press the connecting elements 330 against the target tissue, securing the implant body 300 against the target tissue 340. The sliding tube 310 can be flexible or rigid.

Figure 4A:
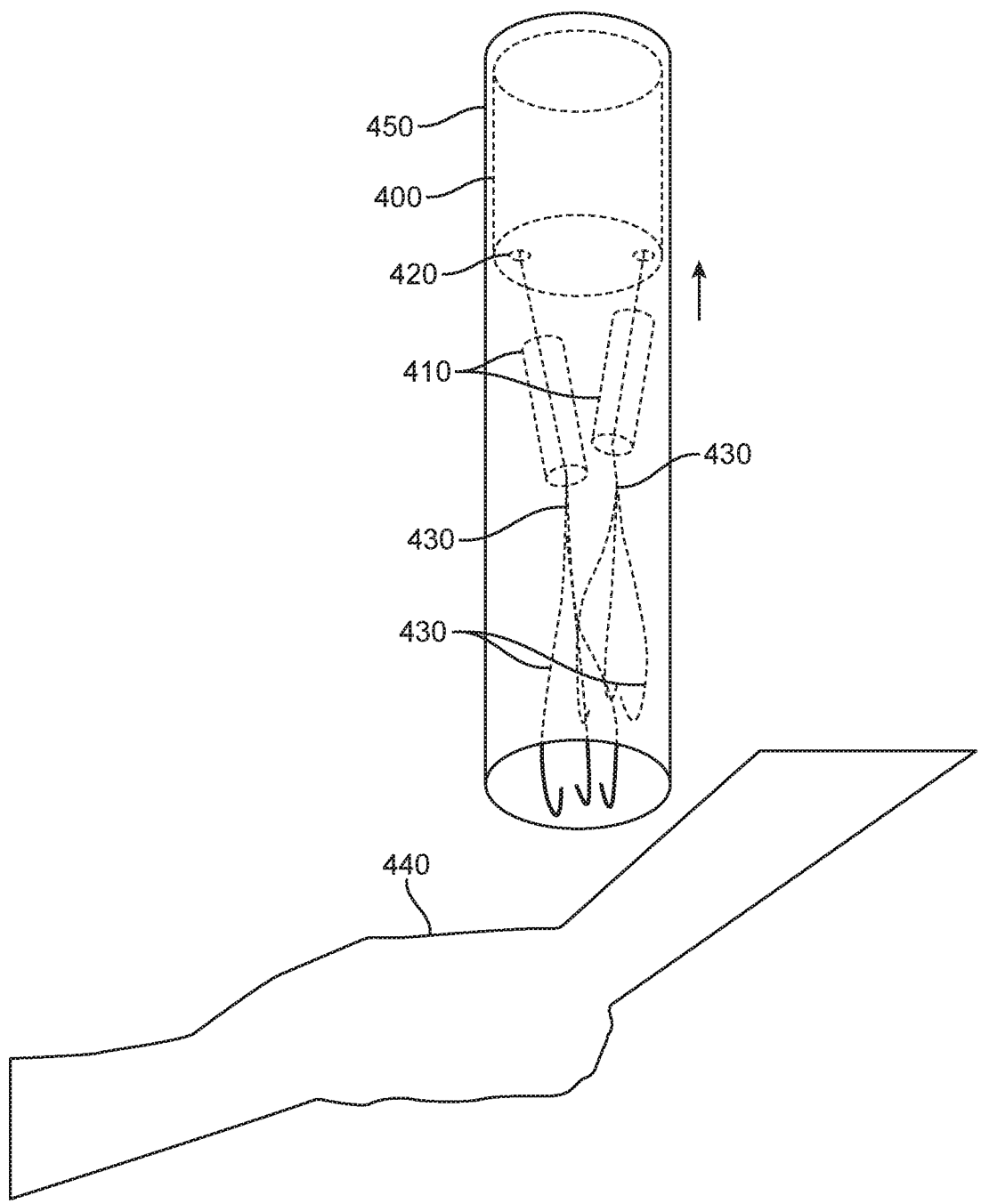
FIGS. 4A, 4B, and 4C illustrate the described attachment apparatus with multiple groups of attaching elements and a method of delivering and attaching said apparatus to target tissue.
Figure 4B:
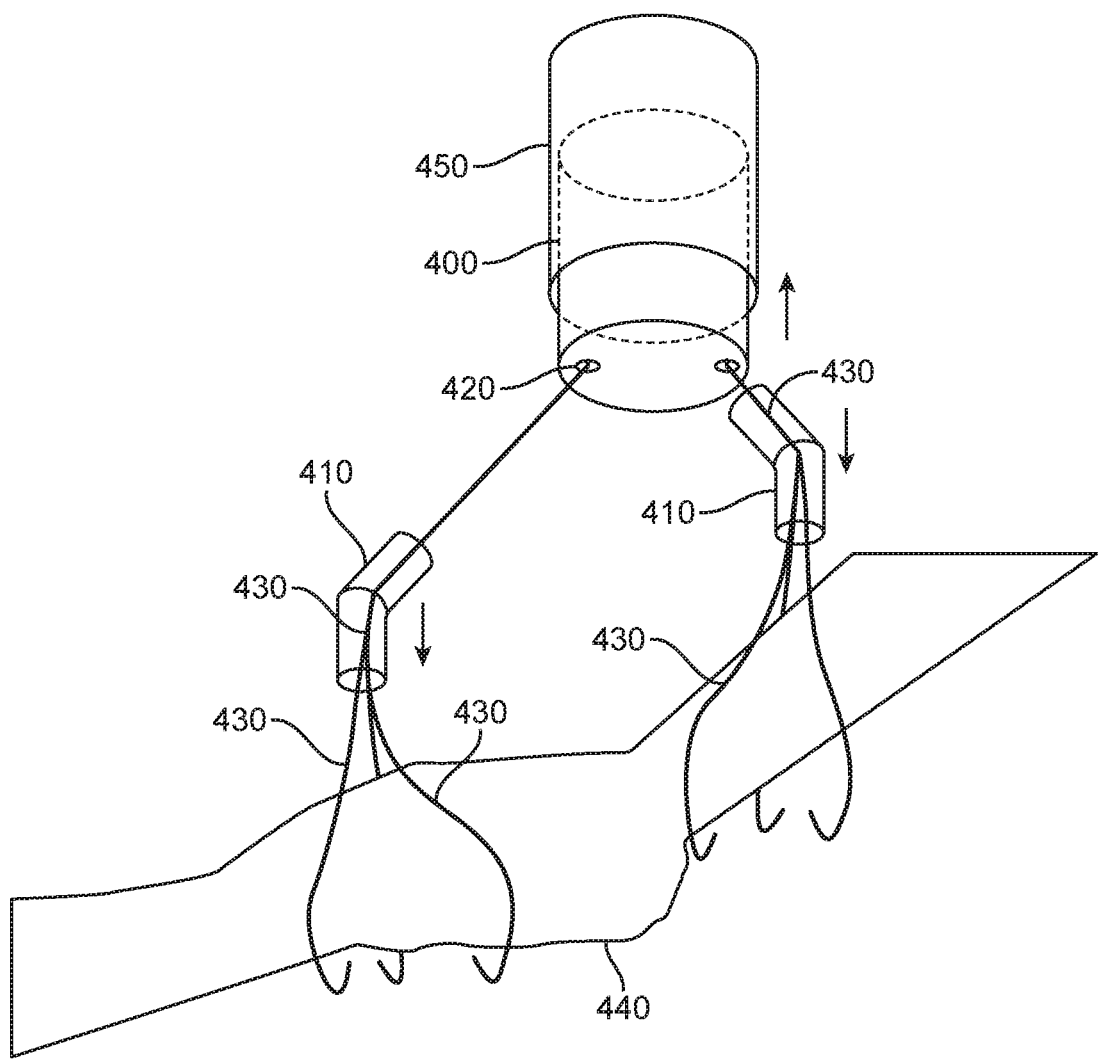
Figure 4C:
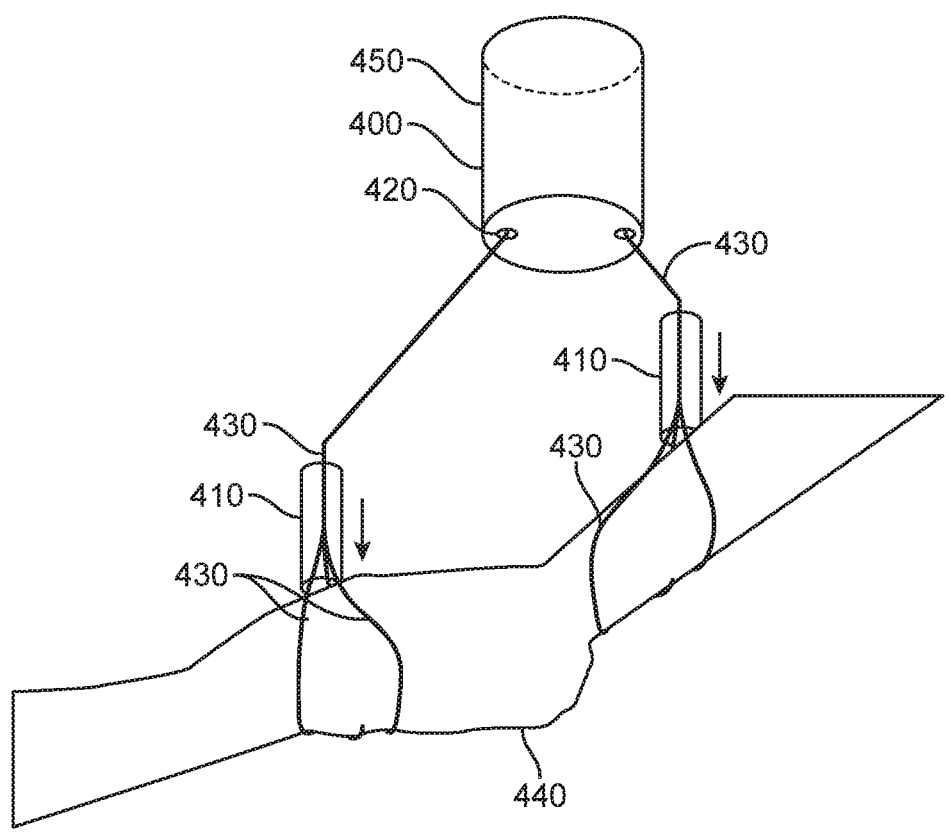

FIGS. 4A-4C show an apparatus and method of securing an implant body 400 with multiple groups of connecting elements 430 to target tissue 440. The apparatus may utilize multiple groups of connecting elements 430 which can be compressed or opened by using at least one sliding tube 410 per group of connecting elements 430. The connecting elements 430 may be coupled to the implant body 400 through feed-throughs 420. Each tube 410 may push connecting elements 430 together similar to the action of a screw-grabber device to secure each group of connecting elements 430 to the desired location on the target tissue 440. FIGS. 4A-4C show a sequence of attaching the implant body 400 to the target tissue 440. As shown in FIG. 4A, the implant body 400 may be positioned completely within an introducer 450 with all groups of connecting elements 430 compressed. As shown in FIG. 4B, the implant body 400 may be slightly advanced along arrows 435 through the introducer 450, opening up the connecting elements 430 and allowing them to expand and be advanced toward the target tissue surrounding the target tissue 440. The sliding tubes 410 may not be completely compressing the connecting elements 430. As shown in FIG. 4C, the implant body 400 has completely ejected from the introducer 450 and the sliding tubes 410 is advanced to a point where all the connecting elements 430 within each group is fully pressed against the target tissue 440, securing each group of connecting elements 430 to the correspondingly desired location on the target tissue 440 and thus fixing/securing the implant body 400 against the target tissue 440. The sliding tubes 410 may be flexible or rigid. All connecting elements 430 within each group can be interconnected together or separately controlled, in order to achieve the desired therapeutic and/or diagnostic outcome(s).

Figure 7:
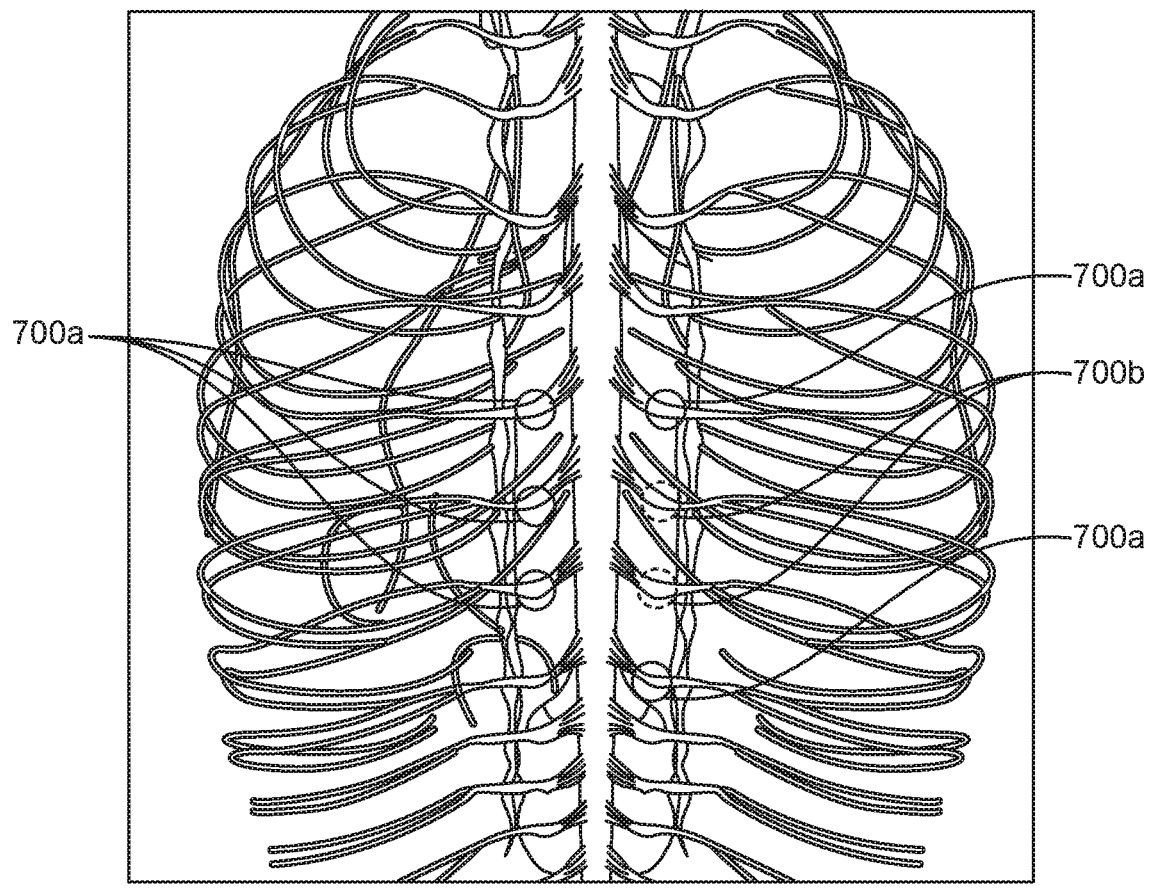
FIG. 7 illustrates a neuromodulation therapy involving multiple modulation sites in which some are active and some are not.

Multiple tissue interfaces, such as electrodes, extending from a single neuromodulator or from multiple neuromodulators can be positioned in the above described manner on multiple nerves, nerve bundles, nerve roots, or other neural tissue. Modulation of multiple nerve sites may be necessary for certain applications and therapies. For instance, in order to treat back pain effectively by completely blocking or masking pain, multiple DRGs, dorsal roots, or nerve bundles at multiple vertebra levels (i.e. T12, L1, L2) and at one or both sides (left and right) can be modulated. Depending on the affected region, the area of coverage can be expanded by activating more and more electrodes until the entire affected region is covered and pain is eliminated, blocked, or masked in its entirety. Unnecessary electrodes will not be activated, saving energy. The multiple interfaces or electrodes can deliver the same modulation profile, different modulation profiles, or same modulation profiles but in a coordinated manner to improve therapeutic outcome and mitigate side effects. This coordination could depend on simultaneous or sequential activation, and may depend on other types of sensed or collected information. For example, in some applications such as when modulating intestines to induce peristalsis, modulation of multiple sites along the intestine at different times but periodically and in coordinated manner with respect to one another is more beneficial to induce wave-like contractions. Similarly, other therapies may require interdependent modulation which can be controlled by a single or multiple controllers which are aware of each individual implant's or electrode's scheduled modulation profile. Also, feedback can be used to sense neural, muscular, biological, physical, or other activity, and this information can inform adjustments to the modulation profile for one or more modulation sites, as shown in FIG. 7. In FIG. 7, five of seven implanted modulation sites are activated (activated sites 700a) to completely alleviate pain in a patient. More interfaces or electrodes are implanted than are necessary to avoid multiple implantation procedures. However, after implantation, specific interfaces or electrodes can be activated or disabled in order to achieve the desired therapeutic effect. The multiple modulation sites may comprise multiple dorsal root ganglion sites on different sides and multiple levels. The selection of which sites to activate and which sites to disable (inactive sites 700b) can be performed by relying on patient feedback in an iterative approach or by sensing and controlling activation in a closed-loop manner.

It may be clinically advantageous for the modulation interface components to be flexible and soft in order to prevent tissue irritation due to its motion, which can result from physical activity or other causes. Metal or other rigid material electrodes are generally not soft enough compared to the surrounding tissue and may cause such irritation and inflammation. This, however, may have to be accomplished with minimal compromise to electrode conductivity and not cause significant degradation in electrode/tissue impedance which would lead to increased power consumption. Soft electrodes can be implemented on flexible, biocompatible printed circuit substrates. In order to reduce electrode/tissue impedance, planar contacts can be implemented of a desired size to accommodate target tissue stimulation. For example, many nerves or nerve ganglia may be on the order of a few millimeters in diameter. Therefore, in order to stimulated the desired ganglion and prevent stimulation of adjacent tissue, the electrode size may be set somewhere on the order of 0.5 mm to 2 mm in diameter. Furthermore, these electrodes can be electroplated or coated with Pt—Ir, Pt, Ir, Au, Pt-black or other similar coatings in order to increase effective surface area of the electrode and reduce its interface impedance. Furthermore, multiple contacts (electrode pads) can be spread around the flexible substrate to improve versatility. These electrode pads can be hard wired (connected in a certain configuration) or can have programmable connections which can be utilized to create current steering and improve therapeutic results. Various flexible substrate electrodes and their securing mechanisms and devices are shown in FIG. 14, FIG. 15, FIG. 16, FIG. 17, FIG. 18, and FIG. 19 as further described below and herein. These may include electrodes which can wrap around target nerves or tissue and can be anchored to the desired tissue using pins, screw-like structures, or any other attachment method. Furthermore, anchoring pins can be electrically connected to the electrodes and can be conductive. This way, if anchoring pins are passing through nerve tissue, current can be conducted from the pins (inside the nerve tissue) to an opposite polarity electrode pad which can be located on the outside of the nerve. Structures which are not implemented on flexible substrates can still be made softer by coating them with softer biocompatible materials such as silicone prior to implantation. The electrode can be left uncoated or can be coated with conductive materials.

Flexible modulation interfaces may be difficult to guide during implantation procedure because of their compressible or otherwise adjustable geometry. In order to make implantation procedure easier, one or more electrodes comprising at least one flexible portion can first be attached to and/or within a rigid or semi-rigid structure, such as a cannula, catheter, or lead, which can be used to advance and navigate the one or more electrodes to the desired location. Once the electrodes are in proximity of the target location, the host rigid or semi-rigid lead can be detached and extracted, leaving behind only the one or more electrodes.

Electrodes can further be coated with drug eluting agents in order to prevent or otherwise reduce inflammation, infection, pain, and/or other adverse effects. The agents may include analgesics, anesthetics, antibiotics, antiseptics, steroids, anti-inflammatory drugs, collagen, pharmaceuticals, and/or other agents with beneficial effects. Examples may include ibuprofen, bupivacaine, lidocaine, maprivacaine, procaine, dexamethasone, betamethasone, and epinephrine. Some applicable antibiotics or antiseptics could include vancomycin or cefalozin. Other agents may be suitable for use in other cases, so this list is not exhaustive.

Figure 5:
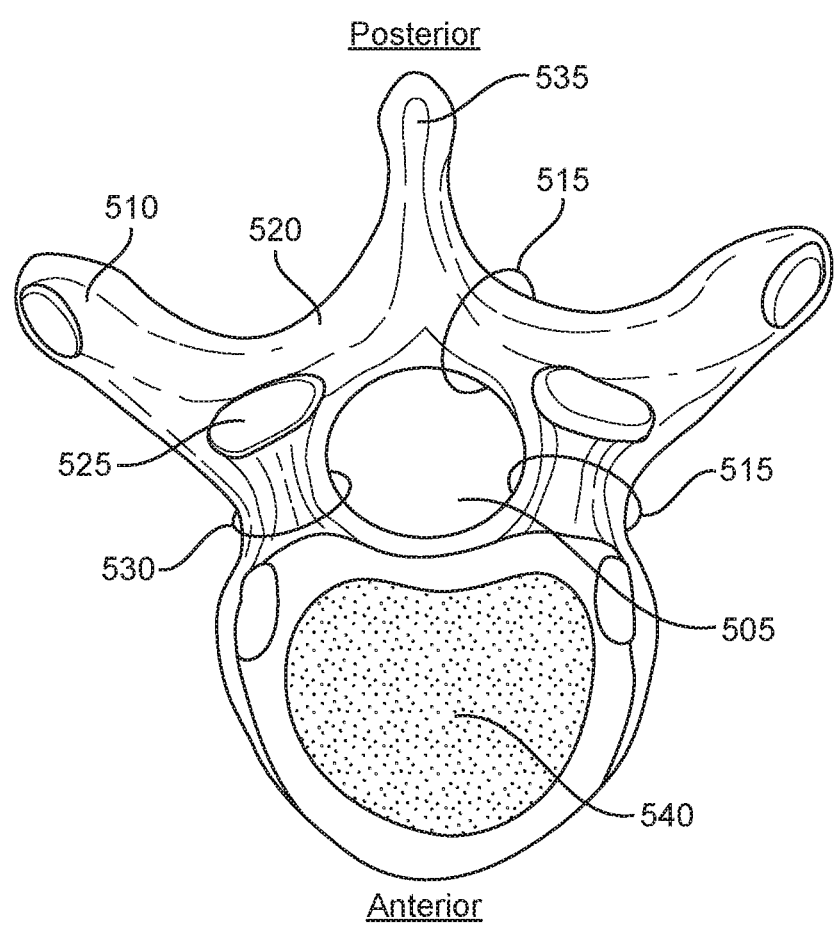
FIG. 5 illustrates the structure of a vertebrae and a description of the different parts.

Using the electrodes and other components of the present invention, nerve bundles and/or ganglia can be relatively simple to target when placing electrodes for nerve modulation. For example, dorsal root ganglion can be located with the assistance of common imaging modalities, such as fluoroscopy, by referencing nearby bone structures and landmarks, such as vertebral foramen 505, spinous or transverse process 510, vertebral arch 515, lamina 520, superior articular process 525, or pedicle 530, as shown in FIG. 5. The position of the dorsal root and dorsal root ganglion with respect to these landmark structures does not vary significantly from patient to patient. Therefore, these structures may provide an easy way to guide positioning of the electrodes and other components of the present invention using common imaging modalities. Further relevant structures include the spinous process 535 and the vertebral body or centrum 540.

The majority of existing neurostimulation treatments rely on electrically activating nerves, and this activation has been effective in a variety of treatments. The behavior of neurons and tissues are often directly influenced by electric currents and voltages, so this is a straightforward way of interacting with these types of tissues. Controlling the parameters of the applied current and voltage can offer additional flexibility and control of the physiological responses. For some nerves, applying electrical modulation at high frequencies can block transmissions, and this modulation can be very effective in managing certain types of pain. Other types of tissue, including smooth muscle, may require modulation pulse widths greater than 2 ms in length to have an effect, and these can be applied with a certain duty cycle and duration. For some patients, high amplitude stimulation may be necessary to have the desired effect. This could be due to a number of factors, including variations in tissue impedance, differences in physiological structure, or differences in the placement of the modulation system. Localizing the placement of the modulation site can reduce energy requirements for inducing the desired physiological responses because less energy is wasted in surrounding tissues. In some cases, smaller electrodes can result in increased impedance at the tissue interface, which can increase the requirements of electrical modulation. This requirement can be mitigated by coating the electrodes with certain materials. In particular, platinum or platinum-iridium coatings or the other previously described coatings are non-toxic and have been shown to dramatically reduce this impedance for several types of modulation systems. Other materials may be advantageous depending on the tissue type and the desired type of modulation. Charge balancing the delivered current can be included because it can reduce voltage and therefore reduce power requirements, and it can minimize adverse effects. There can be numerous methods for balancing charge, and neuromodulation requiring high duty cycles can require sophisticated charge-balancing methods. Charge balancing can be accomplished with electronic circuits that precisely measure delivered current and/or voltage at the interface and use feedback control to properly adjust one or more stimulation parameters. Other methods can intrinsically or passively balance the delivered current in the way current reacts to changes in the applied voltage.

For many applications, alternatives to electrical modulation that can offer significant advantages. Research has shown that mechanical forces or vibrations at nerves or other tissues can induce physiological effects similar to electrical modulation. For most types of tissue, generating mechanical forces can be more power efficient (e.g. because of the relatively high electrical impedances of tissue encountered during electrical stimulation). There can be several ways these mechanical forces can be induced by the apparatus of the present invention. Electromagnetic actuators can be used with either internal or external magnetic fields. These systems may be very power efficient in converting electrical to mechanical energy and function similar to motors. Alternatively or in combination, ultrasonic or other mechanical vibrations can be applied to the tissue directly or to a device with a desired resonance, causing it to vibrate at the desired location. Other methods involve activating nerves with electric or magnetic fields, which can be generated either internal or external to the body. These actuators or devices can be miniaturized and used with similar attachment methods as described herein.

The modulation system of the present invention can monitor impedance or other aspects of the quality of the connection to tissue during and/or outside of stimulation, in order to keep track of the electrode/tissue interface status and electrode status to ensure the contact with tissue remains acceptable. The impedance can be monitored by driving current through tissue and measuring voltage across a known resistor value which is placed in series with electrodes, thus measuring the amplitude of stimulation current, and by measuring the voltage difference between the electrodes. The magnitude of impedance can be calculated from the measured values of stimulation current and voltage. Additionally, relative phase of current can be measured with respect to voltage phase for a given applied stimulation tone to derive the phase of impedance. Alternatively or in combination, the delay between applied voltage and current can be measured to derive the phase information.

Methods for sensing different types of information (e.g. patient information or apparatus information) can also greatly improve both diagnostics and therapies. These types of information include but are not limited to action potentials, neural activity, muscular activity, and other biological, chemical, biochemical, or physiological signals. Electrical activity can be sensed through electrodes at or near the site of interest. There are a variety of known sensors that can detect pressure, chemicals, pH, and other phenomena that may be of interest and may be incorporated into the systems and devices of the present disclosure. Additionally, information from other areas of the body or directly from the patient can be incorporated into the diagnostic or therapy. This information can adapt modulation parameters used on specific nerves or tissues, or it can activate or deactivate certain modulation sites for therapies involving multiple sites. For chronic conditions, the severity can vary and the treatment can adapt to this severity to treat as necessary. Also, it can adapt to changes in the condition or the patient to continue delivering effective treatment. This information can also be used to track the progress of the condition and the treatment, and to keep caretakers informed and to allow them to use their expertise to adjust the treatment if it is needed.

These new methods for modulating, sensing, and/or controlling the therapy or diagnostics can be accomplished with apparatus of the present invention, such as using minimally invasive devices with wireless power transfer and communications. Pulse generation can be done locally on the device or externally transmitted through a transmission system. The implantable devices can also include local energy storage, such as batteries or capacitors. If a more traditional system is used, the new attachment systems and modulation interfaces would allow for precisely locating modulation sites and operating with multiple sites. In particular, different devices may be most suitable for certain applications, and the methods described herein can operate with different types of devices, tissues, or locations within the body.

Figure 6:
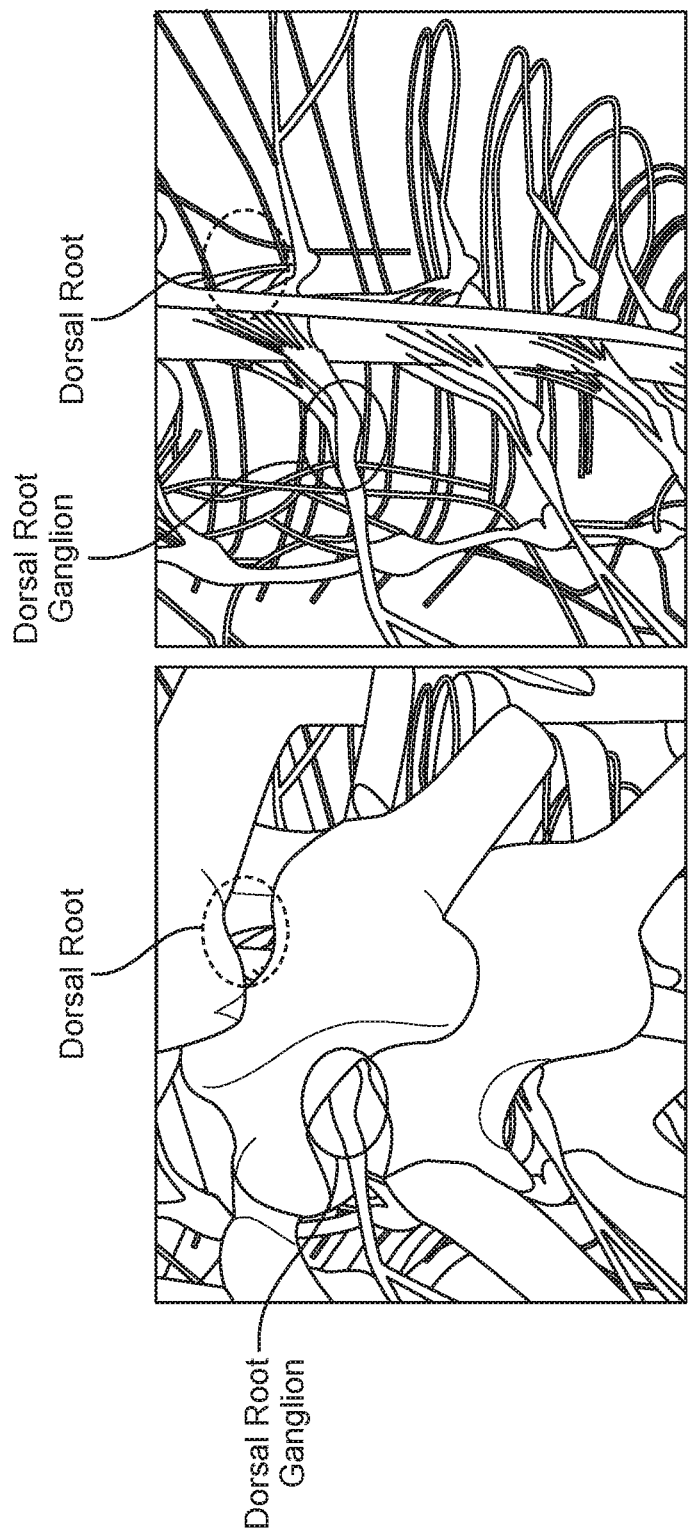
FIG. 6 illustrates the locations of the dorsal root and the dorsal root ganglion with respect to the spinal column.

Referring to FIG. 6, spinal nerves may be stimulated to treat pain. The dorsal root ganglion DRG and the dorsal root DR are shown in FIG. 6. Electrodes or other interfaces can be used to delivery energy to modulate the DRG and/or the DR in order to suppress and/or mask pain. Depending on the selected modulation profile, the propagation of neural activity with pain information can be blocked from the brain or modulation can cause paresthesia (tingling sensation), which can be effectively used to mask pain. Both nerve sites, the DRG and the DR, may provide a simple way to target electrode or interface placement and anchoring, and may be effective locations at which to deliver energy to cause desired therapeutic effect(s).

Referring to FIG. 8, attached electrodes or other interfaces are shown. These attached electrodes or other interfaces may be positioned around different nerves and nerve bundles and to neuromodulator implants which are shown schematically. For example, there may be sets 801 and 802 of four connections to two different dorsal root ganglions, a set 803 of three connections to a dorsal root, a set 804 of attachments with three connections with a fourth center-connection inside the bundle positioned on a peripheral nerve ganglion, a set 805 of attachments with two connections to a dorsal root ganglion. One or more of the connections may be provided with center needle-like electrode may penetrate inside the peripheral nerve bundle and may act as one of the terminals for sinking or sourcing current.

Figure 14:
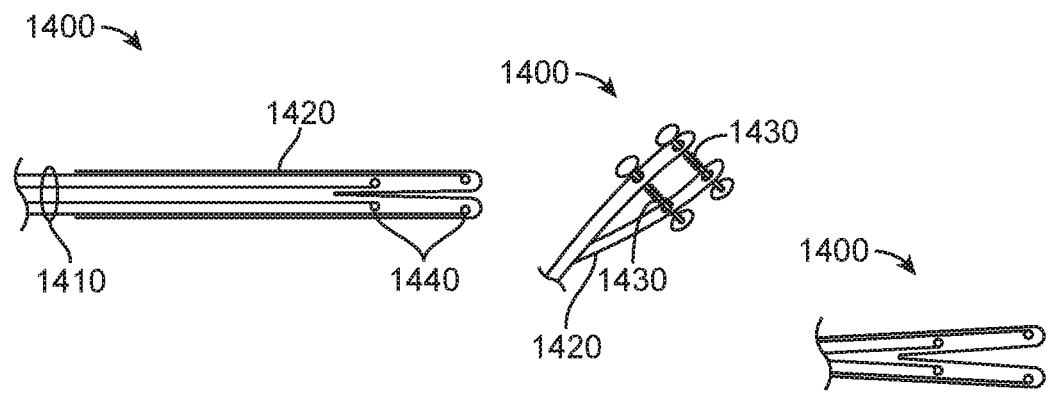
FIG. 14 illustrates a variation of flexible tissue interfaces that connect devices and tissues.

Referring to FIG. 14, embodiments of the present disclosure may provide a flexible interface 1400 comprising flexible interface electrodes 1410 implemented on a flexible printed substrate 1420. The flexible substrate 1420 can split and can have multiple interface sites which would be connected to a therapeutic or diagnostic device. For neuromodulation, the conductive electrodes 1410 may form electrical connections with tissue directly be being in proximity or in contact with it or through conductive pins 1430 which may pass through conductive holes 1440 and through target tissue, securing the electrodes to the tissue.

Figure 15:
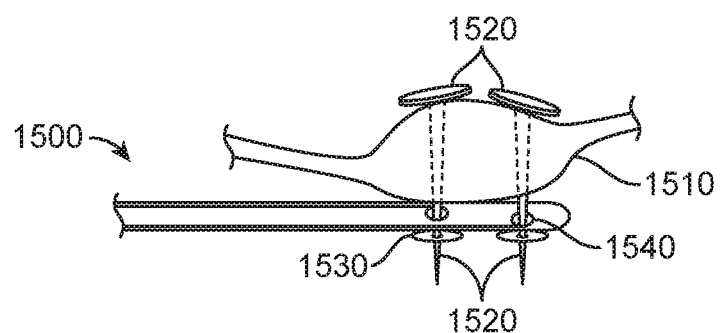
FIG. 15 illustrates an additional variation of flexible tissue interfaces for sensing or modulation of tissue.

Referring to FIG. 15, embodiments of the present disclosure may provide another flexible interface 1500 attached to target tissue 1510 (such as a nerve bundle) using pins 1520. The pins 1520 can be inserted through target tissue and into receiving holes or starting from holes and then through the target tissue 1510. The securing function or anchoring of the pin 1520 can be achieved by utilizing a nut or matching plate 1530 (similar to the head of the pin). The nut 1530 can mate with the pin 1520 and secure the pin 1520 and flexible substrate 1540 of the flexible interface 1500 in place. Conducting pins 1520 can be used to sense or stimulate target tissue from the inside when preferable.

Figure 16:
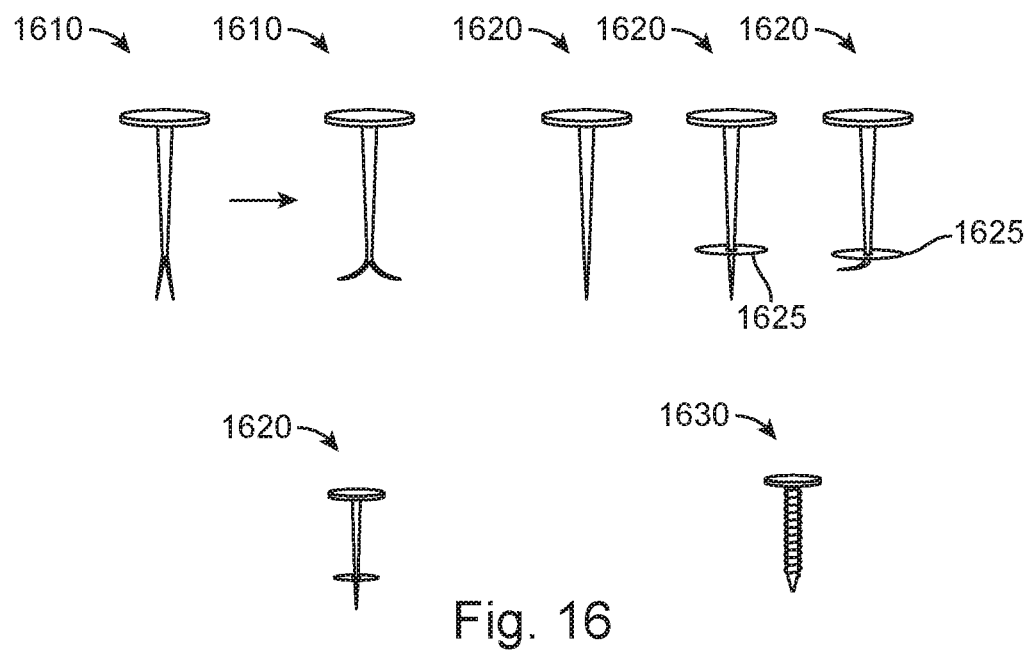
FIG. 16 illustrates different pin configurations for securing the tissue interface in place.

Referring to FIG. 16, several different pin configurations for securing interfaces to target tissue are shown. A pin 1610 may be pre-split and may split open after passing through the desired tissue and interface receptacle, thus securing/anchoring the interface to the target tissue. The split end of the pin 1610 may be beat to secure the pin 1610 in place. One or more bending pieces 1625 can be on the end of a pin 1620. For example, the bending pieces may comprise a nut or similar component that can be used to secure the pin 1620 and to ensure that the beat pin can press through a larger surface area. The pins 1610 and 1620 may be nail-like. Screw-like pins 1630 may be used to screw into tissue and/or through a mating nut or receptacle on an interface electrode. The pins 1610, 1620, and/or 1630 may be conductive.

Figure 17:
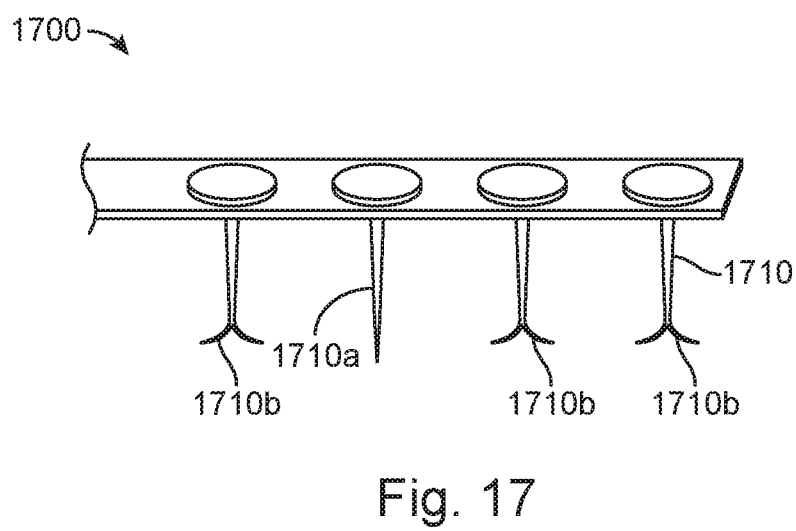
FIG. 17 illustrates a flexible substrate using pins or screws for multiple tissue connections.

Referring to FIG. 17, a flexible interface substrate 1700 is shown. The flexible interface substrate 1700 may comprise multiple tissue-connections and anchoring mechanisms utilizing pins or screws 1710 to secure to target tissue. Secured pins 1710a and unsecured pins 1710b are shown by FIG. 17.

Figure 18:
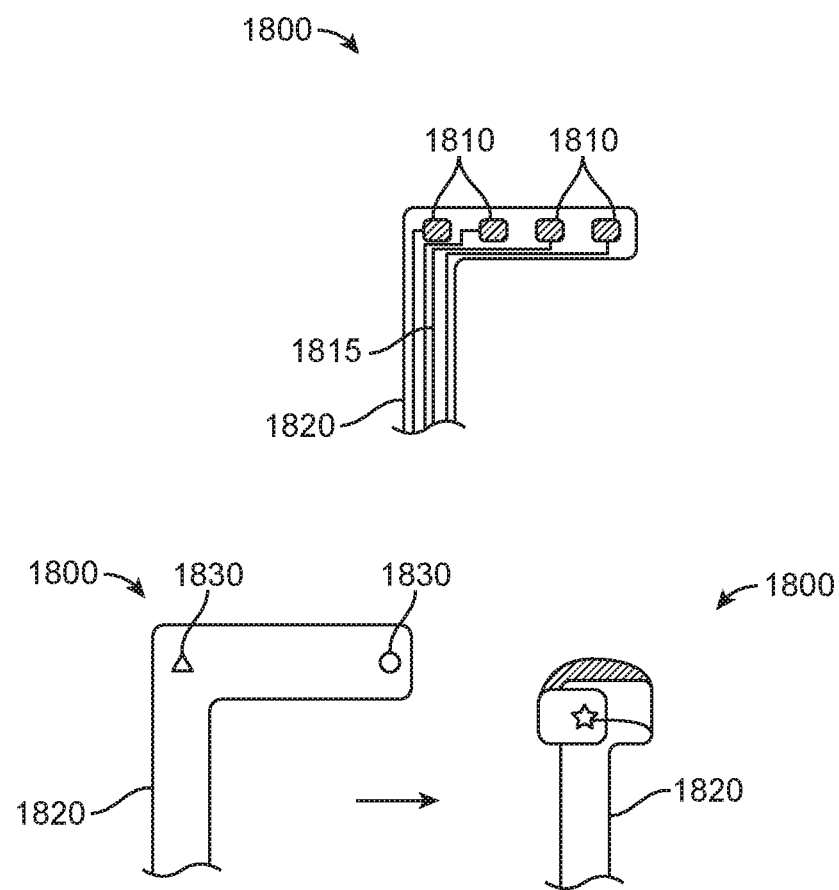
FIG. 18 illustrates a flexible structure that can wrap around target tissues to attach to them.

Referring to FIG. 18, flexible interfaces 1800 which can wrap around target tissue such as nerves are shown. The flexible substrate 1820 of the flexible interfaces 1800 can have conductive wires or electrodes 1815 which may be partially insulated from tissue and may connect electrode plates, pads, or other exposed conductive tissue interfaces 1810 to a pulse generator, sensing interface, modulation interface, or other therapeutic and/or diagnostic device. The flexible interfaces 1800 can have one or more mating terminals 1830 which can be used to secure them by connection after one end is wrapped around the target tissue. This would lock the electrode in the desired wrapped position. Multiple mating terminals can be used to provide flexibility to accommodate multiple target tissue sites. Some examples of mating terminals are materials such as Velcro™, mating pins and holes, and two holes which can be secured with a wire or thread. A T-shaped flexible substrate can be used instead of an L-shaped substrate. Also, cascaded T- or L-shaped extensions (e.g., leaves) can be branching out from the main lead (root) when multiple similar attachments may be necessary.

Figure 19:
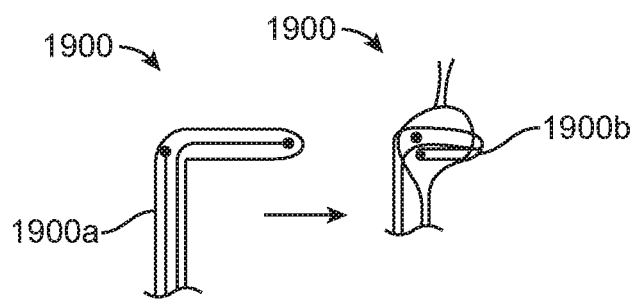
FIG. 19 illustrates a variation of the flexible structure that wraps around targeted tissues using pins or screws.

Referring to FIG. 19, a wrap-around flexible interface 1900 can be secured through pins or screws which can pass through tissue. FIG. 19 shows the flexible interface 1900 in its unwrapped configuration 1900a and its wrapped configuration 1900b.

Figure 20:
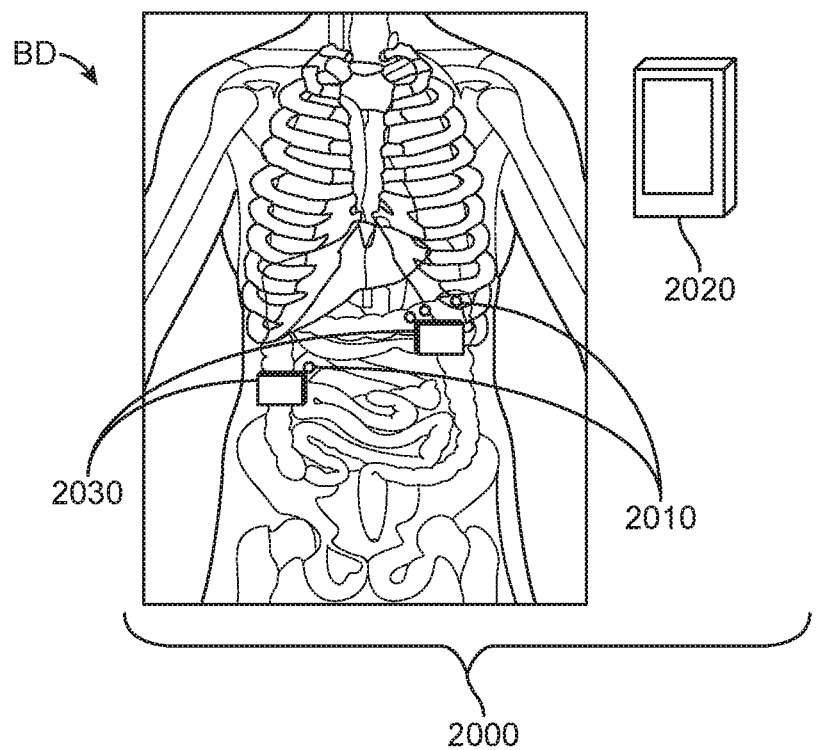
FIG. 20 shows a schematic illustrating the envisioned application of embodiments of the external system operating with one or more implantable devices.
Figure 21:
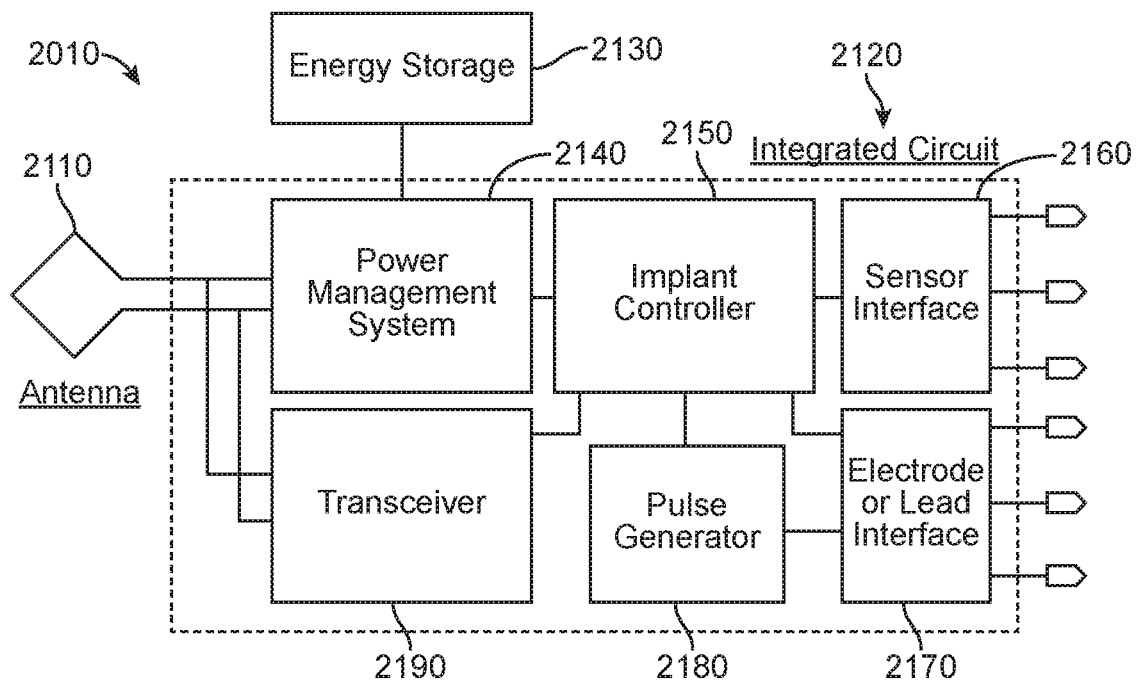
FIG. 21 shows a schematic of a basic block diagram of an implantable device with power harvesting and management, two-way communications, a digital controller, a pulse generator, and an interface for one or more sensors and electrodes.
Figure 22:
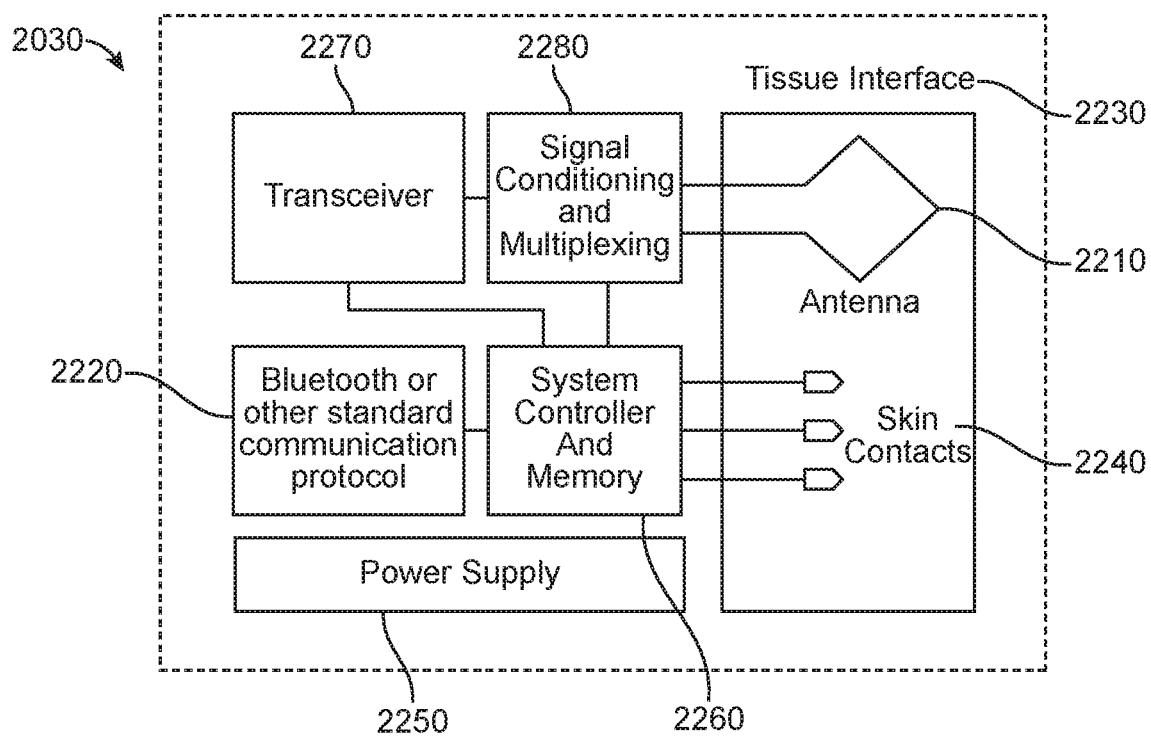
FIG. 22 shows a schematic of a basic block diagram of the external system with the ability to transfer power and communicate with the device or other hardware as well as sensor or electrode interfaces.

Implantable devices may be limited in their design by the power budget (e.g. short-term or long term power requirements), which can restrict both miniaturization and functionality. Neuromodulation devices can require significant power to provide therapy because of the relatively high voltage and current requirements needed to drive stimulation. For fully wireless devices, the power limitation is typically the design constraint and limits the performance of the device. The envisioned usage of embodiment of the present disclosure is shown in FIG. 20. FIG. 20 shows one or more implantable devices 2010 controlled and powered from external device 2030 external to the body BD. The elements of the overall system 2000 can allow for mm and sub-mm neuromodulators while offering the flexibility to operate with different therapies and for different applications. This miniaturization can be accomplished in part by the ability of the overall system 2000 to interface with different antennas and the on-board intelligent power management system. The external device 2030 may include components for power transfer, data transfer, programmability, data management (including processing and visualization) and a user interface for doctors and/or patients, such as a handheld interface 2020. The implantable device 2010 may be implanted minimally invasively and may receive power and data from the external device 2030. The delivery of the implantable device 2010 may be through a needle, an endoscope, or with many other methods. The implantable system may be delivered to any of a variety of implantation sites as described herein to perform neuromodulation therapy or diagnostics. A system diagram of embodiments of the implantable device 2010 is shown in FIG. 21 and an external device 2030 is shown in FIG. 22. The external device 2030 may include a transmission antenna 2210 that can be placed near the surface of the skin in close proximity to the antenna 2110 of the implantable device 2010. This link can transfer both power and data to the implantable device 2010. The external device 2030 can also receive information from the implantable device 2010 via several methods depending on the data protocols of the implantable device 2010. This communication may include a load modulation sub-system in which antenna impedances are sensed, or tissue conduction in which small electrical signals are transferred through the tissue itself. The external device 2030 can operate with either batteries or with a wall outlet. The external device 2030 may also have a separate communication protocol 2220, such as Bluetooth, for interfacing with computers, smart phones, or other devices. The external device 2030 can include an information display with information about the device performance, information about the therapy, or controls for adapting parameters. Data can be transferred at speeds up to and exceeding 20 Mbps to accommodate configuration and control of the device 2030 as well as real-time treatment adjustments, such as between 0.1 and 20 Mbps, or between 0.5 and 4 Mbps. Data and power can also be transferred to multiple devices simultaneously and the high-speed of communication allows for several devices to adapt and adjust in real-time. Sensors can be incorporated with the external device 2030 and also make use of the high-speed communication system for diagnostics or real-time feedback of physiological parameters to inform the doctor or patient of the functionality of the device or to provide feedback to the system to adapt the treatment. This information can be stored locally or transferred securely to other devices or to the cloud where it is accessible from the internet. Data processing and visualization can also be performed locally or on other devices.

The external device 2030 can wirelessly power implantable devices 2010 via either electromagnetic coupling or through a mechanical transfer, such as via an ultrasonic signal. Depending on the application, patient, frequency, number of implants, depth of implants, and other factors, the external device 2030 can operate with a variety of antennas or transmitters of different sizes. The external device 2030 can interface with one or more antennas via RF signal generation and conditioning circuits and matching network which can accommodate a variety of such antennas and operating frequencies. Moreover, the external device 2030 can adjust how much power is transferred to one or more implantable devices 2010 based on feedback from the implants and/or based on externally sensed quantities, such as tissue and system temperature.

For wireless powering and communication using electromagnetic energy the external device 2030 uses one or more antennas 2210. The one or more antennas 2210 can be implemented on a printed circuit board comprising one or more rigid and/or flexible substrates. Alternatively, textile substrates can be used to implement one or more such antennas. Also, multiple external antennas 2210 can be used simultaneously or exclusively in order to provide better coupling between the implantable and external antennas 2110, 2220.

High-speed, efficient communication can be accomplished by combining data transfer into the power signal. This combination can be non-trivial, especially at high frequencies because most modulation methods can have a significant effect on power transfer and using a separate communication system would result in large interference. Asynchronous methods can dramatically reduce system requirements, and power transfer can remain uninterrupted by employing methods that minimally modulate the amplitude. These data transfer methods could also operate with multiple devices simultaneously by assigning each device a specific address or ID. The communication methods described can use encoding and encryption to improve reliability, safety, and security.

The external device 2030 can rely on data from the implantable device 2010 for multiple purposes. These purposes include improved positioning of the external device 2030 to improve coupling between external and implant antennas 2110, 2120, monitoring of various sensed quantities by the implantable device 2010, monitoring of implant status and therapy status. One or more of these sets of data can be used to re-adjust the therapy either in closed-loop or via user input. The reverse data link from the implantable device 2010 to the external device 2030 can be non-trivial and can be accomplished via a variety of methods. Some methods may rely on backscattering signal transmitted by the external device(s) to the implantable device(s) by modulating load on the implant antenna. Other methods may rely on implantable device 2010 having a transmitter circuit which generates a carrier signal and transmits it to the external device 2030. Other methods may include implantable device 2010 relying on volume conduction to communicate with the external device by modulating voltage or current through electrodes connected to tissue. Depending on the selected communication scheme, the external device can be configured to receive and demodulate this signal from one or more implants.

The external device 2030 may also keep track of the desired therapy program and actual applied therapy to the patient. The external device 2030 can collect data from embedded sensors, patient input, and/or one or more implants, and store the data in embedded memory and/or upload it to external storage such as phone or cloud storage system. The external device 2030 can also issue some one or more notifications to the patient, doctor, or even emergency dispatch personnel, based on this sensed and stored data.

Treatment parameters can be controlled remotely via the external device 2030 and adapted based on performance or changes in the condition. The external device 2030 can be controlled by a doctor, the patient, or some combination of the two depending on the intended use. Therefore, the overall device 2000 can accommodate a variety of interface with external infrastructure via existing protocols such as Bluetooth, ZigBee, WiFi, 2net platform interface, and other wireless and wired general or medical protocols and interfaces. These interfaces can rely on built-in encryption or privacy or can incorporate additional custom encryption and error detection and correction encoding.

Other aspects of the external device 2030 are also described herein, such as form factor, user interface features, compliance features, energy storage and recharging, safety, reliability, privacy, and others.

Referring to FIG. 21, the implantable device 2010 may further comprise an integrated circuit 2120 and an energy storage unit 2130 (such as a battery) coupled to the integrated circuit 2120. The integrated circuit 2120 may comprise a power management sub-system 2140 coupled to the energy storage unit 2130, an implant controller 2150 coupled to the power management sub-system 2140, a sensor interface 2160 coupled to the implant controller 2150, an electrode or lead interface 2170, a pulse generator 2180 coupled to the implant controller 2150 and the electrode or lead interface 2170, and a transceiver 2190 coupled to the antenna 2110, the power management sub-system 2140, and the implant controller 2150.

Referring to FIG. 22, the external device 2030 may further comprise a tissue interface 2230 which may comprise the antenna 2210 and skin contacts 2240. The external device 2030 may further comprise a power supply 2250, a system controller and memory 2260 which may be coupled to a Bluetooth or other standard communication protocol 2220, a transceiver 2270 coupled to the system controller and memory 2260, and a signal conditioner and multiplexer 2280 coupled to the transceiver 2270 and the system controller and memory 2260.

Several applications and their preferred embodiments are described as follows.

The physical form of the external device 2030 could take a variety of forms depending on the intended application, the location of the implantable device 2010, and the included features. This form could be a single component or could have multiple components as well, such as separating the transmission antenna from the battery pack and user interface. The size of the antenna 2210 can be determined by the operating frequency, implant depth, and the antenna used in the implantable device 2010. These antennas 2210 can be loops, patterns, or patches on the order of several cm on a side. The external device 2030 can have the ability to interface with a variety of antennas 2210 in order to increase its flexibility for use in different applications. In some embodiments, there is a common connector to each of these different antennas 2210 and the primary external device 2030 has the necessary components (e.g., the signal conditioner and multiplexer 2280) to shift frequencies, power levels, and matching systems or sub-systems to operate with these different devices. The primary external device 2030 may incorporate the power source 2250 and user interface along with electronic components for data communication, management, storage, processing, and visualization. This external device 2030 will likely be dominated by the size of the battery, though should be on the order of ~cm in each dimension.

Figure 26:
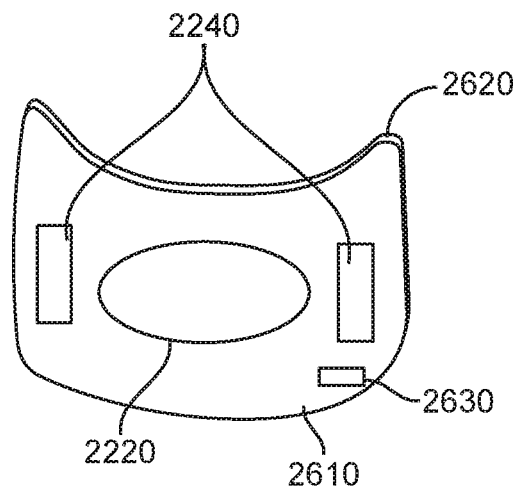
FIG. 26 shows an exemplary external device implemented as a flexible patch.

The external device 2030 can be encased in a single enclosure or multiple enclosures. FIGS. 23a-23d depicts several methods of operation for these devices and methods for networking them with a user interface such as a handheld interface 2020. The enclosure with the antenna 2210 should be placed close to the surface of the skin, and may also include electrical contacts 2240 (e.g., electrodes) with the skin for detecting biological parameters or receiving certain types of information for the implantable device(s). These contacts 2240 can also transmit information to one or more implantable devices 2010 or deliver therapy through body conduction. This antenna enclosure may be incorporated into articles of clothing such as shirts, belts, hats, or other clothing, or it may be a separate system or device adhered to the skin directly. The electronic components for communication, data systems, and user interface should also be enclosed either separately or together with the antenna. This enclosure could be constructed in a way to fit in a pocket or attach to a belt. The external device 2030 can also take a form factor of a self-adhesive patch, which can be placed over the implant. This form factor is depicted in FIG. 26. It can be implemented on a flexible substrate 2610 (e.g., a substrate comprising one or more flexible portions) and can include a battery and other circuitry 2630, adhesives such as an adhesive layer 2620, gels, matching gels for either conduction electrodes, antenna, or both. Gels or pads can also be used to control the separation distance between the antenna and tissue or to remove heat generated due to power transmission. These patches can also be connected to other patches and/or to a handheld controller via tethered (wired)

methods or wirelessly. Tethered methods can use flexible cables, e-textiles, or other cables or wires to provide the power and/or data link.

Figure 23A:
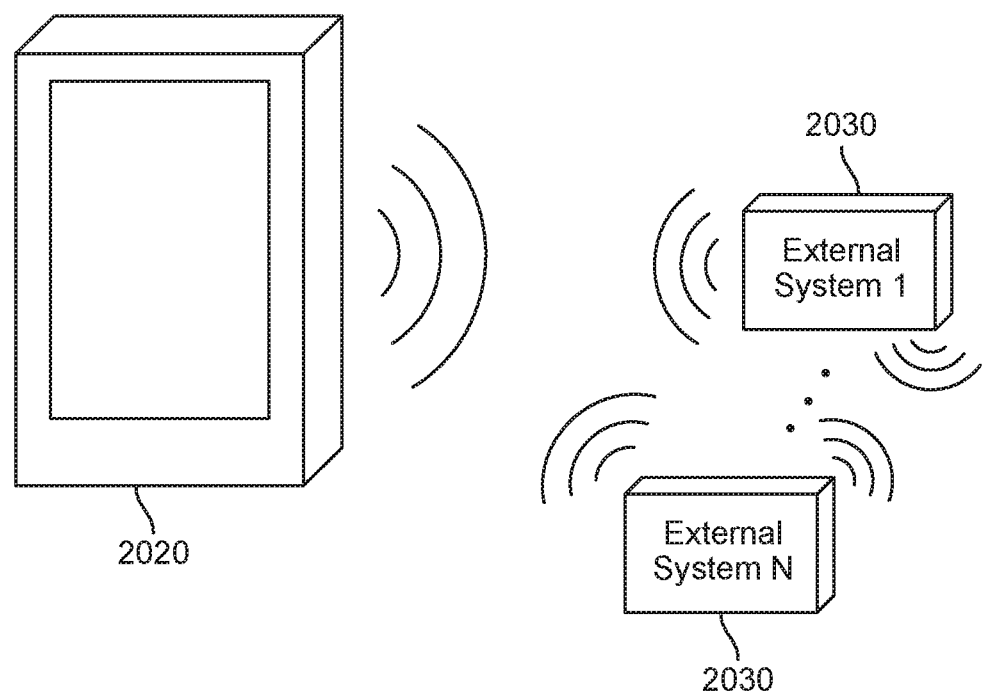
FIGS. 23a, 23b, 23c, and 23d show schematics illustrating user interfaces networked with one or more external devices.
Figure 23B:
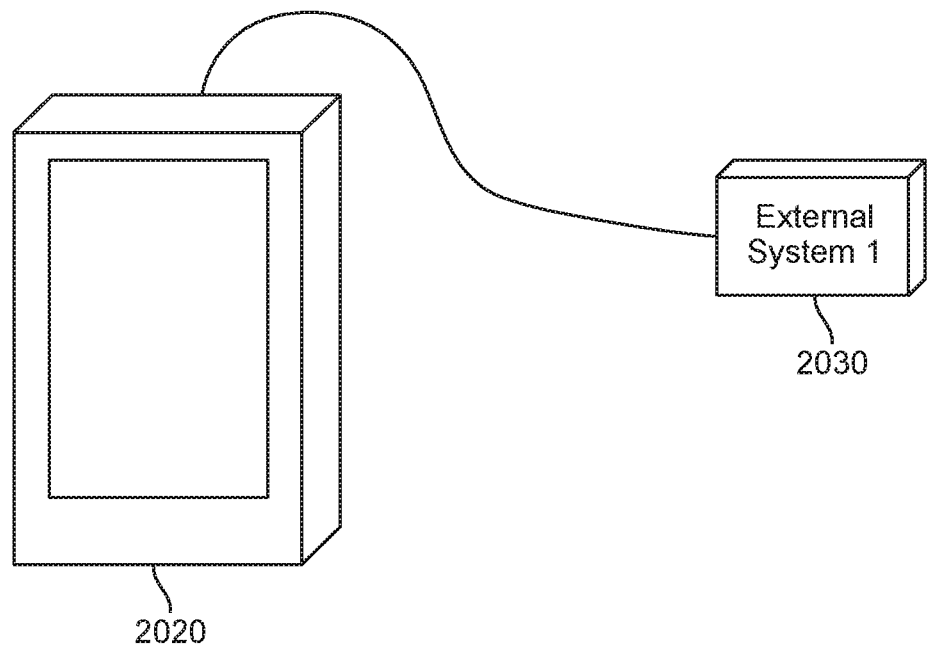
Figure 23C:
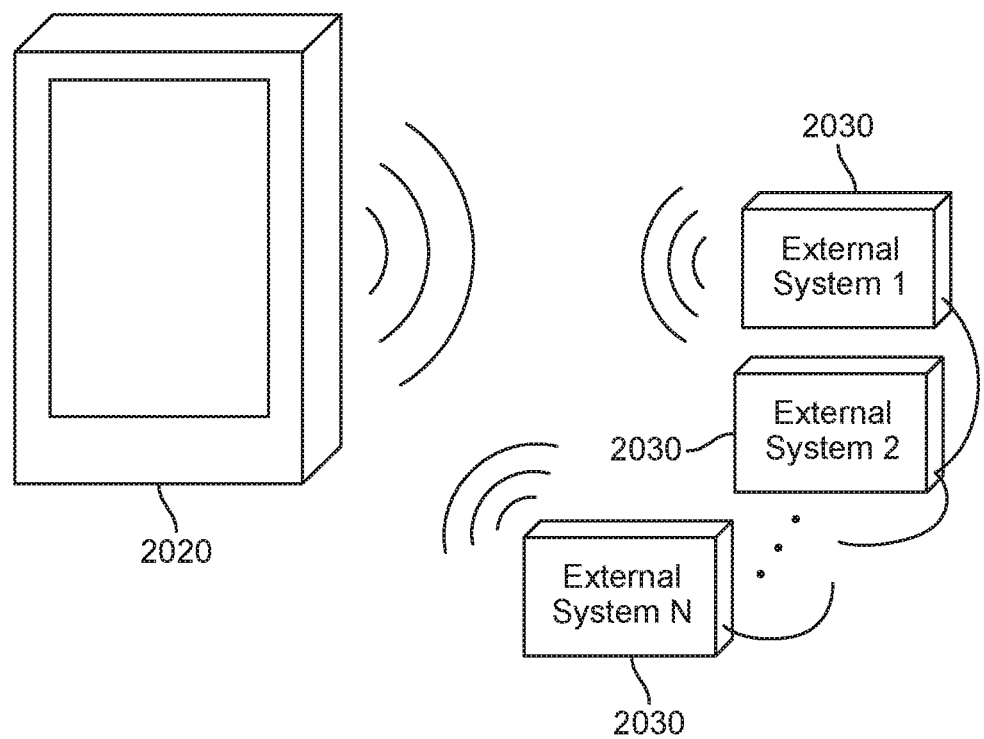
Figure 23D:
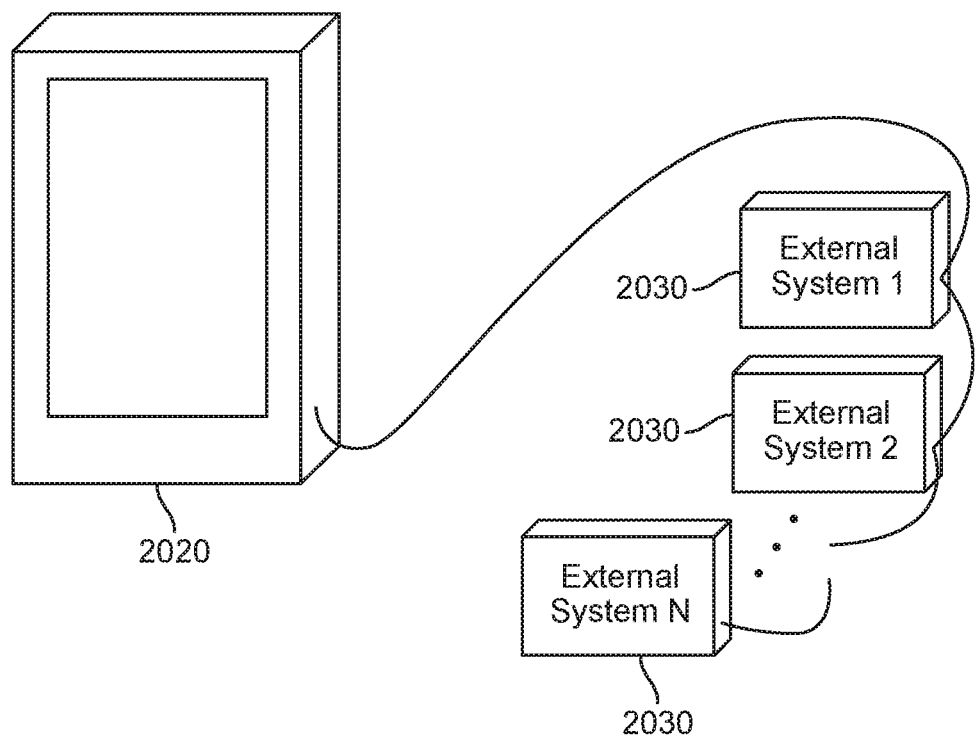

Referring to FIGS. 23a-23d, the handheld interface 2020 may network and tether with multiple external devices. As shown in FIG. 23a, the handheld interface 2020 may communicate wirelessly with two or more external devices 2030 which may communicate wirelessly with one another. As shown in FIG. 23b, the handheld interface 2020 may communicate with an external device 2030 through a wired connection. As shown in FIG. 23c, the handheld interface 202 may through a wireless connection communicate with multiple external devices 2030 which may communicate with each other either wirelessly and/or with a wired connection. As shown in FIG. 24c, the handheld interface 2020 may communicate through a wired connection with multiple external devices 2030, each of which may in turn communicate with each other either wirelessly or with a wired connection.

To transfer energy to the implantable device 2010, an external antenna can be placed in close proximity to the surface of the skin. This placement can be accomplished by incorporating the antenna into one or more articles of clothing or with a separately adhered device such as a patch. This external antenna can be enclosed with the power source or attached via wires to an enclosed device with batteries and other electronics. The size of the external antenna varies with the size of the antenna on the implant, though the external antenna size is typically several cm on a side and a few mm thick. This patch could include additional sensors or electrical contacts to the skin to enhance the features of the overall system. The antenna can collect information from the implant or from its electrical connections and store it or communicate it to other devices.

The frequency of power and data transfer can be tuned to one or more specific implants, and this tuning may require adjusting the external antenna or by adapting the matching circuitry at the input of the antenna itself. Variations in implant location and environment could alter the optimal frequency and this frequency alteration would require adaptations to the matching devices in place. This matching could be accomplished with either discrete or distributed components, and could be adjusted after the implant is placed inside the body. In some embodiments, the external antenna is designed to operate specifically with one or more implanted antennas. Based on the characteristics of the antennas, it is possible to design either passive matching circuitry or active matching circuitry. In some embodiments, the matching is accomplished passively with inductance and capacitance at the input of the antenna and tuned to the specific frequency of the implant. This matching can also be made adaptive by digitally switching in different amounts of capacitance to optimize the setup. If the external antenna is also a receiver for data communications, there can be additional RF components for improving sensitivity and decoupling the transmitted signal and the received signal.

The external device 2030 may transfer power to the implantable device 2010 through the tissue, and can use any of a number of power transfer methods including electromagnetic or mechanical techniques. Ultrasonic powering may involve transmitting high frequency sound waves through tissue (e.g. to be received by piezoelectrics of the implant). Ultrasonic energy has minimal attenuation when traveling through most tissue environments though significant reflection at air or bone interfaces can occur. This ultrasonic power transfer method may also require good contact with the skin, which may include placement of gel at the interface of the transmitter and the skin. Powering can also be accomplished with electromagnetic power transfer as described with regard to FIG. 24, in which electric and/or magnetic fields are altered and the energy in these changing fields is captured through receivers (e.g. inductive coils) on the implant. Attenuation of this energy depends on the frequency and the types of fields transmitted, and the attenuation can be significant for deeply implanted devices. In some embodiments, the implantable device 2010 is powered through RF signals in the low GHz range or high MHz range. This frequency range can allow for very small antennas at the receiver that are capable of receiving sufficient energy for diagnostics or therapeutics. Power transfer can be adapted based on the quality of the transmission link. In some embodiments, data can also be modulated on the power carrier. There are also set safety limits of tissue absorption (Specific Absorption Rate (SAR) and other similar constraints) which must be adhered to for use in medical applications. An additional safety consideration is in the heating of the external device itself, which results from power transmission and other functions. Guidelines about heat should be adhered to in the design of the final overall system and may limit power transfer in some circumstances. Additionally, guidelines from the FCC should also be adhered to, which will most likely require operation in the industrial, scientific, and medical (ISM) frequency bands.

One or more external device antennas 2210 and/or one or more implantable antennas 2110 can utilize link gain optimization techniques using various improvement methods. Some of the improvement methods may include: mechanical positioners; energy focusing techniques, such as beam steering used in far field regions, mid-field energy (power) focusing by generating optimal equivalent currents that focus energy spatially inside tissue; mid-field or near-field focusing by utilizing multiple phase and amplitude adjustable sources or antennas to shape electromagnetic fields inside tissue to achieve focusing and spatial focus steering. Other techniques such as electromagnetic lenses, metamaterials, left-handed materials, phase-adjustable materials, and other similar methods can also improve the link gain or optimize power transfer through better control the electromagnetic energy. Furthermore, conducting elements within the antennas 2110, 2210 can be adjusted to control focusing or improve link gain dynamically.

These methods can be accomplished in real time using feedback signals described in sections for power and link gain adjustments. These optimizations or adjustments can be done with an open loop or closed loop method as needed. They may be a need for these methods only once after implantation, periodically, on-demand, or continuously.

Alignment of antennas can be guided through active methods described in algorithms for positioning, or can utilize more passive or semi-active alignment methods, such as using magnets to align antennas, mechanical protrusions, or electromagnets. The alignment can also be assisted with information about the link from the transmitter and/or the implant.

Power transfer can be combined with data transfer to increase efficiency and reduce system overhead. This can be accomplished with small changes in the amplitude of the power transfer signal that can be detected asynchronously at the implanted receiver. Potential methods of combining data transfer to the implant are described in later sections, and the preferred method is described in detail.

Figure 25:
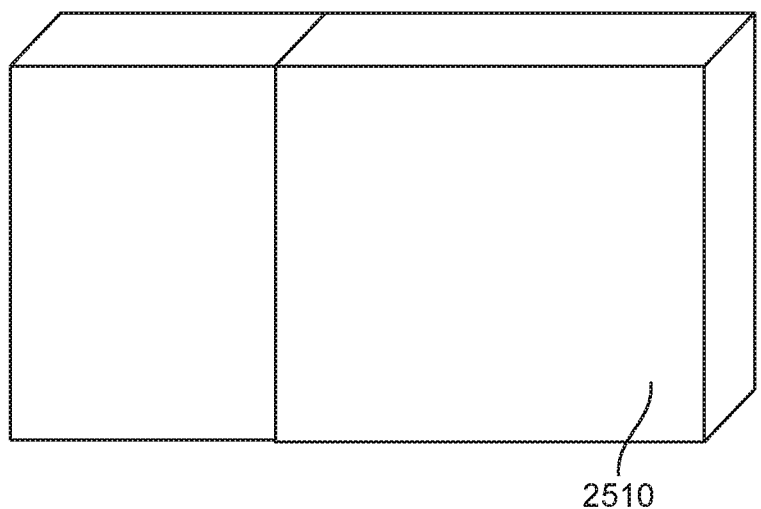
FIG. 25 shows an exemplary external device with a removable rechargeable battery.

The external device 2030 can be powered through batteries or with direct connections to wall outlets. Batteries allow for portable systems and for most applications should operate for several days before requiring recharging. Some applications may be more power intensive and require more frequent recharging. As an additional feature, the system can operate from wall outlets when the patient is at home or in a place where this is convenient. The power source can be located in a separate enclosure from the antenna 2210 to increase the comfort of the overall system. The antenna should be located in close proximity the implantable device, and the battery pack could significantly increase its size and weight, and the ability to carry it in a different location could reduce patient discomfort. Referring to FIG. 25, the external device 2030 may comprise a swappable rechargeable battery 2510 to power the external device 2030. Each external device of the external device 2030 may be provided with one or more swappable rechargeable batteries 2510.

Figure 29:
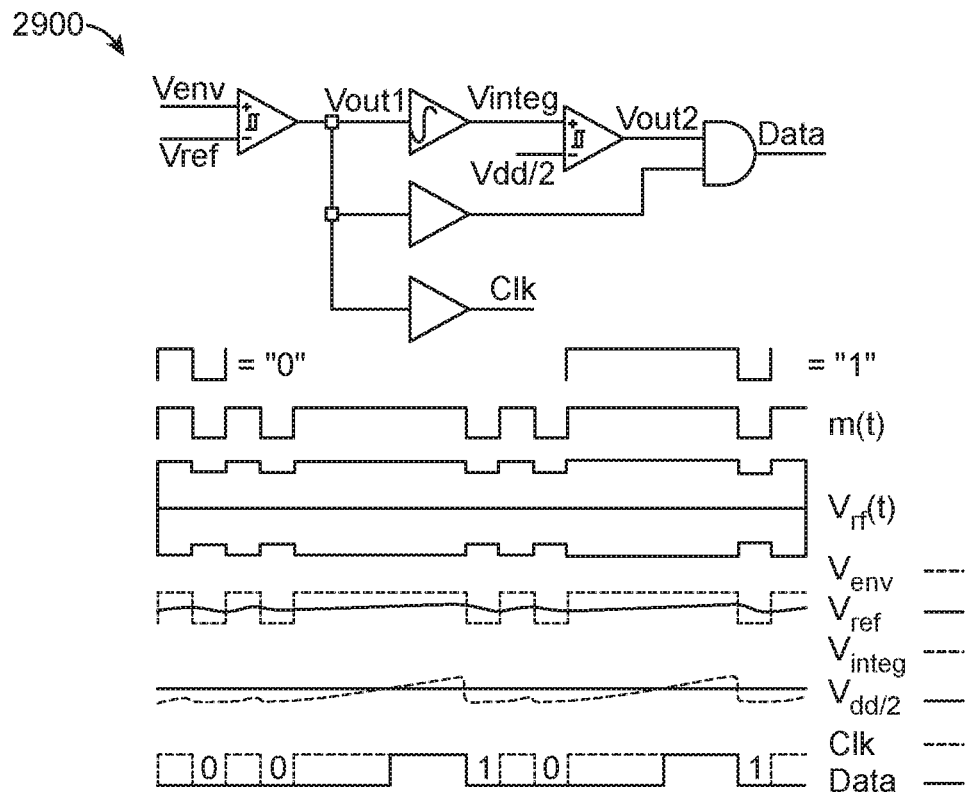
FIG. 29 shows waveforms illustrating the ASK-PW modulation method for data transmission.
Figure 30:
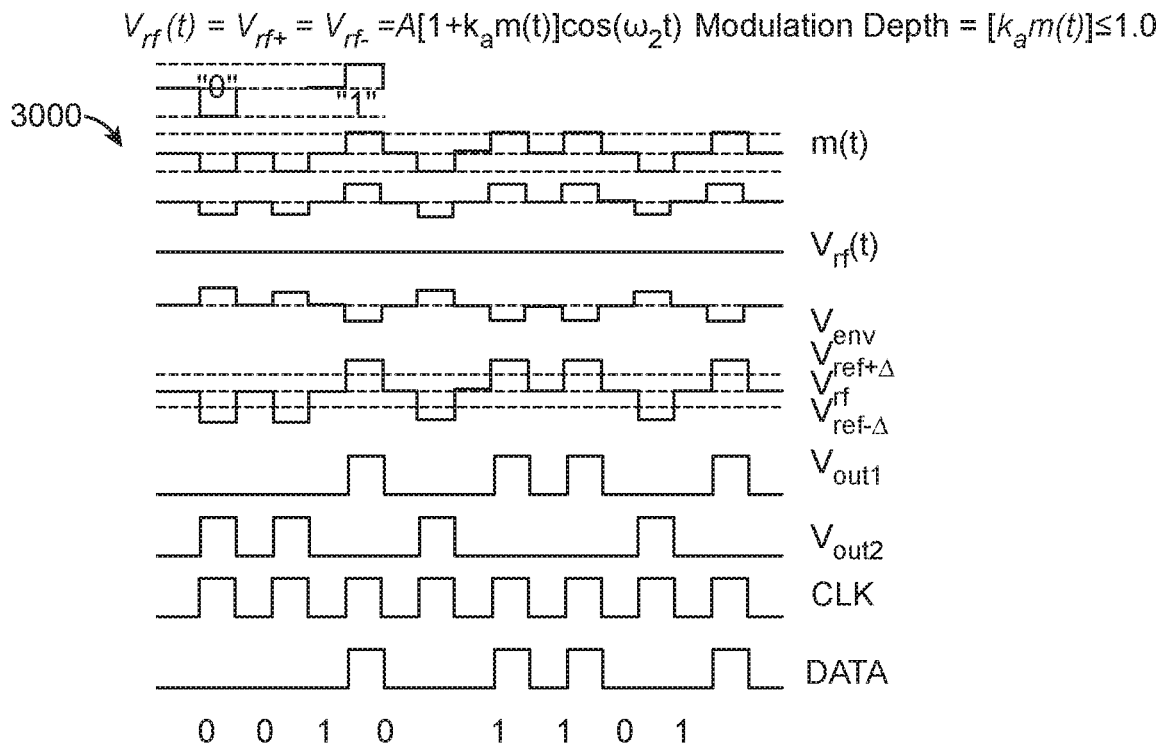
FIG. 30 shows waveforms illustrating an ASK method using multi-level encoding.

There is a two-way communication link between the implanted neuromodulator and the external transmitter. The forward transmission from the external antenna to the implantable device 2010 may provide information for the controller to configure the operation of the device, and can operate at speeds up to and in excess of 20 Mbps. Many forms of modulation can be used including both amplitude and frequency modulation, however combining data with power transmission introduces additional challenges. Conventional forms of data modulation can significantly impact the amount of power transferred, and trying to use multiple antennas or different frequencies would need to contend with large levels of interference from the power carrier. Another more indirect method is for the external device 2030 to have electrical contact with the surface of the skin and transmit small electrical signals through the tissue. In some embodiments, the communication link is combined with the power transfer link in a way that minimizes the effect on power transfer, and operates asynchronously to reduce the overhead on the chip. This method could function very similarly to what is described in U.S. Pub. No. 2013/0215979 (the contents of which are incorporated herein by reference), which uses amplitude shift-keying with data encoded in the pulse-width (ASK-PW). In this method, the amplitude of the power carrier is modulated with minimal depth, which minimizes the impact on power delivery to the device as desired. Data can be encoded in the width of transmitted pulses, allowing for asynchronous operation on the implant, which reduces the complexity of the on-chip circuitry. By eliminating the need for carrier synchronization circuitry, the power consumption on the implant is also minimized. This method can also easily accommodate variable data rates and modulation depth, which gives flexibility in its overall power consumption and also can increase robustness when the antenna link is weaker. A high-level diagram of this method is shown by the operational diagram 2900 in FIG. 29. An envelope detector may extract the envelope of the power carrier, and the resulting signal is converted to a full-swing digital signal. The envelope detector uses a dynamic reference to extract the desired signal because of the inherent fluctuations from wireless powering, and the operation of this system. The digital signal has both long and short pulses that were recovered from envelope of the power carrier, and these pulses are integrated to determine the encoded data. The falling edge of the pulse can be used to clock the data as shown in the figure, and this clock signal can be repurposed for other uses on the chip as well. The diagram 3000 in FIG. 30 also depicts the waveforms of the signals, showing the transmitted envelope, the digital version of the envelope, and the method for extracting data from the pulse width. An alternative to this approach is shown by the circuit diagrams 3100 in FIG. 31, in which multi-level encoding is used for data. This method can allows for a constant clock period in transmission, simplifies dynamic reference settings, and has a more constant average power transmitted.

Figure 31:
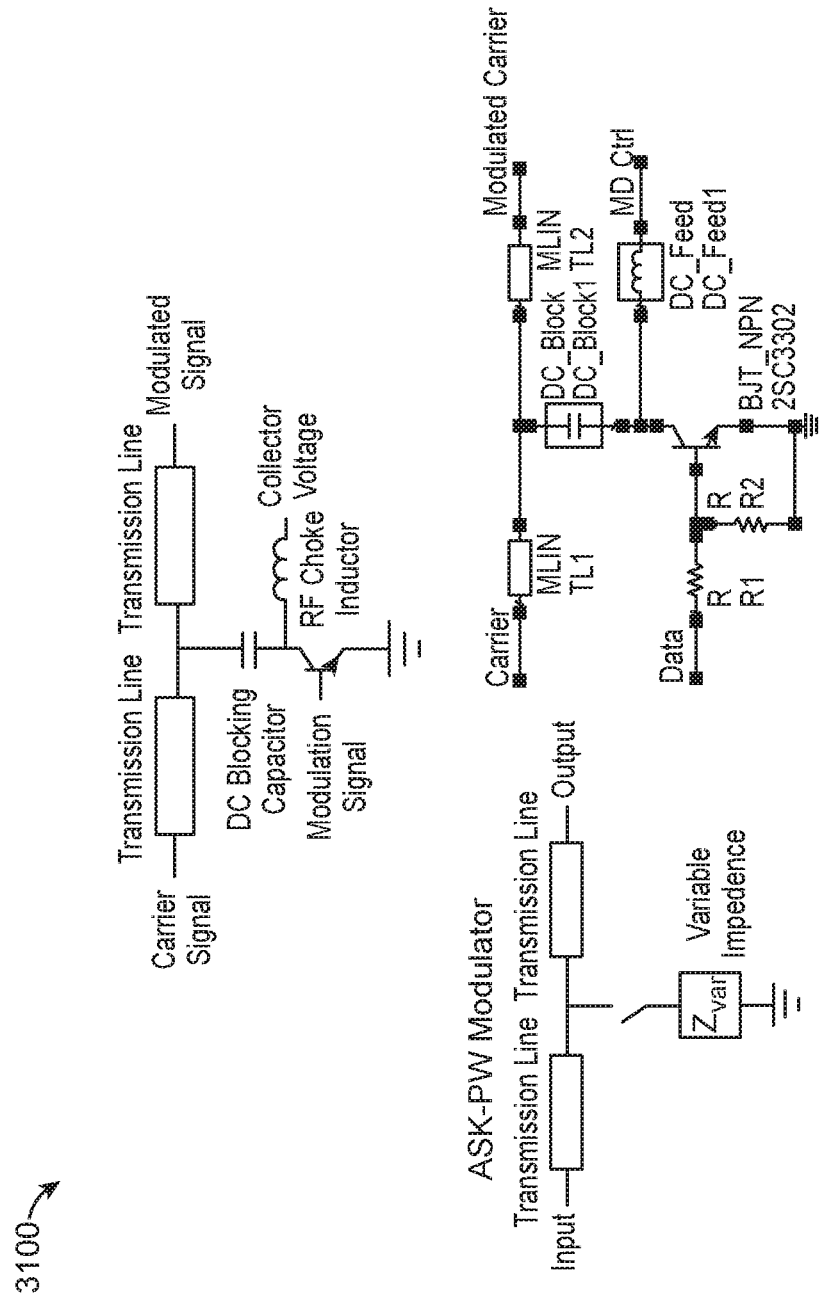
FIG. 31 shows circuit diagrams for modulation methods and circuits for high frequency ASK modulation with adjustable depth.

One way to generate ASK-PW signal to power the implant and send data to it is to first generate a carrier signal, then encode data on it by modulating the amplitude of the carrier signal. The modulated carrier can then be bandpass filtered and amplified to generate desired spectrum and amplitude prior to transmission. The baseband data waveform which modulates the carrier signal can be conditioned prior to mixing it with a carrier signal to achieve desired pulse shapes and spectrum. Variety of pulse shaping techniques can be used to improve signal integrity of the communications. Pulse shaping can be achieved using analog or digital methods. For example, low pass filter can be used as an analog method or digital. Alternatively, baseband data stream can be generated using a digital waveform and then converted to analog signal using a DAC. The modulated RF carrier can also be generated directly using a high speed DAC. In other embodiments, modulation of a carrier signal can be achieved by loading a transmission line with a transistor or a similar controllable component which can modulate impedance of the transmission line through which the signal from carrier generation circuit passes. The baseband data can connect to the control terminal such as gate terminal on a FET transistor or a base terminal on a BJT transistor. This way, the baseband data modulates the impedance of the transmission line, and therefore, the reflection and transmission coefficients, which directly affect amplitude of the carrier signal. The resulting modulated carrier signal can then be conditioned and amplified for transmission to the implant. The baseband data can be analog or digital waveform in the above described method. Digital data stream is preferred because it is easier to decode on the implant when using ASK-PW. Data is encoded in pulse width of the modulating signal. Amplitude modulation depth or modulating index can be adjusted by controlling the bias voltage of the modulating transistor as shown in FIG. 31. Modulation depth can be controlled by adjusting collector-emitter bias voltage on the transistor. The baseband data can be driven by FPGA and resistors R1 and R2 attenuate the signal to the proper level to control the BJT transistor. A large DC block capacitor and a choke inductor are implemented to bias the transistor without interfering with the RF signal. Carrier signal of desired frequency can be generated using well known methods such as voltage controlled oscillator (VCO) or digitally controlled oscillator (DCO). In order to achieve specific carrier frequency, a crystal oscillator can be used for reference frequency in a phase or frequency locked loop (PLL). Numerous methods can be used to generate the carrier signal.

The reverse data transfer from the implantable device to the external device(s) will operate in conjunction with the forward link, and will be capable of data transmission speeds up to and exceeding 2 Mbps, such as 0.1-1 Mbps. It is possible to have an oscillator on-chip for an active transmitter that sends data back to external transmitter. This would require significant power on the implant to operate and would need to contend with interference from the power carrier. Even with these challenges, these implementations may have advantages in certain situations. Other methods require much less power on the chip, and are advantageous in many situations because of the power limitations of the implantable device. One potential method with a minimal power budget is through a backscattering link, in which the loading at the antenna of the implant is altered to introduce mismatch, which can then be sensed at the transmitting antenna. This method is similar to what is used in RFID systems, though transmitting through tissue poses a different set of challenges. This method can be sensitive as the environment changes, and variations are common when operating in tissue. To mitigate the effects of the operating environment, several possible loads can be implemented, and the load that maximizes the received signal can be used. This load satisfies two requirements: maximizing the average backscattered power per bit (max $\{\sigma_1+\sigma_2\}$) and maximizing the Euclidean distance between the reflection coefficients on the Smith chart corresponding to the matched and mismatched loads (max $\{|\Gamma_1-\Gamma_{2,k}|\}$). In this description, $\sigma$ corresponds to the termination-dependent implant antenna radar cross-section and $\Gamma$ are the reflection coefficients corresponding to matched termination and terminated with some load, k. In order to demodulate such signal, direct conversion receiver architecture can be implemented on the external device, as shown in the diagram 3200 of FIG. 32.

Figure 32:
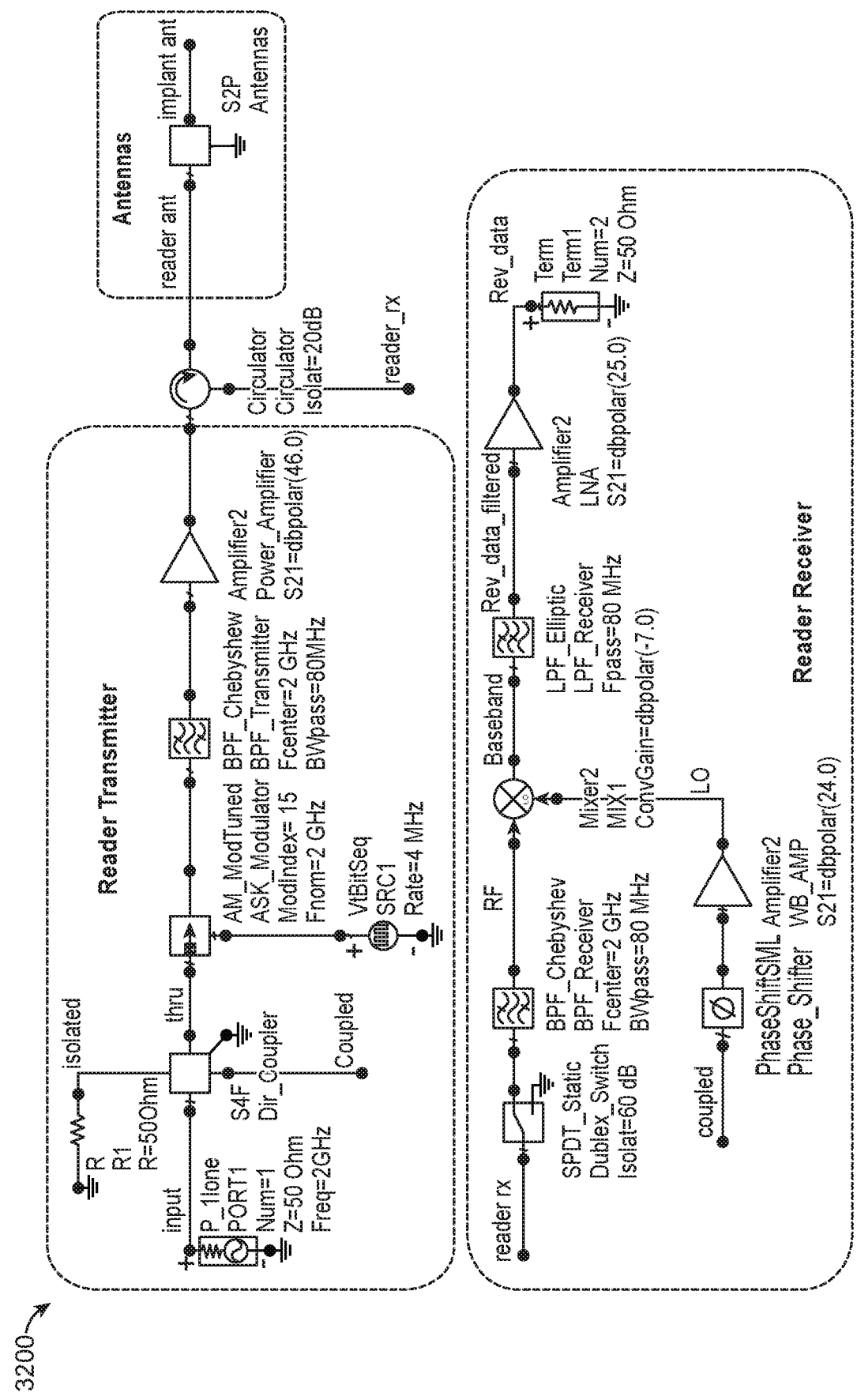
FIG. 32 shows a circuit diagram of a direct conversion receiver for detecting reflected energy.

The external reader may comprise transmit and receive signal paths which are isolated by circulator as shown in FIG. 32. The transmit signal path may comprise a power carrier generator which connects to directional coupler whose through port is connected to ASK modulator. The data may be configured on an FPGA and modulates the power carrier with adjustable modulation depth, ranging between 0 and 100%. The modulated power carrier can then be filtered with 80 MHz bandpass filter around the carrier and can be fed to a power amplifier. The power amplifier may amplify the signal to sufficient power level to provide enough power to the implantable device, which could be between 20 and 36 dBm, depending on chip power consumption requirements, implant environment, and separation distance and medium between the external and implant antennas. The external reader and the implantable device are coupled through a pair of weakly coupled antennas.

As was mentioned earlier, the receive signal path can be isolated with a circulator that provides isolation between the forward and reverse signals of approximately 20-30 dB. However, because the backscattered signal is significantly lower power than the transmit signal, the 20 dB of isolation is not always sufficient to suppress the leaked power carrier and ensure that the amplifier in the receive signal path does not saturate. In those cases, active blocker rejection techniques can be used to further suppress self-interference. Additionally, forward data link modulates the carrier, which causes significant fluctuation in carrier amplitude, further complicating signal processing in the reverse data recovery. Therefore, a duplex switch can be implemented in the receive chain which provides additional 60 dB of isolation during the transmission of the forward data. Because the receive path in this case is implemented using only the in-phase component, it is also important to synchronize the phases of the RF and LO signals at the mixer. Therefore, a passive phase shifter can be implemented to ensure that the signals are in phase. There can be an additional amplifier for the LO signal to ensure that LO signal level is in appropriate amplitude range between 7 and 13 dBm for proper mixer operation. The mixer output can then be filtered by a low pass filter to eliminate undesired high frequency components and can be amplified before decoding the data.

Another method for reverse communication uses the stimulation electrodes to transmit a small signal through the tissue. Here, the external device 2030 may require some form of electrical connection with the surface of the skin to detect the small fluctuations in electrical stimulation. This has potential advantages in that it requires very low-power from the implant, and can operate at frequencies where there won't be interference with the forward link. Additionally, it can operate asynchronously and simultaneously with forward data transfer, whereas backscattering modulation and active transmission through the antenna would be very limited in this type of simultaneous operation. Because there is little or no interference, the external device can have a very sensitive receiver, which means that the electrical signals sent through the tissue can be very small (even below <1% or below 10% of the delivered therapeutic stimulation). If there are multiple devices, this method would allow for rapid communication between the devices and the external device.

In order to demodulate signal which is transferred using volume conduction from the implantable device to the external device, the external device can use one or more electrodes or electrode pairs which are in contact with tissue. The electrodes could detect the voltages generated by the implant and feed these signals to the readout interface. One possible embodiment of sensor interface AFE implementation is shown in the diagram 3300 of FIG. 33. In the FIG. 33, the sensor interface may comprise electrodes connected to tissue which act as a transducer from ionic or electronic current flow in tissue to a voltage difference which can be further sampled and processed by analog front end (AFE) of the implantable device. AC-coupling block could connect to the electrodes and filters out undesirable low frequency content of the sensed signal. Low noise amplifier may amplify the sampled signal to a desired amplitude so that the signal can further be filtered out by the low pass filter. There may be an additional amplifier after the filter. The analog signal at the output of low pass filter may then be converted to digital signal using analog to digital converter. The sampling frequency and resolution may be based on the desired application and data rate. One or more of the parameters of the AFE can be made controllable to make the device versatile for a variety of applications and compatible with a variety of transducers. For example, the high pass filter and low pass filter cutoff frequencies can be made adjustable by the digital controller. Also, the gain of the amplifiers can be made adjustable as in variable gain amplifier and can either be controlled with a feedback loop. Additionally, the sampling frequency and resolution can also be made controllable. One or more of the above described components of the AFE can also be deactivated and bypassed for power savings and versatility. For example, it may be desirable to bypass the AC-coupling block and the low noise amplifier and simply low pass filter the signal and convert it to digital representation if the sensed signal has large amplitude and does not contain large DC component.

The electrodes and electrode interface circuits can also sense action potentials, neural activity signals, muscular activity signals, and other biological, chemical, biochemical, or physiological signals. For electrical signals, electrodes act as transducers to supply signal to the sensing interface. The sensing interface can comprise an optional coupling network, low noise amplifier, variable gain amplifier, tunable filter, and ADC to digitize the signal and feed it to the controller. The above mentioned components make up an analog front end (AFE) for the electrode interface. The AFE for communication can be reconfigured and reused for sensing physiological signals when not being used for communication. Alternatively, a dedicated AFE for physiological signal sensing can be used on the external device. The same electrodes can be used for communication or separate electrodes or electrode pairs can be used for communication and for physiological signal sensing. Additionally, these electrodes and electrode interface circuits can also be used to sense the actual delivered therapy parameters and adjust the parameters based on the measured values. Because in some cases the implantable system and/or device(s) may not include a precise clock reference, it may be difficult to achieve precise timing. Therefore, it is very valuable to have the ability to sense the actual therapy parameters and compare them to desired parameters and then adjust these parameters until actual therapy parameters match the desired parameters. The controller on the external device 2030 can be programmed to control when sensing of these various parameters occurs. For example, during therapy delivery, therapy parameters can be sensed. When therapy is not being delivered and the implantable device 2010 is communicating with external device 2030, the controller can configure the AFE to sense the reverse link data. When neither is occurring, the controller can configure the AFE to sense physiological signals.

Matching gels, adhesive gels, conductive gels, short-wear gels, extended-wear gels, hydrogels, can be used to ensure good contact between the conduction electrodes and tissue. These gels can improve mismatch between impedances, improve conduction, and improve comfort for the patient. They can also improve the safety characteristics of the overall system by offering better heat management and/or impedance control of the interface.

For both the forward and reverse communication systems, the data transfer needs to safe, reliable, and private. The preferred ASK-PW method for forward data transfer may offer advantages in safety because it minimizes effects on power delivery, allowing for higher power transfer efficiency and therefore less tissue heating due to the power carrier. The interaction with the implantable device 2010 is also protected in the sense that the signal may be sent on the power signal, which may be placed on the surface of the skin to send sufficient power for operation. This may ensure that interference from other types of electromagnetic radiation will not disturb the operation of the device. Additionally, the implantable device 2010 may only operate when verified data is received, ensuring that the device is inactive when not given specific instructions. The data sent from the implant can be kept private because sensing it requires an antenna in very close proximity, preventing other devices or antennas from detecting the signal. The communication protocols can be unique to the device and can include encryption to further ensure privacy.

In many embodiments, the transmitter transfers electromagnetic energy to the implant at frequencies in the low-GHz range. This frequency range has advantages for very small antennas operating in tissue environments. The carrier frequency can be generated in a number of ways, including oscillators or signal generators. This carrier may then be modulated by introducing a controllable impedance in the RF path to introduce mismatch and therefore controllably alter the amplitude of the transmitted signal. This method can be implemented with transmission lines and transistors. One implementation uses a BJT transistor tied to the RF path with a transmission line to ground, and by controlling the voltage at the base, a variable impedance can be introduced. This method can modulate the amplitude from 0-100%. Lower depths may have a minimal effect on power transfer, however data is received more robustly with larger modulation depths. The signal may be amplified after modulation and then transmitted through one or more antennas. This antenna may be matched to the frequency of the carrier to maximize the radiated electromagnetic energy. For implantable devices 2010 with backscattering data links, this antenna will be capable of sensing small amounts of reflected energy and recovering the intended information. Alternatively, for implantable devices 2010 transferring data with small electrical signals transferred through tissue, the external device can include electrical contacts with the surface of the skin to sense and recover these signals.

For both the forward and reverse communication links, the data transfer can be transferred digitally, and so any form of conventional error detection and correction can be used. This can accomplished through repetition codes, parity bits, checksums, error correcting codes, or any method that is familiar to those skilled in the art. For the forward data link to the implant, the preferred embodiment includes an ID code and a preamble that may be present before data capture starts. Once the data capture phase completes, error detection and correction can be performed for additional protection against errors. For the reverse data link, there can be significantly more errors because of the difficulty of low-power communication through tissue environments. In these cases, error correction could be essential, and any of the previous correction methods can be used. The transmitter can also acknowledge the data through a handshake with the implant or request that data be resent if errors occurred.

Multiple implantable and/or external devices may need to be deployed for either monitoring physiological activity or delivering therapy at multiple locations in parallel. Because there is a need to get data from and send commands to all of these devices that are located roughly in the same area, it may be necessary to use a multiple access scheme with a single external device. Time division multiple access (TDMA) based scheme. as shown for example by the timing diagram 3500 of FIG. 35, can be used to achieve communication with multiple devices. Each implantable device 2010 may have its own time slot to communicate to the external reader. Each device can be assigned its own unique identification (ID). For example, FIG. 34 shows a method 3400 of assigning unique IDs to each device which can be used in multiple access communication protocols. The external reader may interrogate the individual implantable devices 2010 in a sequential manner by transmitting data packets with an ID for which the data packet is intended. Once the implantable device 2010 receives an ID that matches its own, it will act based on the data contained in the packet and may transmit a reverse data packet to the external reader with its own ID. This way only one implant communicates to the external reader at a time, avoiding data collisions. The interrogation period for all devices is short enough compared to physiological activity to achieve high temporal resolution.

Another multiple access scheme which can be used for reverse data transmission may be code division multiple access (CDMA). A group of orthogonal codes can be used to encode outgoing data packet prior to transmission. Since each device which is communicating back to the external reader would have a code which is orthogonal to that of other devices, data collision can be avoided even if multiple implantable devices communicated with the external device in the same time frame. TDMA scheme can be used for forward data transmission and either CDMA or TDMA may be used for reverse data transmission.

CDMA for reverse data transmission from implants or implantable devices to external device is also beneficial to provide feedback from multiple implanted implantable devices while positioning the external device in the optimal location. With only a single implanted implantable device, there is often no ambiguity which device is transmitting data to the external reader. Therefore, a simplified protocol can be used to derive information about the wireless link quality while positioning the external device. However, when more than one implantable device is implanted, either the protocol has to be more complex to accommodate more implants without ambiguity or devices need to be able to communicate asynchronously and possibly concurrently. More complex wireless link quality feedback and positioning protocol unnecessarily complicates and makes the process of positioning the external device longer and less desirable for the user of such device(s). Therefore, a preferred embodiment uses CDMA scheme where devices can communicate to the external device concurrently while the wireless link is being established. This way, the external device(s) 2030 can receive data from one or multiple implantable devices 2010 unambiguously and provide feedback and guidance to the user on what the optimal position of the external device(s) 2030 is.

In some embodiments, the protocol for positioning of the external device(s) 2030 to achieve wireless link of acceptable quality is outlined in the following. The external device(s) 2030 may transmit a higher power level than usual during the positioning process in order to accelerate and ease the positioning process. When an implantable device 2010 is powered on, power-on-reset (POR) signal can be generated and causes the implantable device controller to reset itself to a known state. This signal also triggers the controller to transmit a data frame to the external device 2030 to indicate that the controller has been reset. This can notify the external device 2030 that the particular implantable device 2010 which transmitted the data has received sufficient amount of power to turn on and reset itself. This limited information may be insufficient to derive information about the wireless link quality, however. Therefore, additional information may be necessary. This additional information can be on the rate of charging of an energy storage element on the implantable device, such as capacitor or battery. For example, the implantable device 2010 could transmit a data packet to the external device when its energy storage is charged to particular percentages of the capacity in certain incremental steps, such as 0% to 100% in 10% increments. The external reader could then interpret how much power is being delivered to the implant. If the storage element gets fully charged, the external device 2030 can transmit a command to discharge the element through a built-in shunting network on the implant, acting as an internal dummy load. Also, the output power level on the external device 2030 can be adjusted to speed up the search for optimal operation parameters, including external antenna position. Therefore, this added information can be used by the external device to derive either relative or absolute information about the wireless link quality and suggest an alternative antenna orientation, output power level, operating frequency, impedance matching network configuration in case it is tunable, and other parameters that affect the wireless link quality.

In case of an implanted system having a single implantable device 2010, the antenna orientation can be adjusted based on a gradient search algorithm until a maximum in the wireless link quality is found based on the feedback received from the implant, as described above. The output power level can then be adjusted based on the therapy parameters and charge and discharge rates on the implant. The power level adjustments can be done when the patch is placed or periodically, to ensure that the implant receives sufficient but not excessive amount of power, which would result in inefficient system operation. This can be accomplished by monitoring charge/discharge rate while starting at a high output power level and slowly reducing the output power level until delivered amount of power becomes insufficient for device operation, which would occur when discharge rate is faster than charge rate.

In case of an implanted system having multiple implantable devices 2010, the antenna orientation can be adjusted based on feedback from multiple implants until all implants receive sufficient amount of power. This can be achieved by monitoring quality of individual wireless links between the external device(s) and each implant. Once optimal position of the external antenna for every implant is known, a good position which accommodates all the implants in the best possible way can be determined. In case there may not be position which accommodates all the implantable devices 2010, priority can be given to certain implants and a biased position which accommodates devices with higher priority can be determined. Algorithms that weigh importance of certain implants can be used and position can be determined based on these weights and priorities. For example, if two implantable devices 2010 are delivering energy to tissue to achieve desired therapeutic effects, a doctor in charge of therapy or potentially even the overall system itself can determine that one of the two implants has a stronger effect than the other and the external antenna position can be biased toward the more important implant while sacrificing the wireless link quality of the less important implant. Overall, this may be more advantageous for the operation of the overall system as a whole. Alternatively, implantable devices 2010 with higher power consumption can be given a higher priority than those with lower power consumption in order to achieve the highest power efficiency of the overall system.

Multiple devices may have the same ID if similar or identical functionality is required in the same time frame. In this case, the external system would act as a broadcasting station for multiple implants or implantable devices. All implantable devices with the matching ID would act upon data which they receive in the forward data packet, causing them to be synchronized to the same external system's clock.

The ID programmability for each external device 2030 can be achieved via wirebonding, solder bumping or a technique which provides an inexpensive yet effective way to reuse the same integrated circuit and same board and simply modify the pattern in which ID pads are wirebonded—either to VDD or GND potential—thus assigning the ID to each device, as shown in FIG. 34. This method 3400 can also be used to program a particular code for every implant if CDMA scheme is used for communications. Alternatively, an external device 2030 can have non-volatile memory or registers which can be programmed, setting the device ID and code if needed.

Figure 35:
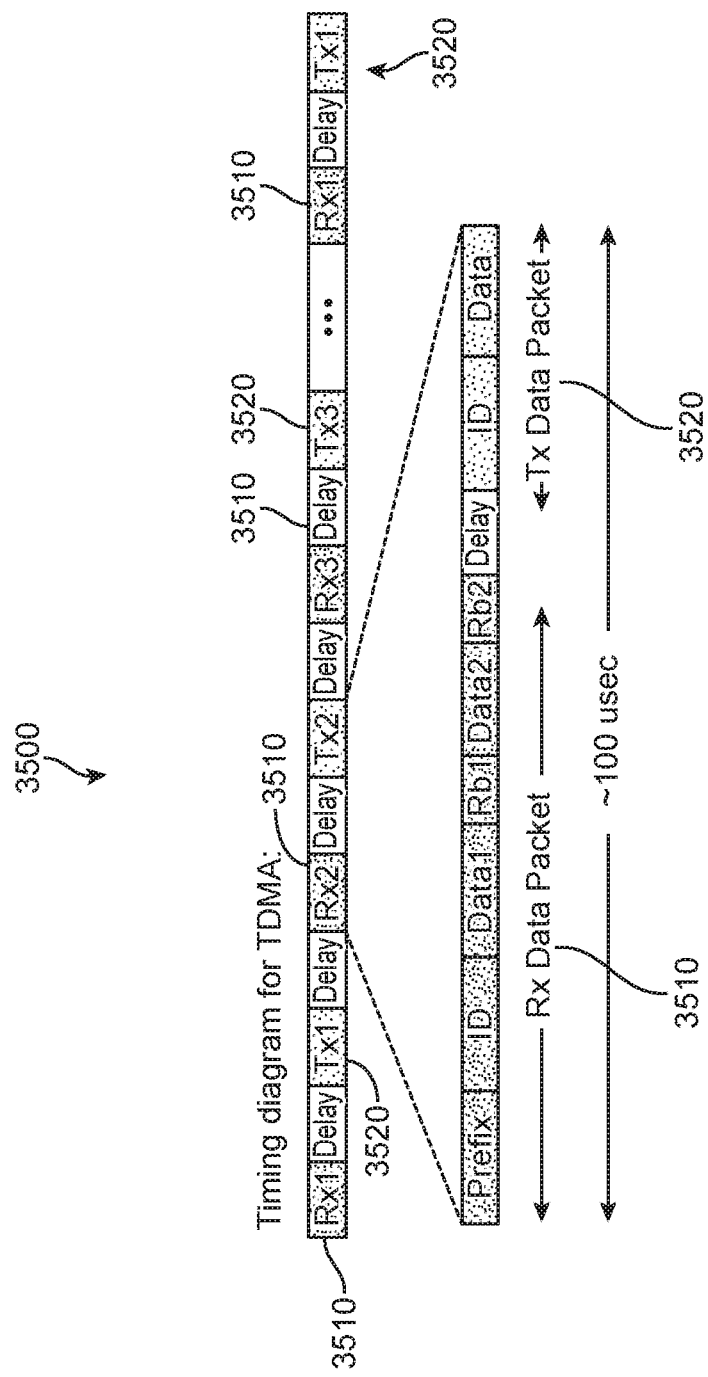
FIG. 35 shows a schematic of a timing diagram for a TDMA protocol with multiple external and/or implantable devices.

A sample timing diagram illustrating TDMA operation is shown in FIG. 35. Forward data from the external reader to the implantable device 2010 is shown by arrows 3510, and reverse data from the implant to the external reader is shown in by arrows 3520. From FIG. 35, it can be seen that the forward data packet comprises a prefix (preamble), implant ID, followed by data which includes encoding to handle errors and improve signal integrity, such as run length limiting codes. Once the implantable device 2010 receives the matching ID and error-free data, the internal clock is enabled and, after some delay, the data is transmitted back from the device to the external reader. The delay may be necessary to ensure that the forward data link does not interfere with the on-chip analog sensing interface which can be sensitive to power supply fluctuations caused by RF amplitude fluctuations. Also, the delay can help demodulate the reverse data packet at the external reader when backscatter or load modulation is used. The reverse data packet contains a preamble, ID, and data which include encoding to handle errors and improve signal integrity. The entire forward and reverse data transaction could take on the order of 50 μsec or more due to high forward and reverse data rates, such as 0.1 μsec to 100 μsec. In some cases including the use of larger packet sizes, the transaction could take more than 100 μsec, such as 100 μsec-5 ms, or 500 μsec-1 ms. In case the implantable device 2010 has a large number of registers which need to be programmed for proper implant operation, the implant can be programmed not within one but within multiple forward data packets. In that case, the forward data packet may contain address and value of the register which needs to be programmed instead of programming all registers at once. It could also take significantly less time than 50 μsec if data rate is increased or if programming is performed with multiple packets.

Feedback data from the implantable device 2010 can be used to adjust the external device 2030 power levels in order to provide sufficient power to one or more implantable devices 2010 while not exceeding the necessary amount of power. This may be beneficial in order to save battery life on the external device 2030. Implantable devices 2010 can provide information to the external device(s) or patch(es) to control the output power level in a closed-loop configuration. This feedback information can be provided periodically, upon request, or continuously depending on the specific use case. The power levels may also need to be adjusted during varying patient physical activity, changing environmental conditions, and other situations that may perturb the link gain between implants and the external patch. The feedback data can include charge and discharge rates of the implants, as described in algorithm for antenna positioning section of this document. The power levels can further be adjusted during data transmission and/or reception phases in order to improve data link quality. The power levels can also be adjusted periodically to improve link gain. For example, bursts of high power transmissions can be used to quickly charge the implants if needed.

The matching network, operating frequency, and other link gain and data link parameters can be adjusted to accommodate varying environment conditions and unpredictable environments. The matching network can utilize an array of components that can be configured using a searching algorithm to select the optimal component or combination of components based on the desired search criterion, such as the maximum link gain or the maximum data rate. Furthermore, the carrier frequency can also be adjusted to select optimum frequency of operation. Two or more parameters can be swept in a nested loop or using a more sophisticated algorithm, such as a gradient search or MSE algorithm to determine optimal parameters for operation. The frequency of operation may be a useful parameter for maximizing link gain, especially in situations when one or more implants do not include an adjustable or tunable matching network. In those cases, the external transmitter can sweep the frequency of operation while adjusting matching network to maintain good match between antenna and transmitting circuits in order to improve power transfer characteristics to the implant. The maximum link gain frequency can then be identified and selected based on the algorithms described earlier, which may require feedback information from the implant. Frequency selection can compensate for unpredictable operating environments or changes in environment, and it can be readjusted if these types of changes reduce performance. The power transmitted can then be adjusted based on the therapy and the link performance to ensure a sufficient amount of power is delivered to one or more implants and that only insignificant amount of power is wasted by minimizing excess output power. Some matching network and link gain optimization techniques are described in U.S. patent application Ser. No. 12/485,641 by Stephen O'Driscoll, et al. Moreover, the described configuration optimization can be carried out periodically, only once after implantation, on demand, or continuously. It can also be done in a closed-loop manner with or without the patient's knowledge, in order to improve therapy adherence. Multiple carrier frequencies can be utilized by the external device to improve link gain with one or more implants. This may be especially beneficial in the case of multiple implants with non-tunable matching networks and unpredictable or varying environments. In those cases, the external transmitter can transmit several carriers at different frequencies to accommodate each individual implant's frequency of operation. The external transmitter can utilize multiple tuned antennas, or broadband antenna(s). Alternatively, a single antenna with tunable matching network could be used with time-domain multiple access approach. Other similar techniques could be utilized to accommodate multiple carriers.

Similar to optimizing power link gain, the data link gain can also be optimized. This optimization can be based on minimizing bit error rate, such as by utilizing a PRBS data and counting errors and adjusting data link parameters based on this feedback. The adjustable data link parameters are described in this document and are also described in U.S. patent application Ser. Nos. 13/734,772 and 14/043,023.

Mismatch in impedances can be sensed using multiple methods, as was described earlier, such as by sensing the reflection coefficient or standing wave ratio by relying on a directional coupler or circulator, or other methods, such as by sensing temperature of the transmitting circuits and/or antenna. Other methods for sensing and adjusting matching network can be found in U.S. patent application Ser. Nos. 12/485,641 and 14/043,023. These methods can also be used to detect failures in the overall system. Once mismatch or temperature exceeds a predetermined threshold, the overall system can classify the event or condition as failure and take appropriate actions in accordance with failure handling algorithms, including disabling the overall system and notifying the users.

The external devices 2030 can also be configured to monitor the activity of the therapy, power link, data link, sensing circuitry, antenna, impedances, and other measurable parameters of the overall system in order to prevent malfunction, failures, or unintended operation. Various failure detection mechanisms can be implemented in the overall system. The power link can be monitored via temperature of the overall system, reflection coefficient to monitor impedance mismatch, electric current draw, and other parameters which would change from baseline during a failure. Bit error rate monitors can be utilized to estimate data link quality. For instance, in the event of an antenna failure, the impedance would be become mismatched, causing a significant reflection of energy. This in turn would cause the reflection coefficient to become high, and could increase the external device temperature. The fault in the overall system operation could be detected by monitoring temperature, reflection coefficient, standing wave ratios, or combinations thereof and the on-system controller could respond to such an event in accordance to a pre-programmed safety protocol. Additionally, in the case of a severe or dangerous failure, an automatic kill-switch could be triggered. One possible action for this failure event could be to shut down the overall system and notify the user of the failure and its specifics. In cases when failures could be catastrophic, emergency personnel, the patient's caregiver and/or doctor could be alerted of this event, as well. Other failure detection mechanisms could involve estimating the quality of the power link and/or data link, a comparison of therapeutic parameters with desired parameters, interference detection from other devices in similar operating frequency band, and/or harsh environments which are adverse to device operation, such as radiation or presence of strong electric or magnetic fields. Appropriate failure handling protocols would cause the overall system to respond to these various conditions in a way to minimize any harm to the patient, the overall system, and surrounding environment. Calibration and/or system adjustments can be done based on the failure monitors. Some of the possible failures also include inadequate or nonexistent power and/or data link or lack of expected response from one or more implantable devices. Other failure mechanisms involve imbalance of delivered charge, failures in hermetic packaging which would cause shift in frequency and changes in performance, impedance changes in leads and tissue-electrode interface, impedance changes in antenna, and other parameters.

Implantable devices 2010 can also have built-in kill-switch or temporary disable switch in order to permanently or temporarily disable device. Disabling of the implantable device 2010 can be done by shorting power and ground terminals of the implant, shorting antenna terminals, and/or shorting all electrodes together. This would prevent the device from harvesting energy and from delivering stimulation energy to tissue. The kill-switch could be activated remotely via magnetic field, such as in a reed switch or relay. Other options could be through fuse, non-volatile memory, mechanical options, physical shorting such as shorting certain terminals.

A linear xy stage can be used by a patient, a doctor, or even be incorporated into the external system in order to automate positioning. The positioning can be done every time when the external system is being positioned, or can even be readjusted periodically. Alternatively, the positioning can be optimized with a specially designed xy stage or a similar positioner and the optimal location of the implant can be marked on the skin of the patient for ease and repeatability of subsequent positioning. Readjustment can be done periodically but with low frequency to ensure that the marked position is still optimal and to compensate for any changes in the operating environment which may affect the optimal position of the antenna 2210 on the external devices=2030.

Figure 27:
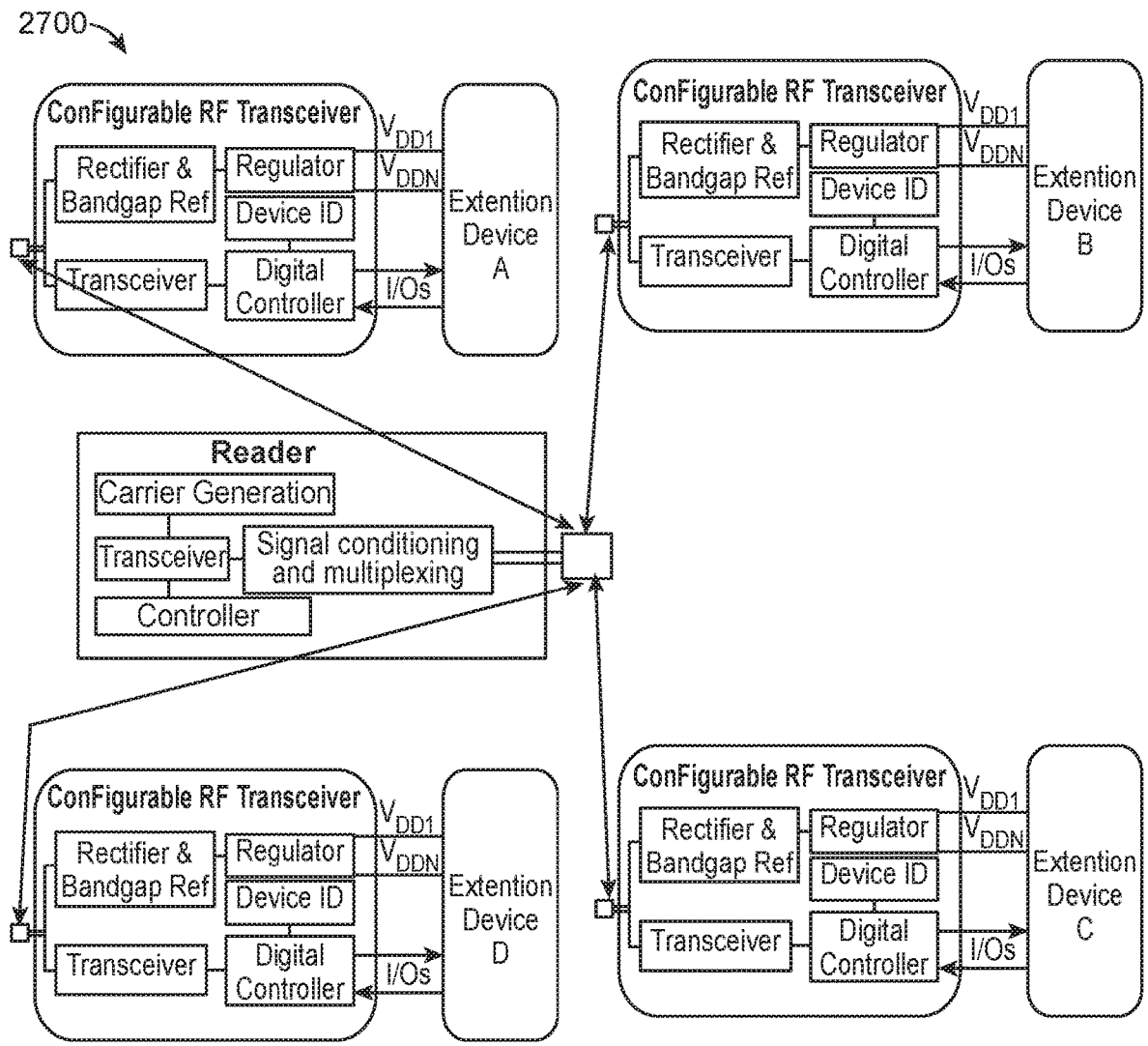
FIG. 27 shows a schematic of a setup for networking a reader with multiple devices.
Figure 28:
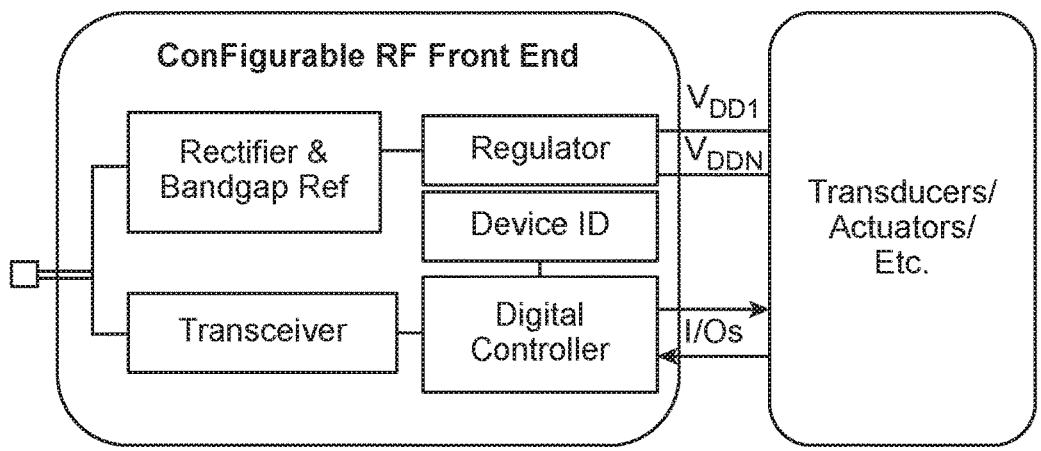
FIG. 28 shows a schematic of a configurable receiver that can interface with sensors, transducers or other devices.

The external device 2030 may be operated by either a doctor or patient depending on the intended use of the external device 2030 and the overall system 2000. This external device 2030 can be powered by batteries or be plugged in to a wall depending on where and how treatment is delivered. The external patch can have built-in or replaceable batteries that can be easily swapped by a patient, as shown in FIG. 25. The batteries can be primary cell or rechargeable. In case there are multiple external patches on a patient, they can be powered by a single battery pack to which they are tethered; or each patch can contain its own battery in order to avoid wired tethering. These setups are depicted in FIGS. 23a-23d, which also shows network configurations. In case networking or therapeutic coordination is necessary between external patches, they can communicate using wireless communication methods or wired communication methods if they are tethered. Each external patch may have multiple devices within its network to coordinate therapies and/or diagnoses. The external devices or patches 2030, furthermore, can be a part of a larger network which is connected to a handheld device and/or another main controller device. This makes up a super-network of coordinated implants which are all part of this network via the external devices or patches 2030. This network can achieve improved therapeutic outcomes with the use of localized and/or distributed diagnostics and/or therapeutics. The synchronization can be done at any level of the network—at implant level, external patch level, or the super node level (handheld controller or other similar device). FIG. 27 shows a possible configuration 2700 of a reader interfacing with multiple devices, and FIG. 28 depicts a configurable interface 2800 that can operate with a variety of sensors, actuators, or other elements. Additionally, other coordination operations can be done on all devices in the network, such as the calibration of devices, therapeutic parameters, sensing parameters, adjustments to environmental conditions, and others. The environmental condition changes may include: changes in patient physical activity; patient stress levels; external environment adjustments to compensate for temperature, humidity, and others; presence of potentially harmful conditions to devices in the network caused by extraneous electric or magnetic fields, such as during MRI, cat-scan, X-Ray, ultrasound, or potentially due to use of defibrillators, or interference from other devices. In those cases, depending on the level of severity of the environmental conditions, the operation and/or therapy can be adjusted to compensate for the changes, or in some cases, the devices can be instructed to be turned off in order to prevent any malfunction, damage, or failure. The network devices may also communicate with computers and/or smart phones to relay information about the operation of the overall system and to allow for reconfiguration of the overall system. In order to communicate with external devices 2030 other than implantable devices 2010, the external device(s) or patch(es) can have additional communication interfaces. These interfaces connect the external device(s) 2030 to the outside and provide an ability to interface with users to program the external device(s) 2030, reconfigure the device(s) in part or in its entirety, program or reconfigure each individual implant of the implantable device(s) 2010 or the external device 2030, monitor the external device 2030 and its functionality and status, monitor individual implant functionality and status, monitor status of the therapy or diagnostic results, securely transfer and save data. This communication with the external infrastructure, such as personal computer, smart phone, or cloud computing, can be accomplished utilizing any existing wireless protocols, such as Bluetooth, ZigBee, WiFi, Qualcomm 2net, MICS, ISM, WMTS, MedRadio, MNN, MBAN, cellular communications, RFID or existing wired protocols, such as USB or ThunderBolt which could also be used to charge the external device(s). Collectively, this interface of the external devices 2030 to things outside of human body is referred to as external interface.

Figure 24:
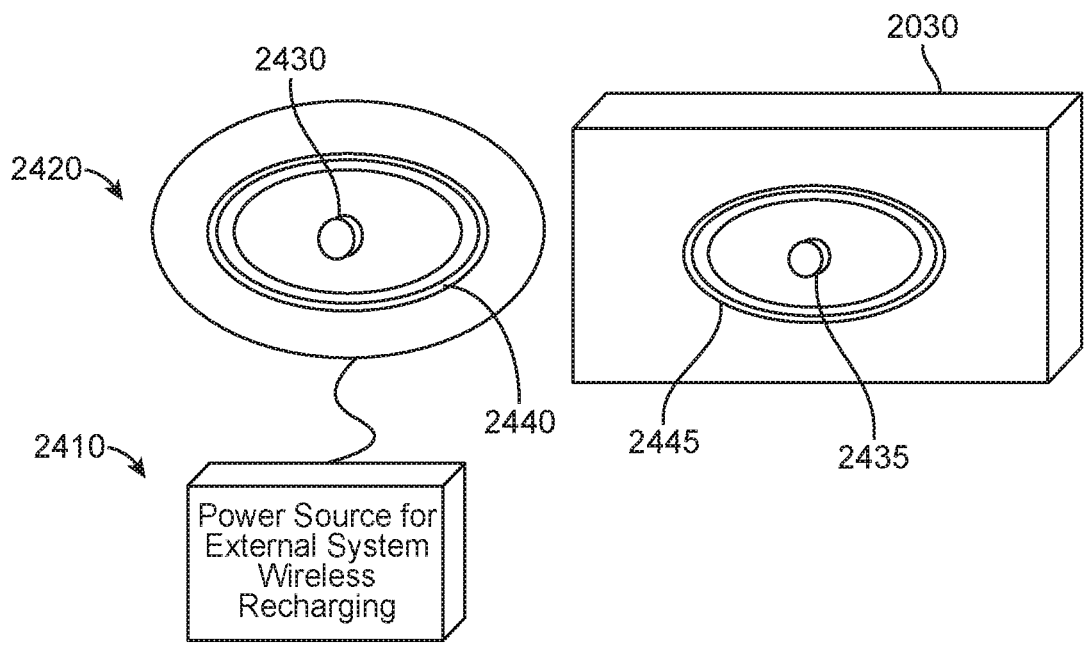
FIG. 24 shows a schematic illustrating a method for wirelessly recharging the external device(s).

The rechargeable battery 2510 can be recharged using tethered methods, such as by plugging into a charger, or wirelessly. The battery 2510 can be recharged wirelessly using inductive coupling, mid-field powering, or far-field beam steering approaches. In case of near-field or mid-field powering, the transmitting antenna can be aligned with the external patch receiving antenna using passive or active alignment methods. Some examples of passive alignment methods include: mating mechanical protrusions which can lock the two antennas in fixed position for recharging;

permanent magnets in the recharger and the external device or patch 2030, such that the magnets align the two antennas; and other similar methods. The active alignment methods may include: using permanent magnet and an electromagnet to align the antennas; sensing coupling between two antennas and providing feedback to one of the antennas to reposition it with respect to the fixed antenna; and other similar methods. FIG. 24 depicts a magnetic alignment sub-system for wireless recharging of the external system or device(s).

Referring to FIG. 24, the external device 2030 may be wirelessly recharged. Power may be supplied with an external power supply 2410 which may power an external charging member 2420 which may comprise a magnet or mating mechanical protrusion 2430 for external coil alignment with a complementary magnet or mechanical protrusion for external coil alignment 2435 of the external device 2030. When the external charging member 2420 and the external device 2030 are aligned, the inductive coils 2440 of the external charging member 2420 may be aligned with the inductive coils 2445 of the external charging member 2420 so that the external device 2030 may be charged.

The external interface may use secure communications in order to prevent any non-secure access to information from unauthorized users or devices. Additionally, authorization can be required to change therapy parameters which would affect the course of treatment. Different authorization tiers can be implemented that enable various levels of access to the programmability and data of the overall system. For example, doctor authorization level provides an ability to change therapeutic parameters of the overall system, and provides access to collected data about therapy status and history as well as any relevant information about collected physiological data. Patient authorization level can provide information about the status of the overall system, such as battery level on the external device(s) as well as some additional information which can be useful for the patient. A patient may also be able to make some minor adjustments to the operation of the overall system which lie within certain boundaries pre-set by a doctor who would not dramatically alter the course of treatment or compromise safety of the patient.

The external device 2030 can also send reminders, alerts, and other types of notifications to authorized people through the external interface. For example, if a patient does not put on the external device 2030 during the programmed therapy window, the overall system may notify the patient and/or the patient's doctor that the therapy is not being followed. These notifications and reminders can improve patient compliance and can also serve as a feedback for a doctor about the therapy effectiveness.

The external device 2030 may also offload some of the processing and storage needs to the external computing infrastructure by transferring raw or partially processed data that it collects through the external interface. The infrastructure can then notify the external device(s) if any action is required, such as change in therapeutic parameters. Notification may also be post-processed data which is formulated for easier visualization by a patient or doctor. For example, in case of seizure prevention the implant can collect raw data and rely on the external device or infrastructure to predict the onset of seizures and then notify the external device that it needs to administer a treatment or stimulate certain parts of brain in order to prevent the seizure.

The handheld device 2020 can contain user interfaces for input and output, such as touch screen display, an LCD or other conventional display, speaker, vibration element, light emitting element, and others for output, and keyboards, buttons, touch screen interface, switches, and other similar input interfaces to program, monitor, and control the therapy and/or diagnostic devices within the network. Multiple external patches can be controlled from the same handheld device. In turn, the handheld device can have access to and control of each individual implantable device via one or more external patches, as described earlier.

Although other components which are essential or optional to the operation of the integrated circuit have not been described explicitly are included implicitly. Such components may include power-on-reset circuit (POR), calibration circuits, memory, timing and delay circuits, and other circuits not explicitly stated in this invention. Their implementation, functionality, and how they fit into the overall system is obvious to those skilled in the art of integrated circuit design can be accomplished with a variety of methods that relate to the overall system architecture.

The one or more external devices and the one or more implantable devices 2010 can work individually or coordinate in a network to treat a variety of conditions. The one or more implantable devices 2010 can be places in one or more of the following sites for sensing and/or treatment: the tibial nerve (and/or sensory fibers that lead to the tibial nerve); the occipital nerve; the sphenopalatine ganglion; the sacral and/or pudendal nerve; target sites in the brain, such as the thalamus; the vagus nerve; baroreceptors in a blood vessel wall, such as in the carotid artery; along, in, or proximal to the spinal cord; one or more muscles; the medial nerve; the hypoglossal nerve and/or one or more muscles of the tongue; cardiac tissue; the anal sphincter; peripheral nerves of the spinal cord, including locations around the back; the dorsal root ganglion; and motor nerves and/or muscles. The system or apparatus can be used to treat one or more of the following: migraine; cluster headaches; urge incontinence; tremor; obsessive compulsive disorder; depression; epilepsy; inflammation; tinnitus; high blood pressure; pain; muscle pain; carpal tunnel syndrome; obstructive sleep apnea; pace or defibrillate the heart; dystonia; interstitial cystitis; gastroparesis; obesity; fecal incontinence; bowel disorders; chronic pain; improving mobility.

These system or apparatuses of the present disclosure can be effective for both chronic and acute treatments, and can withstand long-term implantation and use under various environments. These systems or apparatuses can include devices that produce custom waveforms for stimulation that can be tailored to the treatment and to the specific patient. These systems or apparatuses can incorporate two-way high-speed communication with an external device. These systems or apparatuses (e.g. implantable devices) use novel methods of energy delivery, energy management, communications, activation and suppression of physiological activity as will be described herein. These implantable devices and external devices also have novel form factors and encapsulation, allowing for flexible treatments, simple implantation, and reliable long-term use. There is also a discussion of applications of these methods, systems, and apparatus and potential variations to accommodate different uses, including both therapies and trialing.

Figure 36:
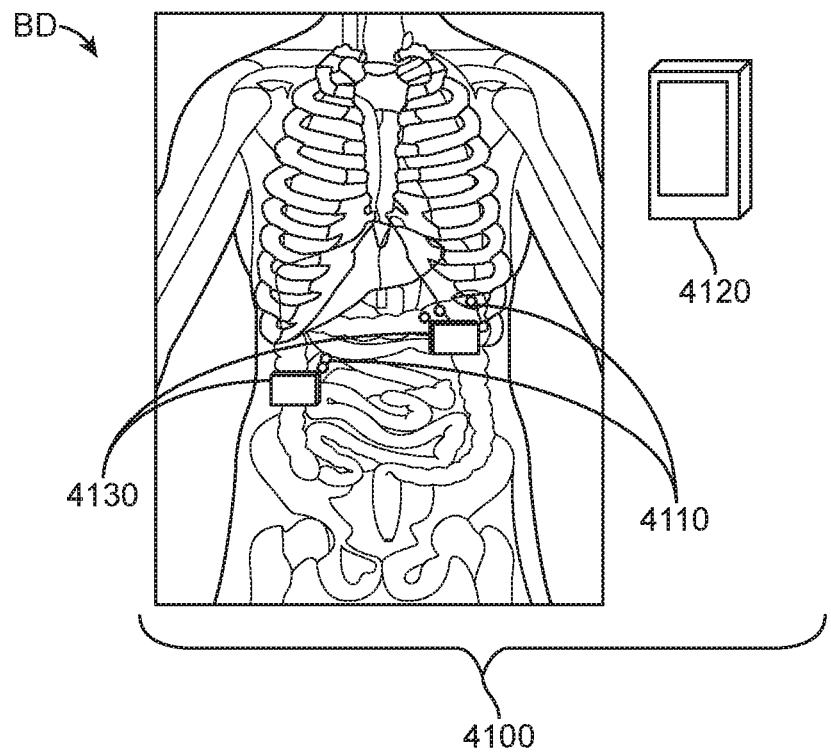
FIG. 36 illustrates an embodiment of an overall system including a needle-injected implantable system to be used with an external system; consistent with the present inventive concepts.
Figure 37:
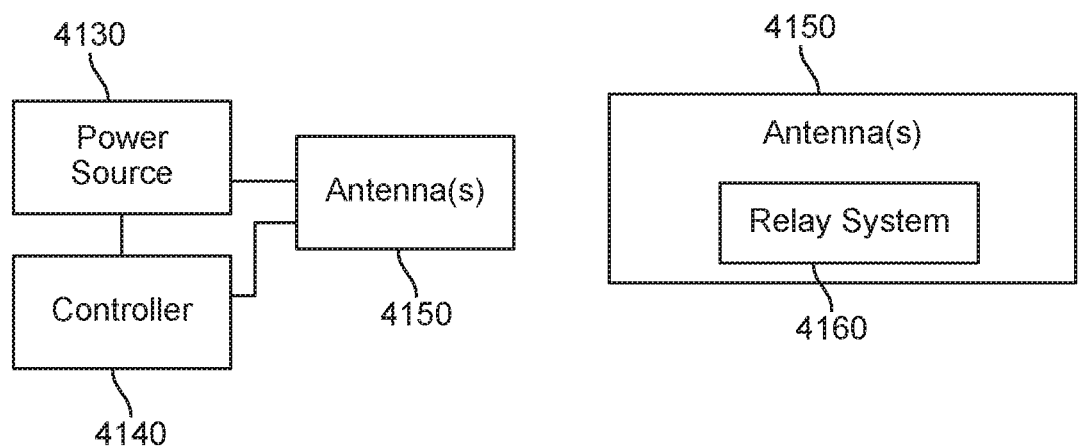
FIG. 37 illustrates a basic system diagram of an implantable system with power harvesting and management, two-way communications, a digital controller, a pulse generator, and an interface for one or more sensors and electrodes; consistent with the present inventive concepts.
Figure 38:
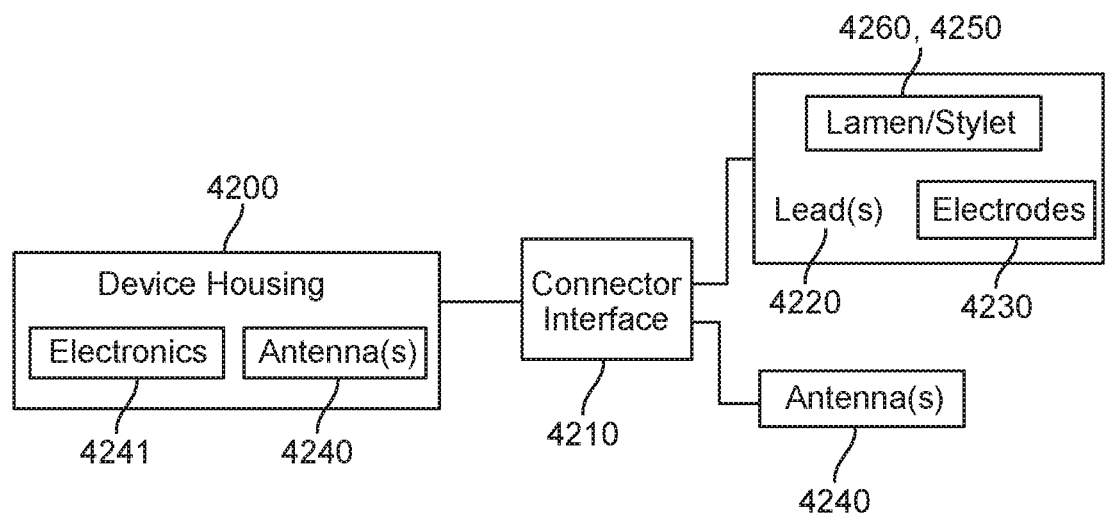
FIG. 38 illustrates a basic block diagram of an implantable system with the ability to receive power and communicate with the external system or other hardware; consistent with the present inventive concepts.

Implantable devices have a limited power budget, which restricts both miniaturization and functionality. Neuromodulation devices can require significant power to provide therapy because of the relatively high voltage and current requirements needed to drive stimulation. For fully wireless devices, the power limitation is typically the design constraint and limits the performance of the device. An overall system 410 of the present inventive concepts is shown in FIG. 36, and is described in more detail in the references incorporated herein. FIG. 36 shows the minimally invasive implantable device 4110 that is controlled and powered from a device external to the body. A basic block diagram of the external device 100 is shown in FIG. 37 and a basic block diagram of the implantable device 4110 is shown in FIG. 38. The external device 4100 can have all its elements integrated into a single component, or it can be divided into several discrete components that are tethered or untethered. Additionally, the overall system 411 can operate with multiple copies of the external devices and/or the internal devices (e.g. multiple discrete external components and/or multiple discrete implantable components) to form a network or system of external and internal devices, respectively. The elements of the system 411 can allow miniaturization to mm and sub-mm sizes while offering the flexibility to operate with different power budgets and offer different features and form factors. These advantages may be partly accomplished by the ability of the implantable device 4110 to interface with different antennas and an on-board intelligent power management sub-system as described above and herein. The implantable device 4110 can include a controller that configures the on-board circuitry, a pulse generator that can produce custom stimulation waveforms to accommodate the intended treatment, and one or more antennas. This pulse generator could control amplitude, timing and frequency, pulse duration, duty cycle, and/or polarity. The small size of the implant 4110 can allow for a minimally invasive implantation process such as with a needle injection system, an endoscope, or a laparoscopic technique as will be described further. The external device 4100 may include one or more transmission antennas that may be placed near the surface of the skin in close proximity to the antenna of the implant 4110, which may be implanted inside the body. This external device 4100 can transfer both power and data to the implantable device 4110, and operates with either batteries or with a wall outlet. The external device 4100 may have a separate communication protocol, such as Bluetooth, for interfacing with computers, smart phones, a handheld device; the Internet; a local area network (LAN); and/or other devices. Data is transferred at speeds up to and exceeding 20 Mbps to accommodate configuration and control of the one or more implantable devices as well as real-time treatment adjustments. Data and/or power can also be transferred to multiple devices (e.g. multiple discrete implantable devices) simultaneously (e.g., power is transferred simultaneously and communications with multiple implantable devices can be done in discrete time slots, as in case of time domain multiple access) and the high-speed of communication allows for several implantable devices to adapt and adjust in real-time. Sensors can be incorporated with the implantable devices and/or external devices and also make use of the high-speed communication for diagnostics or real-time feedback of physiological parameters to inform the doctor or patient of the functionality of overall system 411 (or a component of overall system 411) or to provide patient physiologic information feedback to the overall system 411 to adapt the treatment.

Figure 39:
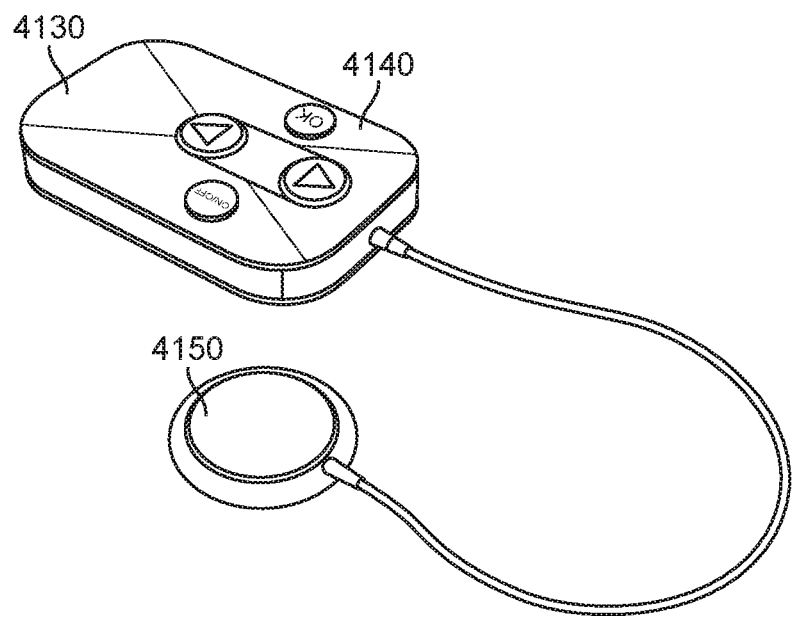
FIG. 39 illustrates an external device with a power source, controller, and tethered antennas; consistent with the present inventive concepts.
Figure 40:
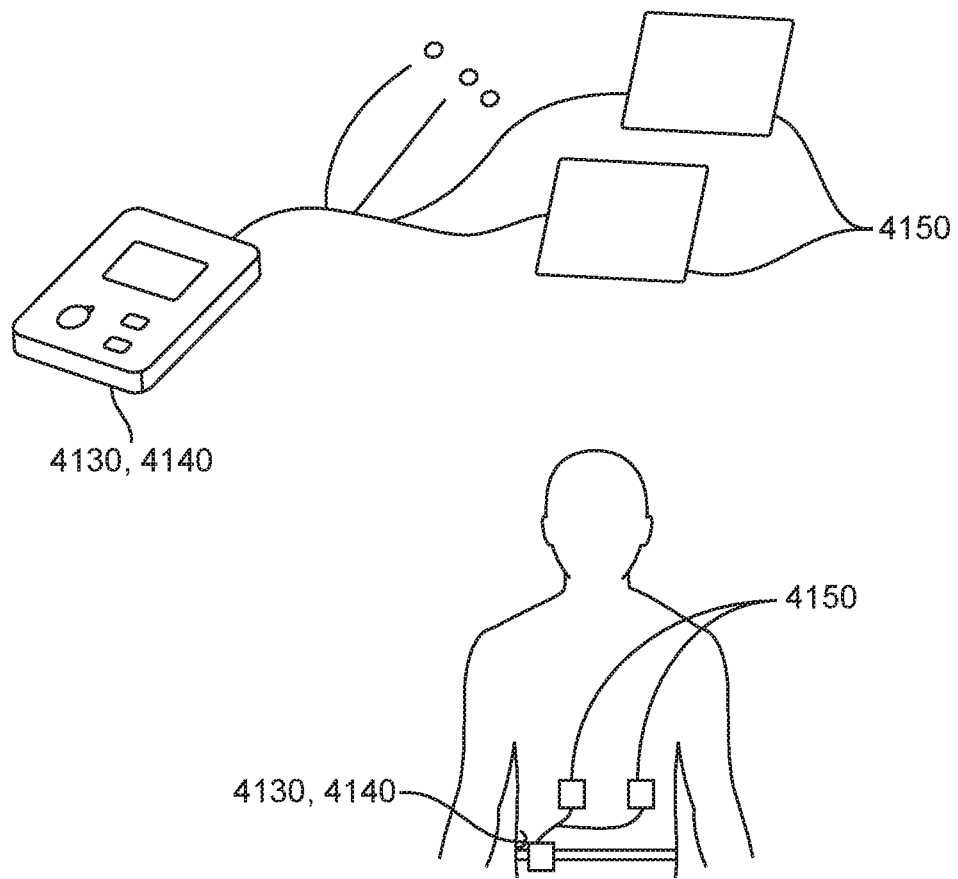
FIG. 40 illustrates an external device with a power source, controller, and one or more tethered antennas; consistent with the present inventive concepts.

The implantable device 4110 is controlled by an external device 4100 that can be designed to accommodate the particular application and its intended use. This external device 4100 can include one or more antennas 4150 for transmitting and receiving RF signals, a controller 4140 for controlling the communications or other operations of the overall system (e.g. therapeutic parameters, neuromodulation parameters, closed-loop adaptation of therapy based on feedback from sensors), and a power source 4130, such as a battery. These external device 4100 elements can be combined into a single discrete component or divided into several components. In some embodiments, a power source 4130 (e.g. battery) and controller are surrounded by a single enclosure, and one or more antennas 4150 are tethered to this enclosure via a wire (e.g. cable or interconnect 4310), as depicted in FIG. 39 and FIG. 40. There, a user interface and/or display may be implemented (e.g. on the enclosure surrounding the power source and controller), allowing the user to view, interact, and/or adapt the operation of the overall system 411. The user interface could comprise button(s), a touchscreen display, knob(s), keyboard, keypad, display, microphone, light, speaker and/or other components configured for user input and/or user output. Depending on the intended use and application of the overall system 411, this user interaction with the system or apparatus can have varying levels of complexity. In these embodiments, one or more antennas 4150 could be attached to the skin directly through an adhesive or attached in close proximity to skin with a belt, band, strap or other attachment element. An enclosure containing power supply 4130 and controller 4140 could be tethered to this antenna and placed in a more comfortable or otherwise convenient location, such as in a pocket or clipped to a belt. The antenna, adhesives, or other attachment elements can be designed to be disposable after several days, weeks, or months of operation. Alternatively, the antenna, adhesives or other attachment elements, or other component of the external device, can be more permanent, lasting years or longer. A battery (or a battery pack) can be charged while in the enclosure, it could be removable from the enclosure to be charged separately, or it could be removable primary cell battery so it can be replaced with another primary cell battery. These battery configurations would allow the user to have multiple batteries for the one external device and charge one battery while the other is in use with the external device.

Figure 41:
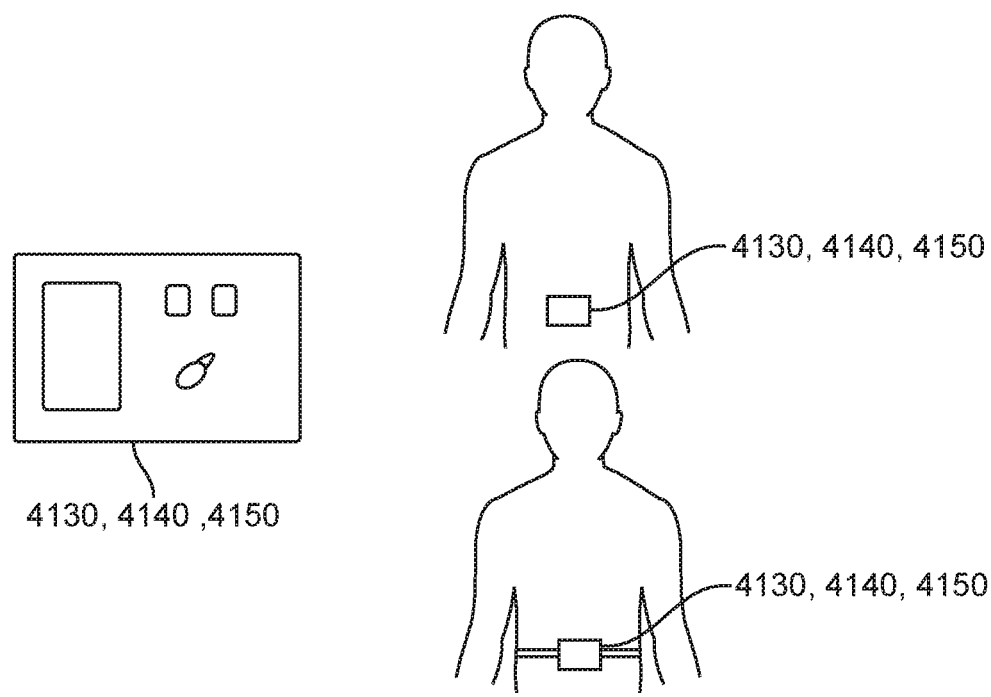
FIG. 41 illustrates an external device with a power source, controller, and antenna integrated in a single enclosure; consistent with the present inventive concepts.

In some embodiments of the external device 4100, a single enclosure surrounds a power supply (e.g. battery) 4130, a controller 4140, and one or more antennas 4150. In these embodiments, the enclosure could be attached directly to the skin through an adhesive or attached in close proximity to the surface of the skin through a belt, band, strap, or other attachment element. An example of these embodiments is depicted in FIG. 41. The user interface could be implemented on the enclosure, allowing the user to view, interact, and/or adapt the operation of the overall system 411. The user interface could comprise button(s), a touchscreen display, knob(s), keyboard, keypad, display, microphone, light, speaker and/or other component configured for user input and/or user output. Depending on the intended use and application, this interaction can have varying levels of complexity. The adhesives or other attachment elements can be separate from the enclosure and can be designed to be disposable after several days, weeks, or months of operation. Alternatively, the adhesives or other attachment elements can be more permanent, lasting years or more. A battery can be charged while in the enclosure, or it could be removable from the enclosure to be charged separately. These battery configurations would allow the user to have multiple batteries for the external device and charge one battery while the other is in use with the external device.

Figure 42:
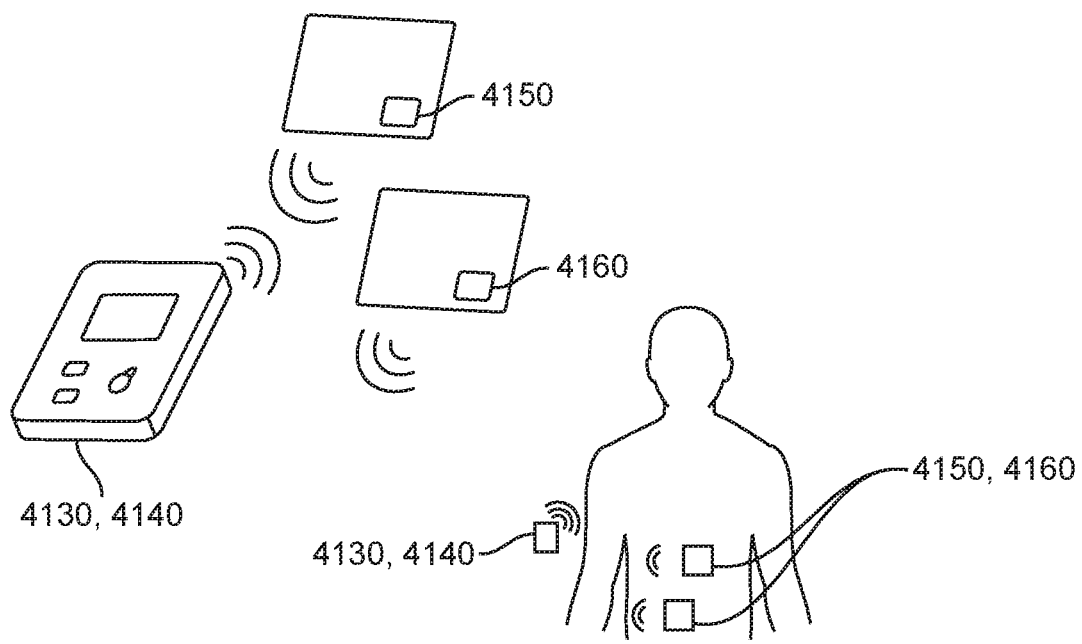
FIG. 42 illustrates an external device with a power source, a controller, and one or more untethered antennas with each antenna attached to a power source and a communications relay; consistent with the present inventive concepts.
Figure 43A:
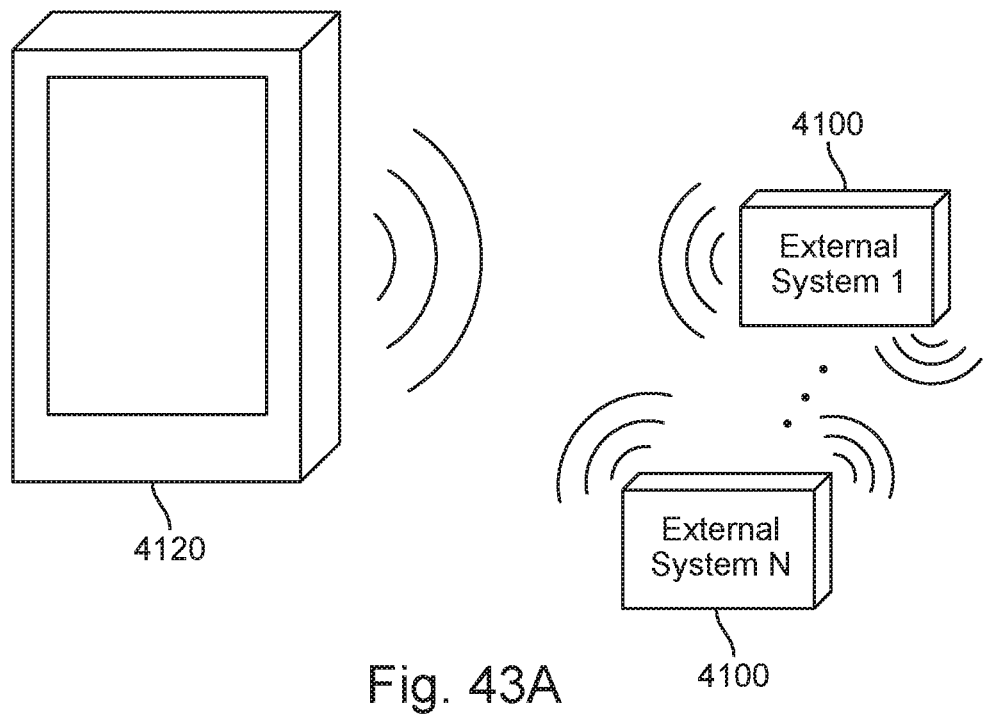
FIGS. 43a, 43b, 43c, and 43d illustrate multiple external devices operating in a network with a handheld controller; consistent with the present inventive concepts.
Figure 43B:
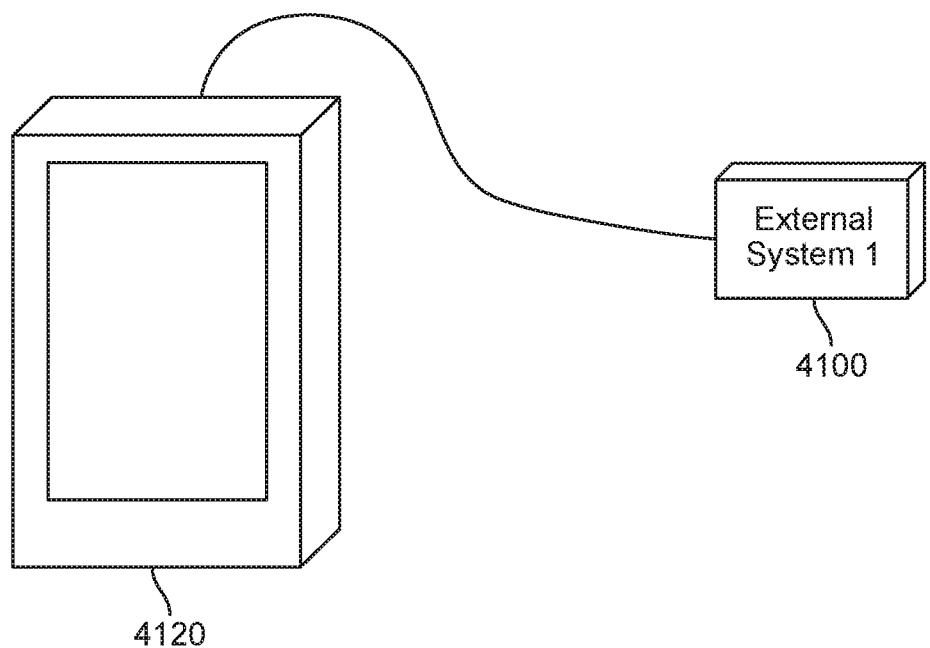
Figure 43C:
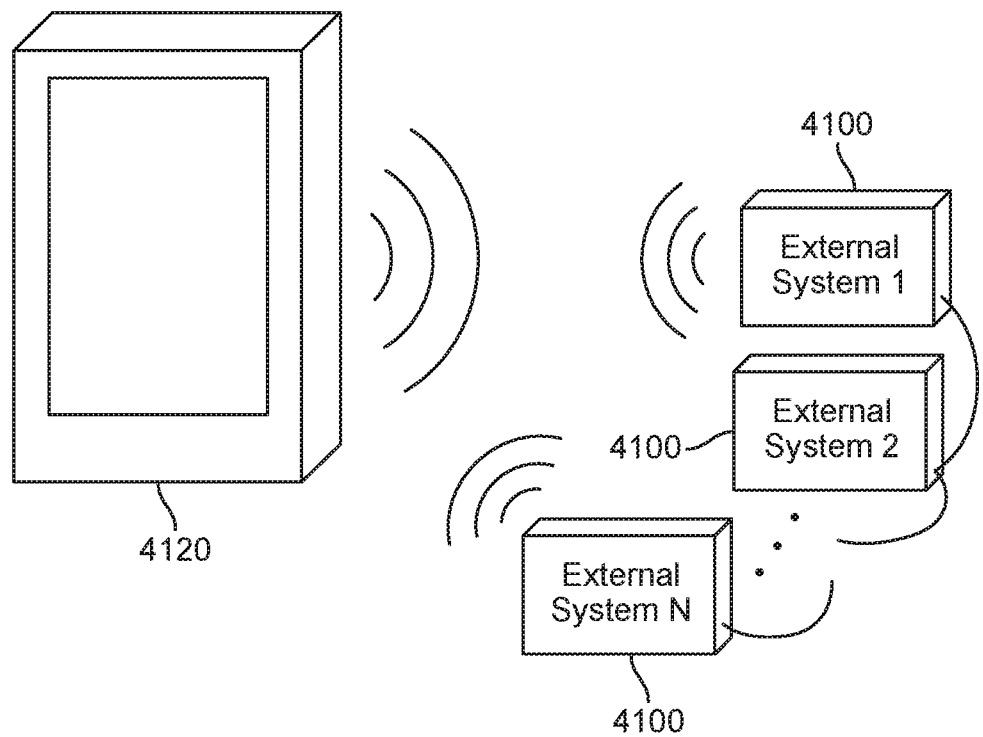
Figure 43D:
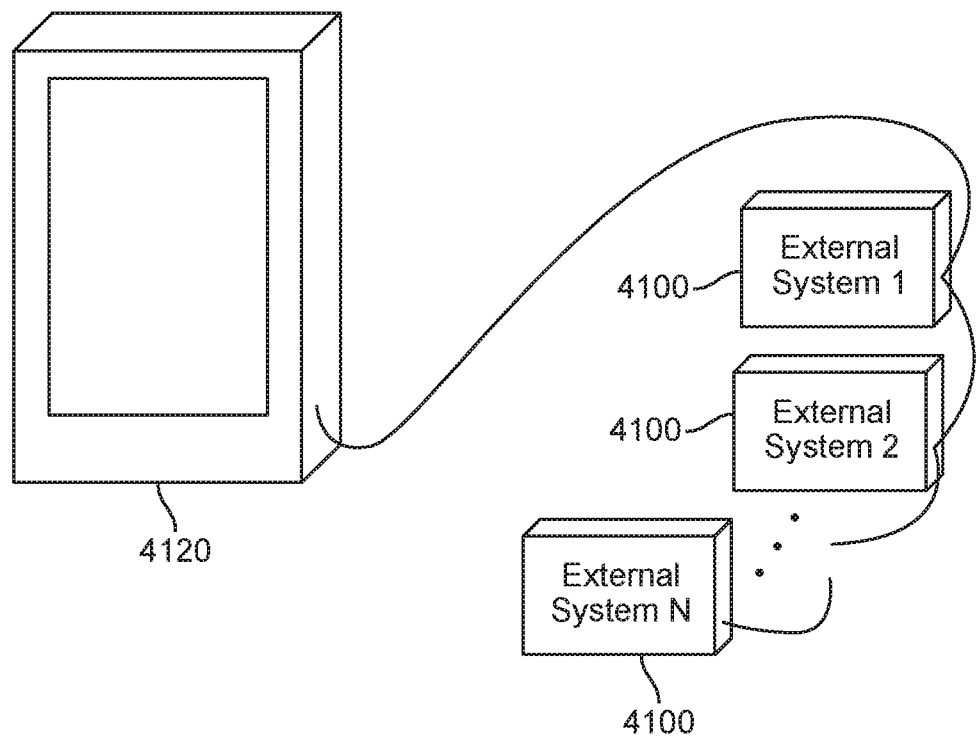

In some embodiments of the external device 4100, a power supply (e.g. battery) 4130 and controller 4140 are surrounded by one enclosure, and one or more antennas 4150, each attached to a relay or communication electronics 4160, have the ability to wirelessly communicate with the controller, such as is depicted in FIG. 42. This wireless communication can be accomplished with Bluetooth, WiFi, ZigBee, Qualcomm 2net, MICS, ISM, WMTS, MedRadio, MNN, MBAN, cellular communications, and/or RFID communications. This arrangement can also be used to configure a network with multiple external devices, and this is depicted in FIG. 43a. In these embodiments, the user interface could be implemented on the enclosure with the power source 4130 and controller 4140 that can wirelessly communicate with the antenna, allowing the user to view, interact, and/or adapt the operation of the overall system. The antenna can have its own power source (e.g. replaceable, swappable, or permanent, as described hereinabove) and communication electronics 4160. The user interface could comprise buttons, a touchscreen display, knob(s), keyboard, keypad, display, microphone, light, speaker and/or other component configured for user input and/or user output. Depending on the intended use and application, this interaction can have varying levels of complexity. With these embodiments, the antenna could be attached to the skin directly through an adhesive or attached in close proximity to skin with a belt, band, strap or other attachment element. The enclosure containing a power source 4130 and controller 4140 could be placed in a more comfortable or otherwise convenient location within the range of the wireless communications to this antenna, such as in a pocket or clipped to a belt. The antenna, adhesives, or other attachment elements can be designed to be disposable after several days, weeks, or months of operation. Alternatively, the antenna, adhesives, and/or other attachment elements can be more permanent, lasting years or longer. Batteries can be charged while in their respective enclosures, or they can be removable from their respective enclosures to be charged separately. These battery configurations would allow the user to have multiple batteries for the external device and charge the extra batteries while the external device is in use.

Figure 44:
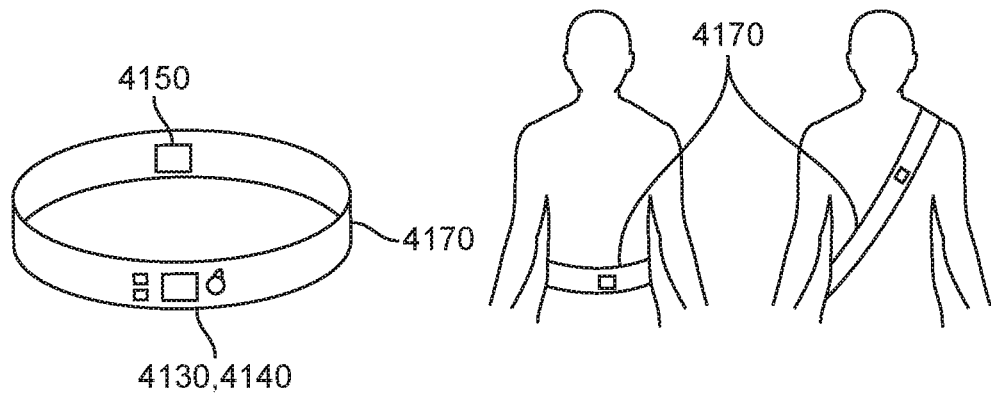
FIG. 44 illustrates an external device with a power source, controller, and one or more antennas integrated into an attachment assembly; consistent with the present inventive concepts.

In some embodiments of the external device 4100, a power supply 4130 (e.g. a battery), a controller 4140, and one or more antennas 4150 are all integrated into an attachment assembly 4170 that may include a belt, band, strap, and/or other article of clothing. In this embodiment, the antenna would be attached in close proximity to the surface of the skin at a designated location on the attachment assembly 4170. This embodiment is depicted in FIG. 44. The user interface can be positioned in a convenient location on the attachment assembly 4170, allowing the user to view, interact, and/or adapt the operation of the overall system 411. Alternatively or additionally, the user interface can be untethered handheld device 4120 for improved convenience of controlling the overall system 411, wirelessly coupled to communicate with the rest of the external system. The user interface could consist of button(s), a touchscreen display, knob(s), keyboard, keypad, display, microphone, light, speaker and/or other component configured for user input and/or user output. Depending on the intended use and application, this interaction can have varying levels of complexity. Elements of the attachment assembly 4170 can be designed to be disposable after days, weeks, or months of operation. A battery can be charged while in the external device(s), or it could be removable from the external device(s) to be charged separately. These battery configurations would allow the user to have multiple batteries for the external device(s) and charge one battery while the other is in use with the external device(s).

Figure 45:
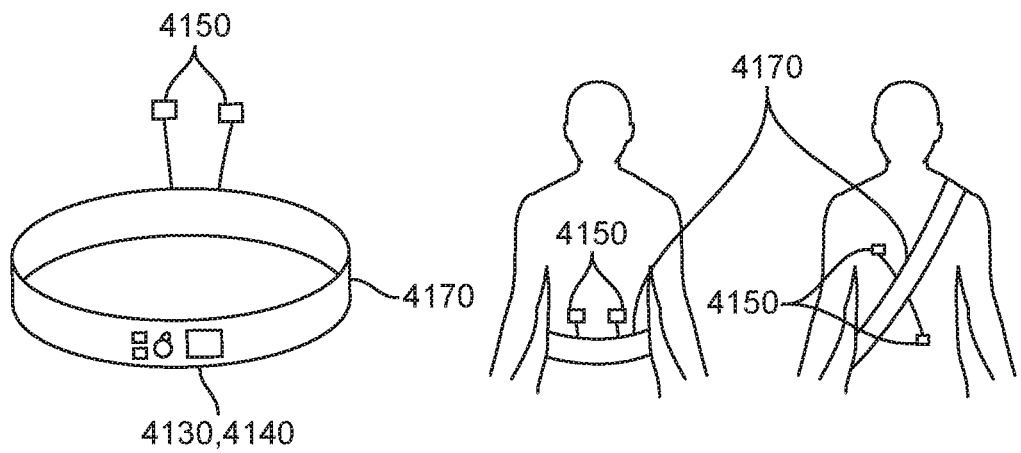
FIG. 45 illustrates an external device with a power source and controller integrated into an attachment assembly with and one or more tethered antennas; consistent with the present inventive concepts.

In some embodiments of the external device 4100, a power supply 4130 (e.g. a battery) and a controller 4140 are integrated into an attachment assembly 4170 that can include a belt, band, strap, or other article of clothing, and one or more antennas 4150 are separately placed in the desired position on the body with an adhesive or other attachment element. The one or more antennas 4150 can be tethered with a wire or untethered and communicate with the controller 4140 through a wireless communication method. This embodiment is depicted in FIG. 45. This system may allow the patient to comfortably adjust the bulk of the components without affecting the antenna placement. The user interface could be implemented in a convenient location on an enclosure of the external device 4100 or through a separate wireless controller, allowing the user to view, interact, and/or adapt the operation of the overall system 411. The user interface could comprise buttons, a touchscreen display, knob(s), keyboard, keypad, display, microphone, light, speaker and/or other component configured for user input and/or user output. Depending on the intended use and application, this interaction can have varying levels of complexity. Elements of the attachment assembly 4170 and/or antenna 4150 can be designed to be disposable after days, weeks, or months of operation. The battery can be charged while in the external device(s), or it could be removable from the external device(s) to be charged separately. These battery configurations would allow the user to have multiple batteries for the external device(s) and charge one battery while the other is in use with the external device(s).

Figure 46:
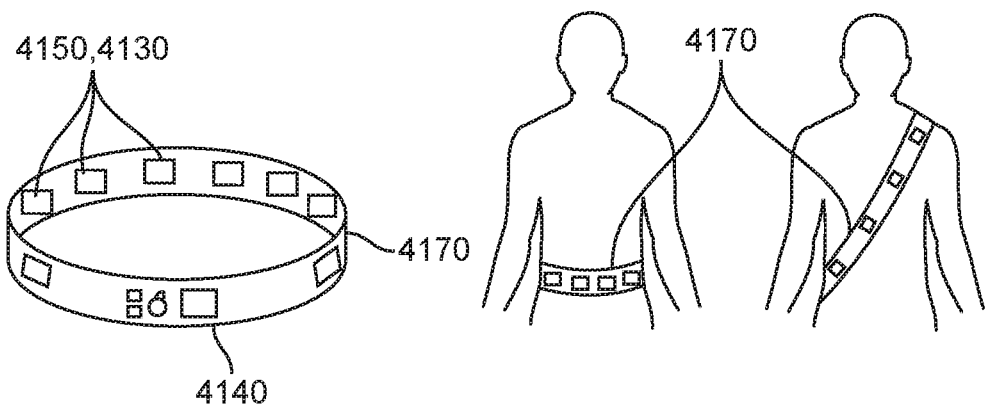
FIG. 46 illustrates an external device integrated into an attachment assembly with one or more distributed antennas and/or distributed power sources; consistent with the present inventive concepts.
Figure 47:
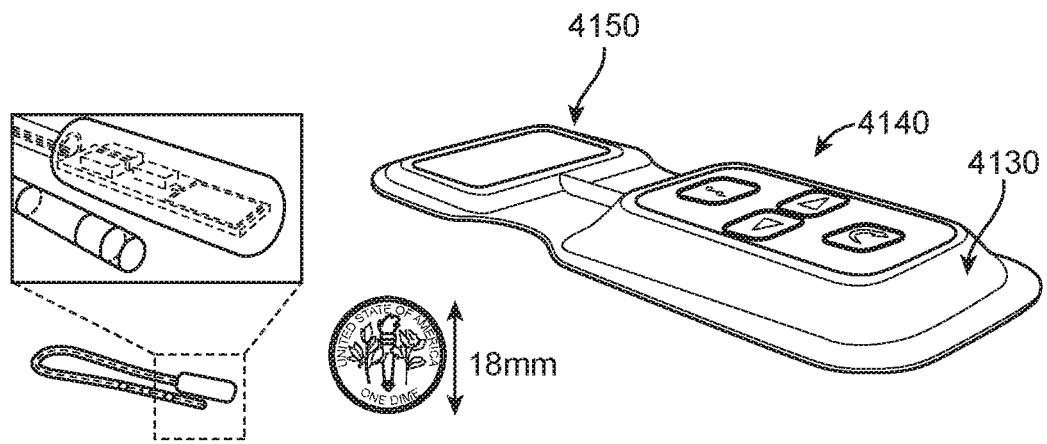
FIG. 47 illustrates an external device with a power source, controller, and antenna next to an implantable device.

In some embodiments of the external device 4100, a power supply 4130 (e.g. a battery) and a controller 4140 are integrated into an attachment assembly 4170 that can include a belt, band, strap, or other article of clothing, and antennas 4150 are interspersed around this attachment assembly 170 to maximize the coverage area of the transmitted signals. This embodiment is depicted in FIG. 46. This configuration would allow the patient to comfortably adjust the bulk of the components while maintaining an effective wireless link with the implantable device 4110. Additionally, this external device 4100 can operate with multiple implantable devices 4110 in different locations. The one or more distributed antennas 4150 can all be activated or a subgroup comprising one or more antennas 4150 can be selectively activated to optimize wireless link gain efficiency while saving power consumption. This optimization can be performed based on feedback from one or more implantable devices 4110. Such link gain feedback and adjustment algorithm is described in more detail in provisional patent application No. 62/053,085 titled "Method and Apparatus for Operation with Minimally Invasive Neuromodulators," filed on Sep. 19, 2014. The user interface could be implemented in a convenient location on the external device 4100 or through a separate wireless device, allowing the user to view, interact, and/or adapt the operation of the overall system 411. The user interface could comprise buttons, a touchscreen display, knob(s), keyboard, keypad, display, microphone, light, speaker and/or other component configured for user input and/or user output. Depending on the intended use and application, this interaction can have varying levels of complexity. Elements of the attachment assembly 4170 and/or antenna can be designed to be disposable after days, weeks, or months of operation. A battery can be charged while in the external device(s), or it could be removable from the external device(s) to be charged separately. These battery configurations may allow the user to have multiple batteries for the external device(s) and charge one battery while the other is in use with the external device(s). As an additional variation to this embodiment, multiple power supplies 4130 (e.g. multiple batteries) could also be distributed along the attachment assembly 4170 (i.e.

positioned at different locations of the attachment assembly), allowing additional power to be stored with a more comfortable or otherwise convenient configuration. With distributed batteries, the thickness of the attachment assembly 4170 could be more uniform and the weight distribution along the attachment assembly 4170 could be more balanced.

In some embodiments of the external device 4100, one or more antennas 4150 can be constructed on a flexible substrate that conforms to the surface of the skin and/or one or more antennas 4150 can be printed on the skin directly using epidermal electronics. These antenna configurations offer additional convenience to the patient without sacrificing performance. One or more antennas 4150 comprising printed epidermal electronics can be electrically connected to a separate enclosure including a power supply 4130 (e.g. a battery) and a controller 4140. Alternatively or additionally, one or more antennas 4150 comprising printed epidermal electronics can wirelessly communicate with a controller 4140, such as is described hereabove. These skin-attached and/or skin-printed antennas may need to be reapplied or replaced periodically, which could be accomplished by either the doctor or the patient.

In some embodiments of the external device, multiple antennas can be used in the place of a single antenna. These antennas could either be tethered or untethered (e.g. tethered or untethered to a controller 4140 and/or external power source 4130). While a single antenna of the external device 4100 can power multiple implants in its relatively close proximity, multiple antennas can be configured to allow implants at different sites to be operated from a single external device 4100. These external device antennas can operate in coordination (e.g. transmit power and/or communication simultaneously to implants), can operate as communication relays (e.g. relay received commands from the controller to one or more implantable devices and from one or more implantable devices to the controller while powering one or more implantable devices due to relay's proximity to one or more implantable devices), and can function as part of a network. Examples of this network are shown in FIG. 43.

In some embodiments of the external device 4100, the entire external device 4100 can be designed to be disposable and replaced over the course of days, weeks, months, or years. This disposable device approach can offer additional convenience to the patient by minimizing the required maintenance for the duration of use. Alternatively, one or more portions of the external device 4100 can be disposable while one or more other portions are reusable. If the antenna 4150 is separate from the controller (either tethered or untethered), it could be designed in a disposable package that simplifies its use for the patient while maintaining high performance for the duration of use, such as when a power supply such as a rechargeable battery and/or the controller are reusable.

In some embodiments of the external device, the antenna can include elements for tuning its position, orientation, and/or operating environment to achieve better performance. This tuning can occur at large or small scales, and the adjustments can be automated or performed manually. Information about communication and/or power links, overall system 411 performance, and/or overall system 411 characteristics can be provided to assist this tuning for either the automatic or manual method.

Figure 51:
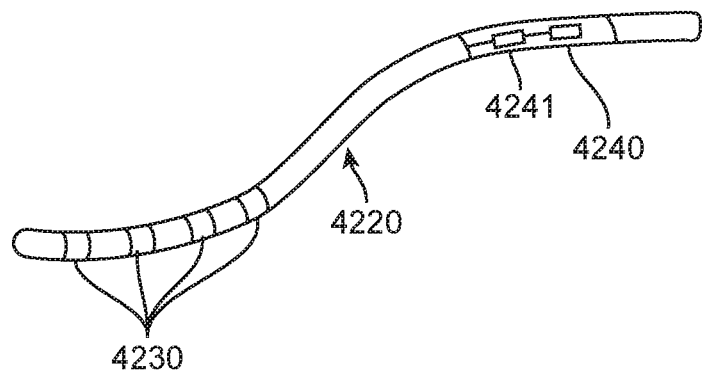
FIG. 51 illustrates an implantable device integrated into a lead with antennas and electrodes; consistent with the present inventive concepts.
Figure 52:
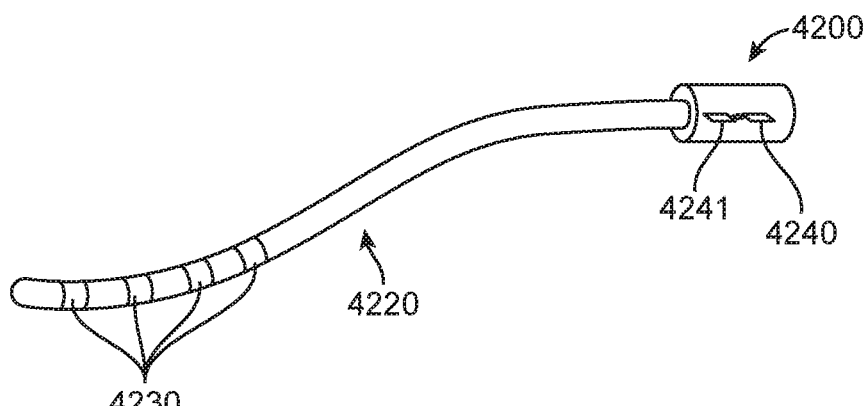
FIG. 52 illustrates an implantable device with a cylindrical encapsulated housing, a lead, electrodes, electronics, and an antenna; consistent with the present inventive concepts.
Figure 53:
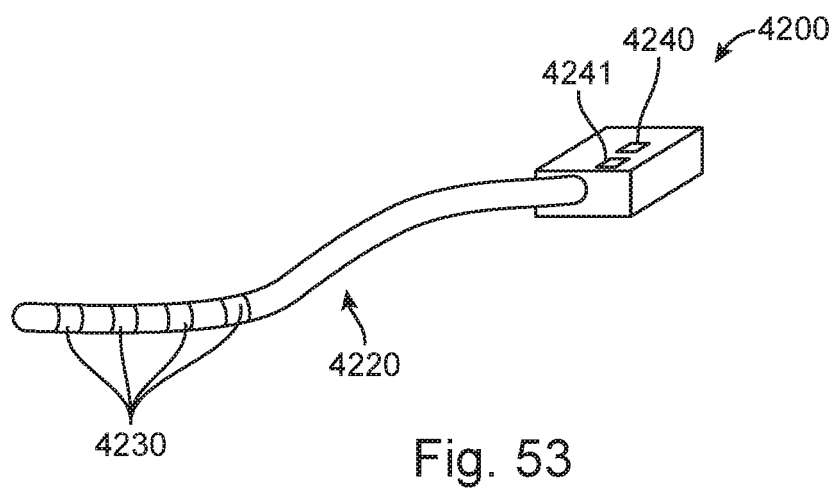
FIG. 53 illustrates an implantable device with a rectangular encapsulated housing, a lead, and electrodes; consistent with the present inventive concepts.

The implantable device 4110 can also comprise several form factors depending on the intended use and the needs of the indication. In some embodiments, the implantable device 4110 comprises: one or more housings 4200, one or more antennas 4240, one or more electrodes 4230, energy harvesting circuit, energy management circuit, one or more energy storage elements, a pulse generator, a controller, stimulation current driver, one or more sensors, communications circuits for receiving and sending data, calibration circuits, startup and power-on-reset circuits, memory circuits, timing circuits, and other auxiliary circuits, such as a matching network, that are necessary for proper implantable device operation and a particular application (collectively electronics or circuits 4241); and combinations of these. Different patients and/or therapies may require different implantation sites, different electrode placement and/or configurations, different stimulation waveforms, and/or different numbers of stimulation channels (e.g. each including independent energy delivery circuitry for one or more electrodes). One embodiment of the implantable device 4110 incorporates circuits 4241, antenna(s) 4240 and/or other elements into an implantable lead 4220, which includes one or more electrodes 4230 for interfacing with tissue. An example of this embodiment is shown in FIG. 51. The electronics and/or antenna in the lead can be sealed (e.g. hermetically or otherwise sealed to prevent contamination from passing into and/or out of an enclosure), for long-term implanted use. In this embodiment, an antenna 4240 can be distributed along the length of the lead to increase its radar cross-section and/or alter its inductance (which alters the resonance). The length of a dipole antenna or the long dimension of a loop antenna could be changed by several centimeters, which increases received power in proportion to the change in length and inductance increases in approximate proportion to the length as well. The lead 4220 itself could include a variable number of connections depending on the treatment (e.g. the number of stimulation channels that are necessary). In some embodiments, the implantable device can support 2, 4, 8, 16, 32, or more channels as any treatment can require (e.g. between one and 64 electrodes). Additionally, the entire lead can be designed to be MRI-compatible by minimizing or eliminating induced currents and/or the use of magnetic materials or ferromagnetic materials. In some embodiments of MRI-compatible leads 4220, the lead 4220 can have conductive shield throughout the lead. In other embodiments, the lead 4220 can have heat spreading elements built into the lead 4220. In yet other embodiments, reed switches or other relays or switches can be used to disconnect electrodes 4230 from the interconnect 4310, to minimize or prevent MRI-induced current from flowing through tissue. The reed switch or other relays can be remotely activated prior to MRI use or by MRI fields and can be de-activated to return the implantable device to normal operating condition after MRI use.

In some embodiments of the implantable device 4110, one or more functional elements (e.g. electronic components) are enclosed in a housing 4200 (e.g. a sealed housing) on one end of a lead 4220. This housing can have a variety of shapes including cylindrical, rectangular, elliptical, spherical, or an irregular shape adapted to the specific requirements of the overall system 411 and/or treatment. Embodiments of this housing are shown in FIG. 48, FIG. 49, FIG. 50, FIG. 51, and FIG. 52. This housing 4200 can be sealed (e.g. hermetically sealed) if desirable with feedthroughs 4201 and/or wired or wireless connector interface 4210 for AC coupled channels (such as RF inputs for the antenna), stimulation channels, and/or sensors. The electrode 4230 can have a variable number of connections depending on the treatment and the number of stimulation channels that are necessary. The device 4110 can support 4, 8, 16, 32, or more channels as any treatment can require (e.g., between one and 64 channels). Additionally, the entire implantable device 4110 including the housing 4200 and the lead 4220 can be designed to be MRI-compatible by minimizing or eliminating induced currents and/or the use of magnetic materials or ferromagnetic materials and as described hereinabove.

In some embodiments of the implantable device 4110, a lead 4220 is integrated into the implantable device 4110 and/or is attached to the implantable device 4110. This lead 4220, with or without an additional housing 4200, can be constructed to include a lumen 4260 to aid with the implantation procedure. A stylet 4250, guide wire and/or other insertable filament (hereinafter "stylet") can be used with this lumen 4260 during the implantation procedure. These stylets 4250 can have bends or curves to assist with the guidance process, and in particular the tip portion (i.e. distal portion) of the stylet 4250 can be straight or curved with a variable stiffness. This stylet configuration allows the lead 4220 to have a more controllable stiffness and therefore allows the implantation to more precisely controlled and guided. After the lead 4220 is positioned in the desired location, the stylet 4250 can be removed. For additional convenience, the stylet 4250 can be prepackaged inside the lumen 4260 of the lead 4220 and/or implantable device 4110, which will save time in the overall procedure.

In some embodiments of the implantable device 4110, the stiffness and/or shape of one or more portions of the implantable device 4110 can have additional control during implantation. This stiffness and/or shape control can be accomplished through the use of shape-memory alloys, which can be reshaped with changes in temperature (or other control parameter, such as applied current or voltage). These and other shape and/or stiffness controllable materials allow for simplified and/or improved manipulation and placement during implantation and post-implantation of one or more portions the implantable device 4110. The implantable device 4110 (or a portion thereof) could be implanted in a configuration that simplifies the procedure, and then reshaped into a new configuration post-implantation. Alternatively, one or more portions of the implantable device could be surrounded by a sheath 4270 of a desired stiffness during implantation, and the sheath could be removed after the implantable device 4110 is placed in the desired position. These sheaths could incorporate bends or other curves (e.g. in a resiliently biased curved portion) to further improve the controllability and guidance of one or more portions of the implantable device 4110 as it is implanted.

Figure 55:
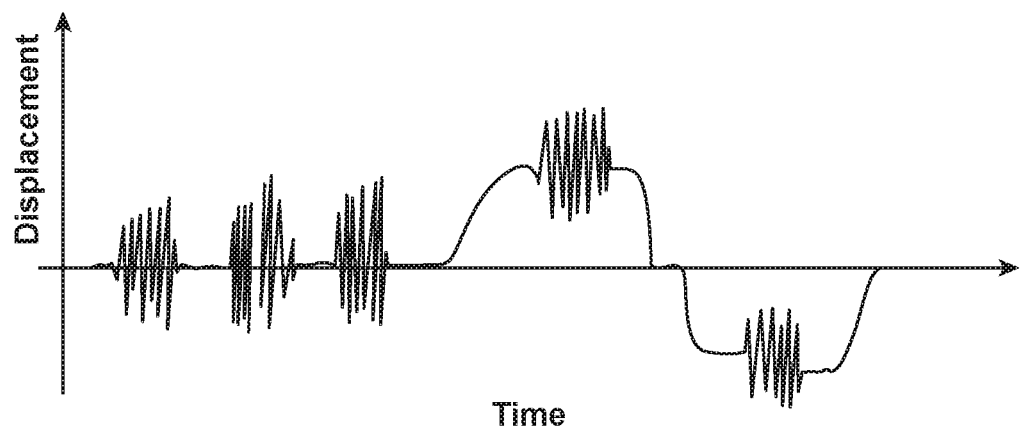
FIG. 55 illustrates example waveforms for mechanical motion that can modulate tissue; consistent with the present inventive concepts.

In some embodiments of the implantable device 4110, the device 4110 is capable of mechanically interacting with tissue, inducing motion in the surrounding tissue, moving, rotating, squeezing, expanding, and/or repositioning itself. This motion could be in the form of vibrations, impulses, linear displacements, and/or angular displacements. These motions could assist (i.e. used in conjunction with) and/or replace electrical neuromodulation of nerves, muscles, and/or other tissues. The equivalent of a stimulation pulse could be applied by a specific duration of vibration and/or displacement, including a displacement offset with vibrations applied in addition. This stimulation delivery could be performed at both low and high frequencies ranging from 1 Hz to 50 kHz and with controllable duty cycles. Additionally, the waveform can be custom designed or irregular in shape to produce the most effective stimulation. A depiction of possible mechanical motion waveforms are shown in FIG. 55. The motion itself can be accomplished with several types of forces including electromagnetics forces, magnetic forces, piezoelectric forces, thermal expansion forces, and combinations thereof. These force methods can be fully enclosed within the device housing 4200, and can apply the mechanical forces without electrical contact with tissue. If used with a lead 4220, the lead body and/or tip can incorporate one or more mechanical interfaces designed for the specific method of force generation. The lead 4220 could be anchored or sutured to the specific site to ensure the precision of long-term treatments. The lead 4220 could also incorporate methods of adjusting position over time to reposition the device and/or interface at the desired location or to improve comfort of the implantable device.

Figure 54:
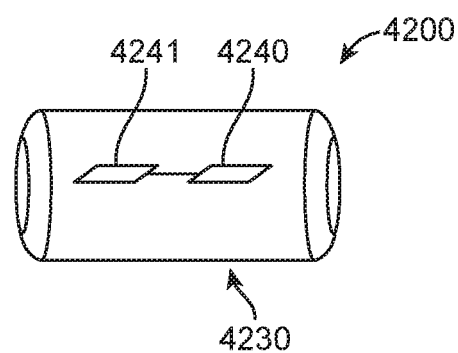
FIG. 54 illustrates an implantable device with an encapsulated housing and feedthroughs for the electrodes with no lead; consistent with the present inventive concepts.
Figure 56:
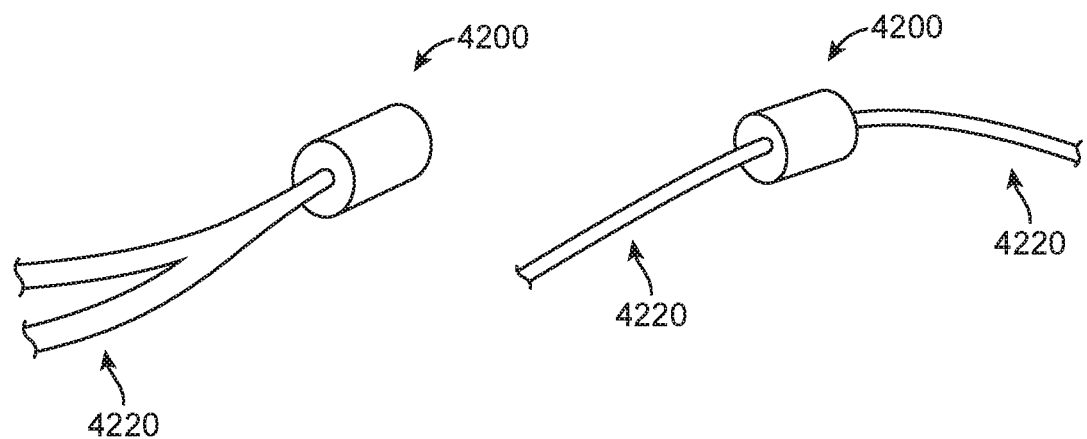
FIG. 56 illustrates a device housing with bifurcated or multiple leads; consistent with the present inventive concepts.
Figure 57:
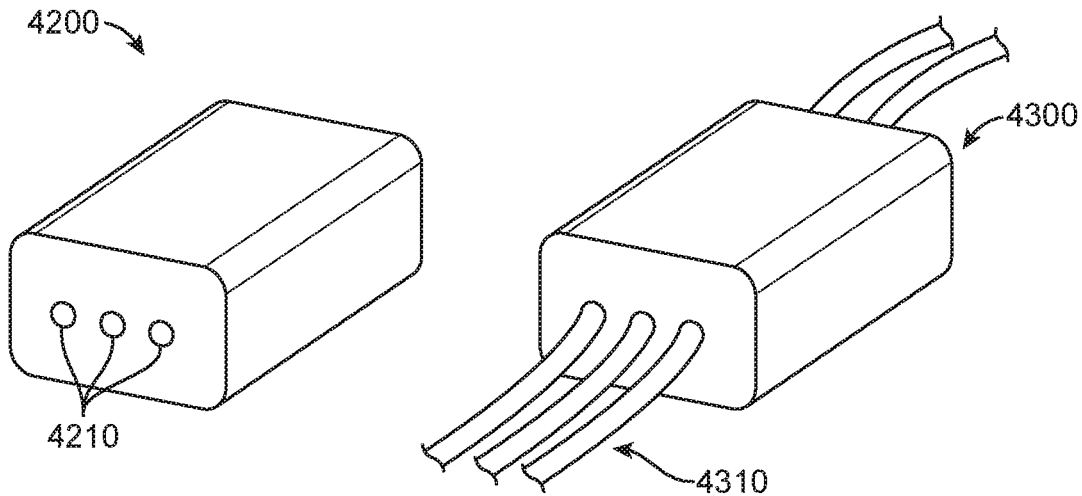
FIG. 57 illustrates a housing with multiple connection interfaces as well as a connection hub; consistent with the present inventive concepts.

In some embodiments of the implantable device 4110, different lead 4220 and/or electrode 4230 configurations can increase the flexibility and versatility of the treatment. Leads can be cylindrical in shape with a variable number of electrodes, including 4, 8, 16, or 32 connections (e.g. between one and 64 connections) as well as other numbers of connections. The electrodes can source and/or sink variable currents and can have adjustable polarity. By controlling the voltages and polarity at the different points of contact, the current can be steered or otherwise directed in certain ways through tissue. This directing of current can be important for targeting specific tissue sites while avoiding stimulation of certain other tissues. The leads 4220 and/or electrodes 4230 could also be configured in the shape of a paddle electrode, in which the electrical connections are arranged across a flat or curved surface. The number of connections could be much larger in a smaller area with this arrangement, including 1 to 64 or more connections depending on the intended use. In spinal cord stimulation, additional stimulation channels and the ability to control or direct current can precisely target the specific nerves experiencing pain while minimizing stimulation to surrounding tissues. In peripheral nerve and/or peripheral field stimulation, multiple leads working in a coordinated way with controllable stimulation channels, polarity, and drive currents offer flexibility in the overall coverage area and enable cross-talk among one or more leads 4220 and/or electrodes 4230. The patterns of placement of these leads 4220 also can influence the coverage of the neuromodulation, and placing electrodes 230 10-50 cm apart across the back can offer effective treatment outcomes. Additionally, placing the electrodes 4230 in a square, rectangular, diamond, circular, elliptical, regular, and/or irregular pattern across the back can also improve coverage of the modulation. A single implantable device 4110 can support multiple leads that are either integrated together or connected as needed. These leads 4220 could bifurcate from the implantable device 4110 and be guided to different locations within the body. Alternatively, the implantable device 4110 could have one or more connection interfaces for other implantable devices 4110, housings 4200, leads 4220, and/or electrodes 4230. Examples of possible arrangements of a device with multiple leads are shown in FIG. 56. These leads 4220 can be coordinated from a single implantable device 4110, or leads 4220 from separate implantable devices 4110 can be coordinated together to achieve the desired result. A connection hub 4300 can also be used to connect together multiple implantable devices 4110 and/or multiple leads 4220 (e.g. multiple leads connected to one or more controllers). These connection hubs 4300 themselves could also be connected to additional connection hubs 4300 to scale the overall system 411 to accommodate additional leads 4220. In one implementation of a connection hub 4300, the hub acts as a binary splitter, doubling the number of potential connection interfaces with each stage of hubs. An example of a housing with one or more connections and a connection hub 4300 is shown in FIG. 57. Leads 4220 and/or implantable devices 4110 could also be connected end to end to accommodate a variable number of leads 4220 and/or electrodes 4230 and additional separation distance of the stimulation sites. For some treatments, it may be necessary to place electrical connections very precisely at specific nerve sites. The device 4110 can incorporate microelectrodes, which are small, independently positioned electrodes that are precisely placed and connected to desired tissue. These electrodes can be wrapped around the site and/or anchored in close proximity of the site. These microelectrodes can protrude from a lead 220, the implantable device 4110, or the device housing 200. Each microelectrode can be independently controlled, and a set of microelectrodes can be coordinated to offer a better treatment. For stimulation of the dorsal root ganglion and many other specific tissues, it can be very important to precisely apply stimulation to avoid stimulating other nearby nerves or tissues. In some cases, the device housing 200 itself can include feedthroughs that directly connect to the desired tissue. An example of this setup is shown in FIG. 54. The device housing 4200 can include one or more connections depending on its size and the feedthrough technology used. Some specific embodiments of microelectrodes and tissue interfaces are described in U.S. Provisional Patent Application #62/015,392, titled "Methods and Apparatus for Neuromodulation Treatments of Pain and Other Conditions," filed on Jun. 21, 2014.

In some embodiments of the implantable device 4110, additional design features to improve MRI compatibility can be incorporated, such as an MRI effect reducing assembly as described herein. The primary concerns associated with MRI compatibility may involve the forces applied to materials by the magnetic field and induced currents in the device. In most embodiments, materials that experience forces in a magnetic field will not be part of the implantable device 4110 or will be minimally used so as not to cause issues. To mitigate the effects of induced currents, heat sinks and/or heat spreaders can be included, shielding can be applied to the implantable device 4110, the lead 4220, and/or any long wires or conductors in the implantable device 4110, and/or the addition of active or passive shorts or other methods of diverting current (e.g. near the lead tips). Heat spreading can be accomplished by using materials with high heat conduction (e.g. via a high heat conduction element) in the areas where heating is most prevalent. A short can be introduced by a reed switch or a mechanical switch that is activated before and/or during MRI use. Additionally, other parallel electrical connections or current diversions can be introduced by mechanical switches, active methods, or passive methods to disperse current and mitigate harmful effects on tissue.

In some embodiments of the implantable device 4110, additional design features are incorporated in the leads 4220, electrodes 4230, and/or other electrical connections to reduce resistance and/or power consumption. This reduction can be accomplished with large wires, multiple wires in parallel for a single connection, and/or shorter wires/distances from the stimulator to the stimulation site. Lower resistance materials can also be used to reduce resistance, and electrode coatings, such as platinum, iridium, gold, alloys of these metals, such as $Pt_x/Ir_{1-x}$, and other metal alloys, and/or carbon nanotube coating, can improve the connection with tissue and reduce the overall impedance of the connection. Multiple channels can also coordinate to reduce the overall need for stimulation, which can also reduce the electrical current required for a desired therapy.

The implantation procedure can vary with indication. However, regardless of the indication, an implantable device 4110 generally should be delivered to a location inside of a human body as quickly and as safely as practical. The specific location is determined based on indication, patient-specific conditions and preferences, anatomy, origin of pathology, physician experience and preferences, and other variables in each particular case. In order to accommodate some of these variables and various device embodiments, the implantation procedure can be assisted with standard tools that are commonly used in the art. In some embodiments however, novel, customized tools are used for implantation of one or more portions of the implantable device.

For example, when implanting a lead for spinal cord stimulation, common tools, techniques, and procedures can greatly simplify the process. Common tools used for lead implantation are: anchors, extensions, needles (~15 gauge, epidural, curved or modified Tuohy), stylets (with bent tip between 10-30 degrees, straight, short, soft, hard), tunneling tools (rods, tips, tube), and others. Also, customized tools or tools adapted from other indications can be used to improve implantation procedure and give operating physicians additional flexibility and options. For example, insertion tools can be used in place of a needle to guide lead 4220 implantation. Example of an insertion tool that can be used is described in U.S. Pat. No. 8,452,421 B2 "Lead Insertion Tool," which is designed for cochlear implant lead insertion, but can be adapted for use in other indications, such as spinal cord stimulation lead implantation. In one embodiment, a lead would be pre-loaded with a most commonly used stylet 250 in a package or kit. The operating physician would use a supplied insertion tool or a needle. The rough procedure for lead implantation for SCS is outlined in the following steps:

1. An incision is made at the lead insertion (lead entry) place to the depth of subcutaneous fascia.

2. Insert supplied needle or insertion tool using a paramedical approach and using imaging modality to guide the insertion. Imaging modality, such as fluoroscopy can be used to guide the insertion. Insert the needle into the epidural space at the appropriate angle until some resistance is encountered from the ligamentum flavum. Preferably, the placement of a lead is not at midline but to either side of the midline because the ligament or spinous process movement can damage the lead over time. The needle or insertion tool should be inserted using a shallow needle-insertion angle (<45°) into the epidural space to reduce the risk of lead damage.

3. Confirm the needle or insertion tool placement using imaging. Adjust as necessary.

4. Rotate the needle or insertion tool such that the angle of entry would as desired. In case of a needle, rotate the needle so that the beveled edge faces the cephalad, remove the needle stylet.

5. Advance the needle or insertion tool and confirm entry into the epidural space using known techniques. For example, loss-of-resistance technique with air or sterile [United States Pharmacopeia—USP] water can be used to confirm the entry. Use of flush or liquids, such as contrast media or saline flush, which would obstruct view or complicate further procedures is not recommended.

6. Using imaging, slowly insert the lead through the needle and advance the lead to the initial target placement site. A stylet may need to be reinserted. Use marking on stylet to determine angle of bending on stylet (when bent tip stylet is used). For example, the bent stylet can be keyed on the stylet handle with key corresponding to same or opposite direction of the distal bent tip, depending on the stylet used. If resistance is encountered when using bent stylet during lead advancement, exchange the bent stylet for the straight stylet and use short, firm movements to advance the lead.

In some embodiments, a guide wire can be used in addition or instead of a stylet 4250, prior to lead advancement. A guide wire would make a track for a lead to follow. That way, a guide wire is inserted first and is guided using an imaging modality until it reaches the desired place where the lead electrodes 4230 need to be positioned. Then the guide wire would be removed and a lead 4220 would be inserted. The lead would follow the tracks made by a guide wire more easily. A stylet 4250 or an inserting sheath 4270 can also be optionally used with the lead 4220 insertion.

In some embodiments, a guiding sheath 4270 or tube can be used to guide lead 4220 implantation. The sheath 4270 could be more rigid than a lead 4220 and could have a curved end. The procedure would be similar to the earlier described procedure, with the exception of using of the described sheath 4270 for lead 4220 advancement. After the lead 4220 insertion and confirmation of the correct location, the sheath 4270 is removed, leaving the lead 4220 and electrodes 4230 in place.

Figure 62:
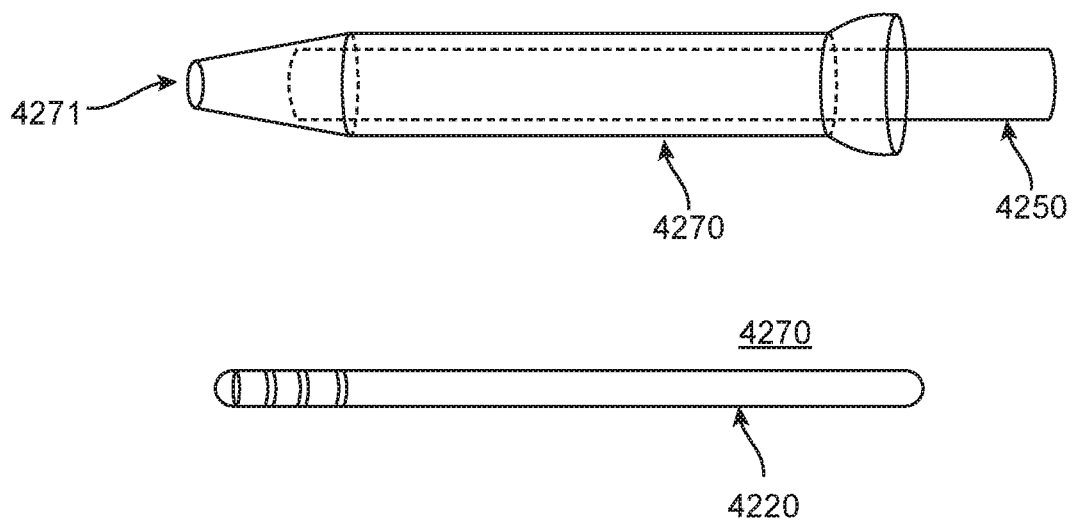
FIG. 62 illustrates a lead implantation sheath with a guide wire, or a lumen inserted in it; consistent with the present inventive concepts.

In some embodiments, a combination of sheath, stylet, guide wire and/or other filament 4250 is used for lead 4220 implantation. A sheath 4270 with a guide wire acting as a stylet 4250 can be used to deliver the distal end of the tube (sheath) 4270 to the correct location. The guide wire 4250 would then be removed from the sheath 4270. The lead 4220 would then be inserted into the sheath 4270 and slidingly advanced until it reaches the desired location. The sheath 4270 could then be removed, leaving the lead and the electrodes 4230 in the correct place for the desired therapy. The sheath 4270 would have a narrowed distal end 4271 to ensure the guide wire 4250 does not extend beyond the distal end of the sheath 4271. The diameter of the narrowed distal end 4271, however, is large enough to allow its removal after lead is inserted but small enough not to let the guide wire through, as shown in FIG. 62. The guide wire in this case has very similar functionality to a stylet 4250. Therefore, it is important to have multiple options for the guide wire 4250. The guide wire 4250 can have varying parameters to accommodate more flexibility during the surgery. These parameters include: rigidity, length, diameter, curved or straight, bent tip.

The sheath 4270 could also accommodate (e.g. provide support for) the usage of a camera (such as fiber optic camera including a visible light fiber), ultrasound fiber, sensing lead, and other tools that can further be used during lead 4220 implantation and can help in determining the correct or the best location for the lead 4220 and electrodes 4230. For example, a lead 4220 with a sensor (e.g. sensing electrodes) can be used with sheath 4270 during lead advancement. In some embodiments, the sheath 4270 includes one or more sensors. The sensors can be used to measure action potentials, neural activity, and/or muscle activity to hone in on the right location. Other sensors and/or transducers can be used (e.g. included in the lead 4220 and/or sheath 4270), such as to measure one or more of pressure, temperature, pH, and others.

In some embodiments, a sheath 4270 with lead 4220 and stylet 4250 are inserted and advanced until they reach the desired location. After the electrode 4230 reaches the desired location, the sheath 4270 can be removed and the lead 4220 can be adjusted and further advanced using the stylet 4250.

The stylet 4250 could then be removed, leaving the lead and electrodes 4230 in the correct location for the desired therapy.

Figure 60:
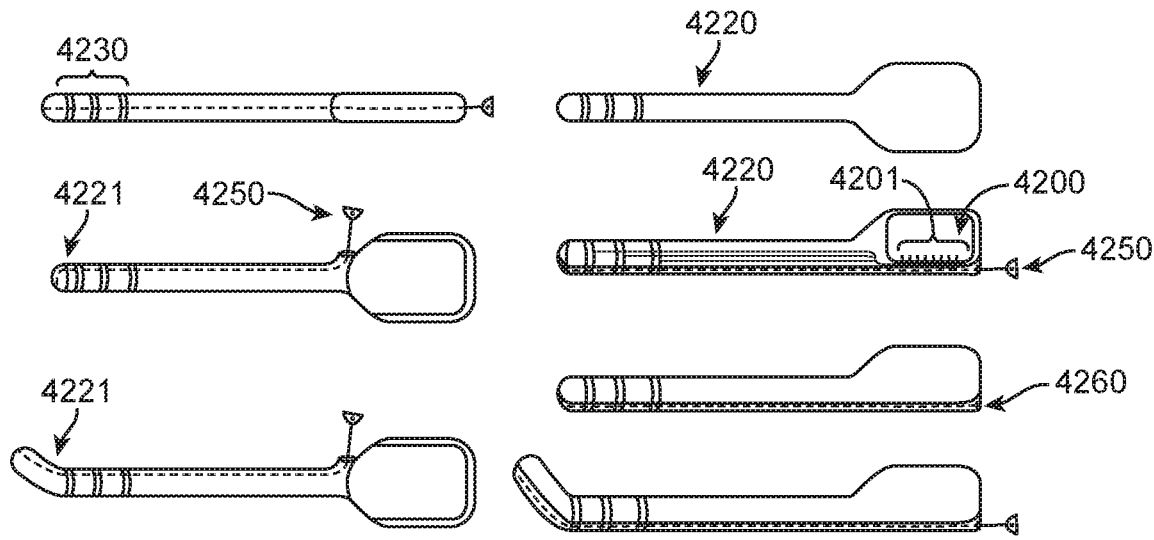
FIG. 60 illustrates various implantable device embodiments with stylets and lumens for stylets and other tools; consistent with the present inventive concepts.
Figure 61:
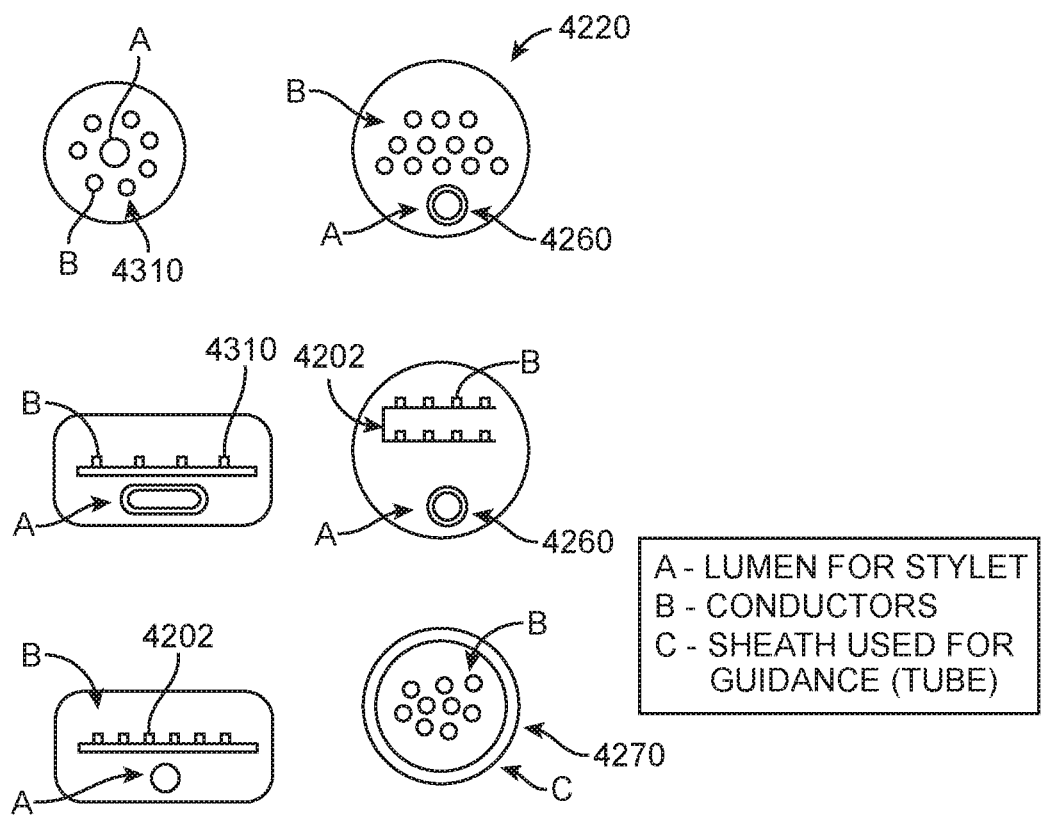
FIG. 61 illustrates cross-sectional view of several embodiments of a lead, showing conductors of an interconnect, lumen for a stylet, and sheath around a lead; consistent with the present inventive concepts.

Several embodiment options for lead which can accommodate a stylet are shown in FIG. 60. Also, several options of a lead cross-section are shown in FIG. 61. As can be seen from the figures, the lead 4220 would include a lumen 4260 through which a stylet 4250 can be inserted. The lumen ends at the distal end of the lead 4221, such that the stylet, effectively, pushes the lead due to its rigidity. The lead 4220 can be circular, oval, rectangular, or other shape in cross section. Also, the stylet lumen 4260 (or lumen which can accommodate other things aside from stylet) can have various cross section shape, depending on the requirements, and can be circular, oval, rectangular, or other shapes. The cross-section also shows insulated conductors 4310 which connect electrodes 4230 to active circuitry (electronics) 4241. The conductors 4310 can be of various types and implemented in various ways. For example, in some embodiments, the conductors 4310 can be implemented on a flexible PCB, can be individual insulated wires, multi-stranded wires, bundles of wires, single strand wires, magnetic wires, and other options. FIG. 60 shows several different embodiments of the implantable device 4110 comprising a lead 4220 with electronics 4241 and one or more antennas 4240 built into the lead (e.g. entire implantable device 4110 is in a lead form factor) or electronics 4241 encapsulated in a sealed package or housing 4200 on proximal end of the lead 4220. In the figures, the lead comprises one or more insulated conductors 4310 and one or more lumens 4260. The conductors 4310 connect electrodes 4230 to the active circuitry 241 that drives stimulation waveforms through the electrodes 4230. The one or more lumens 4260 can be used to accommodate a stylet 250 or other tools that can be used to aid with the lead implantation procedure.

Figure 71:
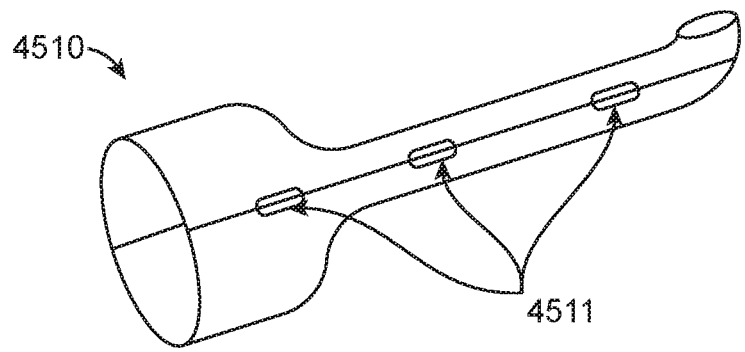
FIG. 71 illustrates a two-piece needle introducer with hinges for minimally invasive implantation of an implantable device; consistent with the present inventive concepts.
Figure 72:
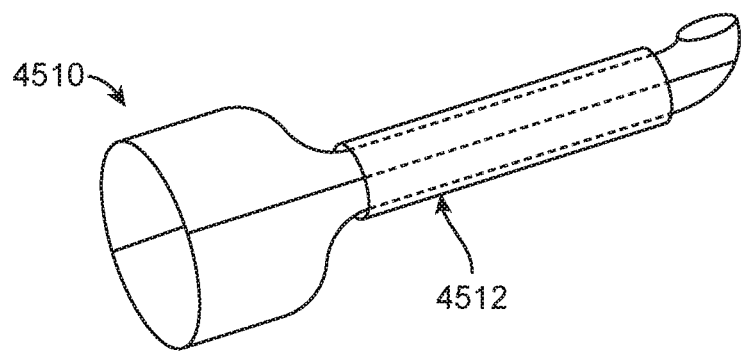
FIG. 72 illustrates a two-piece needle introducer held together with a sheath for implantation of an implantable device; consistent with the present inventive concepts.
Figure 73:
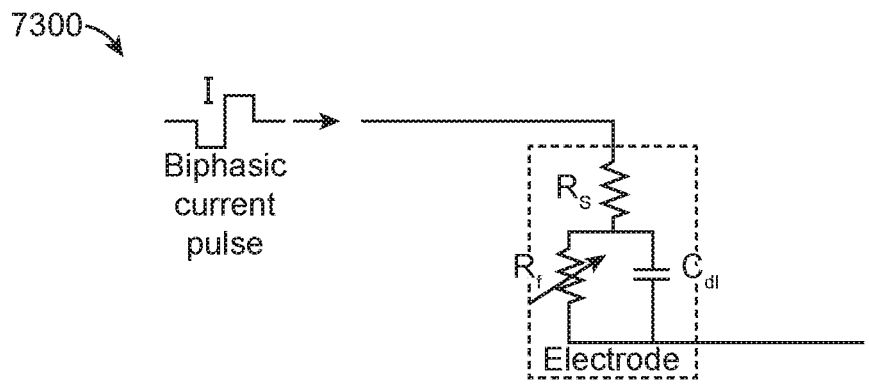
FIG. 73 illustrates a simple circuit model for a typical electrode.

As described in previous sections, some embodiments of the implantable device 4110 comprise one or more leads 4220, possibly bifurcated leads, connected to a sealed package or housing 4200 that houses active and/or passive circuits 4241, antennas 4240, and other components. In case the encapsulation or housing 4200 (e.g. hermetic encapsulation) is not fully integrated into a lead 4220, the sealed housing 4200 can protrude beyond the diameter of the lead. In order to accommodate minimally invasive implantation without surgery, it is important that implantation tools do not block doctor's view of lead entry point and also provide for easy manipulation during lead 4220 and device housing 4200 implantation. If a needle 4510 is used for lead implantation, as described in the steps above, a doctor would need to have an ability to remove the needle 4510 without removing the housing 4200 from the lead 4220 (i.e. in case the housing 4200 is not connectorized to the end of the lead 4220). In order to accommodate needle 4510 removal post lead implantation and to allow for device housing 4200 to be implanted, the needle 4510 can consist of several parts. Some embodiments of the introducer needle are shown in FIG. 71 and FIG. 72. As shown in the FIGS. 71, 72, in some embodiments, the needle 4510 can consist of two parts which are held together with a hinge 4511 that unfolds or breaks apart, or surrounding tube or sheath (similar to shrink wrap tube) 4512 which is biocompatible. The sheath 4512 can be silicone, plastic, or other similar materials. After lead 4220 implantation procedure is complete, the sheath 4512 can be cut enabling the two parts of the needle 4510 to come apart, which could be assisted with perforations along the sheath. Then, the rest of the device package or housing 4200 can be implanted under the skin.

In other embodiments, the lead 4220 can be connectorized to the sealed housing 4200, such that the lead 4220 can be separately implanted using a needle 4510 or insertion device. The needle 4510 would then be removed and the housing 4200 would be connected via connector interface 4210 to the lead 4220 for implantation, allowing a physician to complete the implantable device 4110 implantation procedure.

Figure 63:
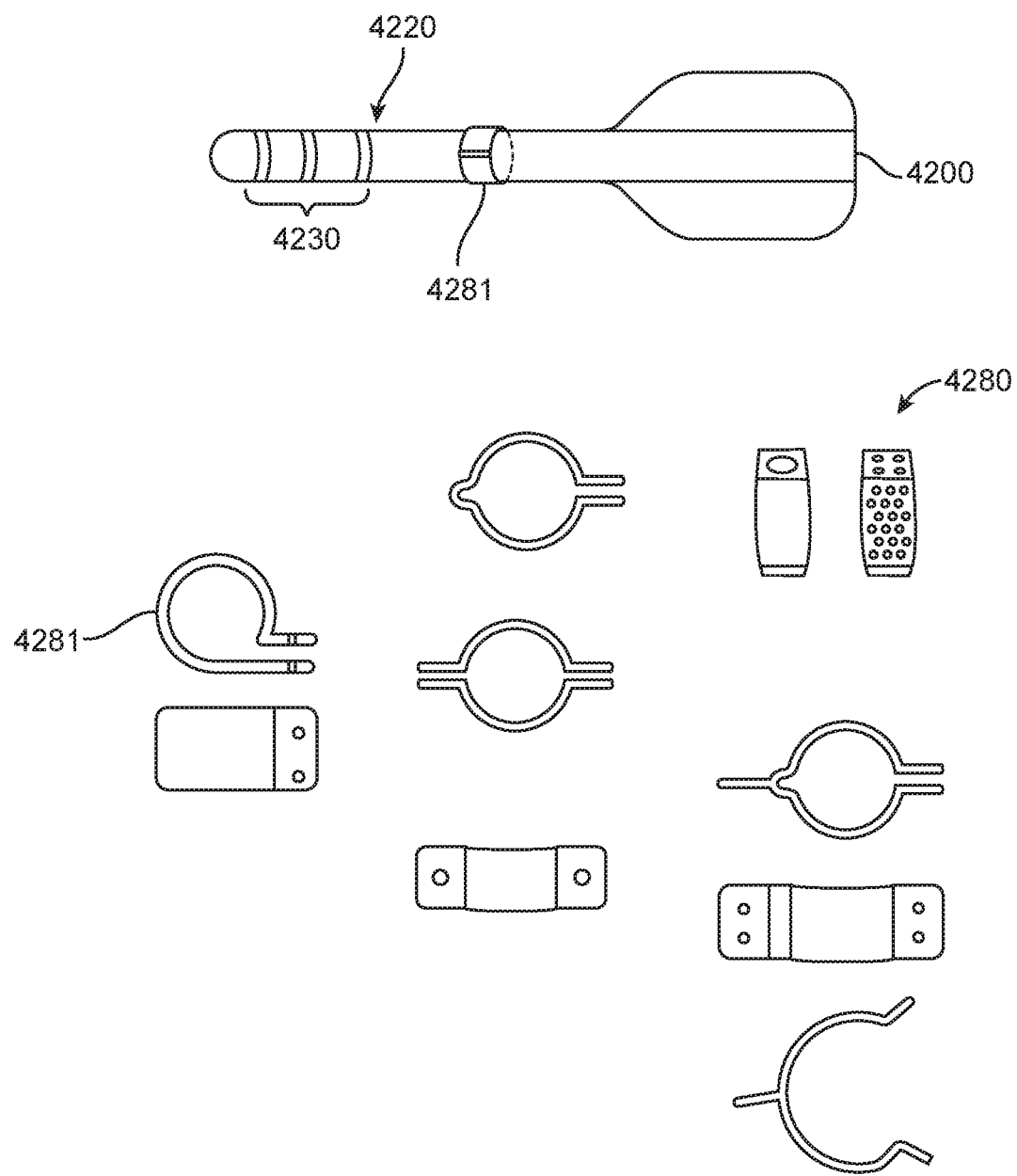
FIG. 63 illustrates several embodiments of a clamp or anchor; consistent with the present inventive concepts.

Some form of anchoring can be used to ensure permanent implantation of the implantable device 4110 by securing or fixating it in place. At least a portion of the implantable device 4110 can be sutured to fix it in place. The implantable housing(s) 4200 can contain built-in eyelets or other suture holes 4280 for sutures. Alternatively, or in addition to eyelets, barbs, staple; fixation parts and/or other anchor elements can be added to the lead 4220 and/or other portion of the implantable device 4110 to serve as additional spots for suturing and permanent fixation within a patient prior to closing the incision spot. These anchor elements 4281 can comprise a texturized pattern for improved grip such that they do not slide along the lead 4220 or device housing 4200 and such that sutures would not slide along the anchor 4281. This anchoring 4281 would effectively enable the sutures to fix the device and/or lead in place permanently. Other anchoring elements 4281 can be in shape of a clamp that can clamp around a lead and/or device. Sutures or staples can be used to close the clamp and prevent it from opening after the implantation and fixation procedure and to hold the device in place. The clamp would contain an extension with one or more holes 4280 for sutures to be inserted through as can be seen in FIG. 63.

Figure 70:
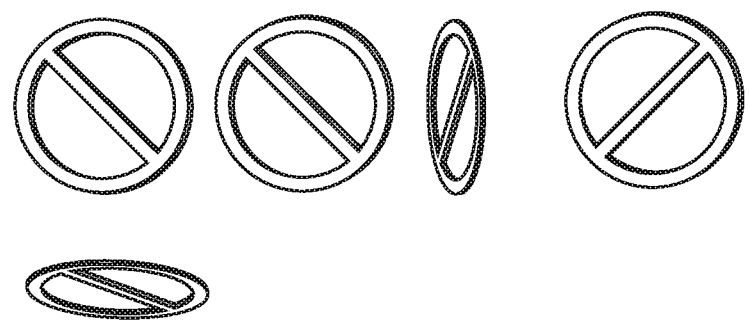
FIG. 70 illustrates an example of a radio-opaque marker in different angles and orientation; consistent with the present inventive concepts.

As previously described, in order to determine the implantable device 4110 position and orientation, an imaging modality can be used. Radio-opaque or other visualizable markers at the lead tip (e.g. distal end of the lead) 4221 can be used to help identify the lead 4220 and electrode 4230 position with regard to the anatomy. Furthermore, imaging can be done from multiple different views, such as anterior-posterior and lateral views, in order to determine the 3-D position and orientation of the lead 4220 and the electrodes 4230. In some embodiments, several radio-opaque markers are included (e.g. on and/or in the lead 4220) with certain predetermined shapes and in pre-determined locations along the lead 4220, such as at the distal end of the lead 4221, in order to further simplify the orientation procedure. For example, if the perceived shape of one or more markers changes with device position, rotation, and orientation, fewer imaging views can be used to establish the 3D position of a lead 4220. Appropriate shape for a visualizable marker can be selected such that it's projection on a 2D plane would reveal additional information about device rotation, tilt, and orientation. FIG. 70 shows several different examples of such visualizable markers in different orientations, rotations, and positions. From the figure, it can be seen that if an implantable device 4110 which includes such visualizable marker is rotated or tilted, the 2D projection of the imaged marker would change. Thus the device position, orientation, rotation, tilt, and general 3D location can be more easily determined with fewer steps, simplifying procedure and reducing the number of images that need to be taken during the procedure. The radio opaque markers can also include the device ID for easy retrieval during implantation, warning labels, and other markers that can be used during implantation, programming, routine use, explanation, servicing, etc.

In order to determine the correct location of the lead 4220 and to ensure that the electrodes 4230 are located in proximity to the nerves or anatomic site that needs to be activated or suppressed via stimulation waveform, the overall system 411 may need to be tested intraoperatively. This testing involves activating the implantable device 4110 and stimulating tissue. During this intraoperative testing or trialing, the patient can be required to provide feedback about the sensation of paresthesia, its location and/or comfort level, for a variety of stimulation parameters and/or electrode configurations. In order to ease with this intraoperative trialing, a special trialing interface 4400 is included in the overall system 411. Since the implantable device 4110 would not be fully implanted yet, the trialing interface 4400 can be of a different configuration than the external patch or other external device component that would normally be used to activate one or more implanted portions of the implantable system of the present inventive concepts. Some example embodiments of the intraoperative trialing interface 4400 are shown in FIG. 64 and FIG. 65.

In some embodiments, the trialing interface 4400 comprises a docking element 4410 (or docking port) which would house or otherwise at least partially surround the at least a portion of the implantable device 4110, such as to surround a proximal end of a lead, such as to wirelessly couple to the implant. The docking element 4410 can fit securely to ensure that the wireless link quality is acceptable and does not vary significantly with surroundings. The shielding from the surroundings can be accomplished by incorporating radio absorptive and/or radio reflective materials 4411 into the construction of the docking element 4410. The doctor could then manually adjust stimulation parameters until a desired set of parameters is determined and/or an acceptable lead 4220 and electrode 4230 location is established. Alternatively, the trialing interface 4400 could incorporate a special search algorithm that would step through the stimulation parameters and based on patient feedback or automatically find the proper set of stimulation parameters. Based on the trial and/or patient feedback, the lead 4220 location may need to be readjusted and trialing redone. After it is determined that the location of the lead 4220 and electrodes 4230 is proper, the implantable device 4110 can be fully implanted, secured in place and the incision closed up.

In some embodiments, the trialing interface 4400 can be connectorized with mating connectors (e.g. electrical connectors) 4210 on the trialing interface 4400 and associated portion of the implantable device 4110 (e.g. lead 4220 or device housing 4200). This wired trialing procedure is similar to the wireless trialing procedure, but with a wired interface 4210. The trialing connector 4210 can be configured to mate with a lead connector 4210 of similar construction to a connectorized sealed housing 4200. Alternatively, the trialing interface 4400 can mate with a connectorized antenna interface. In the case of a lead interface, the trialing interface 4400 would directly drive electrodes 4230 through the leads 4220 and therefore would have to drive stimulation waveforms out of a waveform generator, similar to the functionality of the implantable device electronics 4241. However, in case when a trialing interface mates with a connectorized antenna interface, the trialing interface 4400 would have to mimic RF signal transmission that would normally be received wirelessly during normal operation. Therefore, the trialing interface would include an RF carrier modulated with data but would excite the input to the electronics 4241 of the implantable device 4110 in a wired way. The trialing interface could have its own matching network which matches to the same carrier frequency that would normally be used during operation or to a different frequency. Operation at lower frequency can be advantageous for power savings and lower complexity of the trialing interface, since the size of the trialing interface is not constrained as much as that of an implantable device 4110.

Figure 64:
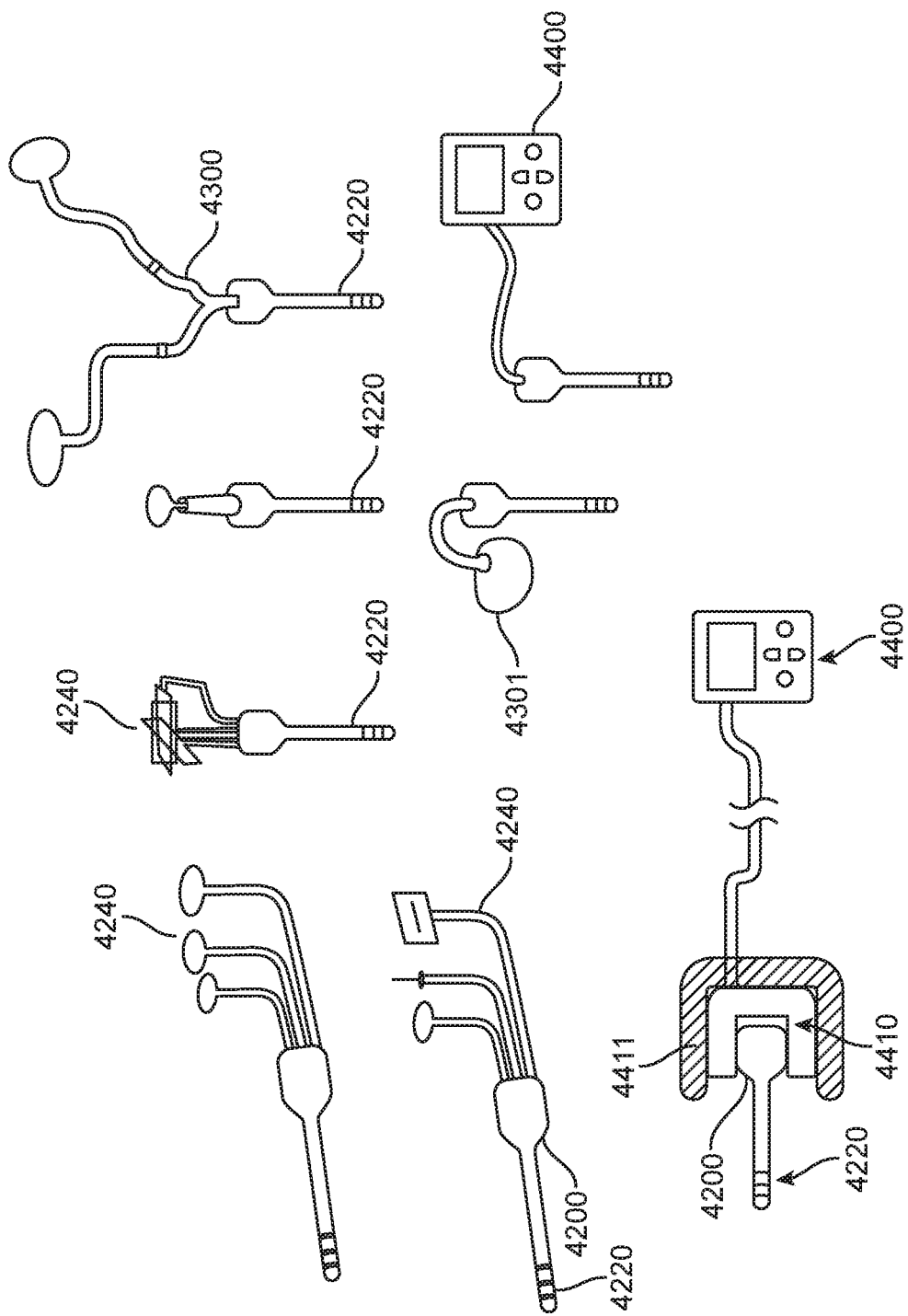
FIG. 64 illustrates several embodiments of extension devices which can connect to the connector interface on an implantable device, including one or more antennas, trialing interface, energy storage, and interposer connector; consistent with the present inventive concepts.
Figure 65:
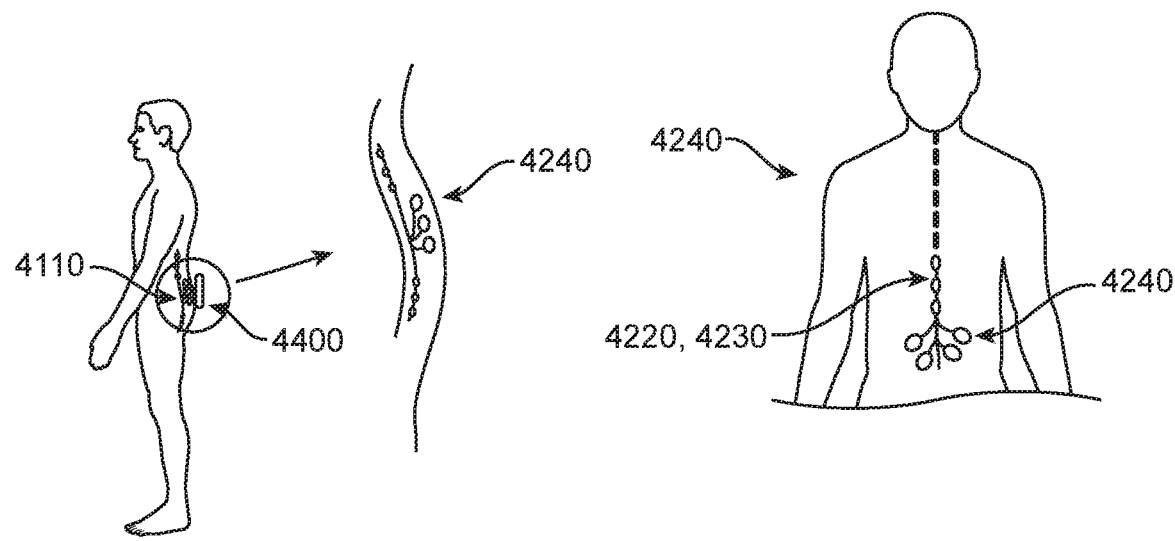
FIG. 65 illustrates an implantable device with distributed antennas and a trialing interface; consistent with the present inventive concepts.
Figure 66:
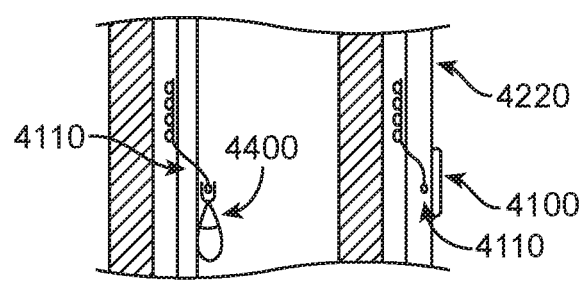
FIG. 66 illustrates an implantable device with electrodes in epidural space, a wireless trialing interface for intraoperative trialing, and an external device for postoperative operation or wireless trailing; consistent with the present inventive concepts.

For certain applications that require deeper implants, higher power budgets, more stringent size requirements for the external battery, and/or link gain improvement, it can be beneficial to have the antenna or multiple antennas located closer to the skin surface than one or more remaining portions of the implantable device, as shown in FIG. 64 and FIG. 65. In order to accommodate this placement configuration, the implant antenna or antennas 4240 could be connected to the rest of the implant or implant housing 4200 with a connecting interface or other connecting element, such as cable, wires, conductive leads, transmission lines, waveguides, distributed matching network, transformer, lumped matching network, or other configuration (hereinafter interconnect) 4310 that allows for the antenna(s) 4240 be separate from the active and/or passive circuits enclosure 4200. The interconnect 4310 between remote antenna 4240 and the rest of the implantable device can thus act as a matching network or simply an electrical connector. The interconnect 4310 can be flexible, rigid, semi-rigid or include at least a flexible portion, and it can be used to position the antenna(s) 4240 independent of the rest of the implantable device. The resulting remote antenna or pig-tail antenna 4240 can be positioned at a location within the body of the patient that optimizes link gain. Furthermore, multiple antennas can be connected this way to the rest of the implant. The position of each antenna can be individually adjusted to optimize link gain for a variety of situations and operating conditions. For example, several antennas can be distributed under the skin to make the link gain less sensitive to external device position (e.g. external patch position), relative orientation, alignment, and/or rotation as shown in FIG. 64 and FIG. 65. Furthermore, one or more remote antennas 4240 can be foldable and unfoldable to enable minimally invasive implantation as described in U.S. Provisional Patent Application No. 61/953,702. Alternatively, or in addition to this, the antenna extensions (i.e. individual remote antennas 4240) can be positioned orthogonally with respect to each other to further desensitize link gain to the position of one or more external device components (e.g. less sensitive to external patch or external antenna 4150 positioning). The remote antenna 4240 physical structure can be optimized for a particular application and can be selected from the list of: loop antenna, multi-loop antenna, orthogonal antennas, polarized antenna structures, dipole antenna, multi-coil antenna, helical antenna, patch antenna, and combinations thereof.

Figure 69:
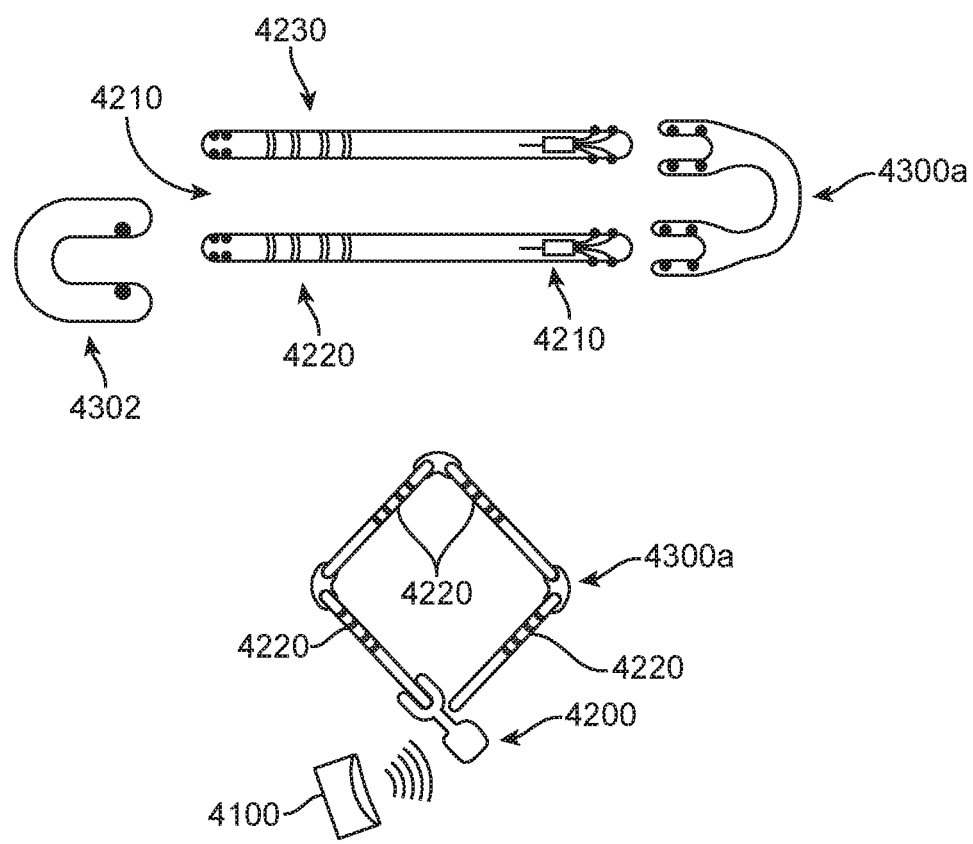
FIG. 69 illustrates connectorized implantable device with active leads connected in series, forming a diamond pattern; consistent with the present inventive concepts.

In some embodiments, one or more remote antennas 4240 can connect to the rest of the implantable device with feedthroughs, resulting in a permanent configuration. In some embodiments, the rest of the implantable device and one or more of the remote antennas can have mating connectors 4210. The connectors 4210 can be standardized such that the same core implantable device housing 4200 can be mated with a specific antenna 4240 that is best optimized for a particular need, indication, use, and/or operating environment. The antennas 4240 could have a specific impedance that would be matched and/or resonant with a component of the implantable device 4110 (e.g. the electronics 4241 housed in a package or housing 4200) at a particular frequency in order to maximize performance. Alternatively, or in addition to this, an interposer matching network 4300a can be used between the antenna 4240 and the housing 4200 (FIG. 69). The interposer 4300a could further include combiners, splitters, and other radio frequency (RF) components to further optimize link gain and make the design of implant electronics 4241 and antennas 4240 more flexible and versatile. With this approach, several antennas 4240 can be supplied with the implantable device 4110 and an operating physician could have a choice of the antenna 4240 to implant in a particular patient to accommodate a particular situation. Similarly, a physician can select an appropriate lead 4220, from several different leads which can be supplied with the implantable device 4110, for a particular situation.

A connectorized interface 4210 for one or more swappable antennas 4240 further offers additional benefits and flexibility. Firstly, it accommodates multiple antennas 4240 to suit a particular need without having to redesign the whole implantable device 4110. Furthermore, other devices and components (extension devices 4301) can be connected to the implant to improve functionality, utility, and/or accommodate different uses. For example, a testing assembly can comprise a power supply such as a battery with a special RF interface that mimics an antenna 4301 can be connected to the implant if application requires for the use of a battery. The RF interface would be designed to provide a signal to the implantable device according to what would be expected at the output of the antenna. The battery could be beneficial for certain applications, such as when external patch is not a viable or at least not a preferred option. Other attachment elements 4301 could include a trialing interface 4400 for intraoperative trialing as shown in FIG. 64 and FIG. 65.

Figure 67:
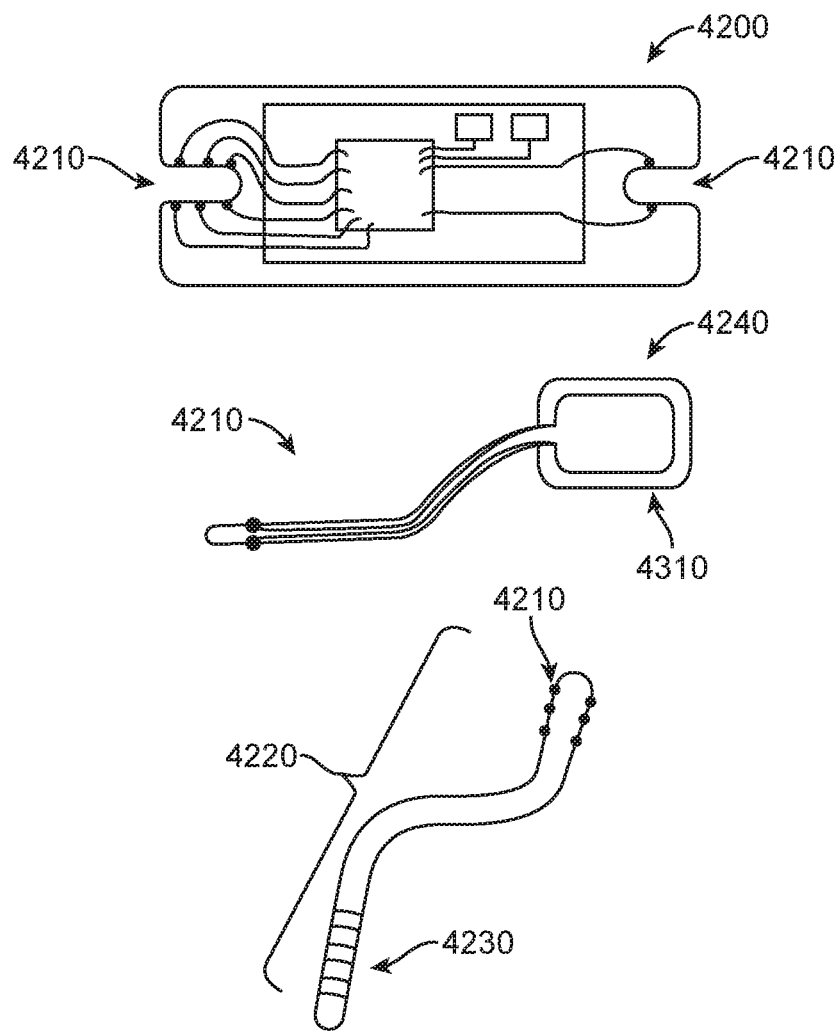
FIG. 67 illustrates connectorized interface of the implantable device, including implant package, lead, and antenna; consistent with the present inventive concepts.
Figure 68:
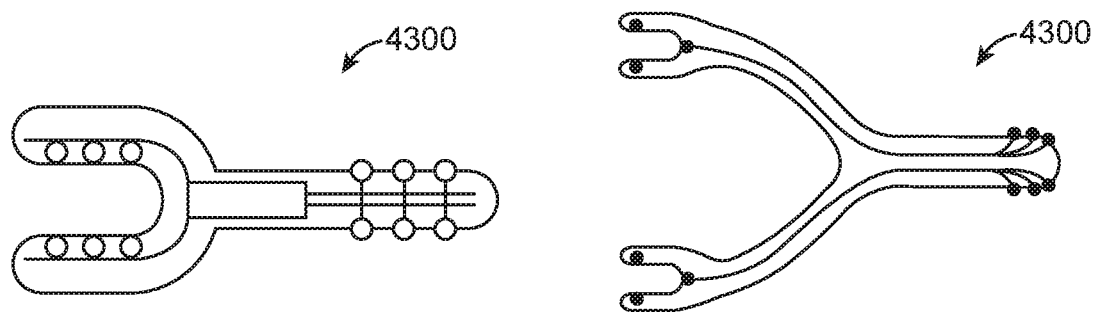
FIG. 68 illustrates adapters, interposers, and connection hubs; consistent with the present inventive concepts.

Similar to connectorized antennas, in some embodiments, it can be preferred to have connectorized lead/electrode interface on the implantable device (e.g. a sealing connector) as shown in FIG. 67. A connectorized lead interface would enable for a simpler implantation procedure as described herein. Also, a connectorized lead interface 4210 provides higher flexibility in adapting the implant to a particular case to meet the therapy requirements. For example, leads of various lengths, diameters and other dimensions, electrode shapes, electrode sizes, electrode configurations, and other lead variables can be accommodated with the same device as long as the connectors are designed to mate to each other. For example, with a connectorized lead interface, the same implant housing 4200 can be used with a variety of leads 4220, such as cylindrical leads, paddle electrodes, microelectrodes, bifurcated lead designs, and other lead options. Also, similar to the connectorized antenna interface, connectorized lead interface can mate with a variety of optional devices and/or adapters, such as splitters for leads; active and/or passive interfaces for leads, such as serializer and/or deserializer for active leads; lead extensions; diagnostic interfaces that can be used to test implant functionality at any point during the lifetime of the device. Other interposer components 4300a and/or devices can also be used by mating with the implant housing 4200 and leads 4220, such as a charge balance device, pulse conversion or pulse shaping device (e.g., DC to pulse burst), filters, etc. As was mentioned before, all these connecting devices or attachment elements, can be passive—such as leads or splitters, passive filters, AC-coupling capacitors for charge balancing, active—such as pulse conversion devices, active filters, active charge balancing circuits, or combinations thereof.

In some embodiments, it can be beneficial to connect active or passive distribution circuits or hubs to the connectors 4210. These distribution circuits can distribute stimulation and/or sensing channels from the device to remote electrodes which can be placed in various locations throughout the anatomy of a patient. These distribution circuits can comprise splitters and/or hubs which interface with one or more connectors on the implantable device 4110 and one or more leads. Each lead 4220 would have one or more electrodes 4230. This way, the connector interface 4210 on the device housing 4200 can be standardized but the leads 4220 can be customized to a particular application with the distribution circuit acting as an interposer or adapter 4300*a*. Unused connectors can be deactivated through active control of the implantable device 4110 or can be blocked with a termination plug 4302 to prevent the connector from contacting the tissue once the implantable device 4110 is implanted. These connectors 4210 can be placed in various locations on the implantable device 4110 or implant housing 4200, such as next to each other, on opposite ends of the implantable device 4110 or implant housing 4200, or distributed throughout the implantable device 4110 or implant housing 4200.

In some embodiments it can be beneficial to have multiple electrodes 4230 distributed throughout the body that can provide cross-talk or can steer current from one electrode to another remote electrode in a different location of the body. In that case it is necessary for the electrodes 4230 to have a common reference node which requires the electrodes to be physically connected to the same active device electronics 4241 with one or more channels. In order to enable this configuration, bifurcated leads can be used which are connected to the same implantable device 4110 or same device housing 4200. Also, it can be beneficial to network multiple leads in series to enable all the implanted portions to have a common reference node. In those configurations, active leads can be used which can send and/or receive commands from one implantable device (e.g. single electronics encapsulating package or housing 4200). A serial communication link with one or more conductors can be used in those configurations. A serial protocol can be used to control these active leads 4220. However, the leads 4220 would have to support this serial protocol. A low power serial interface with connectors 4310 for power, ground, and one or more serial data wires can be used in those configurations. The leads 4220 can have connectors 4210 on both ends of the lead 4220 to enable series connection of one lead to the next in a chain. Each lead could have its own ID code (e.g. an addressable code) and a single controller (e.g. electronics 4241 housed in a package or housing 4200) can program each lead 4220 through the serial communication interface independently, collectively, or in coordinated manner. This concept is illustrated in FIG. 69. Similar to what is described hereinabove, unused connectors 4210 can be closed with a termination plug 4302 in order to prevent the connector 4210 from coming in contact with tissue, which could potentially damage the lead 4220 and/or connectors 4210 over time. The termination plug 4302 can be configured to keep the connector 4210 contacts sealed.

Figure 58:
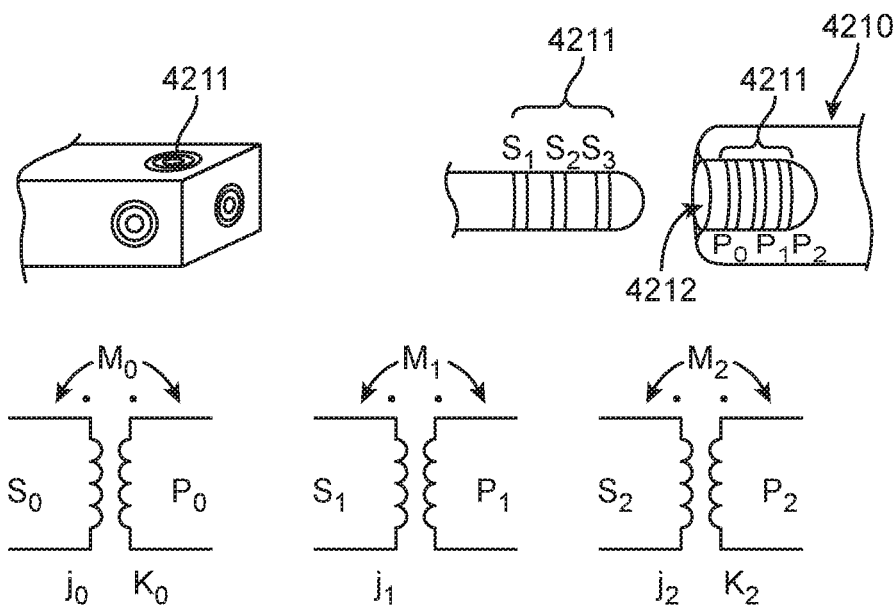
FIG. 58 illustrates a wireless AC-coupled interface implemented using inductive coupling; consistent with the present inventive concepts.

In some embodiments, multiple implantable connectors 4210 can comprise wired connectors with conductive contacts, as normally used with active implantable devices. Alternatively, a connection interface 4210 can be AC-coupled and even wireless. In some embodiments, an implantable device 4110 (e.g. encapsulation package or housing 4200) does not include feedthroughs or a wired connector interface 4210. Instead, the connector interface 4210 is wireless. In a wireless connector interface 4210, connectors do not use conductive interface between the encapsulated package (e.g. hermetically encapsulated package or housing 4200) and extensions 4301, such as antennas 4240, leads 4220, and other possible extension devices as described hereinabove. Instead, signals are coupled and transmitted wirelessly. Absence of feedthroughs can be advantageous for fabrication and/or life expectancy of the implantable device 4110 (e.g. feedthroughs may result in a limited life). Examples of wireless interfaces or AC-coupled interfaces 4210 are described below. In some embodiments, an AC-coupled interface 4210 relies on one or more transformer coils 4211 which form one or more transformers with a primary transformer coil 4211 located inside the package or housing 4200 and a mating (complementary) secondary transformer coil 4211 located in an extension 4301 (such as a lead 4220 or antenna 4240). Depending on the number of turns in each primary and secondary transformer coils 4211, this configuration could further enable voltage/current step up or step down, thereby increasing the interface utility. The transformer coils 4211 can be planar coils in the implant housing 4200 with matching set of planar coils in the extension devices 4301. Alternatively, the transformer coils 4211 could be coplanar coils. In that case, the implantable device package or housing 4200 can have a concave or convex port 4212 which would mate with an extension device port, as shown in FIG. 58. As shown in the figure, in one embodiment, a lead 4220 can be inserted into a port 4212 in sealed housing 4200, aligning all the co-planar transformer coils 4211. Each electrode 4230 can have an associated set of primary and secondary coils 4211 which are inductively coupled. This AC-coupling interface 4210 can comprise a frequency response which accommodates the required stimulation waveforms without unintended filtering. This similar concept of an AC-coupled interface 4210 can be applied to a wireless antenna connector. Because the antenna 4240 normally only supplies RF signal, this interface 4210 is even more practical for antennas 4240 use because smaller transformer coils 4211 for coupling can be used for RF. Ferrite cores can further be used with this transformer-based interface 4210 to further improve coupling and/or adjust frequency response.

Figure 59:
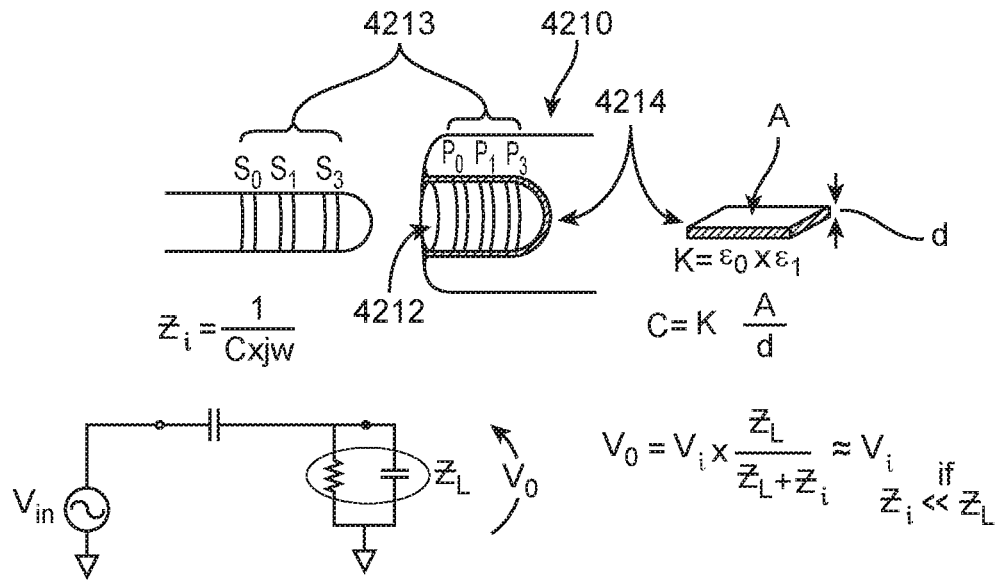
FIG. 59 illustrates a wireless AC-coupled interface implemented using capacitive coupling; consistent with the present inventive concepts.

In some embodiments, the AC-coupling interface 4210 can be implemented using capacitive coupling. The capacitors are formed in a similar manner to inductive wireless interface—by aligning a conductive plate 4213 on implantable device housing 4200 with a plate on extension device 4301 (such as lead 4220 or antenna 4240)—which would form pairs of parallel plates. Some embodiments of the capacitive AC-coupled interface are shown in FIG. 59. The encapsulation between the plates (e.g. capacitor dielectric 4214) can be the same as the rest of the encapsulation or can be selectively made of a material with different dielectric constant, κ. For example, high-κ dielectrics would result in higher capacitive coupling and thus smaller area plates 4213 can be used. Also, encapsulation 4214 can be selectively thinned around (e.g. between) the mating plates 4213 to further increase the capacitance. In some embodiments, the extension device plates 4213 are not encapsulated to reduce the distance between the plates 4213 and increase capacitive coupling. The exposed plates 4213 can be plated with or made of materials that are biocompatible. This construction would not increase the risk of oxidation or corrosion because these nodes are only exposed to AC signals and not DC signals. This type of coupling is also advantageous because it results in charge balancing circuitry without explicit use of discrete AC-coupling capacitors, which enables further miniaturization by reducing number of passive components used in the implantable device 4110.

As was mentioned before, there are multiple ways the implantable device 4110 can be encapsulated and packaged. The actual method of encapsulation and packaging depends on the intended application, because of the tradeoffs involved with each choice. For example, silicone elastomers, such as Silastic, are typically flexible and inert to biological tissue interactions but are permeable with liquids commonly encountered in implantable applications. Therefore, devices that are encapsulated with Silastic or similar silicone elastomers have a shorter lifetime than device that are encapsulated with less permeable encapsulation methods, such as fluorocarbons, crystalline materials, glass, ceramic, or metal packaging methods. The tradeoff with the less permeable encapsulation choices is that they can require feedthroughs for conductive connections which increase the device size with increasing number of feedthroughs due to a fairly low density of feedthroughs. Additional consideration of choosing a less permeable material is the ability of the material to pass the desired wireless signals through the package without significantly attenuating them. For example, metals significantly attenuate electromagnetic waves in a very broad range, including RF and optical range. Therefore, using RF power transfer and RF or optical communication techniques with devices that are encapsulated or enclosed in metal packaging presents additional challenges due to signal attenuation. Glass, ceramic, some nonmetallic crystalline materials, fluorocarbons, and silicone materials do not attenuate electromagnetic waves as much as metals do. Therefore, the use of these materials for encapsulation would be significantly more advantageous to metal encapsulation when implantable devices rely on wireless powering and communications. Other material properties, such as flexibility, resistance to mechanical stress, and other properties need to be accounted when selecting materials for implantable device encapsulation and packaging.

Figure 48:
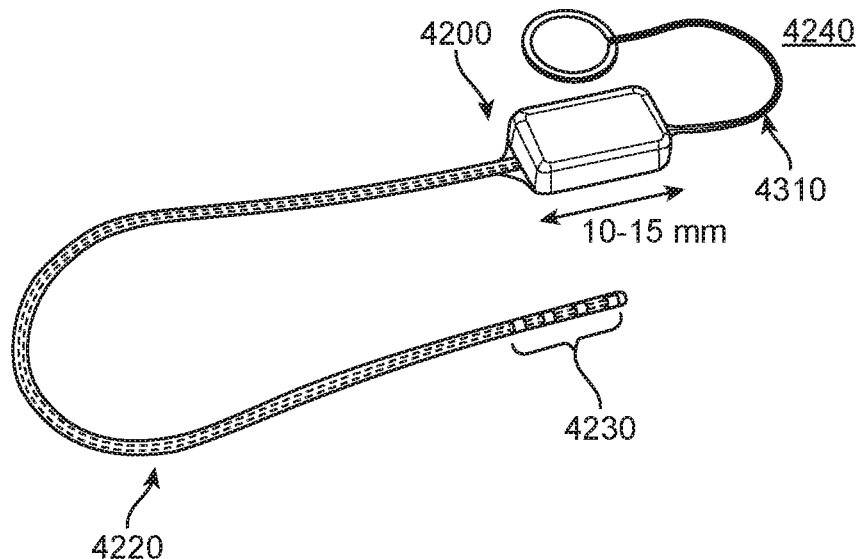
FIG. 48 illustrates an implantable device with an encapsulated housing, a tethered antenna, and a lead; consistent with the present inventive concepts.
Figure 49:
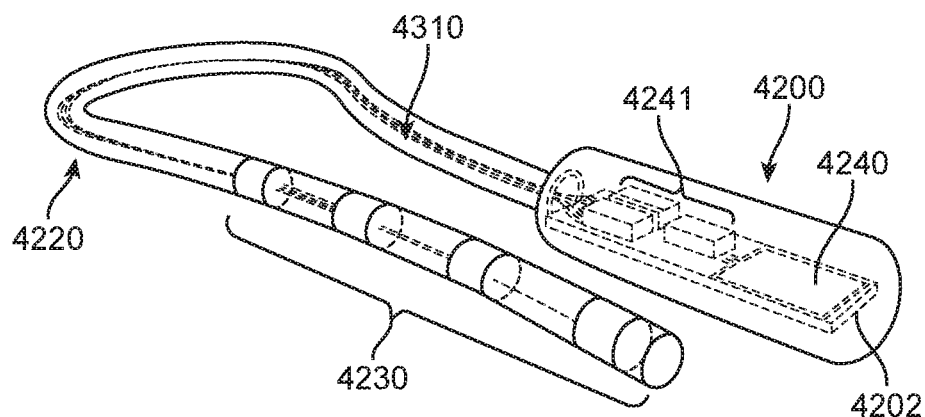
FIG. 49 illustrates an implantable device with an encapsulated housing and a lead; consistent with the present inventive concepts.
Figure 50:
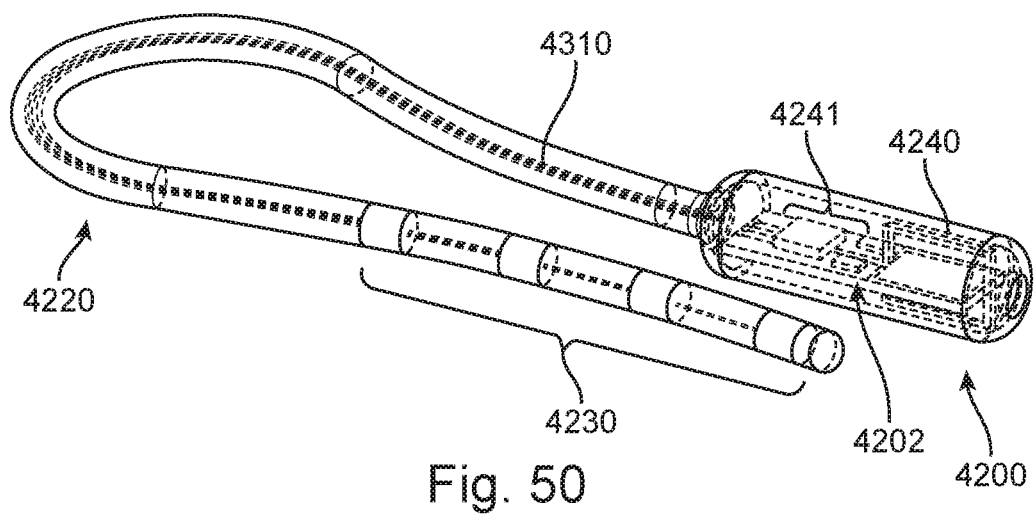
FIG. 50 illustrates an implantable device with an encapsulated housing, orthogonal antennas, and a lead; consistent with the present inventive concepts.

In some embodiments, the implantable device 4110 or at least parts or elements of the implantable device are packaged in a sealed (e.g. hermetically sealed) cylindrical or planar glass encapsulation or housing 4200 with high density feedthroughs 4201 to connect to one or more electrodes 4230 and/or one or more antennas 4240. One of the key advantages with this encapsulation method is that the implantable package or housing 4200 does not attenuate electromagnetic waves, so in configurations in which an antenna 4240 is enclosed within the package or housing 4200, the implantable device 4110 can be powered and can communicate using an RF carrier. Additional benefits are: longer lifetime due to sealed packaging; robust package design which is not susceptible to fractures due to mechanical stress; high density feedthroughs 4201 enable multi-channel and/or multi-electrode therapy and/or diagnostics (sensing); small form factor of the package enables minimally invasive implantation and comfort for patient; significant reduction in implantation time because tunneling is not required for the small form factor package. Several embodiments with cylindrical and planar glass encapsulation technology are shown in FIG. 48, FIG. 49, and FIG. 50. The glass substrate is also bio compatible and bio-stable. The glass substrate can further be encapsulated with silicone or similar compound and overmolded if necessary.

In other embodiments, the implantable device 4110 can be fully integrated into a lead 4220 with electrodes 4230. In those cases, elongated antennas 4240, such as dipole antenna, elongated loop or multi-loop antenna, can be used and can extend along the lead for a larger cross section. Flexible or rigid PCB substrate 4202 can be used to mount electronic components 4241 such as ASIC and other discrete components along the length of the lead 4220. The PCB 4202 can contain conductors 4310 to electrically interconnect the electronic components 4241, one or more antennas 4240, and electrodes 4230. The lead 4220 can be made of a variety of biocompatible materials, including a variety of polymers such as polymethymethacrylate (PMMA), polydimethylsiloxane (PDMS), parylene, polyurethane, polytetrafluoroethylene (PTFE), polycarbonate, and other similar compounds. The form factors can be similar to what was previously described and shown in FIG. 51.

The one or more external devices 4100 and the one or more implantable devices 4110 can work individually or coordinate in a network to treat a variety of conditions. The one or more implantable devices 4110 can be placed in one or more of the following sites for sensing and/or treatment: the tibial nerve (and/or sensory fibers that lead to the tibial nerve); the occipital nerve; the sphenopalatine ganglion; the sacral and/or pudendal nerve; target sites in the brain, such as the thalamus; the vagus nerve; baroreceptors in a blood vessel wall, such as in the carotid artery; along, in, or proximal to the spinal cord; one or more muscles; the medial nerve; the hypoglossal nerve and/or one or more muscles of the tongue; cardiac tissue; the anal sphincter; peripheral nerves of the spinal cord, including locations around the back; the dorsal root ganglion; and motor nerves and/or muscles. The overall system 411 can be used to treat one or more of the following: migraine; cluster headaches; urge incontinence; tremor; obsessive compulsive disorder; depression; epilepsy; inflammation; tinnitus; high blood pressure; pain; muscle pain; carpal tunnel syndrome; obstructive sleep apnea; pace or defibrillate the heart; dystonia; interstitial cystitis; gastroparesis; obesity; fecal incontinence; bowel disorders; chronic pain; improving mobility; SCS for heart failure.

The following describes challenges and approaches to of ensuring charge balance safety in an SCS application while minimizing the size penalty of DC-blocking capacitors, which may be applicable to many embodiments of the present disclosure.

In conventional neurostimulators, DC-blocking caps are generally placed in circuit between any active electronics and each (or all but one) electrode. The object of the capacitors is to prevent any net DC current flow through tissue, which would otherwise cause irreversible electrochemical reactions at the electrode-tissue interface and result in tissue damage. These capacitors generally perform two interrelated functions:

A) During normal stimulation with fully functional electronics, the capacitors can prevent net DC current through tissue that would otherwise occur due mismatches in the current sources or other non-ideal characteristics of the electronics. Each capacitor may be in series with an electrode during both the stimulation (charge) phase and the opposite-polarity recovery (discharge) phase, so any net difference in charge transfer between the two phases cause a voltage to build up across the capacitor. This voltage may ultimately cause the larger-magnitude phase to go into compliance limit and thus achieves charge balance.

B) The DC-blocking capacitors may prevent tissue exposure to DC current in the case of an electronics failure within the stimulator, such as a leaky IC pad, a stuck DAC bit, etc. The assumption may be that these capacitors would protect against any single-point failure; a multi-point failure that involves a capacitor itself would not be addressed.

The following sections discuss these two aspects of charge balance and DC protection, and approaches to eliminating the need for DC-blocking capacitors. The schemes described below and herein may be applicable to any of the stimulation systems, devices, and apparatuses described above and herein.

1) P/NDAC Imbalance.

In theory, the typical ~5% potential mismatch between P and N current sources could be addressed by using an H-bridge-like configuration where the same P and N sources are switched between stimulating and indifferent electrodes in the two phases of a biphasic pulse. The weaker of the two sources may determine the current, so the only mismatch between the two phases should be due to the effective impedance of the current source and the output DC bias delta over the course of the two phases. Cascoded current sources typically have effective parallel impedances in the megohm range; e.g., for a 5 megohm source impedance and a 5 V bias delta between the two phases, the resulting mismatch will be 1 uA. Assuming a ⅟₂₀ pulse duty cycle (250 us pulse width at a 200 Hz rate), the average current imbalance may be 50 nA. This may be in technically below the 100 nA safety limit, but higher than desirable. In addition, if the stimulating and recovery phases of the biphasic pulse are asymmetric, then the INL of the DACs may also be a potential source of imbalance. INL can possibly be improved by creative DAC architectures; e.g., if the DAC is composed of 4 equal sections, these could be switched so as to drive in parallel during the stimulation phase and sequentially during a recovery phase that is one fourth the current and four times the duration of the simulation phase, so that each section contributes the same amount of charge in each phase. In any case, even with optimal current source design, a small residual charge imbalance will likely exist after the biphasic pulse.

2) Shorting.

At first glance, shorting may seem like a good option to remove any residual charge imbalance for an SCS application, due to the long interval between pulses relative to the time constant of the electrode-tissue interface. Referring to the simplified electrode model 7200 shown in FIG. 72 taken from Ji-Jon Sit's PhD thesis (Sit, Ji-Jon "An asynchronous, low-power architecture for interleaved neural stimulation, using envelope and phase information" PhD Thesis, MIT, 2007).

The electrode-tissue interface may comprise the double-layer capacitance, Cdl, the solution spreading resistance, Rs, and the Faradaic resistance, Rf. For a typical cochlear implant electrode, Cdl can be in the 5-15 nF range and Rs in the 2-20 Kohm range, so an upper bound for the time constant to discharge Cdl through Rs is on the order of 300 us. For SCS with a larger electrode, Cdl may be higher and Rs lower, so it's probable that the time constant falls in a similar range. Thus with a 200 Hz pulse rate, there could be roughly 10 time constants available to discharge Cdl through shorting, which again sounds like an easy proposition.

A difficulty may be that during the biphasic stimulation pulse, some current also passes through Rf. The Faradic resistance may be due to electrolytic reactions at the electrode interface, which are not always reversible, and are potentially destructive to tissue. At the end of the biphasic pulse the net current through Rf is non-zero, even if the two phases are perfectly charge-balanced, since the net voltage across Rf is non-zero. Thus if Rf is sufficiently small, shorting is counter-productive, since it prevents Cdl from discharging through Rf and equalizing the Rf current. It can be demonstrated mathematically that for Rf is greater than 1 megohm, shorting should not present a problem, and proposes using a shorting interval of about 3 time constants to remove ~0.4% residual mismatch from his active charge-balanced DAC design. The safety of this assumption may have to be verified experimentally.

3) DAC Linearity and Compliance Limits.

Even assuming well-balanced current sources and that shorting can be used to remove small residual charges, it may all fall apart if either current source approaches its compliance limit, since the resulting reduction in current output will not be balanced in the opposite phase. And from experience with cochlear implants, it seems likely that typical use cases will bump up against the compliance limit occasionally if not often.

Figure 74:
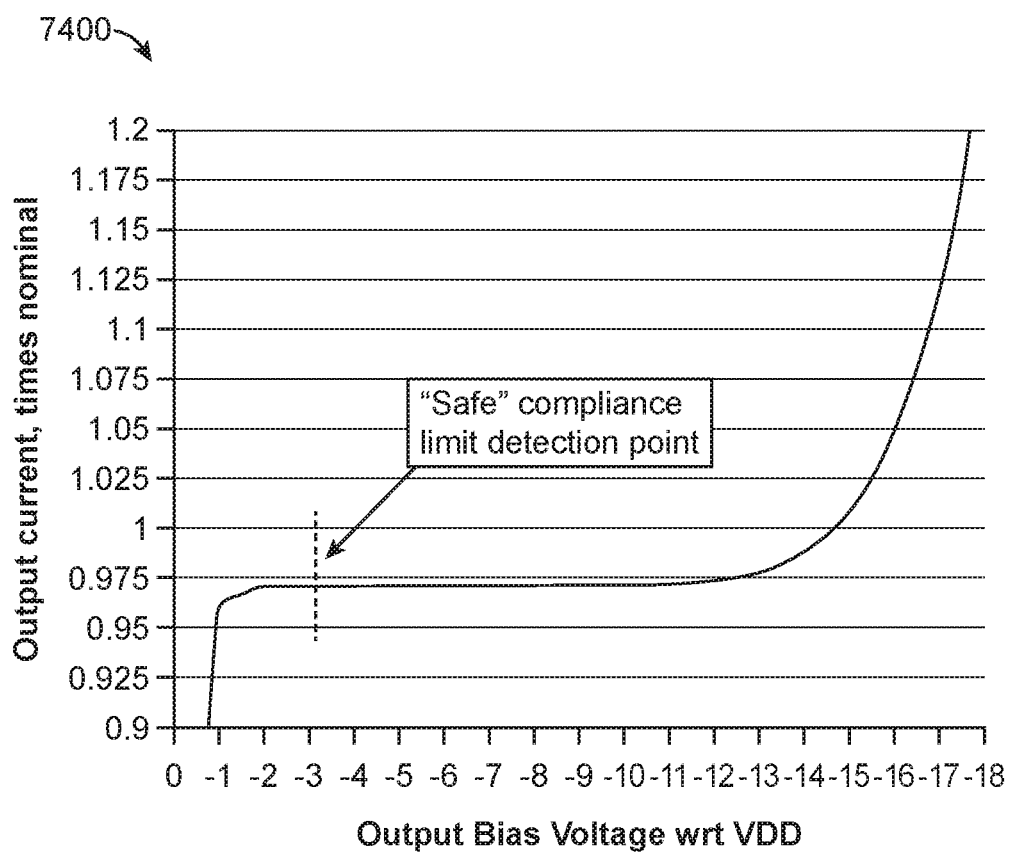
FIG. 74 illustrates a chart of output current versus output bias voltage for a stimulator, according to many embodiments.

The chart 7400 in FIG. 74 below shows I-V performance of a cascoded PFET current mirror, typical of the positive source of a stimulator output. At the left side of the chart, the current source is in compliance limit, with output current starting to drop off at about 2V below VDD, and dropping off steeply at 1V. This is the current-source "dropout" voltage, and is one of the overhead power costs of a current-based stimulator. To the right of the dropout voltage point is long flat region, where effective output impedance is typically in the megohm range. This is where the source needs to operate if we want to ensure charge balance by means of the current source matching. To the right of the linear region the current starts to climb in an uncontrolled manner as the output devices exceed their breakdown voltage. This should be avoided in practice by use of correctly-specified high-voltage output devices and limiting maximum VDD.

One way to address the problem of compliance limits may be to add a voltage detection circuit at the current source output. When the approach of compliance limit is detected, the current source can be turned off. This can either be treated as an error condition and halt stimulation, or if this occurs during the stimulation phase, the time at which detection occurs can be latched and used to reduce the duration of the recovery phase, so that charge balance is preserved. In order to do this in a reliably safe manner, the detector may have to be very conservatively specified, so that stimulation is stopped while output voltage is still in the linear range, accounting for process and voltage corners. This might mean a detection point set at a volt or so higher than the start of the dropout region, which means effectively an additional volt of dropout. This may be ameliorated somewhat by the fact that the DC-blocking cap that such a circuit helps eliminate would also contribute to additional dropout (e.g., a 2.2 uF DC blocking cap will develop ~1V across it during the course of a 10 mA current pulse of 200 us duration.) So the efficiency loss due to an early compliance detection point may turn out to be roughly a "wash" with the elimination of the DC-blocking cap.

4) Simple Single-Channel Stimulator

Figure 75A:
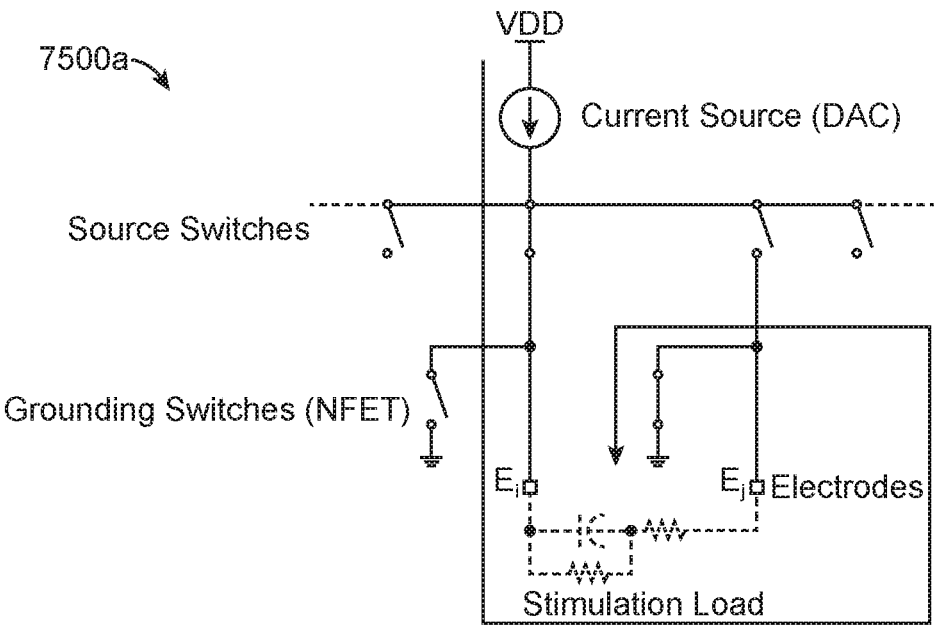
FIGS. 75a and 75b show current paths for a single-channel stimulator, according to many embodiments.
Figure 75B:
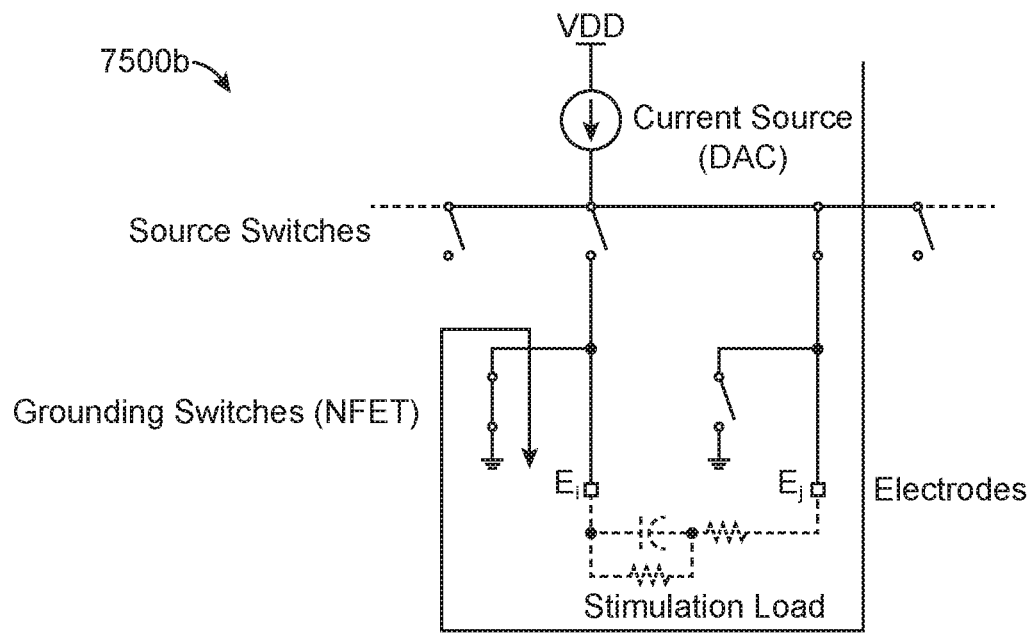

In the case where only a single channel (electrode pair) is stimulated at a given time, a single current source can be used in a H-bridge configuration, with switches to a supply node forming the return path. This is shown in FIGS. 75*a* and 75*b*, with current paths 7500*a*, 7500*b* indicated for the stimulation and recovery phases. The same current source can be used for both stimulation and recovery, and so as long as its output bias voltage remains in the linear region, charge balance will be close to optimal. (With the caveat and possible workaround regarding INL if stimulation and recovery phases are asymmetric, as described in 1) above.) Multiple single source H-bridges can be activated together during the stimulation phase, and can be activated sequentially during the recovery phase. This would require that each of the single current sources have a common sink (if driving from the high voltage side) or a common source (if pulling from the low voltage side).

A few other notes about this approach:

As shown in FIGS. 75a and 75b, there may be one source switch and one grounding switch for each electrode; these need to be physically large devices to reduce series resistance. The good news, however, is that grounding switches at least may not need to be complementary transmission-gate switches; NFETs alone should be sufficient.

As discussed in 3), above, charge balance can break down when the current source goes into compliance and one mitigation is suggested there. Another option that retains some benefit of simplicity may be a hybrid approach using a single off-chip DC blocking cap that is available as common resource, and connected to the active electrodes by switches, as shown in FIGS. 76a and 76b by circuit diagrams 7600a and 7600b, respectively. This can solve the compliance issue, though not the single-point-failure risk, which is discussed in subsequent sections. This approach may have the obvious cost of one large off-chip capacitor, but is still much more compact than the traditional approach of one capacitor for each electrode.

If an off-chip DC-blocking capacitor is used, the relative values/volumes of the DC-blocking capacitor and the VDD bulk or "tank" capacitor should be considered. As it pertains to loss of compliance voltage during the stimulation and recovery phases, the DC-blocking and tank capacitors can be effectively in series with each other, as both develop a voltage drop as current is delivered to the load. For this reason, trying to make the tank capacitor much larger than the DC-blocking capacitor may not be beneficial, and making them close to equal in value may allow a larger DC-blocking cap than otherwise possible and a more optimal solution. For example, if both capacitors are 4.7 uF, the total compliance loss over a 10 uA, 200 us pulse will be 0.85 V. On the other hand, if the DC-blocking capacitor is 1 uF and the tank capacitor is 10 uF, the compliance loss will be about 2 V.

Figure 77:
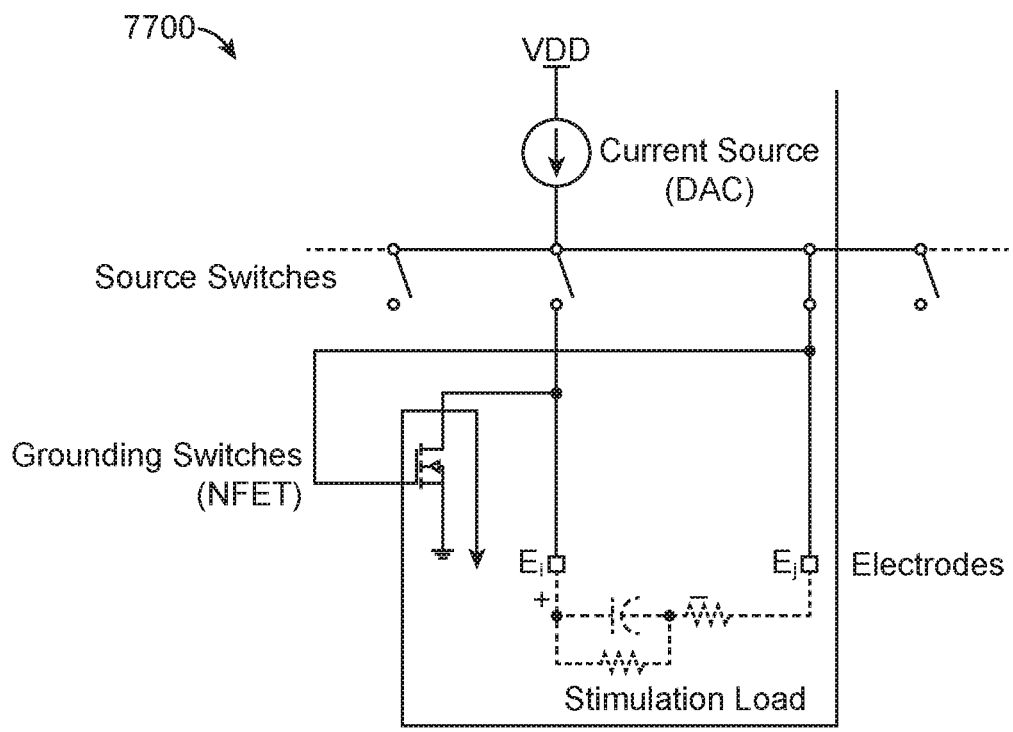
FIG. 77 shows a circuit diagram of a single-channel stimulator using a grounding load during recovery, according to many embodiments.

Finally, one thing that might need to be considered given that the stimulator will be driving a capacitive load: During the recovery phase, the more-positively-charged terminal of the load will be connected to ground, and so the other terminal could initially go below ground and possibly forward-bias ESD protection diodes, which will reduce the accuracy of the current source. One possible way to mitigate that is to make the grounding switch act more like a linear load; a simplified version is shown by circuit diagram 7700 in FIG. 77.

5) Multi-Channel Stimulation

If there is a requirement to stimulate more than one channel (electrode pair) simultaneously, than the single-channel scheme above may not simply be replicated across multiple channels. In order to maintain per-electrode charge balance, the return electrode in each pair cannot just be switched to a supply rail (voltage source). The distribution of impedance, and therefore current, within the tissue is often not well controlled, so current from the multiple current sources may flow to the return electrodes (connected to voltage sources) in an unpredictable manner. For this reason, each stimulation channel will require both a positive (P) and a negative (N) current source, which are switched between the two electrodes in an H-bridge manner.

This may also mean that the P and N current sources in each channel much be very accurately matched to each other; the idea of the weaker source limiting the stronger will not work in this case, again because flow of current from multiple sources is not well controlled through tissue. Matching could be done by means of characterization during wafer-sort and trimming. It may also be possible to characterize and re-trim in vivo, for example by using a small on-chip capacitor to accumulate charge difference between the two sources during a non-stimulation calibration phase. Note, however, that in order to trim to within, say, 5 uA, an 8-bit DAC with a 10 mA full-scale output would require a trimming resolution on the order of ⅛ LSB. This may be a significant practical issue.

One other possible approach may be to have two off-chip DC blocking capacitors with switches to two active electrodes at a time, and always use monopolar stimulation, where current for both channels returns to a single indifferent electrode.

6) Single-Point Failure Protection

Figure 78:
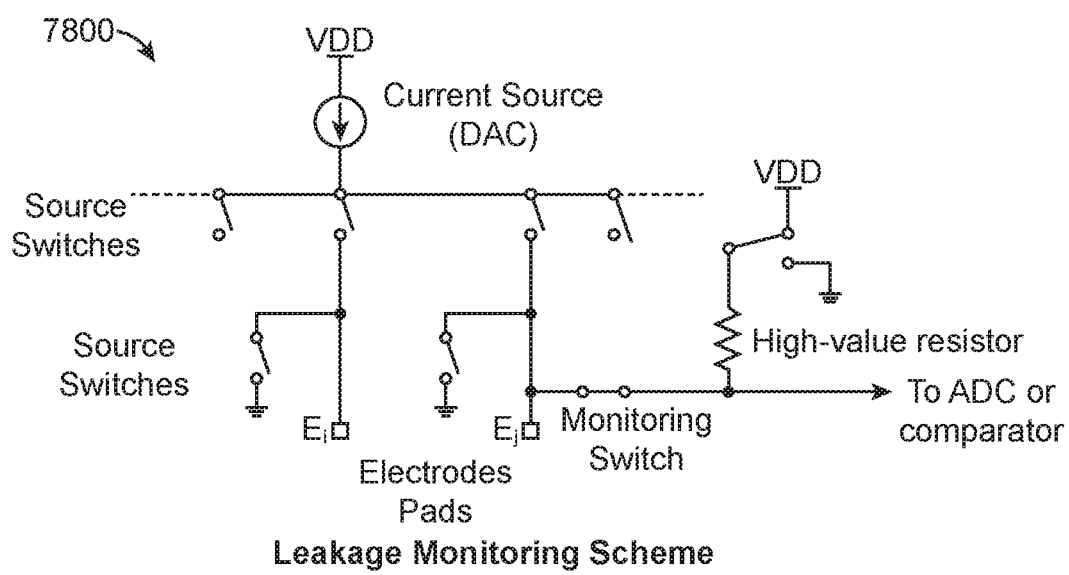
FIG. 78 shows a circuit diagram of an electrode pad leakage monitoring scheme, according to many embodiments.

As presented, the single- and multi-channel schemes in 4) and 5), above, do not protect against DC exposure in the case of a single-point electronic failure. This may even be true for the hybrid approach with the single DC-blocking capacitor, since there is circuitry between the capacitor and tissue. One approach to mitigating the risk may be to have a means to periodically monitor the "health" of the IC. The in vivo P-N calibration operation discussed in 5), above, could be performed periodically to check for any bit failures within the DACs. In addition, leakage to electrode pads at the IC could be measured by using a high-value resistor that is switched into the circuit during non-stimulation intervals. This is shown by circuit diagram 7800 in FIG. 78.

During a period of non-stimulation, say at startup and/or periodically thereafter, all normal stimulation switches may be opened, and a high-value resistor is switched to one IC electrode pad at a time. The opposite end of the resistor may be alternately switched to VDD and ground, and the drop across the resistor measured with the on-chip ADC or a fixed-threshold comparator. Assuming a 10 megohm resistor, a leakage level of 10 nA will cause a 100 mV drop, which should not require heroic circuit design to measure. One drawback of this approach may be the time required: if one assumes that the single-layer capacitance of the electrode interface will be in the circuit, the time constant will be on the order of 10 megohm*10 nF=0.1 s, meaning that it will take on the order of 10 seconds to measure leakage on 8 electrode pads.

Figure 79:
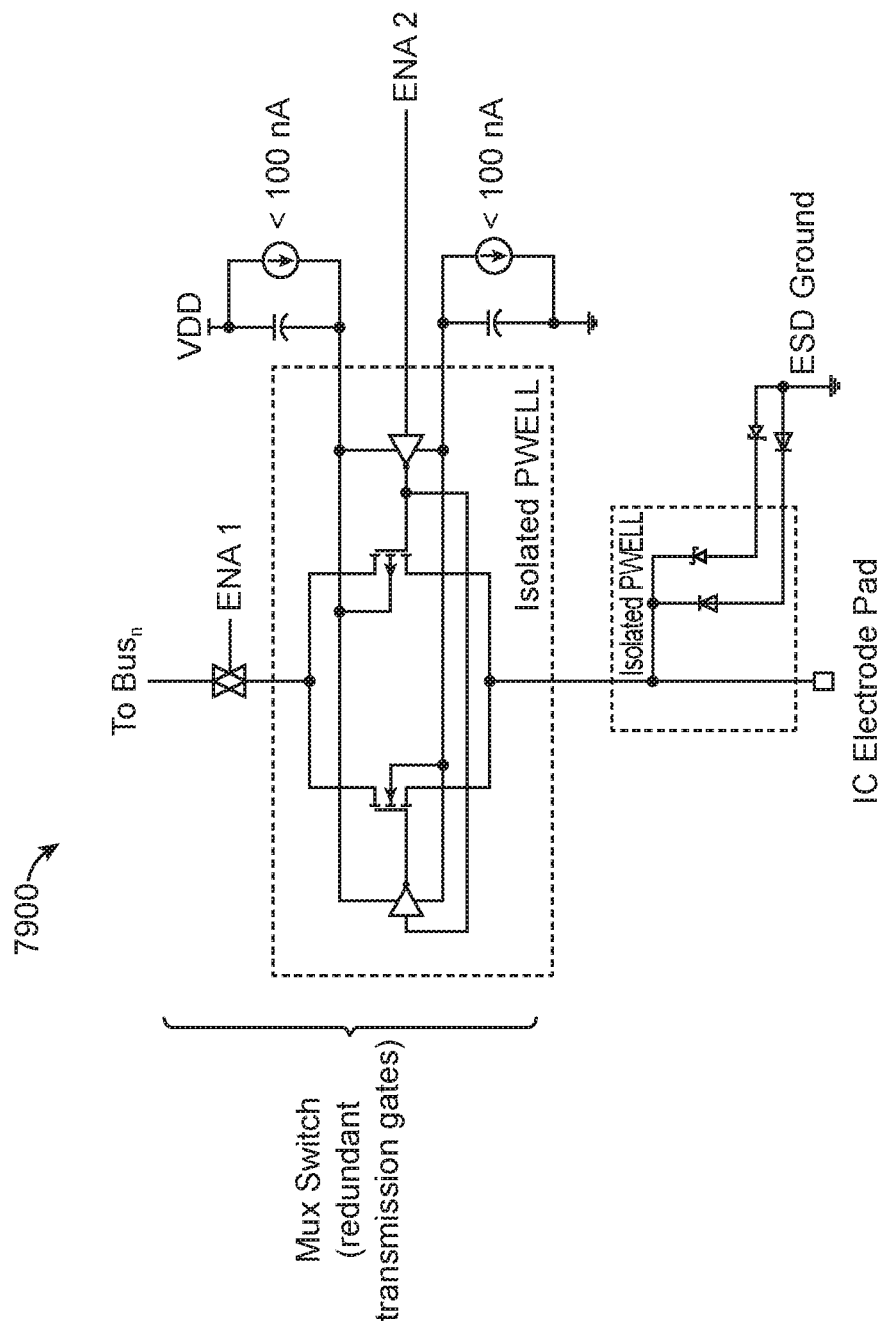
FIG. 79 shows a circuit diagram of a scheme to mitigate single-point on-chip failures, according to many embodiments.

Another way to address single-fault failures (with the assumption that there are multiple potential failure points on-chip, as opposed to the idea that the entire chip is a single potential failure point) is to provide redundancy in control circuits and blockage of potential leakage paths. An example of this approach is shown by the circuit diagram 7900 in FIG. 79.

Several mitigations are shown in diagram 7900. First, the mux switch can employ redundancy in both transmission gates and controls. If one transmission gate develops source-to-drain leakage, the other may still block current flow when it is disabled. Likewise, redundant digital enable lines can prevent leakage if one is stuck on. Within each transmission gate, isolated well structures may be used and gate and bulk biases have very limited current drive, so that if a leakage defect occurs, tissue exposure to DC current will be below the harm threshold. A similar approach could be used for pad ESD protection structures: redundant series low-side diodes and high-side clamps provide overall leakage protection even if one such device is leaky.

There may be a couple of drawbacks to these mitigations: One may be size—a redundant series transmission gate with the same ON resistance as a single, non-redundant gate will require four times the area; e.g., if a 50 ohm complementary switch requires 0.1 mm$^2$ in a given high-voltage process, a 50 ohm redundant switch will require 0.4 mm$^2$. For the "hybrid" approach is section 5), two such switches per electrode are required, so the area required here may be prohibitive. Another potential drawback may be that dual series high-side ESD clamps are probably not available in standard ESD protections libraries, and so likely would have to be developed.

7) High-Frequency Current-Switching

Two papers by Liu, Demosthenous, and Donaldson, "In vitro evaluation of a high-frequency current-switching stimulation technique for FES applications" and "An Integrated Stimulator With DC-Isolation and Fine Current Control for Implanted Nerve Tripoles" describe the use of small-value, on-chip capacitors switched at high frequency to replace large DC blocking capacitors. In the first paper the authors claim that this approach both A) achieves charge-balanced stimulation and B) protects tissue against DC current in the event of a single-point failure. The general approach is shown by diagram 8000 in FIG. 80.

Capacitors C1 and C2 pump charge from the current source ($I_{DAC}$) to the load, and as with any switched-cap circuit, capacitor size can be traded off for frequency, thus allowing small, on-chip capacitors.

The claim of charge-balance, A), however, may appear flawed for at least the following reason: In a conventional stimulator (a), a DC-blocking capacitor may enforces charge balance because it is in both the charge and discharge paths of the load, and so any imbalance between charge and discharge phases results in a net voltage being developed across the cap, which will eventually limit current in one or the other phase and thus enforce charge balance. In the high-frequency current-switching approach, however, the capacitors' charge path may be through the load but the discharge path is not, so the capacitors cannot enforce charge balance. The authors in fact achieve charge balance through passive shorting after the stimulation pulse, and again referring to Sit's thesis, there appears to some potential safety risk in relying on passive shorting to provide more than just a minimal "fine adjustment" of charge balance.

In the second paper, the authors back away from the charge-balance claim but provide substantiation for the single-point-failure-protection claim B). This appears somewhat more reasonable: The switched capacitors C1 and C2 would limit DC leakage due to a failure in the positive current source, and the controls for the ground-return and discharge switches are capacitively coupled, to avoid DC leakage paths in the case of a failure. However, the overall protection afforded seems limited: Switched capacitors behave like resistors in circuit, so while they will limit maximum current in the case of a gross short, they will not limit total charge delivered. Another issue is size; to achieve an equivalent 50 ohm series resistance using a 5 Mhz switching frequency, C1 and C2 would each have to have a value of 4 nf, requiring a total of 2 mm² of area in a typical process. This is roughly a factor of 5 larger than the redundant complementary switch discussed in section 6). In addition, the authors use an SOI process to achieve supply isolation, so some work would have to be done to see if sufficient isolation could be achieved using a standard high-voltage bulk-CMOS process. (And availability of depletion-mode FETs are required in the process, to protect the charge-balance function of the shorting switch in the case that $\Phi_{DISCHAGE}$ fails open.)

In short, because of the limited capabilities for both charge balancing and fault protection, this approach may not appear to be very promising to replace large off-chip capacitors as safety elements.

8) Other Approaches

Figure 81:
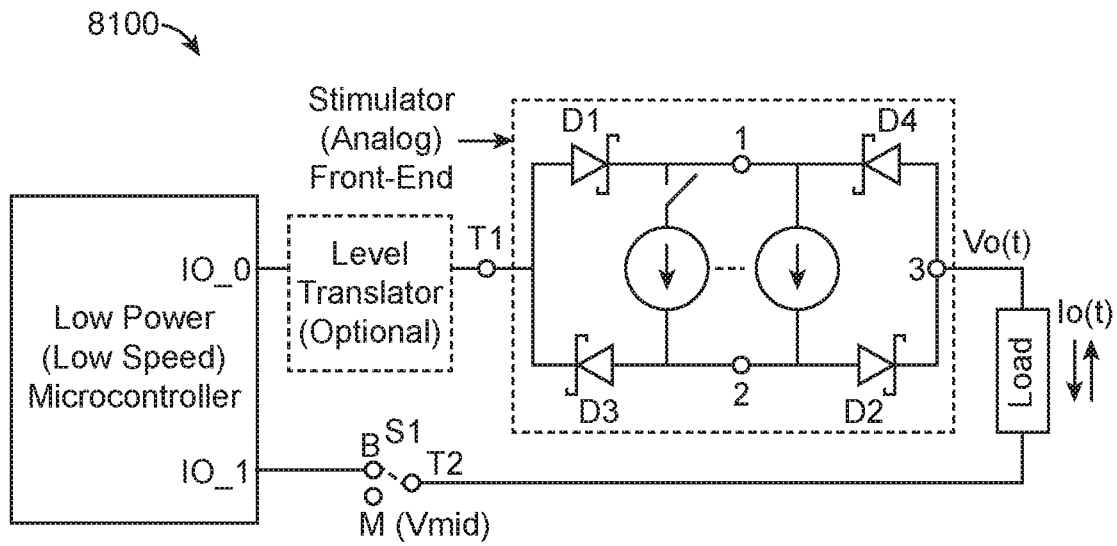
FIG. 81 shows a circuit diagram of an H-bridge stimulator architecture, according to many embodiments.

In their paper "Flexible Charge-Balanced Stimulator with 5.6 fC Accuracy for 140 nC Injections" authors Nag, Jia, Thakor, and Sharma describe the use of an H-bridge stimulator architecture with a single floating current source, as shown in the diagram 8100 in FIG. 81.

This may be similar to the simple single-channel stimulator described in section 4), above, in that a single current source is used for both the stimulation and recovery phases, and so ensures charge balance, assuming the source is linear. This latter approach may use diodes instead of switches in some places, and so switch chip area could possibly be traded off with the fixed ~0.7V drop of each diode (there is some question whether high-current on-chip Schottky diodes can be realized practically). However, to mux the single current source across multiple electrode pairs, switches would still be required, so the saving might be moot. Also, issues of compliance limits, multi-channel simultaneous stimulation, and single-point failure protection are not addressed by this design. Finally, the authors give no explanation of what is probably the most challenging part of the design, i.e., how to design a floating current source. (On the other hand, they do detail the measurement setup used to characterized charge balance accuracy of their design).

Figure 82:
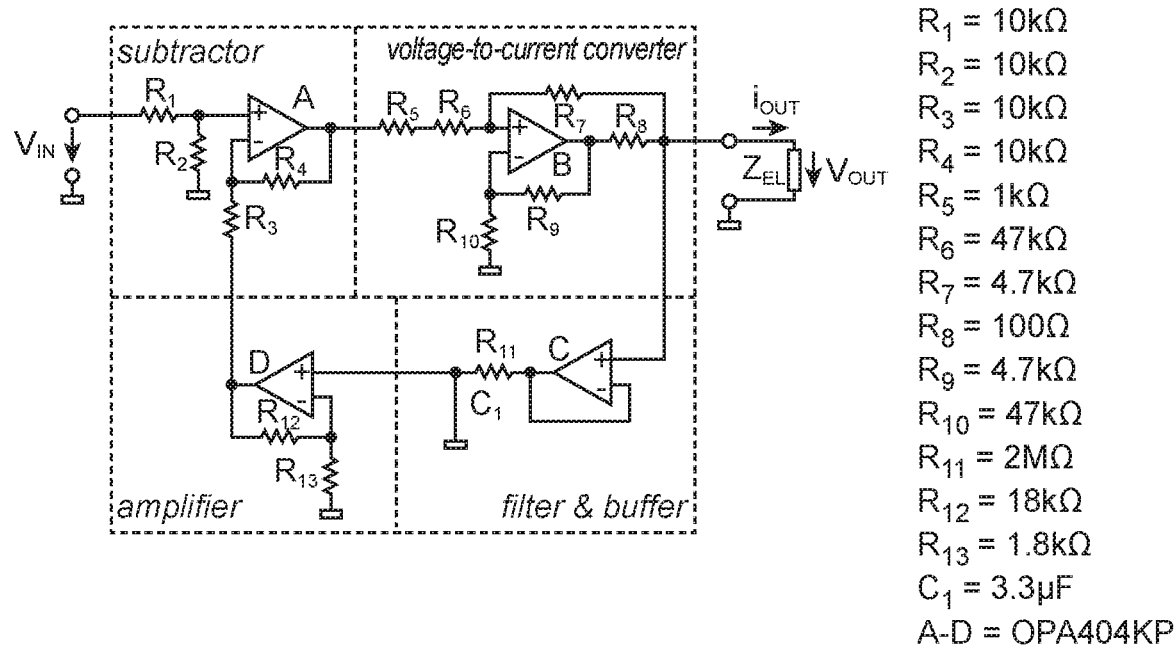
FIG. 82 show a circuit diagram of a scheme using regulated electrode bias-voltage for safe neural stimulation, according to many embodiments.

In their paper "A voltage-controlled current source with regulated electrode bias-voltage for safe neural stimulation," authors Schuettler, Franke, Krueger, and Stieglitz describe a purely analog approach that is very elegant in its simplicity, but likely has practical limitations in a real application. The basic circuit is shown in the diagram 8200 in FIG. 82.

In this approach, amplifier C may integrate voltage across the load using a long time constant, and any non-zero average voltage (and therefore current) acts as an error term that corrects the bipolar current source. The primarily limitation to this approach may be that the DC accuracy required to ensure charge safety; assuming a target of 10 nA net DC maximum and a 1 Kohm stimulation load, the circuit would have to be accurate to 10 uV; this falls into the "heroics" category. Even if we use an additional shorting step to resolve small charge balance errors, the circuit may still need to be accurate to a few mVs. A secondary issue may be that if we want to use a single positive power supply node, the voltage measurement may have to be differential.

Figure 83:
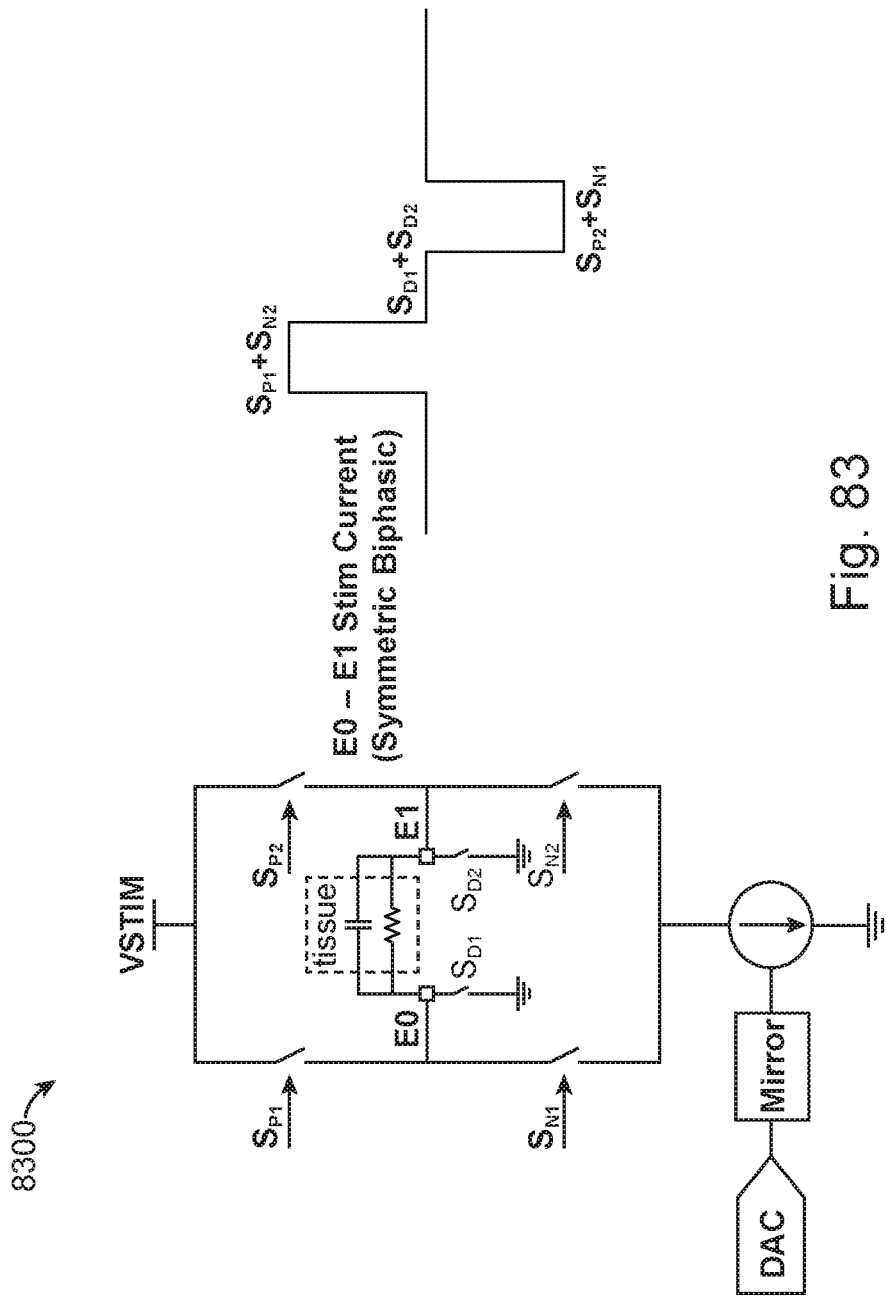
FIG. 83 shows a circuit diagram of a scheme of a current-sink H-bridge approach, according to many embodiments.

Finally, Cactus proposes the following current-sink H-bridge approach shown by circuit diagram 8300 in FIG. 83. This may be identical in principal to the simple single-channel stimulator described in 5), above. A difference may be in the use of an NFET (sink) current source instead of a PFET source. Cactus's use of NFETs may likely be advantageous in terms of chip area. On the other hand, PFETs are less prone to issues with leakage due to impact ionization at high drain currents/voltages. Also, the inventors here may find discomfort in connecting the positive supply to tissue through a switch while the ESD devices in the pads are connected to ground. Granted, it may require a double-point failure to apply uncontrolled current to tissue, so this may fall into the category of "superstition."

The one point that Cactus may seem on slightly shaky ground is whether this can be scaled to multi-channel simultaneous stimulation; again, the problem is one of per-electrode charge balance if more than one electrode is connected to a voltage source in a given stimulation phase.

While preferred embodiments of the present disclosure have been shown and described herein, it will be obvious to those skilled in the art that such embodiments are provided by way of example only. Numerous variations, changes, and substitutions will now occur to those skilled in the art without departing from the scope of the present disclosure. It should be understood that various alternatives to the embodiments of the present disclosure described herein may be employed in practicing the inventions of the present disclosure. It is intended that the following claims define the scope of the invention and that methods and structures within the scope of these claims and their equivalents be covered thereby.

What is claimed is:

1. An apparatus for delivering stimulation energy to tissue, comprising:
   an implantable device comprising an implantable energy storage element and at least one implantable antenna, the implantable device configured to deliver stimulation energy to tissue;
   an external device comprising an external antenna, the external device configured to transmit power and data to the implantable device via a wireless link;
   wherein the apparatus is configured to reduce a power level of the external device transmissions until a discharge rate of the implantable energy storage element is faster than the charge rate of the implantable energy storage element.

2. The apparatus according to claim 1, wherein the apparatus is further configured to assess at least one of relative wireless link quality information or absolute wireless quality link information.

3. The apparatus according to claim 1, wherein a quality of the wireless link is adjustable by a user adjusting external antenna orientation.

4. The apparatus according to claim 1, wherein a quality of the wireless link is adjustable by adjusting a parameter selected from the group consisting of: external device antenna position; external device output power level; external device operating frequency; parameter of an impedance matching network; and combinations thereof.

5. The apparatus according to claim 1, wherein the apparatus is further configured to notify the external device when the implantable device has received sufficient power to turn on.

6. The apparatus according to claim 1, wherein the apparatus is further configured to adjust the power level of the external device transmissions to the implantable device.

7. The apparatus according to claim 6, wherein the apparatus is configured to increase the power level of the external device transmissions during an assessment of the quality of the wireless link.

8. The apparatus according to claim 7, wherein increasing the power level increases speed of the assessment of the quality of the wireless link.

9. The apparatus according to claim 6, wherein the apparatus is configured to adjust the power level based on a parameter selected from the group consisting of: a stimulation therapy parameter; charge rate of the implantable energy storage element; discharge rate of the implantable energy storage element; and combinations thereof.

10. The apparatus according to claim 6, wherein the apparatus is configured to adjust the power level during an event selected from the group consisting of: event in which patient physical activity varies; event in which environmental conditions change; event in which wireless link gain changes; and combinations thereof.

11. The apparatus according to claim 6, wherein the apparatus is configured to adjust the power level during data transmission and/or reception phases.

12. The apparatus according to claim 6, wherein the adjusting of the power level can comprise bursts of power delivered by the external device to charge the implantable energy storage element.

13. The apparatus according to claim 1, wherein the apparatus is further configured to prevent unintended operation by monitoring a parameter selected from the group consisting of: a therapy parameter; a wireless data link parameter; wireless power link parameter; a sensing circuitry parameter; an antenna parameter; an impedance parameter; and combinations thereof.

14. The apparatus according to claim 1, wherein the apparatus is further configured to maximize quality of the wireless link.

15. The apparatus according to claim 1, wherein the apparatus further comprises a safety protocol and a kill switch, wherein the apparatus is further configured to shut down and notify a user if an undesired condition is detected.

16. The apparatus according to claim 15, wherein the safety protocol is configured to monitor a parameter selected from the group consisting of: temperature of the apparatus; temperature of the external device; a wireless power link parameter; impedance mismatch; electric current draw; bit error rate; antenna failure; reflection coefficient; standing wave ratio; and combinations thereof.

17. The apparatus according to claim 16, wherein the apparatus is configured to perform a calibration of an undesired condition if determined by the safety protocol.

18. The apparatus according to claim 1, wherein the external device is configured to deliver power at a first power level during stimulation and a second power level during an assessment of the quality of the wireless link, and wherein the second power level is higher than the first power level.

19. The apparatus according to claim 1, wherein the external device comprises an adhesive layer, and wherein the adhesive layer is a configured to adhesively attach to patient skin at a location over the implantable device.

20. The apparatus according to claim 1, wherein the implantable device comprises a shunting network, and wherein the implantable device is configured to discharge the implantable energy storage element via the shunting network based on a command from the external device.

21. The apparatus according to claim 1, wherein the implantable energy storage element comprises at least one of a battery or a capacitor.

* * * * *